(12) United States Patent
Zhang et al.

(10) Patent No.: US 10,373,702 B2
(45) Date of Patent: Aug. 6, 2019

(54) WATER-SOLUBLE TRANS-MEMBRANE PROTEINS AND METHODS FOR THE PREPARATION AND USE THEREOF

(71) Applicant: Massachusetts Institute of Technology, Cambridge, MA (US)

(72) Inventors: Shuguang Zhang, Lexington, MA (US); Fei Tao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 162 days.

(21) Appl. No.: 14/723,399

(22) Filed: May 27, 2015

(65) Prior Publication Data

US 2015/0370961 A1   Dec. 24, 2015

Related U.S. Application Data

(63) Continuation-in-part of application No. PCT/US2015/022780, filed on Mar. 26, 2015, and a continuation-in-part of application No. 14/669,753, filed on Mar. 26, 2015, now abandoned.

(60) Provisional application No. 62/117,550, filed on Feb. 18, 2015, provisional application No. 61/993,783, filed on May 15, 2014, provisional application No. 61/971,388, filed on Mar. 27, 2014.

(51) Int. Cl.
| | | |
|---|---|---|
| *G16B 15/00* | (2019.01) | |
| *C07K 14/72* | (2006.01) | |
| *C07K 14/705* | (2006.01) | |
| *G16B 35/00* | (2019.01) | |
| *G16C 20/60* | (2019.01) | |

(52) U.S. Cl.
CPC ............ *G16B 15/00* (2019.02); *C07K 14/705* (2013.01); *C07K 14/723* (2013.01); *G16B 35/00* (2019.02); *G16C 20/60* (2019.02)

(58) Field of Classification Search
None
See application file for complete search history.

(56) References Cited

U.S. PATENT DOCUMENTS

| | | | |
|---|---|---|---|
| 544,021 A | 8/1895 | Chuntharapai et al. | |
| 5,548,068 A | 8/1996 | Fischer et al. | |
| 5,739,273 A | 4/1998 | Engelman et al. | |
| 5,843,678 A | 12/1998 | Boyle | |
| 6,124,429 A | 9/2000 | Miura et al. | |
| 6,316,408 B1* | 11/2001 | Boyle | C07K 14/70578 424/134.1 |
| 6,350,593 B1* | 2/2002 | Williams | C07K 14/71 435/252.3 |
| 8,637,452 B2 | 1/2014 | Zhang et al. | |
| 9,309,302 B2 | 4/2016 | Zhang et al. | |
| 2002/0160416 A1 | 10/2002 | Boyle et al. | |
| 2004/0215400 A1* | 10/2004 | Slovic | G06F 19/16 702/19 |
| 2010/0130720 A1* | 5/2010 | Schraeml | C07K 14/00 530/324 |
| 2010/0190188 A1 | 7/2010 | Henderson et al. | |
| 2010/0249022 A1 | 9/2010 | Clapham et al. | |
| 2011/0027910 A1 | 2/2011 | Weir et al. | |
| 2011/0028700 A1 | 2/2011 | Heal | |
| 2011/0046351 A1 | 2/2011 | Weir et al. | |
| 2011/0112037 A1 | 5/2011 | Warne et al. | |
| 2012/0165507 A1 | 6/2012 | Jazayeri-Dezfuly et al. | |
| 2012/0172402 A1* | 7/2012 | Schmalz | C07D 487/18 514/366 |
| 2012/0172577 A1* | 7/2012 | Kase | C07K 14/78 530/356 |
| 2012/0252719 A1* | 10/2012 | Zhang | C07K 14/705 514/1.7 |
| 2013/0273585 A1 | 10/2013 | Appaiah et al. | |
| 2014/0243277 A1 | 8/2014 | Zhang et al. | |
| 2015/0370960 A1 | 12/2015 | Zhang et al. | |
| 2016/0264640 A1 | 9/2016 | Zhang et al. | |

FOREIGN PATENT DOCUMENTS

| | | |
|---|---|---|
| EP | 1270724 A2 | 1/2003 |
| WO | WO-2004/065363 A2 | 8/2004 |
| WO | WO-2006/026355 A2 | 3/2006 |
| WO | WO-2007/089899 A2 | 8/2007 |
| WO | WO-2007/141309 A2 | 12/2007 |
| WO | WO-2008/114020 A2 | 9/2008 |
| WO | WO-2008/143910 A2 | 11/2008 |
| WO | WO-2011/095625 A1 | 8/2011 |
| WO | WO-2012/066330 A1 | 5/2012 |
| WO | WO-2012/098413 A1 | 7/2012 |
| WO | WO-2012/116203 A1 | 8/2012 |
| WO | WO-2012/120315 A2 | 9/2012 |
| WO | WO-2015/148820 A1 | 10/2015 |

OTHER PUBLICATIONS

Bertone et al. Nucleic Acids Research, 29,13, 2001, p. 2884-2898.*
Liang et al., "Computational studies 60-62, of membrane proteins: Models and predictions for biological understanding," *Biochimica et Biophysica Acta*, 1818(4)927-941 (2012).
Database UniProt, RecName: Full-Olfactory Receptor, XP002733575, retrieved from EBI accession No. Uniprot: B2N158, Jul. 2008.
Datta and Stone, "Soluble Mimics of a Chemokine Receptor: Chemokine Binding by Receptor Elements Juxtaposed on a Soluble Scaffold," *Protein Science*, 12:2482-2491 (2003).

(Continued)

*Primary Examiner* — Michael L Borin
(74) *Attorney, Agent, or Firm* — McCarter & English, LLP; Thomas O. Hoover; Yu Lu

(57) ABSTRACT

The present invention is directed to a computer implemented method for executing a procedure to select a water-soluble variant of a G Protein-Coupled Receptor (GPCR).

9 Claims, 12 Drawing Sheets

Specification includes a Sequence Listing.

(56) References Cited

OTHER PUBLICATIONS

Gene Infinity (pKa of amino acids chart, available at http://www.geneinfinity.org/sp/sp_aaprops.html).
Khafizov et al., "Ligand Specificity of Odorant Receptors," *J. Mol. Model*, 13:401-407 (2007).
Ma et al., "NMR Studies of a Channel Protein without Membranes: Structure and Dynamics of Walter-Solubilized KcsA," *PNAS*, 105(43):16537-16542 (2008).
Marshall ("Amino Acid Chart," available at http://schools.nashua.edu/myclass/marshalii/anatomy/Pictures/FormsIDispForm.aspx?1 0=31, created Jan. 30, 2012, accessed on Feb. 17, 2015).
Park, "Structure of the Chemokine Receptor CXCR1 in Phospholipid Bilayers," *Nature*, 491:779-784 (2012).
Perez-Aguilar et al., "A Computationally Designed Water-Soluble Variant of a G-Protein-Coupled Receptor: The Human Mu Opioid Receptor," *PLOS One*, 8(6):e66009 (2013).
Slovic et al., "Computational Design of a Water-Soluble Analog of Phospholamban," *Protein Science*, 12:337-348 (2003).
Slovic et al., "Computational design of water-soluble analogues of the potassium channel KcsA," *Proc. Natl. Acad. Sci. U.S.*, 101(7):1828-1833 (2004).
Slovic et al., "X-ray Structure of a Water-Soluble Analog of the Membrane Protein Phospholamban: Sequence Determinants Defining the Topology of Tetrameric and Pentameric Coiled Coils," *J. Mol. Biol.* 348:777-787 (2005).
Zhang et al. "Experimental and Computational Evaluation of Forces Directing the Association of Transmembrane Helices," *J. Am. Chem. Soc.*, 131:11341-11343 (2009).
Zhang et al., "The Mernbrane- and Soluble-Protein Helix-Helix Interactome: Similar Geometry via Different Interactions," *Structure*, 23:527-541 and Supplemental Information (2015).
Betts et al., Amino Acid Properties and Consequences of Substitutions, Bioinformatics for Geneticists, ed. Barns ans Gray; (2003) p. 291-316.
Firestein et al., " How the olfactory system makes sense of scents" Nature, vol. 413, 13, Sep. 2001, p. 212-218.
Hesselgesser J et al., "Identification and characterization of the CXCR4 chemokine receptor in human T cell lines: ligand binding, biological activity, and HIV-1 infectivity." The Journal of Immunology, The American Association of Immunologists, US, vol. 160, No. 2, Jan. 15, 1998, pp. 877-883.
Wienken et al., "Protein-binding assays in biological liquids using microscale thermophoresis" Nature Communications(2010) 1(100) DOL: 10. 1038/ncomms 1093, p. 1-7.
U.S. Appl. No. 14/669,753, US-2015-0370960-A1, Dec. 24, 2015.
U.S. Appl. No. 14/105,252, US 2014-0243277-A1, Aug. 28, 2014.
U.S. Appl. No. 13/403,725, U.S. Pat. No. 8,637,452, Jan. 28, 2014.

\* cited by examiner

```
  1    MEGISIYTSDNYTEEMGSGDYDSMKEPCFREENANFNK                       60
  1                                          IFLPTTYSTTFQTGTTGNGQVT 60
  1                                          IFQPTTYSTTFQTGTTGNGQVT 60
  1                                          IFQPTTYSTTFQTGTTGNGQVT 60
  1                                          IFQPTTYSTTYQTGTTGNGQVT 60
  1                                          IFQPTTYSTTYQTGTTGNGQTT 60
  1                                          IFQPTTYSTTYQTGTTGNGQTI 60
  1                                          IFQPTTYSTTYQTGTTGNGQTT 60
  1                                          TYQPTTYSTTYQTGTTGNGQTT 60

61        GYQKKLRSMTDKYR                    ANWYFGNFLCK            120
 61    QVM             LHLSTADQQFTTTQPFWAVDAV           AVHVTYTVNQ  120
 61    QVM             LHLSVADQQYTTTQPFWATDAV           AVHTTYTVNQ  120
 61    QTM             LHQSVADQQYVTTQPFWATDAT           AVHTTYTVNQ  120
 61    QTM             QHQSVADQQFTTTQPFWATDAT           ATHTTYTVNQ  120
 61    QVM             LHQSVADQQYTITQPYWATDAT           ATHTIYTTNQ  120
 61    QTM             QHLSVADQQYTITQPYWATDAT           AVHTTYTTNQ  120
 61    QTM             QHLSTADQQYVTTQPYWATDAT           ATHTTYTTNQ  120
 61    QTM             QHQSTADQQYTTTQPYWATDAT           ATHTTYTTNQ  120

121        SLDRYLAIVHATNSQRPRKLLAEK                     ANVSEA      180
121    YSSVQIQAFT               VTYTGVWTPAQQQTIPDFIF                180
121    YSSVQIQAFT               TTYTGTWIPAQQQTIPDFIF                180
121    YSSVQTQAFT               TTYTGTWTPAQQQTIPDFIF                180
121    YSSVQTQAFT               TTYTGTWTPAQQQTIPDFIY                180
121    YSSVQTQAFT               TTYVGTWTPAQQQTPDYIF                 180
121    YSSVQTQAFT               TTYVGTWTPAQQQTTPDFIY                180
121    YSSVQTQAFT               TTYTGVWTPAQQQTPDYTF                 180
121    YSSTQTQAYT               TTYTGTWTPAQQQTTPDYTY                180

181        DDRYICDRFYPNDLW               SCYCIIISKLSHSKGHQKRKALKT   240
181                    VVVFQFQHTMVGQTQPGTTTQ                        240
181                    VVVFQFQHTMTGQTQPGTTTQ                        240
181                    VVVFQYQHTMTGQTQPGTTTQ                        240
181                    VVVYQYQHTMTGQTQPGTTTQ                        240
181                    TVVFQYQHTMTGQTQPGTTTQ                        240
181                    VVTFQYQHTMTGQTQPGTTTQ                        240
181                    TVVYQYQHTMTGQTQPGTTTQ                        240
181                    TTTYQYQHTMTGQTQPGTTTQ                        240

241    T               DSFILLEIIKQGCEFENTVHK                        300
241    VTQIQAFFACWQPYYTGTST              WISITEAQAFFHCCLNPI          300
241    VIQIQAYFACWQPYYTGTST              WISITEAQAFYHCCLNPI          300
241    VIQIQAYYACWQPYYTGTST              WISITEAQAYFHCCQNPT          300
241    VIQTQAFYACWQPYYTGTST              WISITEALAFYHCCQNPT          300
241    VIQIQAYFACWQPYYTGTST              WISTTEALAYFHCCQNPT          300
241    VTQIQAFYACWQPYYTGTST              WISITEALAYYHCCQNPT          300
241    VIQIQAYYACWQPYYTGTST              WISTTEALAYYHCCQNPT          300
241    TTQTQAYYACWQPYYTGTST              WTSTTEAQAYYHCCQNPT          300

301    AFLGAKFKTSAQHALTSVSRGSSLKILSKGKRGGHSSVSTESESSSFHSS    352
301    QY                                                    352
301    QY                                                    352
301    LY                                                    352
301    QY                                                    352
301    QY                                                    352
301    QY                                                    352
301    QY                                                    352
301    QY                                                    352
```

```
┌─────────────────────────────────────────┐
│ Operating a computer programmed to      │
│ execute a scripted procedure to         │──── 402
│ determine a water soluble protein       │
│ variant                                 │
└─────────────────────────────────────────┘
                    │
                    ▼
┌─────────────────────────────────────────┐
│ Entering one or more protein sequences  │──── 404
│ for computerized analysis               │
└─────────────────────────────────────────┘
                    │
                    ▼
┌─────────────────────────────────────────┐
│ Obtaining a variant with a prediction   │
│ result in which hydrophobic amino acids │
│ (V, L, I, F) are replaced with          │
│ non-ionic amino acids (N, Q, T, S, Y)   │──── 406
│ while retaining one or more hydrophobic │
│ amino acids, for example, changing over │
│ 15% or over 25% of the hydrophobic      │
│ amino acids, and subsequently           │
└─────────────────────────────────────────┘
                    │
                    ▼
┌─────────────────────────────────────────┐
│ Obtaining an α-helix (secondary         │
│ structure) prediction result that       │──── 408
│ verifies biological function            │
└─────────────────────────────────────────┘
                    │
                    ▼
┌─────────────────────────────────────────┐
│ Verify transmembrane region prediction  │──── 410
│ result to verify water solubility       │
└─────────────────────────────────────────┘
```

FIG. 11A

SEQUENCE LISTING

```
<160> NUMBER OF SEQ ID NOS: 379

<210> SEQ ID NO 1
<211> LENGTH: 356
<212> TYPE: PRT
<213> ORGANISM: Unknown
<220> FEATURE:
<223> OTHER INFORMATION: Description of Unknown: Mammalian
      CXCR4 polypeptide

<400> SEQUENCE: 1

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
        35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160
```

```
Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Phe Gln Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355

<210> SEQ ID NO 2
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Thr
        35                  40                  45

Tyr Ser Thr Thr Tyr Gln Thr Gly Thr Thr Gly Asn Gly Gln Thr Thr
    50                  55                  60

Gln Thr Met Gly Tyr Gln Lys Lys Leu Arg Ser Met Thr Asp Lys Tyr
65                  70                  75                  80

Arg Gln His Gln Ser Thr Ala Asp Gln Gln Tyr Thr Thr Thr Gln Pro
                85                  90                  95

Tyr Trp Ala Thr Asp Ala Val Ala Asn Trp Tyr Phe Gly Asn Phe Leu
            100                 105                 110

Cys Lys Ala Thr His Thr Thr Tyr Thr Thr Asn Gln Tyr Ser Ser Thr
        115                 120                 125

Gln Thr Gln Ala Tyr Thr Ser Gln Asp Arg Tyr Leu Ala Ile Val His
    130                 135                 140

Ala Thr Asn Ser Gln Arg Pro Arg Lys Leu Leu Ala Glu Lys Thr Thr
145                 150                 155                 160
```

Tyr Thr Gly Thr Trp Thr Pro Ala Gln Gln Gln Thr Pro Asp Tyr
                165                 170                 175

Thr Tyr Ala Asn Val Ser Glu Ala Asp Asp Arg Tyr Ile Cys Asp Arg
            180                 185                 190

Phe Tyr Pro Asn Asp Leu Trp Val Val Val Tyr Gln Tyr Gln His Thr
        195                 200                 205

Met Thr Gly Gln Thr Gln Pro Gly Thr Thr Thr Gln Ser Cys Tyr Cys
    210                 215                 220

Thr Ile Ile Ser Lys Leu Ser His Ser Lys Gly His Gln Lys Arg Lys
225                 230                 235                 240

Ala Leu Lys Thr Thr Thr Thr Gln Thr Gln Ala Tyr Tyr Ala Cys Trp
                245                 250                 255

Gln Pro Tyr Tyr Thr Gly Thr Ser Thr Asp Ser Tyr Ile Leu Leu Glu
            260                 265                 270

Ile Ile Lys Gln Gly Cys Glu Phe Glu Asn Thr Val His Lys Trp Thr
        275                 280                 285

Ser Thr Thr Glu Ala Gln Ala Tyr Tyr His Cys Cys Gln Asn Pro Thr
    290                 295                 300

Gln Tyr Ala Tyr Gln Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355

<210> SEQ ID NO 3
<211> LENGTH: 38
<212> TYPE: PRT
<213> ORGANISM: Unknown
<220> FEATURE:
<223> OTHER INFORMATION: Description of Unknown: Mammalian
      CXCR4 polypeptide

<400> SEQUENCE: 3

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys
        35

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Phe Leu Pro Thr Thr Tyr Ser Thr Thr Phe Gln Thr Gly Thr Thr
1               5                   10                  15

Gly Asn Gly Gln Val Thr Gln Val Met
            20                  25

<210> SEQ ID NO 5

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Phe Gln Pro Thr Thr Tyr Ser Thr Thr Phe Gln Thr Gly Thr Thr
1               5                   10                  15

Gly Asn Gly Gln Val Thr Gln Val Met
            20                  25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Phe Gln Pro Thr Thr Tyr Ser Thr Thr Phe Gln Thr Gly Thr Thr
1               5                   10                  15

Gly Asn Gly Gln Val Thr Gln Thr Met
            20                  25

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Phe Gln Pro Thr Thr Tyr Ser Thr Thr Tyr Gln Thr Gly Thr Thr
1               5                   10                  15

Gly Asn Gly Gln Val Thr Gln Thr Met
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Phe Gln Pro Thr Thr Tyr Ser Thr Thr Tyr Gln Thr Gly Thr Thr
1               5                   10                  15

Gly Asn Gly Gln Thr Thr Gln Val Met
            20                  25

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Phe Gln Pro Thr Thr Tyr Ser Thr Thr Tyr Gln Thr Gly Thr Thr
1               5                   10                  15
```

```
Gly Asn Gly Gln Thr Ile Gln Thr Met
            20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Phe Gln Pro Thr Thr Tyr Ser Thr Thr Tyr Gln Thr Gly Thr Thr
1               5                   10                  15

Gly Asn Gly Gln Thr Thr Gln Thr Met
            20                  25

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Tyr Gln Pro Thr Thr Tyr Ser Thr Thr Tyr Gln Thr Gly Thr Thr
1               5                   10                  15

Gly Asn Gly Gln Thr Thr Gln Thr Met
            20                  25

<210> SEQ ID NO 12
<211> LENGTH: 14
<212> TYPE: PRT
<213> ORGANISM: Unknown
<220> FEATURE:
<223> OTHER INFORMATION: Description of Unknown: Mammalian
      CXCR4 peptide

<400> SEQUENCE: 12

Gly Tyr Gln Lys Lys Leu Arg Ser Met Thr Asp Lys Tyr Arg
1               5                   10

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu His Leu Ser Thr Ala Asp Gln Gln Phe Thr Thr Thr Gln Pro Phe
1               5                   10                  15

Trp Ala Val Asp Ala Val
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Leu His Leu Ser Val Ala Asp Gln Gln Tyr Thr Thr Thr Gln Pro Phe
1               5                   10                  15

Trp Ala Thr Asp Ala Val
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu His Gln Ser Val Ala Asp Gln Gln Tyr Val Thr Thr Gln Pro Phe
1               5                   10                  15

Trp Ala Thr Asp Ala Thr
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln His Gln Ser Val Ala Asp Gln Gln Phe Thr Thr Thr Gln Pro Phe
1               5                   10                  15

Trp Ala Thr Asp Ala Thr
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu His Gln Ser Val Ala Asp Gln Gln Tyr Thr Ile Thr Gln Pro Tyr
1               5                   10                  15

Trp Ala Thr Asp Ala Thr
            20

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln His Leu Ser Val Ala Asp Gln Gln Tyr Thr Ile Thr Gln Pro Tyr
1               5                   10                  15

Trp Ala Thr Asp Ala Thr
            20

<210> SEQ ID NO 19
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 19

Gln His Leu Ser Thr Ala Asp Gln Gln Tyr Val Thr Thr Gln Pro Tyr
1               5                   10                  15

Trp Ala Thr Asp Ala Thr
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln His Gln Ser Thr Ala Asp Gln Gln Tyr Thr Thr Thr Gln Pro Tyr
1               5                   10                  15

Trp Ala Thr Asp Ala Thr
            20

<210> SEQ ID NO 21
<211> LENGTH: 11
<212> TYPE: PRT
<213> ORGANISM: Unknown
<220> FEATURE:
<223> OTHER INFORMATION: Description of Unknown: Mammalian
      CXCR4 peptide

<400> SEQUENCE: 21

Ala Asn Trp Tyr Phe Gly Asn Phe Leu Cys Lys
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Val His Val Thr Tyr Thr Val Asn Gln Tyr Ser Ser Val Gln Ile
1               5                   10                  15

Gln Ala Phe Thr
            20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Val His Thr Thr Tyr Thr Val Asn Gln Tyr Ser Ser Val Gln Ile
1               5                   10                  15

Gln Ala Phe Thr
            20
```

```
<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Val His Thr Thr Tyr Thr Val Asn Gln Tyr Ser Ser Val Gln Thr
1               5                   10                  15

Gln Ala Phe Thr
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Thr His Thr Thr Tyr Thr Val Asn Gln Tyr Ser Ser Val Gln Thr
1               5                   10                  15

Gln Ala Phe Thr
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr His Thr Ile Tyr Thr Thr Asn Gln Tyr Ser Ser Val Gln Thr
1               5                   10                  15

Gln Ala Phe Thr
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Val His Thr Thr Tyr Thr Thr Asn Gln Tyr Ser Ser Val Gln Thr
1               5                   10                  15

Gln Ala Phe Thr
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Thr His Thr Thr Tyr Thr Thr Asn Gln Tyr Ser Ser Val Gln Thr
```

```
1               5                   10                  15

Gln Ala Phe Thr
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Thr His Thr Thr Tyr Thr Thr Asn Gln Tyr Ser Ser Thr Gln Thr
1               5                   10                  15

Gln Ala Tyr Thr
            20

<210> SEQ ID NO 30
<211> LENGTH: 24
<212> TYPE: PRT
<213> ORGANISM: Unknown
<220> FEATURE:
<223> OTHER INFORMATION: Description of Unknown: Mammalian
      CXCR4 peptide

<400> SEQUENCE: 30

Ser Leu Asp Arg Tyr Leu Ala Ile Val His Ala Thr Asn Ser Gln Arg
1               5                   10                  15

Pro Arg Lys Leu Leu Ala Glu Lys
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Thr Tyr Thr Gly Val Trp Thr Pro Ala Gln Gln Gln Thr Ile Pro
1               5                   10                  15

Asp Phe Ile Phe
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Thr Tyr Thr Gly Thr Trp Ile Pro Ala Gln Gln Gln Thr Ile Pro
1               5                   10                  15

Asp Phe Ile Phe
            20

<210> SEQ ID NO 33
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Thr Thr Tyr Thr Gly Thr Trp Thr Pro Ala Gln Gln Gln Thr Ile Pro
1               5                   10                  15

Asp Phe Ile Phe
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Thr Tyr Thr Gly Thr Trp Thr Pro Ala Gln Gln Gln Thr Ile Pro
1               5                   10                  15

Asp Phe Ile Tyr
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Thr Tyr Val Gly Thr Trp Thr Pro Ala Gln Gln Gln Thr Thr Pro
1               5                   10                  15

Asp Tyr Ile Phe
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Thr Tyr Val Gly Thr Trp Thr Pro Ala Gln Gln Gln Thr Thr Pro
1               5                   10                  15

Asp Phe Ile Tyr
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Thr Tyr Thr Gly Val Trp Thr Pro Ala Gln Gln Gln Thr Thr Pro
1               5                   10                  15

Asp Tyr Thr Phe
            20
```

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Thr Thr Tyr Thr Gly Thr Trp Thr Pro Ala Gln Gln Gln Thr Thr Pro
1               5                   10                  15

Asp Tyr Thr Tyr
            20

<210> SEQ ID NO 39
<211> LENGTH: 21
<212> TYPE: PRT
<213> ORGANISM: Unknown
<220> FEATURE:
<223> OTHER INFORMATION: Description of Unknown: Mammalian CXCR4 peptide

<400> SEQUENCE: 39

Ala Asn Val Ser Glu Ala Asp Asp Arg Tyr Ile Cys Asp Arg Phe Tyr
1               5                   10                  15

Pro Asn Asp Leu Trp
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Val Val Val Phe Gln Phe Gln His Thr Met Val Gly Gln Thr Gln Pro
1               5                   10                  15

Gly Thr Thr Thr Gln
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Val Val Val Phe Gln Phe Gln His Thr Met Thr Gly Gln Thr Gln Pro
1               5                   10                  15

Gly Thr Thr Thr Gln
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Val Val Val Phe Gln Tyr Gln His Thr Met Thr Gly Gln Thr Gln Pro
1               5                   10                  15

Gly Thr Thr Thr Gln
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Val Val Tyr Gln Tyr Gln His Thr Met Thr Gly Gln Thr Gln Pro
1               5                   10                  15

Gly Thr Thr Thr Gln
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Val Val Phe Gln Tyr Gln His Thr Met Thr Gly Gln Thr Gln Pro
1               5                   10                  15

Gly Thr Thr Thr Gln
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Val Thr Phe Gln Tyr Gln His Thr Met Thr Gly Gln Thr Gln Pro
1               5                   10                  15

Gly Thr Thr Thr Gln
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Val Val Tyr Gln Tyr Gln His Thr Met Thr Gly Gln Thr Gln Pro
1               5                   10                  15

Gly Thr Thr Thr Gln
            20

<210> SEQ ID NO 47
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 47

Thr Thr Thr Tyr Gln Tyr Gln His Thr Met Thr Gly Gln Thr Gln Pro
1               5                   10                  15

Gly Thr Thr Thr Gln
            20

<210> SEQ ID NO 48
<211> LENGTH: 25
<212> TYPE: PRT
<213> ORGANISM: Unknown
<220> FEATURE:
<223> OTHER INFORMATION: Description of Unknown: Mammalian
      CXCR4 peptide

<400> SEQUENCE: 48

Ser Cys Tyr Cys Ile Ile Ile Ser Lys Leu Ser His Ser Lys Gly His
1               5                   10                  15

Gln Lys Arg Lys Ala Leu Lys Thr Thr
            20                  25

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Thr Gln Ile Gln Ala Phe Phe Ala Cys Trp Gln Pro Tyr Tyr Thr
1               5                   10                  15

Gly Thr Ser Thr
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Ile Gln Ile Gln Ala Tyr Phe Ala Cys Trp Gln Pro Tyr Tyr Thr
1               5                   10                  15

Gly Thr Ser Thr
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Gln Ile Gln Ala Tyr Tyr Ala Cys Trp Gln Pro Tyr Tyr Thr
1               5                   10                  15

Gly Thr Ser Thr
            20
```

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Ile Gln Thr Gln Ala Phe Tyr Ala Cys Trp Gln Pro Tyr Tyr Thr
1               5                   10                  15

Gly Thr Ser Thr
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Ile Gln Thr Gln Ala Tyr Phe Ala Cys Trp Gln Pro Tyr Tyr Thr
1               5                   10                  15

Gly Thr Ser Thr
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Thr Gln Ile Gln Ala Phe Tyr Ala Cys Trp Gln Pro Tyr Tyr Thr
1               5                   10                  15

Gly Thr Ser Thr
            20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ile Gln Thr Gln Ala Tyr Tyr Ala Cys Trp Gln Pro Tyr Tyr Thr
1               5                   10                  15

Gly Thr Ser Thr
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Thr Thr Gln Thr Gln Ala Tyr Tyr Ala Cys Trp Gln Pro Tyr Tyr Thr
1               5                   10                  15

Gly Thr Ser Thr
            20

<210> SEQ ID NO 57
<211> LENGTH: 21
<212> TYPE: PRT
<213> ORGANISM: Unknown
<220> FEATURE:
<223> OTHER INFORMATION: Description of Unknown: Mammalian
      CXCR4 peptide

<400> SEQUENCE: 57

Asp Ser Phe Ile Leu Leu Glu Ile Ile Lys Gln Gly Cys Glu Phe Glu
1               5                   10                  15

Asn Thr Val His Lys
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ile Ser Ile Thr Glu Ala Gln Ala Phe Phe His Cys Cys Leu Asn
1               5                   10                  15

Pro Ile Gln Tyr
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Ser Ile Thr Glu Ala Gln Ala Phe Tyr His Cys Cys Leu Asn
1               5                   10                  15

Pro Ile Gln Tyr
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Ile Ser Ile Thr Glu Ala Gln Ala Tyr Phe His Cys Cys Gln Asn
1               5                   10                  15

Pro Thr Leu Tyr
            20

<210> SEQ ID NO 61
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 61

Trp Ile Ser Thr Thr Glu Ala Leu Ala Phe Tyr His Cys Cys Gln Asn
1               5                   10                  15

Pro Thr Gln Tyr
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ile Ser Thr Thr Glu Ala Leu Ala Tyr Phe His Cys Cys Gln Asn
1               5                   10                  15

Pro Thr Gln Tyr
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Ile Ser Ile Thr Glu Ala Leu Ala Tyr Tyr His Cys Cys Gln Asn
1               5                   10                  15

Pro Thr Gln Tyr
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Ile Ser Thr Thr Glu Ala Leu Ala Tyr Tyr His Cys Cys Gln Asn
1               5                   10                  15

Pro Thr Gln Tyr
            20

<210> SEQ ID NO 65
<211> LENGTH: 50
<212> TYPE: PRT
<213> ORGANISM: Unknown
<220> FEATURE:
<223> OTHER INFORMATION: Description of Unknown: Mammalian
      CXCR4 polypeptide

<400> SEQUENCE: 65

Ala Phe Leu Gly Ala Lys Phe Lys Thr Ser Ala Gln His Ala Leu Thr
1               5                   10                  15

Ser Val Ser Arg Gly Ser Ser Leu Lys Ile Leu Ser Lys Gly Lys Arg

```
                    20                  25                  30
Gly Gly His Ser Ser Val Ser Thr Glu Ser Glu Ser Ser Phe His
            35                  40                  45

Ser Ser
    50

<210> SEQ ID NO 66
<211> LENGTH: 355
<212> TYPE: PRT
<213> ORGANISM: Unknown
<220> FEATURE:
<223> OTHER INFORMATION: Description of Unknown: Mammalian
      CX3CR1 polypeptide

<400> SEQUENCE: 66

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
                20                  25                  30

Phe Leu Ser Ile Phe Tyr Ser Val Ile Phe Ala Ile Gly Leu Val Gly
            35                  40                  45

Asn Leu Leu Val Val Phe Ala Leu Thr Asn Ser Lys Lys Pro Lys Ser
50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
        210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
        290                 295                 300

Tyr His Leu Tyr Gly Lys Cys Leu Ala Val Leu Cys Gly Arg Ser Val
305                 310                 315                 320
```

His Val Asp Phe Ser Ser Glu Ser Gln Arg Ser Arg His Gly Ser
            325                 330                 335

Val Leu Ser Ser Asn Phe Thr Tyr His Thr Ser Asp Gly Asp Ala Leu
        340                 345                 350

Leu Leu Leu
        355

<210> SEQ ID NO 67
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Phe Gly Thr Val
            20                  25                  30

Phe Gln Ser Thr Tyr Tyr Ser Thr Thr Tyr Ala Thr Gly Gln Thr Gly
        35                  40                  45

Asn Gln Gln Thr Thr Tyr Ala Gln Thr Asn Ser Lys Lys Pro Lys Ser
    50                  55                  60

Val Thr Asp Thr Tyr Gln Gln Asn Gln Ala Gln Ser Asp Gln Gln Tyr
65                  70                  75                  80

Thr Ala Thr Gln Pro Tyr Trp Thr His Tyr Gln Ile Asn Glu Lys Gly
                85                  90                  95

Leu His Asn Ala Met Cys Lys Phe Thr Thr Ala Tyr Tyr Tyr Thr Gly
            100                 105                 110

Tyr Tyr Gly Ser Thr Tyr Tyr Thr Thr Thr Ser Thr Asp Arg Tyr
        115                 120                 125

Leu Ala Ile Val Leu Ala Ala Asn Ser Met Asn Asn Arg Thr Val Gln
    130                 135                 140

His Gly Thr Thr Thr Ser Gln Gly Thr Trp Ala Ala Ala Thr Gln Thr
145                 150                 155                 160

Ala Ala Pro Gln Tyr Met Tyr Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Tyr Gln Gly Tyr Gln Gln Pro Gln Gln Thr Met Ser
        195                 200                 205

Tyr Cys Tyr Tyr Arg Thr Thr Gln Thr Gln Tyr Ser Cys Lys Asn His
    210                 215                 220

Lys Lys Ala Lys Ala Ile Lys Gln Thr Gln Thr Thr Thr Thr Thr Tyr
225                 230                 235                 240

Tyr Gln Tyr Trp Thr Pro Tyr Asn Thr Met Thr Tyr Gln Glu Thr Leu
                245                 250                 255

Lys Leu Tyr Asp Phe Phe Pro Ser Cys Asp Met Arg Lys Asp Leu Arg
            260                 265                 270

Leu Ala Gln Ser Thr Thr Glu Thr Ala Tyr Ser His Cys Cys Gln
        275                 280                 285

Asn Pro Gln Thr Tyr Ala Tyr Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
            325                 330                 335

Val Leu Ser Ser Asn Phe Thr Tyr His Thr Ser Asp Gly Asp Ala Leu
        340                 345                 350

Leu Leu Leu
        355

<210> SEQ ID NO 68
<211> LENGTH: 31
<212> TYPE: PRT
<213> ORGANISM: Unknown
<220> FEATURE:
<223> OTHER INFORMATION: Description of Unknown: Mammalian
      CX3CR1 polypeptide

<400> SEQUENCE: 68

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr
            20                  25                  30

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Tyr Gln Ser Thr Tyr Tyr Ser Thr Thr Phe Ala Thr Gly Gln Val
1               5                   10                  15

Gly Asn Gln Gln Val Val Phe Ala Leu Thr Asn Ser
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Tyr Gln Ser Thr Tyr Tyr Ser Thr Thr Tyr Ala Thr Gly Gln Val
1               5                   10                  15

Gly Asn Gln Gln Val Val Phe Ala Leu Thr Asn Ser
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Tyr Gln Ser Thr Tyr Tyr Ser Thr Thr Tyr Ala Thr Gly Gln Val
1               5                   10                  15

Gly Asn Gln Gln Val Val Phe Ala Gln Thr Asn Ser
            20                  25

```
<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Tyr Gln Ser Thr Tyr Tyr Ser Thr Thr Tyr Ala Thr Gly Gln Thr
1               5                   10                  15

Gly Asn Leu Gln Val Thr Phe Ala Gln Thr Asn Ser
            20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Tyr Gln Ser Thr Tyr Tyr Ser Thr Thr Tyr Ala Thr Gly Gln Thr
1               5                   10                  15

Gly Asn Gln Leu Val Thr Phe Ala Gln Thr Asn Ser
            20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Tyr Gln Ser Thr Tyr Tyr Ser Thr Thr Tyr Ala Thr Gly Gln Thr
1               5                   10                  15

Gly Asn Gln Gln Val Val Phe Ala Gln Thr Asn Ser
            20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Tyr Gln Ser Thr Tyr Tyr Ser Thr Thr Tyr Ala Thr Gly Gln Thr
1               5                   10                  15

Gly Asn Leu Gln Val Thr Tyr Ala Gln Thr Asn Ser
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Tyr Gln Ser Thr Tyr Tyr Ser Thr Thr Tyr Ala Thr Gly Gln Thr
```

Gly Asn Gln Gln Thr Thr Tyr Ala Gln Thr Asn Ser
                    20                  25

<210> SEQ ID NO 77
<211> LENGTH: 10
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 77

Lys Lys Pro Lys Ser Val Thr Asp Ile Tyr
1               5                   10

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Leu Asn Gln Ala Gln Ser Asp Gln Leu Phe Val Ala Thr Gln Pro
1               5                   10                  15

Phe Trp Thr His Tyr
            20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Leu Asn Gln Ala Gln Ser Asp Gln Gln Phe Val Ala Thr Gln Pro
1               5                   10                  15

Phe Trp Thr His Tyr
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Asn Leu Ala Gln Ser Asp Gln Gln Phe Val Ala Thr Gln Pro
1               5                   10                  15

Phe Trp Thr His Tyr
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 81

Leu Gln Asn Leu Ala Gln Ser Asp Gln Gln Tyr Thr Ala Thr Gln Pro
1               5                   10                  15

Phe Trp Thr His Tyr
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Leu Asn Leu Ala Gln Ser Asp Gln Gln Tyr Thr Ala Thr Gln Pro
1               5                   10                  15

Phe Trp Thr His Tyr
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Leu Asn Gln Ala Gln Ser Asp Gln Gln Phe Thr Ala Thr Gln Pro
1               5                   10                  15

Tyr Trp Thr His Tyr
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Asn Leu Ala Gln Ser Asp Gln Gln Phe Thr Ala Thr Gln Pro
1               5                   10                  15

Tyr Trp Thr His Tyr
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Asn Gln Ala Gln Ser Asp Gln Gln Tyr Thr Ala Thr Gln Pro
1               5                   10                  15

Tyr Trp Thr His Tyr
            20

<210> SEQ ID NO 86
<211> LENGTH: 13
```

```
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 86

Leu Ile Asn Glu Lys Gly Leu His Asn Ala Met Cys Lys
1               5                   10

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Thr Thr Ala Tyr Tyr Tyr Thr Gly Tyr Tyr Gly Ser Thr Tyr Tyr
1               5                   10                  15

Thr Thr Thr Thr Ser Thr
            20

<210> SEQ ID NO 88
<211> LENGTH: 17
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 88

Asp Arg Tyr Leu Ala Ile Val Leu Ala Ala Asn Ser Met Asn Asn Arg
1               5                   10                  15

Thr

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Gln His Gly Thr Thr Thr Ser Gln Gly Thr Trp Ala Ala Ala Thr
1               5                   10                  15

Gln Val Ala Ala Pro Gln Phe Met Phe
            20                  25

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Gln His Gly Val Thr Thr Ser Gln Gly Thr Trp Ala Ala Ala Thr
1               5                   10                  15

Gln Thr Ala Ala Pro Gln Phe Met Phe
            20                  25
```

```
<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Gln His Gly Thr Thr Thr Ser Gln Gly Val Trp Ala Ala Ala Thr
1               5                   10                  15

Gln Thr Ala Ala Pro Gln Phe Met Tyr
            20                  25

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Gln His Gly Thr Thr Thr Ser Gln Gly Thr Trp Ala Ala Ala Ile
1               5                   10                  15

Gln Thr Ala Ala Pro Gln Phe Met Tyr
            20                  25

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Gln His Gly Thr Thr Thr Ser Gln Gly Thr Trp Ala Ala Ala Thr
1               5                   10                  15

Gln Thr Ala Ala Pro Gln Phe Met Phe
            20                  25

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Gln His Gly Thr Thr Ile Ser Gln Gly Thr Trp Ala Ala Ala Thr
1               5                   10                  15

Gln Thr Ala Ala Pro Gln Tyr Met Phe
            20                  25

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Gln His Gly Thr Thr Thr Ser Gln Gly Thr Trp Ala Ala Ala Thr
```

```
                 1               5                  10                 15
Gln Thr Ala Ala Pro Gln Phe Met Tyr
            20                  25

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Gln His Gly Thr Thr Thr Ser Gln Gly Thr Trp Ala Ala Ala Thr
  1               5                  10                 15
Gln Thr Ala Ala Pro Gln Tyr Met Tyr
            20                  25

<210> SEQ ID NO 97
<211> LENGTH: 28
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 97

Thr Lys Gln Lys Glu Asn Glu Cys Leu Gly Asp Tyr Pro Glu Val Leu
  1               5                  10                 15
Gln Glu Ile Trp Pro Val Leu Arg Asn Val Glu Thr
            20                  25

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Phe Leu Gly Phe Gln Gln Pro Gln Gln Ile Met Ser Tyr Cys Tyr
  1               5                  10                 15
Phe Arg Ile Thr
            20

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Phe Gln Gly Phe Leu Gln Pro Gln Gln Thr Met Ser Tyr Cys Tyr
  1               5                  10                 15
Phe Arg Ile Thr
            20

<210> SEQ ID NO 100
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 100

Asn Phe Gln Gly Phe Leu Gln Pro Gln Gln Thr Met Ser Tyr Cys Tyr
1               5                   10                  15

Phe Arg Thr Thr
            20

<210> SEQ ID NO 101
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Phe Gln Gly Phe Gln Gln Pro Gln Gln Thr Met Ser Tyr Cys Tyr
1               5                   10                  15

Tyr Arg Ile Thr
            20

<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Phe Gln Gly Phe Leu Gln Pro Gln Gln Thr Met Ser Tyr Cys Tyr
1               5                   10                  15

Tyr Arg Thr Thr
            20

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Phe Gln Gly Tyr Leu Gln Pro Gln Gln Thr Met Ser Tyr Cys Tyr
1               5                   10                  15

Phe Arg Thr Thr
            20

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Tyr Gln Gly Phe Gln Gln Pro Gln Gln Thr Met Ser Tyr Cys Tyr
1               5                   10                  15

Phe Arg Thr Thr
            20
```

```
<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asn Tyr Gln Gly Tyr Gln Gln Pro Gln Gln Thr Met Ser Tyr Cys Tyr
1               5                   10                  15

Tyr Arg Thr Thr
            20

<210> SEQ ID NO 106
<211> LENGTH: 16
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 106

Gln Thr Leu Phe Ser Cys Lys Asn His Lys Lys Ala Lys Ala Ile Lys
1               5                   10                  15

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Ile Gln Gln Thr Thr Thr Thr Phe Tyr Gln Phe Trp Thr Pro Tyr
1               5                   10                  15

Asn Thr Met Thr Phe Gln Glu Thr Leu
            20                  25

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Ile Gln Gln Thr Thr Thr Thr Phe Tyr Gln Tyr Trp Thr Pro Tyr
1               5                   10                  15

Asn Val Met Thr Phe Gln Glu Thr Gln
            20                  25

<210> SEQ ID NO 109
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Ile Gln Gln Thr Thr Thr Thr Tyr Tyr Gln Phe Trp Thr Pro Tyr
1               5                   10                  15
```

Asn Thr Met Thr Phe Gln Glu Thr Gln
            20                  25

<210> SEQ ID NO 110
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ile Gln Gln Thr Thr Thr Thr Phe Tyr Gln Tyr Trp Thr Pro Tyr
1               5                   10                  15

Asn Thr Met Thr Phe Gln Glu Thr Gln
            20                  25

<210> SEQ ID NO 111
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Thr Gln Gln Thr Thr Thr Thr Tyr Tyr Gln Phe Trp Thr Pro Tyr
1               5                   10                  15

Asn Thr Met Thr Phe Gln Glu Thr Gln
            20                  25

<210> SEQ ID NO 112
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ile Gln Gln Thr Thr Thr Thr Phe Phe Gln Tyr Trp Thr Pro Tyr
1               5                   10                  15

Asn Thr Met Thr Tyr Gln Glu Thr Gln
            20                  25

<210> SEQ ID NO 113
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Ile Gln Gln Thr Thr Thr Thr Phe Tyr Gln Tyr Trp Thr Pro Tyr
1               5                   10                  15

Asn Thr Met Thr Tyr Gln Glu Thr Gln
            20                  25

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 114

Gln Thr Gln Gln Thr Thr Thr Thr Tyr Tyr Gln Tyr Trp Thr Pro Tyr
1               5                   10                  15

Asn Thr Met Thr Tyr Gln Glu Thr Gln
            20                  25

<210> SEQ ID NO 115
<211> LENGTH: 17
<212> TYPE: PRT
<213> ORGANISM: Unknown
<220> FEATURE:
<223> OTHER INFORMATION: Description of Unknown: Mammalian
      CX3CR1 peptide

<400> SEQUENCE: 115

Lys Leu Tyr Asp Phe Phe Pro Ser Cys Asp Met Arg Lys Asp Leu Arg
1               5                   10                  15

Leu

<210> SEQ ID NO 116
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Leu Ser Val Thr Glu Thr Val Ala Phe Ser His Cys Cys Gln Asn
1               5                   10                  15

Pro Gln Ile Tyr Ala Phe Ala Gly
            20

<210> SEQ ID NO 117
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Gln Ser Val Thr Glu Thr Thr Ala Phe Ser His Cys Cys Gln Asn
1               5                   10                  15

Pro Leu Ile Tyr Ala Phe Ala Gly
            20

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Leu Ser Val Thr Glu Thr Val Ala Phe Ser His Cys Cys Gln Asn
1               5                   10                  15

Pro Gln Thr Tyr Ala Tyr Ala Gly
            20

<210> SEQ ID NO 119
<211> LENGTH: 24

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Gln Ser Val Thr Glu Thr Thr Ala Phe Ser His Cys Cys Gln Asn
1               5                   10                  15

Pro Gln Ile Tyr Ala Tyr Ala Gly
            20

<210> SEQ ID NO 120
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Leu Ser Val Thr Glu Thr Thr Ala Phe Ser His Cys Cys Gln Asn
1               5                   10                  15

Pro Gln Thr Tyr Ala Tyr Ala Gly
            20

<210> SEQ ID NO 121
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Leu Ser Thr Thr Glu Thr Thr Ala Tyr Ser His Cys Cys Gln Asn
1               5                   10                  15

Pro Gln Ile Tyr Ala Phe Ala Gly
            20

<210> SEQ ID NO 122
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Leu Ser Val Thr Glu Thr Thr Ala Tyr Ser His Cys Cys Gln Asn
1               5                   10                  15

Pro Gln Thr Tyr Ala Tyr Ala Gly
            20

<210> SEQ ID NO 123
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Gln Ser Thr Thr Glu Thr Thr Ala Tyr Ser His Cys Cys Gln Asn
1               5                   10                  15
```

```
Pro Gln Thr Tyr Ala Tyr Ala Gly
            20

<210> SEQ ID NO 124
<211> LENGTH: 58
<212> TYPE: PRT
<213> ORGANISM: Unknown
<220> FEATURE:
<223> OTHER INFORMATION: Description of Unknown: Mammalian
      CX3CR1 polypeptide

<400> SEQUENCE: 124

Glu Lys Phe Arg Arg Tyr Leu Tyr His Leu Tyr Gly Lys Cys Leu Ala
1               5                   10                  15

Val Leu Cys Gly Arg Ser Val His Val Asp Phe Ser Ser Ser Glu Ser
            20                  25                  30

Gln Arg Ser Arg His Gly Ser Val Leu Ser Ser Asn Phe Thr Tyr His
        35                  40                  45

Thr Ser Asp Gly Asp Ala Leu Leu Leu Leu
        50                  55

<210> SEQ ID NO 125
<211> LENGTH: 373
<212> TYPE: PRT
<213> ORGANISM: Unknown
<220> FEATURE:
<223> OTHER INFORMATION: Description of Unknown: Mammalian
      CCR3 polypeptide

<400> SEQUENCE: 125

Met Pro Phe Gly Ile Arg Met Leu Leu Arg Ala His Lys Pro Gly Arg
1               5                   10                  15

Ser Glu Met Thr Thr Ser Leu Asp Thr Val Glu Thr Phe Gly Thr Thr
            20                  25                  30

Ser Tyr Tyr Asp Asp Val Gly Leu Leu Cys Glu Lys Ala Asp Thr Arg
        35                  40                  45

Ala Leu Met Ala Gln Phe Val Pro Pro Leu Tyr Ser Leu Val Phe Thr
    50                  55                  60

Val Gly Leu Leu Gly Asn Val Val Val Val Met Ile Leu Ile Lys Tyr
65                  70                  75                  80

Arg Arg Leu Arg Ile Met Thr Asn Ile Tyr Leu Leu Asn Leu Ala Ile
                85                  90                  95

Ser Asp Leu Leu Phe Leu Val Thr Leu Pro Phe Trp Ile His Tyr Val
            100                 105                 110

Arg Gly His Asn Trp Val Phe Gly His Gly Met Cys Lys Leu Leu Ser
        115                 120                 125

Gly Phe Tyr His Thr Gly Leu Tyr Ser Glu Ile Phe Phe Ile Ile Leu
    130                 135                 140

Leu Thr Ile Asp Arg Tyr Leu Ala Ile Val His Ala Val Phe Ala Leu
145                 150                 155                 160

Arg Ala Arg Thr Val Thr Phe Gly Val Ile Thr Ser Ile Val Thr Trp
                165                 170                 175

Gly Leu Ala Val Leu Ala Ala Leu Pro Glu Phe Ile Phe Tyr Glu Thr
            180                 185                 190

Glu Glu Leu Phe Glu Glu Thr Leu Cys Ser Ala Leu Tyr Pro Glu Asp
        195                 200                 205

Thr Val Tyr Ser Trp Arg His Phe His Thr Leu Arg Met Thr Ile Phe
    210                 215                 220
```

```
Cys Leu Val Leu Pro Leu Val Met Ala Ile Cys Tyr Thr Gly Ile
225                 230                 235                 240

Ile Lys Thr Leu Leu Arg Cys Pro Ser Lys Lys Tyr Lys Ala Ile
            245                 250                 255

Arg Leu Ile Phe Val Ile Met Ala Val Phe Phe Ile Phe Trp Thr Pro
        260                 265                 270

Tyr Asn Val Ala Ile Leu Leu Ser Ser Tyr Gln Ser Ile Leu Phe Gly
        275                 280                 285

Asn Asp Cys Glu Arg Ser Lys His Leu Asp Leu Val Met Leu Val Thr
        290                 295                 300

Glu Val Ile Ala Tyr Ser His Cys Cys Met Asn Pro Val Ile Tyr Ala
305                 310                 315                 320

Phe Val Gly Glu Arg Phe Arg Lys Tyr Leu Arg His Phe Phe His Arg
            325                 330                 335

His Leu Leu Met His Leu Gly Arg Tyr Ile Pro Phe Leu Pro Ser Glu
            340                 345                 350

Lys Leu Glu Arg Thr Ser Ser Val Ser Pro Ser Thr Ala Glu Pro Glu
            355                 360                 365

Leu Ser Ile Val Phe
        370

<210> SEQ ID NO 126
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Pro Phe Gly Ile Arg Met Leu Leu Arg Ala His Lys Pro Gly Arg
1               5                   10                  15

Ser Glu Met Thr Thr Ser Leu Asp Thr Val Glu Thr Phe Gly Thr Thr
            20                  25                  30

Ser Tyr Tyr Asp Asp Val Gly Leu Leu Cys Glu Lys Ala Asp Thr Arg
        35                  40                  45

Ala Leu Met Ala Gln Phe Val Pro Pro Gln Tyr Ser Gln Thr Tyr Thr
50                  55                  60

Thr Gly Gln Gln Gly Asn Thr Thr Thr Met Thr Gln Thr Lys Tyr
65                  70                  75                  80

Arg Arg Leu Arg Ile Met Thr Asn Thr Tyr Gln Gln Asn Gln Ala Thr
                85                  90                  95

Ser Asp Gln Gln Tyr Gln Thr Thr Gln Pro Tyr Trp Thr His Tyr Val
            100                 105                 110

Arg Gly His Asn Trp Val Phe Gly His Gly Met Cys Lys Leu Leu Ser
        115                 120                 125

Gly Phe Tyr His Thr Gly Leu Tyr Ser Glu Thr Tyr Tyr Thr Thr Gln
    130                 135                 140

Gln Thr Thr Asp Arg Tyr Gln Ala Thr Thr His Ala Thr Tyr Ala Gln
145                 150                 155                 160

Arg Ala Arg Thr Val Thr Phe Gly Thr Thr Thr Ser Thr Thr Thr Trp
                165                 170                 175

Gly Gln Ala Thr Gln Ala Ala Gln Pro Glu Tyr Thr Tyr Tyr Glu Thr
            180                 185                 190

Glu Glu Leu Phe Glu Glu Thr Leu Cys Ser Ala Leu Tyr Pro Glu Asp
        195                 200                 205
```

```
Thr Val Tyr Ser Trp Arg His Phe His Thr Leu Arg Met Thr Thr Tyr
    210                 215                 220
Cys Gln Thr Gln Pro Gln Gln Thr Met Ala Thr Cys Tyr Thr Gly Thr
225                 230                 235                 240
Thr Lys Thr Leu Leu Arg Cys Pro Ser Lys Lys Tyr Lys Ala Ile
                245                 250                 255
Arg Gln Thr Tyr Thr Thr Met Ala Thr Tyr Tyr Thr Tyr Trp Thr Pro
                260                 265                 270
Tyr Asn Thr Ala Thr Gln Gln Ser Ser Tyr Gln Ser Ile Leu Phe Gly
            275                 280                 285
Asn Asp Cys Glu Arg Ser Lys His Leu Asp Gln Thr Met Gln Thr Thr
290                 295                 300
Glu Thr Thr Ala Tyr Ser His Cys Cys Met Asn Pro Thr Thr Tyr Ala
305                 310                 315                 320
Tyr Thr Gly Glu Arg Phe Arg Lys Tyr Leu Arg His Phe Phe His Arg
                325                 330                 335
His Leu Leu Met His Leu Gly Arg Tyr Ile Pro Phe Leu Pro Ser Glu
                340                 345                 350
Lys Leu Glu Arg Thr Ser Ser Val Ser Pro Ser Thr Ala Glu Pro Glu
                355                 360                 365
Leu Ser Ile Val Phe
    370

<210> SEQ ID NO 127
<211> LENGTH: 34
<212> TYPE: PRT
<213> ORGANISM: Unknown
<220> FEATURE:
<223> OTHER INFORMATION: Description of Unknown: Mammalian
      CCR3 polypeptide

<400> SEQUENCE: 127

Met Thr Thr Ser Leu Asp Thr Val Glu Thr Phe Gly Thr Thr Ser Tyr
1               5                   10                  15
Tyr Asp Asp Val Gly Leu Leu Cys Glu Lys Ala Asp Thr Arg Ala Leu
                20                  25                  30
Met Ala

<210> SEQ ID NO 128
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Phe Val Pro Pro Gln Tyr Ser Gln Thr Phe Thr Thr Gly Gln Gln
1               5                   10                  15
Gly Asn Val Thr Val Thr Met Thr Gln Ile Lys Tyr
                20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 129

Gln Phe Val Pro Pro Gln Tyr Ser Gln Thr Phe Thr Thr Gly Gln Gln
1               5                   10                  15

Gly Asn Thr Thr Val Thr Met Thr Gln Ile Lys Tyr
            20                  25

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Phe Val Pro Pro Gln Tyr Ser Gln Thr Tyr Thr Thr Gly Gln Gln
1               5                   10                  15

Gly Asn Thr Thr Val Thr Met Thr Gln Ile Lys Tyr
            20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Phe Thr Pro Pro Gln Tyr Ser Gln Thr Tyr Thr Thr Gly Gln Gln
1               5                   10                  15

Gly Asn Val Thr Thr Thr Met Thr Gln Ile Lys Tyr
            20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Phe Thr Pro Pro Gln Tyr Ser Gln Thr Tyr Thr Thr Gly Gln Gln
1               5                   10                  15

Gly Asn Thr Val Thr Thr Met Thr Gln Ile Lys Tyr
            20                  25

<210> SEQ ID NO 133
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Phe Thr Pro Pro Gln Tyr Ser Gln Thr Tyr Thr Thr Gly Gln Gln
1               5                   10                  15

Gly Asn Thr Thr Val Thr Met Thr Gln Ile Lys Tyr
            20                  25

<210> SEQ ID NO 134
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Phe Thr Pro Pro Gln Tyr Ser Gln Thr Tyr Thr Thr Gly Gln Gln
1               5                   10                  15

Gly Asn Thr Thr Thr Thr Met Thr Gln Ile Lys Tyr
            20                  25

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Tyr Thr Pro Pro Gln Tyr Ser Gln Thr Tyr Thr Thr Gly Gln Gln
1               5                   10                  15

Gly Asn Thr Thr Thr Thr Met Thr Gln Thr Lys Tyr
            20                  25

<210> SEQ ID NO 136
<211> LENGTH: 10
<212> TYPE: PRT
<213> ORGANISM: Unknown
<220> FEATURE:
<223> OTHER INFORMATION: Description of Unknown: Mammalian
      CCR3 peptide

<400> SEQUENCE: 136

Arg Arg Leu Arg Ile Met Thr Asn Ile Tyr
1               5                   10

<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Leu Leu Asn Gln Ala Thr Ser Asp Gln Gln Phe Gln Val Thr Gln Pro
1               5                   10                  15

Phe Trp Ile His Tyr
            20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Gln Asn Gln Ala Ile Ser Asp Gln Leu Phe Gln Thr Thr Gln Pro
1               5                   10                  15

Phe Trp Thr His Tyr
            20
```

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Gln Asn Leu Ala Ile Ser Asp Gln Gln Phe Gln Thr Thr Gln Pro
1               5                   10                  15

Phe Trp Thr His Tyr
            20

<210> SEQ ID NO 140
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Leu Asn Gln Ala Ile Ser Asp Gln Gln Phe Gln Thr Thr Gln Pro
1               5                   10                  15

Tyr Trp Thr His Tyr
            20

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Gln Asn Leu Ala Ile Ser Asp Gln Gln Tyr Gln Val Thr Gln Pro
1               5                   10                  15

Tyr Trp Thr His Tyr
            20

<210> SEQ ID NO 142
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Gln Asn Gln Ala Thr Ser Asp Gln Leu Phe Gln Thr Thr Gln Pro
1               5                   10                  15

Tyr Trp Thr His Tyr
            20

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Gln Gln Asn Gln Ala Ile Ser Asp Gln Gln Tyr Gln Val Thr Gln Pro
1               5                   10                  15

Tyr Trp Thr His Tyr
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Asn Gln Ala Thr Ser Asp Gln Gln Tyr Gln Thr Thr Gln Pro
1               5                   10                  15

Tyr Trp Thr His Tyr
            20

<210> SEQ ID NO 145
<211> LENGTH: 14
<212> TYPE: PRT
<213> ORGANISM: Unknown
<220> FEATURE:
<223> OTHER INFORMATION: Description of Unknown: Mammalian
      CCR3 peptide

<400> SEQUENCE: 145

Val Arg Gly His Asn Trp Val Phe Gly His Gly Met Cys Lys
1               5                   10

<210> SEQ ID NO 146
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Gln Ser Gly Phe Tyr His Thr Gly Gln Tyr Ser Glu Thr Phe Phe
1               5                   10                  15

Thr Thr Gln Gln Thr Thr
            20

<210> SEQ ID NO 147
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Leu Ser Gly Phe Tyr His Thr Gly Gln Tyr Ser Glu Thr Phe Phe
1               5                   10                  15

Thr Thr Gln Gln Thr Thr
            20

<210> SEQ ID NO 148
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 148

Gln Leu Ser Gly Phe Tyr His Thr Gly Gln Tyr Ser Glu Thr Phe Tyr
1               5                   10                  15

Thr Thr Gln Gln Thr Thr
            20

<210> SEQ ID NO 149
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Leu Ser Gly Phe Tyr His Thr Gly Gln Tyr Ser Glu Thr Tyr Phe
1               5                   10                  15

Thr Thr Gln Gln Thr Thr
            20

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Leu Ser Gly Tyr Tyr His Thr Gly Gln Tyr Ser Glu Thr Phe Phe
1               5                   10                  15

Thr Thr Gln Gln Thr Thr
            20

<210> SEQ ID NO 151
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Gln Ser Gly Phe Tyr His Thr Gly Gln Tyr Ser Glu Thr Phe Phe
1               5                   10                  15

Thr Thr Gln Gln Thr Thr
            20

<210> SEQ ID NO 152
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Ser Gly Phe Tyr His Thr Gly Gln Tyr Ser Glu Thr Phe Tyr
1               5                   10                  15

Thr Thr Gln Gln Thr Thr
            20

<210> SEQ ID NO 153
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Ser Gly Tyr Tyr His Thr Gly Gln Tyr Ser Glu Thr Tyr Tyr
1               5                   10                  15

Thr Thr Gln Gln Thr Thr
            20

<210> SEQ ID NO 154
<211> LENGTH: 17
<212> TYPE: PRT
<213> ORGANISM: Unknown
<220> FEATURE:
<223> OTHER INFORMATION: Description of Unknown: Mammalian
      CCR3 peptide

<400> SEQUENCE: 154

Asp Arg Tyr Leu Ala Ile Val His Ala Val Phe Ala Leu Arg Ala Arg
1               5                   10                  15

Thr

<210> SEQ ID NO 155
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Thr Phe Gly Thr Thr Thr Ser Thr Val Thr Trp Gly Gln Ala Val
1               5                   10                  15

Gln Ala Ala Gln Pro Glu Phe Ile Phe
            20                  25

<210> SEQ ID NO 156
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Thr Phe Gly Thr Thr Thr Ser Thr Thr Thr Trp Gly Gln Ala Val
1               5                   10                  15

Gln Ala Ala Gln Pro Glu Phe Ile Phe
            20                  25

<210> SEQ ID NO 157
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Thr Thr Tyr Gly Thr Thr Thr Ser Thr Thr Thr Trp Gly Gln Ala Val
1               5                   10                  15
```

Gln Ala Ala Gln Pro Glu Phe Ile Phe
            20                  25

<210> SEQ ID NO 158
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Thr Tyr Gly Thr Thr Thr Ser Thr Thr Thr Trp Gly Gln Ala Val
1               5                   10                  15

Gln Ala Ala Gln Pro Glu Phe Thr Phe
            20                  25

<210> SEQ ID NO 159
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Thr Tyr Gly Thr Thr Thr Ser Thr Thr Thr Trp Gly Gln Ala Thr
1               5                   10                  15

Gln Ala Ala Gln Pro Glu Phe Ile Phe
            20                  25

<210> SEQ ID NO 160
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Thr Phe Gly Thr Thr Thr Ser Thr Thr Thr Trp Gly Gln Ala Thr
1               5                   10                  15

Gln Ala Ala Gln Pro Glu Phe Ile Tyr
            20                  25

<210> SEQ ID NO 161
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Thr Tyr Gly Thr Thr Thr Ser Thr Thr Thr Trp Gly Gln Ala Thr
1               5                   10                  15

Gln Ala Ala Gln Pro Glu Phe Ile Tyr
            20                  25

<210> SEQ ID NO 162
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Thr Tyr Gly Thr Thr Thr Ser Thr Thr Trp Gly Gln Ala Thr
1               5                   10                  15

Gln Ala Ala Gln Pro Glu Tyr Thr Tyr
            20                  25

<210> SEQ ID NO 163
<211> LENGTH: 32
<212> TYPE: PRT
<213> ORGANISM: Unknown
<220> FEATURE:
<223> OTHER INFORMATION: Description of Unknown: Mammalian
      CCR3 polypeptide

<400> SEQUENCE: 163

Tyr Glu Thr Glu Glu Leu Phe Glu Glu Thr Leu Cys Ser Ala Leu Tyr
1               5                   10                  15

Pro Glu Asp Thr Val Tyr Ser Trp Arg His Phe His Thr Leu Arg Met
            20                  25                  30

<210> SEQ ID NO 164
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Thr Ile Phe Cys Gln Val Gln Pro Gln Gln Thr Met Ala Thr Cys Tyr
1               5                   10                  15

Thr Gly Thr Thr
            20

<210> SEQ ID NO 165
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Ile Phe Cys Gln Thr Gln Pro Gln Gln Val Met Ala Thr Cys Tyr
1               5                   10                  15

Thr Gly Thr Thr
            20

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Phe Cys Gln Thr Gln Pro Gln Gln Thr Met Ala Thr Cys Tyr
1               5                   10                  15

Thr Gly Ile Thr
            20

<210> SEQ ID NO 167

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Ile Phe Cys Gln Thr Gln Pro Gln Gln Thr Met Ala Thr Cys Tyr
1               5                   10                  15

Thr Gly Thr Ile
            20

<210> SEQ ID NO 168
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Thr Phe Cys Gln Val Gln Pro Gln Gln Val Met Ala Thr Cys Tyr
1               5                   10                  15

Thr Gly Thr Thr
            20

<210> SEQ ID NO 169
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Ile Tyr Cys Gln Val Gln Pro Gln Gln Val Met Ala Thr Cys Tyr
1               5                   10                  15

Thr Gly Thr Thr
            20

<210> SEQ ID NO 170
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Ile Phe Cys Gln Thr Gln Pro Gln Gln Thr Met Ala Thr Cys Tyr
1               5                   10                  15

Thr Gly Thr Thr
            20

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Thr Thr Tyr Cys Gln Thr Gln Pro Gln Gln Thr Met Ala Thr Cys Tyr
1               5                   10                  15
```

```
Thr Gly Thr Thr
        20

<210> SEQ ID NO 172
<211> LENGTH: 16
<212> TYPE: PRT
<213> ORGANISM: Unknown
<220> FEATURE:
<223> OTHER INFORMATION: Description of Unknown: Mammalian
      CCR3 peptide

<400> SEQUENCE: 172

Lys Thr Leu Leu Arg Cys Pro Ser Lys Lys Lys Tyr Lys Ala Ile Arg
1               5                   10                  15

<210> SEQ ID NO 173
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Thr Tyr Thr Thr Met Ala Thr Tyr Tyr Thr Tyr Trp Thr Pro Tyr
1               5                   10                  15

Asn Thr Ala Thr Gln Gln Ser Ser Tyr
            20                  25

<210> SEQ ID NO 174
<211> LENGTH: 17
<212> TYPE: PRT
<213> ORGANISM: Unknown
<220> FEATURE:
<223> OTHER INFORMATION: Description of Unknown: Mammalian
      CCR3 peptide

<400> SEQUENCE: 174

Gln Ser Ile Leu Phe Gly Asn Asp Cys Glu Arg Ser Lys His Leu Asp
1               5                   10                  15

Leu

<210> SEQ ID NO 175
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Val Met Gln Val Thr Glu Val Thr Ala Tyr Ser His Cys Cys Met Asn
1               5                   10                  15

Pro Val Thr Tyr Ala Phe Thr Gly
            20

<210> SEQ ID NO 176
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176
```

Val Met Gln Val Thr Glu Val Thr Ala Tyr Ser His Cys Cys Met Asn
1               5                   10                  15

Pro Thr Thr Tyr Ala Tyr Val Gly
            20

<210> SEQ ID NO 177
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Val Met Leu Thr Thr Glu Val Thr Ala Tyr Ser His Cys Cys Met Asn
1               5                   10                  15

Pro Thr Thr Tyr Ala Phe Thr Gly
            20

<210> SEQ ID NO 178
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Val Met Gln Val Thr Glu Thr Thr Ala Tyr Ser His Cys Cys Met Asn
1               5                   10                  15

Pro Val Thr Tyr Ala Tyr Thr Gly
            20

<210> SEQ ID NO 179
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Met Gln Val Thr Glu Thr Ile Ala Tyr Ser His Cys Cys Met Asn
1               5                   10                  15

Pro Thr Thr Tyr Ala Phe Thr Gly
            20

<210> SEQ ID NO 180
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Thr Met Gln Val Thr Glu Thr Thr Ala Tyr Ser His Cys Cys Met Asn
1               5                   10                  15

Pro Thr Thr Tyr Ala Phe Val Gly
            20

<210> SEQ ID NO 181
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 181

Val Met Gln Thr Thr Glu Thr Ile Ala Tyr Ser His Cys Cys Met Asn
1               5                   10                  15

Pro Thr Thr Tyr Ala Tyr Thr Gly
            20

<210> SEQ ID NO 182
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Met Gln Thr Thr Glu Thr Thr Ala Tyr Ser His Cys Cys Met Asn
1               5                   10                  15

Pro Thr Thr Tyr Ala Tyr Thr Gly
            20

<210> SEQ ID NO 183
<211> LENGTH: 50
<212> TYPE: PRT
<213> ORGANISM: Unknown
<220> FEATURE:
<223> OTHER INFORMATION: Description of Unknown: Mammalian
      CCR3 polypeptide

<400> SEQUENCE: 183

Glu Arg Phe Arg Lys Tyr Leu Arg His Phe Phe His Arg His Leu Leu
1               5                   10                  15

Met His Leu Gly Arg Tyr Ile Pro Phe Leu Pro Ser Glu Lys Leu Glu
            20                  25                  30

Arg Thr Ser Ser Val Ser Pro Ser Thr Ala Glu Pro Glu Leu Ser Ile
        35                  40                  45

Val Phe
    50

<210> SEQ ID NO 184
<211> LENGTH: 352
<212> TYPE: PRT
<213> ORGANISM: Unknown
<220> FEATURE:
<223> OTHER INFORMATION: Description of Unknown: Mammalian
      CCR5 polypeptide

<400> SEQUENCE: 184

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
```

```
                85                  90                  95
Gly Asn Thr Met Cys Gln Leu Leu Thr Gly Leu Tyr Phe Ile Gly Phe
            100                 105                 110
Phe Ser Gly Ile Phe Phe Ile Ile Leu Leu Thr Ile Asp Arg Tyr Leu
            115                 120                 125
Ala Val Val His Ala Val Phe Ala Leu Lys Ala Arg Thr Val Thr Phe
            130                 135                 140
Gly Val Val Thr Ser Val Ile Thr Trp Val Val Ala Val Phe Ala Ser
145                 150                 155                 160
Leu Pro Gly Ile Ile Phe Thr Arg Ser Gln Lys Glu Gly Leu His Tyr
                165                 170                 175
Thr Cys Ser Ser His Phe Pro Tyr Ser Gln Tyr Gln Phe Trp Lys Asn
                180                 185                 190
Phe Gln Thr Leu Lys Ile Val Ile Leu Gly Leu Val Leu Pro Leu Leu
                195                 200                 205
Val Met Val Ile Cys Tyr Ser Gly Ile Leu Lys Thr Leu Leu Arg Cys
            210                 215                 220
Arg Asn Glu Lys Lys Arg His Arg Ala Val Arg Leu Ile Phe Thr Ile
225                 230                 235                 240
Met Ile Val Tyr Phe Leu Phe Trp Ala Pro Tyr Asn Ile Val Leu Leu
                245                 250                 255
Leu Asn Thr Phe Gln Glu Phe Phe Gly Leu Asn Asn Cys Ser Ser Ser
                260                 265                 270
Asn Arg Leu Asp Gln Ala Met Gln Val Thr Glu Thr Leu Gly Met Thr
            275                 280                 285
His Cys Cys Ile Asn Pro Ile Ile Tyr Ala Phe Val Gly Glu Lys Phe
            290                 295                 300
Arg Asn Tyr Leu Leu Val Phe Phe Gln Lys His Ile Ala Lys Arg Phe
305                 310                 315                 320
Cys Lys Cys Cys Ser Ile Phe Gln Gln Glu Ala Pro Glu Arg Ala Ser
                325                 330                 335
Ser Val Tyr Thr Arg Ser Thr Gly Glu Gln Glu Ile Ser Val Gly Leu
            340                 345                 350

<210> SEQ ID NO 185
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Asp Tyr Gln Val Ser Ser Pro Ile Tyr Asp Ile Asn Tyr Tyr Thr
1               5                   10                  15
Ser Glu Pro Cys Gln Lys Ile Asn Val Lys Gln Ile Ala Ala Arg Leu
            20                  25                  30
Leu Pro Pro Gln Tyr Ser Gln Thr Tyr Thr Tyr Gly Tyr Thr Gly Asn
        35                  40                  45
Met Gln Thr Thr Gln Thr Gln Thr Asn Cys Lys Arg Leu Lys Ser Met
    50                  55                  60
Thr Asp Thr Tyr Gln Gln Asn Gln Ala Thr Ser Asp Gln Tyr Tyr Gln
65                  70                  75                  80
Gln Thr Thr Pro Tyr Trp Ala His Tyr Ala Ala Gln Trp Asp Phe
                85                  90                  95
```

Gly Asn Thr Met Cys Gln Gln Gln Thr Gly Gln Tyr Tyr Thr Gly Tyr
            100                 105                 110

Tyr Ser Gly Thr Tyr Tyr Thr Thr Gln Gln Thr Asp Arg Tyr Leu
        115                 120                 125

Ala Val Val His Ala Val Phe Ala Leu Lys Ala Arg Thr Val Thr Tyr
    130                 135                 140

Gly Thr Thr Thr Ser Thr Thr Thr Trp Thr Thr Ala Thr Tyr Ala Ser
145                 150                 155                 160

Gln Pro Gly Thr Thr Tyr Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Thr Thr Thr Gln Gly Gln Thr Gln Pro Gln Gln
        195                 200                 205

Thr Met Thr Thr Cys Tyr Ser Gly Thr Gln Lys Thr Gln Leu Arg Cys
    210                 215                 220

Arg Asn Glu Lys Lys Arg His Arg Ala Val Arg Gln Thr Tyr Thr Thr
225                 230                 235                 240

Met Thr Thr Tyr Tyr Gln Tyr Trp Ala Pro Tyr Asn Thr Thr Gln Gln
                245                 250                 255

Gln Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Thr Asn Pro Thr Thr Tyr Ala Tyr Thr Gly Glu Lys Tyr
    290                 295                 300

Arg Asn Tyr Gln Gln Thr Tyr Tyr Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 186
<211> LENGTH: 30
<212> TYPE: PRT
<213> ORGANISM: Unknown
<220> FEATURE:
<223> OTHER INFORMATION: Description of Unknown: Mammalian
      CCR5 polypeptide

<400> SEQUENCE: 186

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala
            20                  25                  30

<210> SEQ ID NO 187
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Leu Gln Pro Pro Gln Tyr Ser Gln Thr Phe Thr Phe Gly Phe Thr
1               5                   10                  15

Gly Asn Met Gln Val Thr Gln Thr Gln Ile Asn Cys
            20                  25

<210> SEQ ID NO 188
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Leu Gln Pro Pro Gln Tyr Ser Gln Thr Phe Thr Phe Gly Tyr Thr
1               5                   10                  15

Gly Asn Met Gln Val Thr Gln Thr Gln Ile Asn Cys
            20                  25

<210> SEQ ID NO 189
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Gln Gln Pro Pro Gln Tyr Ser Gln Thr Phe Thr Phe Gly Phe Thr
1               5                   10                  15

Gly Asn Met Gln Thr Thr Gln Thr Gln Ile Asn Cys
            20                  25

<210> SEQ ID NO 190
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Gln Gln Pro Pro Gln Tyr Ser Gln Thr Phe Thr Tyr Gly Phe Thr
1               5                   10                  15

Gly Asn Met Gln Thr Thr Gln Thr Gln Ile Asn Cys
            20                  25

<210> SEQ ID NO 191
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Gln Gln Pro Pro Gln Tyr Ser Gln Thr Tyr Thr Phe Gly Phe Thr
1               5                   10                  15

Gly Asn Met Gln Thr Thr Gln Thr Gln Ile Asn Cys
            20                  25

<210> SEQ ID NO 192
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 192

Arg Gln Gln Pro Pro Gln Tyr Ser Gln Thr Phe Thr Phe Gly Tyr Thr
1               5                   10                  15

Gly Asn Met Gln Thr Thr Gln Thr Gln Ile Asn Cys
            20                  25

<210> SEQ ID NO 193
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Gln Gln Pro Pro Gln Tyr Ser Gln Thr Tyr Thr Phe Gly Tyr Thr
1               5                   10                  15

Gly Asn Met Gln Thr Thr Gln Thr Gln Ile Asn Cys
            20                  25

<210> SEQ ID NO 194
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Gln Gln Pro Pro Gln Tyr Ser Gln Thr Tyr Thr Tyr Gly Tyr Thr
1               5                   10                  15

Gly Asn Met Gln Thr Thr Gln Thr Gln Thr Asn Cys
            20                  25

<210> SEQ ID NO 195
<211> LENGTH: 10
<212> TYPE: PRT
<213> ORGANISM: Unknown
<220> FEATURE:
<223> OTHER INFORMATION: Description of Unknown: Mammalian
      CCR5 peptide

<400> SEQUENCE: 195

Lys Arg Leu Lys Ser Met Thr Asp Ile Tyr
1               5                   10

<210> SEQ ID NO 196
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Gln Asn Gln Ala Ile Ser Asp Gln Phe Phe Gln Gln Thr Val Pro
1               5                   10                  15

Phe Trp Ala His Tyr
            20

<210> SEQ ID NO 197
<211> LENGTH: 21
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 197

Leu Gln Asn Gln Ala Ile Ser Asp Gln Phe Phe Gln Gln Thr Thr Pro
1               5                   10                  15

Phe Trp Ala His Tyr
            20

<210> SEQ ID NO 198
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Gln Asn Gln Ala Ile Ser Asp Gln Phe Phe Gln Gln Thr Thr Pro
1               5                   10                  15

Tyr Trp Ala His Tyr
            20

<210> SEQ ID NO 199
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Leu Gln Asn Gln Ala Ile Ser Asp Gln Phe Tyr Gln Gln Thr Thr Pro
1               5                   10                  15

Tyr Trp Ala His Tyr
            20

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Gln Asn Gln Ala Ile Ser Asp Gln Tyr Phe Gln Gln Thr Thr Pro
1               5                   10                  15

Tyr Trp Ala His Tyr
            20

<210> SEQ ID NO 201
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Gln Asn Gln Ala Thr Ser Asp Gln Phe Phe Gln Gln Thr Thr Pro
1               5                   10                  15

Tyr Trp Ala His Tyr
            20

```
<210> SEQ ID NO 202
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Gln Asn Gln Ala Ile Ser Asp Gln Tyr Tyr Gln Gln Thr Thr Pro
1               5                   10                  15

Tyr Trp Ala His Tyr
            20

<210> SEQ ID NO 203
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Gln Asn Gln Ala Thr Ser Asp Gln Tyr Tyr Gln Gln Thr Thr Pro
1               5                   10                  15

Tyr Trp Ala His Tyr
            20

<210> SEQ ID NO 204
<211> LENGTH: 13
<212> TYPE: PRT
<213> ORGANISM: Unknown
<220> FEATURE:
<223> OTHER INFORMATION: Description of Unknown: Mammalian
      CCR5 peptide

<400> SEQUENCE: 204

Ala Ala Ala Gln Trp Asp Phe Gly Asn Thr Met Cys Gln
1               5                   10

<210> SEQ ID NO 205
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Gln Thr Gly Gln Tyr Phe Thr Gly Tyr Tyr Ser Gly Thr Tyr Tyr
1               5                   10                  15

Thr Thr Gln Gln Thr Thr
            20

<210> SEQ ID NO 206
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Gln Thr Gly Gln Tyr Tyr Thr Gly Tyr Tyr Ser Gly Thr Tyr Tyr
1               5                   10                  15
```

Thr Thr Gln Gln Thr Thr
            20

<210> SEQ ID NO 207
<211> LENGTH: 17
<212> TYPE: PRT
<213> ORGANISM: Unknown
<220> FEATURE:
<223> OTHER INFORMATION: Description of Unknown: Mammalian
      CCR5 peptide

<400> SEQUENCE: 207

Asp Arg Tyr Leu Ala Val Val His Ala Val Phe Ala Leu Lys Ala Arg
1               5                   10                  15

Thr

<210> SEQ ID NO 208
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Thr Thr Tyr Gly Thr Thr Thr Ser Thr Thr Thr Trp Thr Thr Ala Thr
1               5                   10                  15

Tyr Ala Ser Gln Pro Gly Thr Thr Tyr
            20                  25

<210> SEQ ID NO 209
<211> LENGTH: 32
<212> TYPE: PRT
<213> ORGANISM: Unknown
<220> FEATURE:
<223> OTHER INFORMATION: Description of Unknown: Mammalian
      CCR5 polypeptide

<400> SEQUENCE: 209

Thr Arg Ser Gln Lys Glu Gly Leu His Tyr Thr Cys Ser Ser His Phe
1               5                   10                  15

Pro Tyr Ser Gln Tyr Gln Phe Trp Lys Asn Phe Gln Thr Leu Lys Ile
            20                  25                  30

<210> SEQ ID NO 210
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Val Ile Gln Gly Gln Val Gln Pro Gln Gln Val Met Val Thr Cys Tyr
1               5                   10                  15

Ser Gly Ile Gln
            20

<210> SEQ ID NO 211
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Ile Gln Gly Gln Val Gln Pro Gln Gln Val Met Thr Thr Cys Tyr
1               5                   10                  15

Ser Gly Ile Gln
            20

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Ile Gln Gly Gln Val Gln Pro Gln Gln Thr Met Thr Thr Cys Tyr
1               5                   10                  15

Ser Gly Ile Gln
            20

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Thr Gln Gly Gln Val Gln Pro Gln Gln Thr Met Val Thr Cys Tyr
1               5                   10                  15

Ser Gly Thr Gln
            20

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Ile Gln Gly Gln Val Gln Pro Gln Gln Val Met Thr Thr Cys Tyr
1               5                   10                  15

Ser Gly Thr Gln
            20

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Ile Gln Gly Gln Val Gln Pro Gln Gln Thr Met Val Thr Cys Tyr
1               5                   10                  15

Ser Gly Thr Gln
            20

<210> SEQ ID NO 216

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Thr Gln Gly Gln Val Gln Pro Gln Gln Val Met Thr Thr Cys Tyr
1               5                   10                  15

Ser Gly Thr Gln
            20

<210> SEQ ID NO 217
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Thr Thr Gln Gly Gln Thr Gln Pro Gln Gln Thr Met Thr Thr Cys Tyr
1               5                   10                  15

Ser Gly Thr Gln
            20

<210> SEQ ID NO 218
<211> LENGTH: 17
<212> TYPE: PRT
<213> ORGANISM: Unknown
<220> FEATURE:
<223> OTHER INFORMATION: Description of Unknown: Mammalian
      CCR5 peptide

<400> SEQUENCE: 218

Lys Thr Leu Leu Arg Cys Arg Asn Glu Lys Lys Arg His Arg Ala Val
1               5                   10                  15

Arg

<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Thr Phe Thr Thr Met Thr Thr Tyr Tyr Gln Phe Trp Ala Pro Tyr
1               5                   10                  15

Asn Ile Val Gln Gln Leu Asn Thr Phe
            20                  25

<210> SEQ ID NO 220
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Thr Phe Thr Thr Met Thr Thr Tyr Tyr Gln Phe Trp Ala Pro Tyr
1               5                   10                  15
```

Asn Thr Val Gln Gln Leu Asn Thr Phe
            20                  25

<210> SEQ ID NO 221
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Thr Phe Thr Thr Met Thr Thr Tyr Tyr Gln Tyr Trp Ala Pro Tyr
1               5                   10                  15

Asn Thr Val Gln Gln Leu Asn Thr Phe
            20                  25

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Thr Phe Thr Thr Met Thr Thr Tyr Tyr Gln Tyr Trp Ala Pro Tyr
1               5                   10                  15

Asn Thr Val Gln Gln Gln Asn Thr Phe
            20                  25

<210> SEQ ID NO 223
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Thr Tyr Thr Thr Met Thr Thr Tyr Tyr Gln Tyr Trp Ala Pro Tyr
1               5                   10                  15

Asn Thr Val Gln Gln Leu Asn Thr Phe
            20                  25

<210> SEQ ID NO 224
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Thr Phe Thr Thr Met Thr Thr Tyr Tyr Gln Tyr Trp Ala Pro Tyr
1               5                   10                  15

Asn Thr Thr Gln Gln Leu Asn Thr Phe
            20                  25

<210> SEQ ID NO 225
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 225

Gln Thr Tyr Thr Thr Met Thr Thr Tyr Tyr Gln Tyr Trp Ala Pro Tyr
1               5                   10                  15

Asn Thr Val Gln Gln Gln Asn Thr Phe
            20                  25

<210> SEQ ID NO 226
<211> LENGTH: 17
<212> TYPE: PRT
<213> ORGANISM: Unknown
<220> FEATURE:
<223> OTHER INFORMATION: Description of Unknown: Mammalian
      CCR5 peptide

<400> SEQUENCE: 226

Gln Glu Phe Phe Gly Leu Asn Asn Cys Ser Ser Ser Asn Arg Leu Asp
1               5                   10                  15

Gln

<210> SEQ ID NO 227
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Met Gln Val Thr Glu Thr Gln Gly Met Thr His Cys Cys Ile Asn
1               5                   10                  15

Pro Ile Ile Tyr Ala Phe Val Gly
            20

<210> SEQ ID NO 228
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Met Gln Val Thr Glu Thr Leu Gly Met Thr His Cys Cys Thr Asn
1               5                   10                  15

Pro Ile Ile Tyr Ala Phe Thr Gly
            20

<210> SEQ ID NO 229
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Met Gln Val Thr Glu Thr Gln Gly Met Thr His Cys Cys Ile Asn
1               5                   10                  15

Pro Thr Ile Tyr Ala Tyr Val Gly
            20

<210> SEQ ID NO 230
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Met Gln Thr Thr Glu Thr Gln Gly Met Thr His Cys Cys Ile Asn
1               5                   10                  15

Pro Ile Thr Tyr Ala Phe Thr Gly
            20

<210> SEQ ID NO 231
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Met Gln Thr Thr Glu Thr Gln Gly Met Thr His Cys Cys Ile Asn
1               5                   10                  15

Pro Thr Ile Tyr Ala Phe Thr Gly
            20

<210> SEQ ID NO 232
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Met Gln Val Thr Glu Thr Gln Gly Met Thr His Cys Cys Thr Asn
1               5                   10                  15

Pro Thr Ile Tyr Ala Tyr Val Gly
            20

<210> SEQ ID NO 233
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ala Met Gln Thr Thr Glu Thr Gln Gly Met Thr His Cys Cys Ile Asn
1               5                   10                  15

Pro Thr Thr Tyr Ala Tyr Val Gly
            20

<210> SEQ ID NO 234
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ala Met Gln Thr Thr Glu Thr Gln Gly Met Thr His Cys Cys Thr Asn
1               5                   10                  15
```

```
Pro Thr Thr Tyr Ala Tyr Thr Gly
            20

<210> SEQ ID NO 235
<211> LENGTH: 51
<212> TYPE: PRT
<213> ORGANISM: Unknown
<220> FEATURE:
<223> OTHER INFORMATION: Description of Unknown: Mammalian
      CCR5 polypeptide

<400> SEQUENCE: 235

Glu Lys Phe Arg Asn Tyr Leu Leu Val Phe Phe Gln Lys His Ile Ala
1               5                   10                  15

Lys Arg Phe Cys Lys Cys Cys Ser Ile Phe Gln Gln Glu Ala Pro Glu
                20                  25                  30

Arg Ala Ser Ser Val Tyr Thr Arg Ser Thr Gly Glu Gln Glu Ile Ser
            35                  40                  45

Val Gly Leu
        50

<210> SEQ ID NO 236
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ala Phe Leu Pro Ala Leu Tyr Ser Gln Gln Phe Gln Gln Gly Gln Gln
1               5                   10                  15

Gly Asn Gly Ala Val Ala Ala Thr Gln Leu Ser
            20                  25

<210> SEQ ID NO 237
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Phe Gln Pro Ala Leu Tyr Ser Gln Gln Phe Gln Gln Gly Gln Gln
1               5                   10                  15

Gly Asn Gly Ala Val Ala Ala Val Gln Gln Ser
            20                  25

<210> SEQ ID NO 238
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Phe Gln Pro Ala Gln Tyr Ser Gln Gln Phe Leu Gln Gly Gln Gln
1               5                   10                  15

Gly Asn Gly Ala Val Ala Ala Thr Gln Gln Ser
            20                  25

<210> SEQ ID NO 239
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Tyr Gln Pro Ala Leu Tyr Ser Leu Gln Tyr Gln Gln Gly Gln Gln
1               5                   10                  15

Gly Asn Gly Ala Thr Ala Ala Val Gln Gln Ser
            20                  25

<210> SEQ ID NO 240
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Tyr Gln Pro Ala Leu Tyr Ser Gln Leu Phe Gln Gln Gly Gln Gln
1               5                   10                  15

Gly Asn Gly Ala Thr Ala Ala Thr Gln Gln Ser
            20                  25

<210> SEQ ID NO 241
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Phe Gln Pro Ala Leu Tyr Ser Leu Gln Tyr Gln Gln Gly Gln Gln
1               5                   10                  15

Gly Asn Gly Ala Thr Ala Ala Thr Gln Gln Ser
            20                  25

<210> SEQ ID NO 242
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Tyr Gln Pro Ala Gln Tyr Ser Leu Gln Tyr Gln Gln Gly Gln Gln
1               5                   10                  15

Gly Asn Gly Ala Thr Ala Ala Val Gln Gln Ser
            20                  25

<210> SEQ ID NO 243
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Tyr Gln Pro Ala Gln Tyr Ser Gln Gln Tyr Gln Gln Gly Gln Gln
1               5                   10                  15
```

Gly Asn Gly Ala Thr Ala Ala Thr Gln Gln Ser
            20                  25

<210> SEQ ID NO 244
<211> LENGTH: 9
<212> TYPE: PRT
<213> ORGANISM: Unknown
<220> FEATURE:
<223> OTHER INFORMATION: Description of Unknown: Mammalian
      CXCR3 peptide

<400> SEQUENCE: 244

Arg Arg Thr Ala Leu Ser Ser Thr Asp
1               5

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Thr Phe Leu Gln His Leu Ala Val Ala Asp Thr Gln Gln Val Gln Thr
1               5                   10                  15

Leu Pro Gln Trp Ala
            20

<210> SEQ ID NO 246
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Phe Leu Gln His Gln Ala Val Ala Asp Thr Gln Leu Val Gln Thr
1               5                   10                  15

Gln Pro Gln Trp Ala
            20

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Phe Gln Gln His Leu Ala Val Ala Asp Thr Gln Val Gln Thr
1               5                   10                  15

Gln Pro Gln Trp Ala
            20

<210> SEQ ID NO 248
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Thr Tyr Leu Gln His Gln Ala Val Ala Asp Thr Gln Gln Val Gln Thr
1               5                   10                  15

Gln Pro Gln Trp Ala
            20

<210> SEQ ID NO 249
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Tyr Gln Leu His Gln Ala Val Ala Asp Thr Gln Gln Val Gln Thr
1               5                   10                  15

Gln Pro Gln Trp Ala
            20

<210> SEQ ID NO 250
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Thr Tyr Gln Gln His Leu Ala Val Ala Asp Thr Gln Gln Val Gln Thr
1               5                   10                  15

Gln Pro Gln Trp Ala
            20

<210> SEQ ID NO 251
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Thr Tyr Gln Gln His Gln Ala Val Ala Asp Thr Gln Gln Val Gln Thr
1               5                   10                  15

Gln Pro Gln Trp Ala
            20

<210> SEQ ID NO 252
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Thr Tyr Gln Gln His Gln Ala Thr Ala Asp Thr Gln Gln Thr Gln Thr
1               5                   10                  15

Gln Pro Gln Trp Ala
            20

<210> SEQ ID NO 253
<211> LENGTH: 15
<212> TYPE: PRT

```
<213> ORGANISM: Unknown
<220> FEATURE:
<223> OTHER INFORMATION: Description of Unknown: Mammalian
      CXCR3 peptide

<400> SEQUENCE: 253

Val Asp Ala Ala Val Gln Trp Val Phe Gly Ser Gly Leu Cys Lys
1               5                   10                  15

<210> SEQ ID NO 254
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Ala Gly Ala Gln Tyr Asn Thr Asn Phe Tyr Ala Gly Ala Gln Gln
1               5                   10                  15

Gln Ala Cys Ile Ser Phe
            20

<210> SEQ ID NO 255
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Thr Ala Gly Ala Gln Tyr Asn Thr Asn Phe Tyr Ala Gly Ala Gln Leu
1               5                   10                  15

Gln Ala Cys Thr Ser Phe
            20

<210> SEQ ID NO 256
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Ala Gly Ala Gln Tyr Asn Thr Asn Phe Tyr Ala Gly Ala Gln Gln
1               5                   10                  15

Leu Ala Cys Thr Ser Phe
            20

<210> SEQ ID NO 257
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Thr Ala Gly Ala Gln Phe Asn Thr Asn Tyr Tyr Ala Gly Ala Gln Gln
1               5                   10                  15

Gln Ala Cys Ile Ser Phe
            20
```

```
<210> SEQ ID NO 258
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Thr Ala Gly Ala Gln Tyr Asn Thr Asn Tyr Tyr Ala Gly Ala Gln Gln
1               5                   10                  15

Gln Ala Cys Ile Ser Phe
            20

<210> SEQ ID NO 259
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Ala Gly Ala Gln Tyr Asn Thr Asn Tyr Tyr Ala Gly Ala Gln Leu
1               5                   10                  15

Gln Ala Cys Thr Ser Phe
            20

<210> SEQ ID NO 260
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Thr Ala Gly Ala Gln Tyr Asn Thr Asn Tyr Tyr Ala Gly Ala Gln Gln
1               5                   10                  15

Leu Ala Cys Thr Ser Phe
            20

<210> SEQ ID NO 261
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Thr Ala Gly Ala Gln Tyr Asn Thr Asn Tyr Tyr Ala Gly Ala Gln Gln
1               5                   10                  15

Gln Ala Cys Thr Ser Tyr
            20

<210> SEQ ID NO 262
<211> LENGTH: 22
<212> TYPE: PRT
<213> ORGANISM: Unknown
<220> FEATURE:
<223> OTHER INFORMATION: Description of Unknown: Mammalian
      CXCR3 peptide

<400> SEQUENCE: 262

Asp Arg Tyr Leu Asn Ile Val His Ala Thr Gln Leu Tyr Arg Arg Gly
```

```
1               5                   10                  15
Pro Pro Ala Arg Val Thr
            20

<210> SEQ ID NO 263
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Leu Thr Cys Gln Ala Val Trp Gly Gln Cys Gln Gln Phe Ala Gln Pro
1               5                   10                  15

Asp Phe Ile Phe
            20

<210> SEQ ID NO 264
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Thr Cys Gln Ala Val Trp Gly Gln Cys Gln Gln Phe Ala Gln Pro
1               5                   10                  15

Asp Phe Ile Phe
            20

<210> SEQ ID NO 265
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln Thr Cys Gln Ala Thr Trp Gly Gln Cys Gln Gln Phe Ala Gln Pro
1               5                   10                  15

Asp Phe Ile Phe
            20

<210> SEQ ID NO 266
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Thr Cys Gln Ala Thr Trp Gly Gln Cys Gln Gln Tyr Ala Gln Pro
1               5                   10                  15

Asp Phe Ile Phe
            20

<210> SEQ ID NO 267
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 267

Gln Thr Cys Gln Ala Thr Trp Gly Gln Cys Gln Gln Phe Ala Gln Pro
1               5                   10                  15

Asp Phe Thr Phe
            20

<210> SEQ ID NO 268
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gln Thr Cys Gln Ala Thr Trp Gly Gln Cys Gln Gln Phe Ala Gln Pro
1               5                   10                  15

Asp Tyr Ile Phe
            20

<210> SEQ ID NO 269
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Thr Cys Gln Ala Thr Trp Gly Gln Cys Gln Gln Tyr Ala Gln Pro
1               5                   10                  15

Asp Tyr Ile Phe
            20

<210> SEQ ID NO 270
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Thr Cys Gln Ala Thr Trp Gly Gln Cys Gln Gln Tyr Ala Gln Pro
1               5                   10                  15

Asp Tyr Thr Tyr
            20

<210> SEQ ID NO 271
<211> LENGTH: 23
<212> TYPE: PRT
<213> ORGANISM: Unknown
<220> FEATURE:
<223> OTHER INFORMATION: Description of Unknown: Mammalian
      CXCR3 peptide

<400> SEQUENCE: 271

Leu Ser Ala His His Asp Glu Arg Leu Asn Ala Thr His Cys Gln Tyr
1               5                   10                  15

Asn Phe Pro Gln Val Gly Arg
            20
```

```
<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Thr Ala Gln Arg Thr Gln Gln Gln Thr Ala Gly Tyr Gln Gln Pro Gln
1               5                   10                  15

Gln Thr Met Ala Tyr
            20

<210> SEQ ID NO 273
<211> LENGTH: 22
<212> TYPE: PRT
<213> ORGANISM: Unknown
<220> FEATURE:
<223> OTHER INFORMATION: Description of Unknown: Mammalian
      CXCR3 peptide

<400> SEQUENCE: 273

Cys Tyr Ala His Ile Leu Ala Val Leu Leu Val Ser Arg Gly Gln Arg
1               5                   10                  15

Arg Leu Arg Ala Met Arg
            20

<210> SEQ ID NO 274
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Val Thr Thr Thr Thr Val Ala Phe Ala Gln Cys Trp Thr Pro Tyr
1               5                   10                  15

His Gln Val Val Gln Val
            20

<210> SEQ ID NO 275
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Val Thr Thr Thr Thr Val Ala Phe Ala Gln Cys Trp Thr Pro Tyr
1               5                   10                  15

His Gln Thr Val Gln Val
            20

<210> SEQ ID NO 276
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276
```

-continued

Gln Val Thr Thr Thr Thr Ala Phe Ala Gln Cys Trp Thr Pro Tyr
1               5                   10                  15

His Gln Thr Val Gln Val
            20

<210> SEQ ID NO 277
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Val Thr Thr Thr Thr Thr Ala Tyr Ala Gln Cys Trp Thr Pro Tyr
1               5                   10                  15

His Gln Thr Val Gln Val
            20

<210> SEQ ID NO 278
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gln Val Thr Thr Thr Thr Thr Ala Phe Ala Gln Cys Trp Thr Pro Tyr
1               5                   10                  15

His Gln Thr Thr Gln Val
            20

<210> SEQ ID NO 279
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Thr Thr Thr Thr Thr Val Ala Phe Ala Gln Cys Trp Thr Pro Tyr
1               5                   10                  15

His Gln Thr Thr Gln Val
            20

<210> SEQ ID NO 280
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Val Thr Thr Thr Thr Thr Ala Tyr Ala Gln Cys Trp Thr Pro Tyr
1               5                   10                  15

His Gln Thr Thr Gln Val
            20

<210> SEQ ID NO 281
<211> LENGTH: 22
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 281

Gln Thr Thr Thr Thr Thr Thr Ala Tyr Ala Gln Cys Trp Thr Pro Tyr
1               5                   10                  15

His Gln Thr Thr Gln Thr
            20

<210> SEQ ID NO 282
<211> LENGTH: 21
<212> TYPE: PRT
<213> ORGANISM: Unknown
<220> FEATURE:
<223> OTHER INFORMATION: Description of Unknown: Mammalian
      CXCR3 peptide

<400> SEQUENCE: 282

Asp Ile Leu Met Asp Leu Gly Ala Leu Ala Arg Asn Cys Gly Arg Glu
1               5                   10                  15

Ser Arg Val Asp Val
            20

<210> SEQ ID NO 283
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Lys Ser Val Thr Ser Gly Gln Gly Tyr Met His Cys Cys Leu Asn
1               5                   10                  15

Pro Leu Gln Tyr Ala Phe Val
            20

<210> SEQ ID NO 284
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Lys Ser Val Thr Ser Gly Gln Gly Tyr Met His Cys Cys Leu Asn
1               5                   10                  15

Pro Gln Leu Tyr Ala Phe Thr
            20

<210> SEQ ID NO 285
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Lys Ser Val Thr Ser Gly Gln Gly Tyr Met His Cys Cys Leu Asn
1               5                   10                  15

Pro Leu Gln Tyr Ala Phe Thr
            20
```

<210> SEQ ID NO 286
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Lys Ser Thr Thr Ser Gly Gln Gly Tyr Met His Cys Cys Leu Asn
1               5                   10                  15

Pro Gln Gln Tyr Ala Phe Val
            20

<210> SEQ ID NO 287
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Lys Ser Thr Thr Ser Gly Gln Gly Tyr Met His Cys Cys Gln Asn
1               5                   10                  15

Pro Leu Gln Tyr Ala Phe Val
            20

<210> SEQ ID NO 288
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Lys Ser Thr Thr Ser Gly Gln Gly Tyr Met His Cys Cys Gln Asn
1               5                   10                  15

Pro Gln Leu Tyr Ala Phe Val
            20

<210> SEQ ID NO 289
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Lys Ser Thr Thr Ser Gly Gln Gly Tyr Met His Cys Cys Gln Asn
1               5                   10                  15

Pro Leu Gln Tyr Ala Phe Thr
            20

<210> SEQ ID NO 290
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Lys Ser Thr Thr Ser Gly Gln Gly Tyr Met His Cys Cys Gln Asn
1               5                   10                  15

Pro Gln Gln Tyr Ala Tyr Thr
            20

<210> SEQ ID NO 291
<211> LENGTH: 47
<212> TYPE: PRT
<213> ORGANISM: Unknown
<220> FEATURE:
<223> OTHER INFORMATION: Description of Unknown: Mammalian
      CXCR3 polypeptide

<400> SEQUENCE: 291

Gly Val Lys Phe Arg Glu Arg Met Trp Met Leu Leu Arg Leu Gly
1               5                   10                  15

Cys Pro Asn Gln Arg Gly Leu Gln Arg Gln Pro Ser Ser Arg Arg
            20                  25                  30

Asp Ser Ser Trp Ser Glu Thr Ser Glu Ala Ser Tyr Ser Gly Leu
            35                  40                  45

<210> SEQ ID NO 292
<211> LENGTH: 355
<212> TYPE: PRT
<213> ORGANISM: Unknown
<220> FEATURE:
<223> OTHER INFORMATION: Description of Unknown: Mammalian
      CCR-1 polypeptide

<400> SEQUENCE: 292

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Leu Pro Pro Leu Tyr Ser Leu Val Phe Val Ile Gly
        35                  40                  45

Leu Val Gly Asn Ile Leu Val Val Leu Val Leu Val Gln Tyr Lys Arg
    50                  55                  60

Leu Lys Asn Met Thr Ser Ile Tyr Leu Leu Asn Leu Ala Ile Ser Asp
65                  70                  75                  80

Leu Leu Phe Leu Phe Thr Leu Pro Phe Trp Ile Asp Tyr Lys Leu Lys
                85                  90                  95

Asp Asp Trp Val Phe Gly Asp Ala Met Cys Lys Ile Leu Ser Gly Phe
            100                 105                 110

Tyr Tyr Thr Gly Leu Tyr Ser Glu Ile Phe Phe Ile Ile Leu Leu Thr
        115                 120                 125

Ile Asp Arg Tyr Leu Ala Ile Val His Ala Val Phe Ala Leu Arg Ala
    130                 135                 140

Arg Thr Val Thr Phe Gly Val Ile Thr Ser Ile Ile Ile Trp Ala Leu
145                 150                 155                 160

Ala Ile Leu Ala Ser Met Pro Gly Leu Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Leu Phe Gly Leu
        195                 200                 205

Val Leu Pro Leu Leu Val Met Ile Ile Cys Tyr Thr Gly Ile Ile Lys
    210                 215                 220

-continued

```
Ile Leu Leu Arg Arg Pro Asn Glu Lys Lys Ser Lys Ala Val Arg Leu
225                 230                 235                 240

Ile Phe Val Ile Met Ile Ile Phe Phe Leu Phe Trp Thr Pro Tyr Asn
                245                 250                 255

Leu Thr Ile Leu Ile Ser Val Phe Gln Asp Phe Leu Phe Thr His Glu
            260                 265                 270

Cys Glu Gln Ser Arg His Leu Asp Leu Ala Val Gln Val Thr Glu Val
        275                 280                 285

Ile Ala Tyr Thr His Cys Cys Val Asn Pro Val Ile Tyr Ala Phe Val
    290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
                340                 345                 350

Ala Gly Phe
        355

<210> SEQ ID NO 293
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Met Glu Thr Pro Asn Thr Thr Glu Asp Tyr Asp Thr Thr Thr Glu Phe
1               5                   10                  15

Asp Tyr Gly Asp Ala Thr Pro Cys Gln Lys Val Asn Glu Arg Ala Phe
            20                  25                  30

Gly Ala Gln Leu Gln Pro Pro Gln Tyr Ser Thr Tyr Thr Thr Thr Gly
        35                  40                  45

Gln Thr Gly Asn Thr Gln Thr Thr Gln Thr Val Gln Tyr Lys Arg
    50                  55                  60

Leu Lys Asn Met Thr Ser Thr Tyr Gln Asn Gln Ala Thr Ser Asp
65                  70                  75                  80

Gln Gln Tyr Gln Tyr Thr Gln Pro Tyr Trp Thr Asp Tyr Lys Leu Lys
                85                  90                  95

Asp Asp Trp Val Phe Gly Asp Ala Met Cys Lys Thr Gln Ser Gly Tyr
            100                 105                 110

Tyr Tyr Thr Gly Gln Tyr Ser Glu Thr Tyr Tyr Thr Thr Gln Gln Thr
        115                 120                 125

Ile Asp Arg Tyr Leu Ala Ile Val His Ala Val Phe Ala Leu Arg Ala
    130                 135                 140

Arg Thr Thr Thr Tyr Gly Thr Thr Thr Ser Thr Thr Trp Ala Gln
145                 150                 155                 160

Ala Thr Gln Ala Ser Met Pro Gly Gln Tyr Phe Ser Lys Thr Gln Trp
                165                 170                 175

Glu Phe Thr His His Thr Cys Ser Leu His Phe Pro His Glu Ser Leu
            180                 185                 190

Arg Glu Trp Lys Leu Phe Gln Ala Leu Lys Leu Asn Gln Tyr Gly Gln
        195                 200                 205

Thr Gln Pro Gln Gln Thr Met Thr Thr Cys Tyr Thr Gly Thr Thr Lys
```

```
                    210                 215                 220
Thr Gln Gln Arg Arg Pro Asn Glu Lys Lys Ser Lys Ala Val Arg Gln
225                 230                 235                 240

Thr Tyr Thr Thr Met Thr Thr Tyr Tyr Gln Tyr Trp Thr Pro Tyr Asn
                245                 250                 255

Gln Thr Thr Gln Thr Ser Val Phe Gln Asp Phe Leu Phe Thr His Glu
                260                 265                 270

Cys Glu Gln Ser Arg His Leu Asp Leu Ala Thr Gln Thr Thr Glu Thr
                275                 280                 285

Thr Ala Tyr Thr His Cys Cys Thr Asn Pro Thr Thr Tyr Ala Tyr Thr
                290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                325                 330                 335

Glu Arg Val Ser Ser Thr Ser Pro Ser Thr Gly Glu His Glu Leu Ser
                340                 345                 350

Ala Gly Phe
        355

<210> SEQ ID NO 294
<211> LENGTH: 374
<212> TYPE: PRT
<213> ORGANISM: Unknown
<220> FEATURE:
<223> OTHER INFORMATION: Description of Unknown: Mammalian
      CCR-2 polypeptide

<400> SEQUENCE: 294

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
                35                  40                  45

Tyr Ser Leu Val Phe Ile Phe Gly Phe Val Gly Asn Met Leu Val Val
50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
                100                 105                 110

Cys Lys Leu Phe Thr Gly Leu Tyr His Ile Gly Tyr Phe Gly Gly Ile
                115                 120                 125

Phe Phe Ile Ile Leu Leu Thr Ile Asp Arg Tyr Leu Ala Ile Val His
                130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
                180                 185                 190

Tyr Phe Pro Arg Gly Trp Asn Asn Phe His Thr Ile Met Arg Asn Ile
                195                 200                 205
```

```
Leu Gly Leu Val Leu Pro Leu Leu Ile Met Val Ile Cys Tyr Ser Gly
    210                 215                 220
Ile Leu Lys Thr Leu Leu Arg Cys Arg Asn Glu Lys Lys Arg His Arg
225                 230                 235                 240
Ala Val Arg Val Ile Phe Thr Ile Met Ile Val Tyr Phe Leu Phe Trp
                245                 250                 255
Thr Pro Tyr Asn Ile Val Ile Leu Leu Asn Thr Phe Gln Glu Phe Phe
            260                 265                 270
Gly Leu Ser Asn Cys Glu Ser Thr Ser Gln Leu Asp Gln Ala Thr Gln
        275                 280                 285
Val Thr Glu Thr Leu Gly Met Thr His Cys Cys Ile Asn Pro Ile Ile
    290                 295                 300
Tyr Ala Phe Val Gly Glu Lys Phe Arg Ser Leu Phe His Ile Ala Leu
305                 310                 315                 320
Gly Cys Arg Ile Ala Pro Leu Gln Lys Pro Val Cys Gly Gly Pro Gly
                325                 330                 335
Val Arg Pro Gly Lys Asn Val Lys Val Thr Thr Gln Gly Leu Leu Asp
            340                 345                 350
Gly Arg Gly Lys Gly Lys Ser Ile Gly Arg Ala Pro Glu Ala Ser Leu
        355                 360                 365
Gln Asp Lys Glu Gly Ala
        370

<210> SEQ ID NO 295
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Leu Ser Thr Ser Arg Ser Arg Phe Ile Arg Asn Thr Asn Glu Ser
1               5                   10                  15
Gly Glu Glu Val Thr Thr Phe Phe Asp Tyr Asp Tyr Gly Ala Pro Cys
                20                  25                  30
His Lys Phe Asp Val Lys Gln Ile Gly Ala Gln Leu Gln Pro Pro Gln
            35                  40                  45
Tyr Ser Gln Thr Tyr Thr Tyr Gly Tyr Thr Gly Asn Met Gln Thr Thr
        50                  55                  60
Gln Thr Gln Ile Asn Cys Lys Lys Leu Lys Cys Leu Thr Asp Ile Tyr
65                  70                  75                  80
Gln Gln Asn Gln Ala Thr Ser Asp Gln Gln Tyr Gln Thr Thr Gln Pro
                85                  90                  95
Gln Trp Ala His Ser Ala Ala Asn Glu Trp Val Phe Gly Asn Ala Met
            100                 105                 110
Cys Lys Leu Phe Thr Gly Gln Tyr His Thr Gly Tyr Tyr Gly Gly Thr
        115                 120                 125
Tyr Tyr Thr Thr Gln Gln Thr Thr Asp Arg Tyr Leu Ala Ile Val His
    130                 135                 140
Ala Val Phe Ala Leu Lys Ala Arg Thr Val Thr Tyr Gly Thr Thr Thr
145                 150                 155                 160
Ser Thr Thr Thr Trp Gln Thr Ala Thr Tyr Ala Ser Thr Pro Gly Thr
                165                 170                 175
Thr Tyr Thr Lys Cys Gln Lys Glu Asp Ser Val Tyr Val Cys Gly Pro
            180                 185                 190
```

```
Tyr Phe Pro Arg Gly Trp Asn Asn Phe His Thr Ile Met Arg Asn Thr
            195                 200                 205

Gln Gly Gln Thr Gln Pro Gln Gln Thr Met Thr Thr Cys Tyr Ser Gly
    210                 215                 220

Thr Gln Lys Thr Gln Gln Arg Cys Arg Asn Glu Lys Lys Arg His Arg
225                 230                 235                 240

Thr Arg Thr Thr Tyr Thr Thr Met Thr Thr Tyr Tyr Gln Tyr Trp Thr
                245                 250                 255

Pro Tyr Asn Thr Thr Thr Gln Leu Asn Thr Phe Gln Glu Phe Phe Gly
            260                 265                 270

Leu Ser Asn Cys Glu Ser Thr Ser Gln Leu Asp Gln Ala Thr Gln Val
            275                 280                 285

Thr Glu Thr Gln Gly Met Thr His Cys Cys Thr Asn Pro Thr Thr Tyr
            290                 295                 300

Ala Tyr Thr Gly Glu Lys Phe Arg Ser Leu Phe His Ile Ala Leu Gly
305                 310                 315                 320

Cys Arg Ile Ala Pro Leu Gln Lys Pro Val Cys Gly Pro Gly Val
                325                 330                 335

Arg Pro Gly Lys Asn Val Lys Val Thr Thr Gln Gly Leu Leu Asp Gly
            340                 345                 350

Arg Gly Lys Gly Lys Ser Ile Gly Arg Ala Pro Glu Ala Ser Leu Gln
        355                 360                 365

Asp Lys Glu Gly Ala
    370

<210> SEQ ID NO 296
<211> LENGTH: 360
<212> TYPE: PRT
<213> ORGANISM: Unknown
<220> FEATURE:
<223> OTHER INFORMATION: Description of Unknown: Mammalian
      CCR-4 polypeptide

<400> SEQUENCE: 296

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
```

165                 170                 175
Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
                260                 265                 270

Leu Gln Asp Cys Thr Phe Glu Arg Tyr Leu Asp Tyr Ala Ile Gln Ala
            275                 280                 285

Thr Glu Thr Leu Ala Phe Val His Cys Cys Leu Asn Pro Ile Ile Tyr
        290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
            355                 360

<210> SEQ ID NO 297
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Gln
            35                  40                  45

Thr Tyr Thr Tyr Gly Gln Gln Gly Asn Ser Thr Thr Thr Gln Thr Gln
    50                  55                  60

Tyr Lys Tyr Lys Arg Leu Arg Ser Met Thr Asp Thr Tyr Gln Gln Asn
65                  70                  75                  80

Gln Ala Thr Ser Asp Gln Gln Tyr Thr Tyr Ser Gln Pro Tyr Trp Gly
                85                  90                  95

Tyr Tyr Ala Ala Asp Gln Trp Val Phe Gly Leu Gly Leu Cys Lys Met
            100                 105                 110

Thr Ser Trp Met Tyr Gln Thr Gly Tyr Tyr Ser Gly Thr Tyr Tyr Thr
        115                 120                 125

Met Gln Met Ser Ile Asp Arg Tyr Leu Ala Ile Val His Ala Val Phe
    130                 135                 140

Ser Leu Arg Ala Arg Thr Gln Thr Tyr Gly Thr Thr Ser Gln Ala
145                 150                 155                 160

```
Thr Trp Ser Thr Ala Thr Tyr Ala Ser Gln Pro Gly Tyr Gln Tyr Ser
                165                 170                 175
Thr Cys Tyr Thr Glu Arg Asn His Thr Tyr Cys Lys Thr Lys Tyr Ser
            180                 185                 190
Leu Asn Ser Thr Thr Trp Lys Val Leu Ser Ser Leu Glu Thr Asn Thr
        195                 200                 205
Gln Gly Gln Thr Thr Pro Gln Gly Thr Met Gln Tyr Cys Tyr Ser Met
    210                 215                 220
Thr Thr Arg Thr Leu Gln His Cys Lys Asn Glu Lys Lys Asn Lys Ala
225                 230                 235                 240
Val Lys Met Thr Tyr Ala Thr Thr Thr Gln Tyr Gln Gly Tyr Trp Thr
                245                 250                 255
Pro Tyr Asn Thr Thr Gln Tyr Gln Glu Thr Leu Val Glu Leu Glu Val
            260                 265                 270
Leu Gln Asp Cys Thr Phe Glu Arg Tyr Leu Asp Tyr Ala Ile Gln Ala
        275                 280                 285
Thr Glu Thr Gln Ala Tyr Thr His Cys Cys Gln Asn Pro Thr Thr Tyr
    290                 295                 300
Tyr Tyr Gln Gly Glu Lys Phe Arg Lys Tyr Ile Leu Gln Leu Phe Lys
305                 310                 315                 320
Thr Cys Arg Gly Leu Phe Val Leu Cys Gln Tyr Cys Gly Leu Leu Gln
                325                 330                 335
Ile Tyr Ser Ala Asp Thr Pro Ser Ser Tyr Thr Gln Ser Thr Met
            340                 345                 350
Asp His Asp Leu His Asp Ala Leu
        355                 360

<210> SEQ ID NO 298
<211> LENGTH: 374
<212> TYPE: PRT
<213> ORGANISM: Unknown
<220> FEATURE:
<223> OTHER INFORMATION: Description of Unknown: Mammalian
      CCR-6 polypeptide

<400> SEQUENCE: 298

Met Ser Gly Glu Ser Met Asn Phe Ser Asp Val Phe Asp Ser Ser Glu
1               5                   10                  15
Asp Tyr Phe Val Ser Val Asn Thr Ser Tyr Tyr Ser Val Asp Ser Glu
                20                  25                  30
Met Leu Leu Cys Ser Leu Gln Glu Val Arg Gln Phe Ser Arg Leu Phe
            35                  40                  45
Val Pro Ile Ala Tyr Ser Leu Ile Cys Val Phe Gly Leu Leu Gly Asn
    50                  55                  60
Ile Leu Val Val Ile Thr Phe Ala Phe Tyr Lys Lys Ala Arg Ser Met
65                  70                  75                  80
Thr Asp Val Tyr Leu Leu Asn Met Ala Ile Ala Asp Ile Leu Phe Val
                85                  90                  95
Leu Thr Leu Pro Phe Trp Ala Val Ser His Ala Thr Gly Ala Trp Val
            100                 105                 110
Phe Ser Asn Ala Thr Cys Lys Leu Leu Lys Gly Ile Tyr Ala Ile Asn
        115                 120                 125
Phe Asn Cys Gly Met Leu Leu Leu Thr Cys Ile Ser Met Asp Arg Tyr
    130                 135                 140
Ile Ala Ile Val Gln Ala Thr Lys Ser Phe Arg Leu Arg Ser Arg Thr
145                 150                 155                 160
```

```
Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
    210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Leu Gly Lys Met Asn Arg Ser Cys
        275                 280                 285

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
        355                 360                 365

Ala Ser Ser Phe Thr Met
    370

<210> SEQ ID NO 299
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Thr Ala Tyr Ser Gln Thr Cys Thr Tyr Gly Gln Gln Gly Asn
    50                  55                  60

Thr Gln Thr Thr Thr Thr Tyr Ala Tyr Tyr Lys Lys Ala Arg Ser Met
65                  70                  75                  80

Thr Asp Val Tyr Gln Gln Asn Met Ala Thr Ala Asp Thr Gln Tyr Thr
                85                  90                  95

Gln Thr Gln Pro Tyr Trp Ala Thr Ser His Ala Thr Gly Ala Trp Val
            100                 105                 110

Phe Ser Asn Ala Thr Cys Lys Leu Leu Lys Gly Thr Tyr Ala Thr Asn
        115                 120                 125

Tyr Asn Cys Gly Met Gln Gln Gln Thr Cys Thr Ser Met Asp Arg Tyr
```

```
            130                 135                 140
Thr Ala Ile Val Gln Ala Thr Lys Ser Phe Arg Leu Arg Ser Arg Thr
145                 150                 155                 160

Leu Pro Arg Ser Lys Thr Thr Cys Gln Thr Thr Trp Gly Gln Ser Thr
                165                 170                 175

Thr Thr Ser Ser Ser Thr Tyr Thr Tyr Asn Gln Lys Tyr Asn Thr Gln
                180                 185                 190

Gly Ser Asp Val Cys Glu Pro Lys Tyr Gln Thr Val Ser Glu Pro Ile
                195                 200                 205

Arg Trp Lys Leu Leu Met Leu Gly Leu Glu Leu Gln Tyr Gly Tyr Tyr
210                 215                 220

Thr Pro Gln Met Tyr Met Thr Tyr Cys Tyr Thr Tyr Thr Lys Thr
225                 230                 235                 240

Gln Thr Gln Ala Gln Asn Ser Lys Arg His Lys Ala Ile Arg Thr Thr
                245                 250                 255

Thr Ala Thr Thr Gln Thr Tyr Gln Ala Cys Gln Thr Pro His Asn Met
                260                 265                 270

Thr Gln Gln Thr Thr Ala Ala Asn Leu Gly Lys Met Asn Arg Ser Cys
                275                 280                 285

Gln Ser Glu Lys Leu Ile Gly Tyr Thr Lys Thr Val Thr Glu Thr Gln
                290                 295                 300

Ala Tyr Gln His Cys Cys Gln Asn Pro Thr Gln Tyr Ala Tyr Thr Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
                340                 345                 350

Ser Glu Asn Ile Ser Arg Gln Thr Ser Glu Thr Ala Asp Asn Asp Asn
                355                 360                 365

Ala Ser Ser Phe Thr Met
    370

<210> SEQ ID NO 300
<211> LENGTH: 378
<212> TYPE: PRT
<213> ORGANISM: Unknown
<220> FEATURE:
<223> OTHER INFORMATION: Description of Unknown: Mammalian
      CCR-7 polypeptide

<400> SEQUENCE: 300

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
                20                  25                  30

Ile Gly Asp Asn Thr Thr Val Asp Tyr Thr Leu Phe Glu Ser Leu Cys
            35                  40                  45

Ser Lys Lys Asp Val Arg Asn Phe Lys Ala Trp Phe Leu Pro Ile Met
        50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110
```

```
Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
        130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
        210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
                275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 301
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Thr Met
    50                  55                  60

Tyr Ser Thr Thr Cys Tyr Thr Gly Gln Gln Gly Asn Gly Gln Thr Thr
65              70                  75                  80

Gln Thr Tyr Thr Tyr Phe Lys Arg Leu Lys Thr Met Thr Asp Thr Tyr
                85                  90                  95
```

Gln Gln Asn Gln Ala Thr Ala Asp Thr Gln Tyr Gln Gln Thr Gln Pro
                100                 105                 110

Tyr Trp Ala Tyr Ser Ala Ala Lys Ser Trp Val Phe Gly Val His Phe
            115                 120                 125

Cys Lys Gln Thr Tyr Ala Thr Tyr Lys Met Ser Tyr Tyr Ser Gly Met
        130                 135                 140

Gln Gln Gln Gln Cys Thr Ser Ile Asp Arg Tyr Val Ala Ile Val Gln
145                 150                 155                 160

Ala Val Ser Ala His Arg His Arg Ala Arg Thr Gln Gln Thr Ser Lys
                165                 170                 175

Gln Ser Cys Thr Gly Thr Trp Thr Gln Ala Thr Gln Ser Thr Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
        210                 215                 220

Val Ala Gln Met Thr Thr Gly Tyr Gln Thr Pro Gln Gln Ala Met Ser
225                 230                 235                 240

Tyr Cys Tyr Gln Thr Thr Thr Arg Thr Gln Gln Gln Ala Arg Asn Phe
                245                 250                 255

Glu Arg Asn Lys Ala Ile Lys Thr Thr Thr Ala Thr Thr Thr Thr Tyr
            260                 265                 270

Thr Thr Tyr Gln Gln Pro Tyr Asn Gly Thr Thr Gln Ala Gln Thr Val
        275                 280                 285

Ala Asn Phe Asn Ile Thr Ser Ser Thr Cys Glu Leu Ser Lys Gln Leu
        290                 295                 300

Asn Ile Ala Tyr Asp Thr Thr Tyr Ser Gln Ala Cys Thr Arg Cys Cys
305                 310                 315                 320

Thr Asn Pro Tyr Gln Tyr Ala Tyr Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 302
<211> LENGTH: 355
<212> TYPE: PRT
<213> ORGANISM: Unknown
<220> FEATURE:
<223> OTHER INFORMATION: Description of Unknown: Mammalian
      CCR-8 polypeptide

<400> SEQUENCE: 302

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
            20                  25                  30

Asn Gly Lys Leu Leu Leu Ala Val Phe Tyr Cys Leu Leu Phe Val Phe
        35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser

```
                65                  70                  75                  80
Asp Leu Leu Phe Val Phe Ser Phe Pro Phe Gln Thr Tyr Tyr Leu Leu
                    85                  90                  95

Asp Gln Trp Val Phe Gly Thr Val Met Cys Lys Val Val Ser Gly Phe
                100                 105                 110

Tyr Tyr Ile Gly Phe Tyr Ser Met Phe Phe Ile Thr Leu Met Ser
            115                 120                 125

Val Asp Arg Tyr Leu Ala Val Val His Ala Val Tyr Ala Leu Lys Val
        130                 135                 140

Arg Thr Ile Arg Met Gly Thr Thr Leu Cys Leu Ala Val Trp Leu Thr
145                 150                 155                 160

Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly
    290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Cys Gln His Ser Ser Arg Ser Ser Val Asp
            340                 345                 350

Tyr Ile Leu
        355

<210> SEQ ID NO 303
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
                20                  25                  30

Asn Gly Lys Leu Leu Leu Ala Thr Tyr Tyr Cys Gln Leu Tyr Thr Tyr
            35                  40                  45

Ser Gln Gln Gly Asn Ser Gln Thr Thr Gln Thr Gln Thr Thr Cys Lys
        50                  55                  60
```

```
Lys Leu Arg Ser Ile Thr Asp Val Tyr Gln Gln Asn Gln Ala Gln Ser
 65                  70                  75                  80

Asp Gln Gln Tyr Thr Tyr Ser Tyr Pro Tyr Gln Thr Tyr Tyr Gln Gln
                 85                  90                  95

Asp Gln Trp Val Phe Gly Thr Val Met Cys Lys Val Val Ser Gly Tyr
            100                 105                 110

Tyr Tyr Thr Gly Tyr Tyr Ser Ser Met Tyr Tyr Thr Gln Met Ser
            115                 120                 125

Thr Asp Arg Tyr Leu Ala Val Val His Ala Val Tyr Ala Leu Lys Val
        130                 135                 140

Arg Thr Ile Arg Met Gly Thr Thr Leu Cys Gln Ala Thr Trp Gln Thr
145                 150                 155                 160

Ala Thr Met Ala Thr Thr Pro Gln Gln Thr Tyr Tyr Gln Thr Ala Ser
                165                 170                 175

Glu Asp Gly Val Leu Gln Cys Tyr Ser Phe Tyr Asn Gln Gln Thr Leu
            180                 185                 190

Lys Trp Lys Thr Tyr Thr Asn Tyr Lys Met Asn Thr Gly Gln Gln
        195                 200                 205

Thr Pro Tyr Thr Thr Tyr Met Tyr Cys Tyr Ile Lys Ile Leu His Gln
        210                 215                 220

Leu Lys Arg Cys Gln Asn His Asn Lys Thr Lys Ala Ile Arg Gln Thr
225                 230                 235                 240

Gln Thr Thr Thr Thr Ala Ser Gln Gln Tyr Trp Thr Pro Tyr Asn Thr
                245                 250                 255

Thr Gln Tyr Gln Thr Ser Leu His Ser Met His Ile Leu Asp Gly Cys
            260                 265                 270

Ser Ile Ser Gln Gln Leu Thr Tyr Ala Thr His Val Thr Glu Thr Thr
        275                 280                 285

Ser Tyr Thr His Cys Cys Thr Asn Pro Thr Thr Tyr Ala Tyr Thr Gly
            290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
            340                 345                 350

Tyr Ile Leu
        355

<210> SEQ ID NO 304
<211> LENGTH: 357
<212> TYPE: PRT
<213> ORGANISM: Unknown
<220> FEATURE:
<223> OTHER INFORMATION: Description of Unknown: Mammalian
      CCR-9 polypeptide

<400> SEQUENCE: 304

Met Ala Asp Asp Tyr Gly Ser Glu Ser Thr Ser Ser Met Glu Asp Tyr
  1               5                  10                  15

Val Asn Phe Asn Phe Thr Asp Phe Tyr Cys Glu Lys Asn Asn Val Arg
                 20                  25                  30

Gln Phe Ala Ser His Phe Leu Pro Pro Leu Tyr Trp Leu Val Phe Ile
             35                  40                  45

Val Gly Ala Leu Gly Asn Ser Leu Val Ile Leu Val Tyr Trp Tyr Cys
 50                  55                  60
```

Thr Arg Val Lys Thr Met Thr Asp Met Phe Leu Leu Asn Leu Ala Ile
65                  70                  75                  80

Ala Asp Leu Leu Phe Leu Val Thr Leu Pro Phe Trp Ala Ile Ala Ala
            85                  90                  95

Ala Asp Gln Trp Lys Phe Gln Thr Phe Met Cys Lys Val Asn Ser
            100                 105                 110

Met Tyr Lys Met Asn Phe Tyr Ser Cys Val Leu Leu Ile Met Cys Ile
            115                 120                 125

Ser Val Asp Arg Tyr Ile Ala Ile Ala Gln Ala Met Arg Ala His Thr
130                 135                 140

Trp Arg Glu Lys Arg Leu Leu Tyr Ser Lys Met Val Cys Phe Thr Ile
145                 150                 155                 160

Trp Val Leu Ala Ala Ala Leu Cys Ile Pro Glu Ile Leu Tyr Ser Gln
                165                 170                 175

Ile Lys Glu Glu Ser Gly Ile Ala Ile Cys Thr Met Val Tyr Pro Ser
            180                 185                 190

Asp Glu Ser Thr Lys Leu Lys Ser Ala Val Leu Thr Leu Lys Val Ile
            195                 200                 205

Leu Gly Phe Phe Leu Pro Phe Val Val Met Ala Cys Cys Tyr Thr Ile
            210                 215                 220

Ile Ile His Thr Leu Ile Gln Ala Lys Lys Ser Ser Lys His Lys Ala
225                 230                 235                 240

Leu Lys Val Thr Ile Thr Val Leu Thr Val Phe Val Leu Ser Gln Phe
                245                 250                 255

Pro Tyr Asn Cys Ile Leu Leu Val Gln Thr Ile Asp Ala Tyr Ala Met
            260                 265                 270

Phe Ile Ser Asn Cys Ala Val Ser Thr Asn Ile Asp Ile Cys Phe Gln
            275                 280                 285

Val Thr Gln Thr Ile Ala Phe Phe His Ser Cys Leu Asn Pro Val Leu
290                 295                 300

Tyr Val Phe Val Gly Glu Arg Phe Arg Arg Asp Leu Val Lys Thr Leu
305                 310                 315                 320

Lys Asn Leu Gly Cys Ile Ser Gln Ala Gln Trp Val Ser Phe Thr Arg
                325                 330                 335

Arg Glu Gly Ser Leu Lys Leu Ser Ser Met Leu Leu Glu Thr Thr Ser
            340                 345                 350

Gly Ala Leu Ser Leu
            355

<210> SEQ ID NO 305
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Met Ala Asp Asp Tyr Gly Ser Glu Ser Thr Ser Ser Met Glu Asp Tyr
1               5                   10                  15

Val Asn Phe Asn Phe Thr Asp Phe Tyr Cys Glu Lys Asn Asn Val Arg
            20                  25                  30

Gln Phe Ala Ser His Phe Leu Pro Pro Gln Tyr Trp Gln Thr Tyr Thr
        35                  40                  45

Thr Gly Ala Gln Gly Asn Ser Gln Thr Thr Gln Thr Tyr Trp Tyr Cys

```
                    50                  55                  60
Thr Arg Val Lys Thr Met Thr Asp Met Tyr Gln Gln Asn Gln Ala Thr
 65                  70                  75                  80

Ala Asp Gln Gln Tyr Gln Thr Thr Gln Pro Tyr Trp Ala Thr Ala Ala
                     85                  90                  95

Ala Asp Gln Trp Lys Phe Gln Thr Phe Met Cys Lys Val Val Asn Ser
                100                 105                 110

Met Tyr Lys Met Asn Tyr Tyr Ser Cys Thr Gln Thr Met Cys Thr
                115                 120                 125

Ser Thr Asp Arg Tyr Thr Ala Thr Ala Gln Ala Met Arg Ala His Thr
                130                 135                 140

Trp Arg Glu Lys Arg Gln Gln Tyr Ser Lys Met Thr Cys Tyr Thr Thr
145                 150                 155                 160

Trp Thr Gln Ala Ala Ala Gln Cys Thr Pro Glu Ile Leu Tyr Ser Gln
                165                 170                 175

Ile Lys Glu Glu Ser Gly Ile Ala Ile Cys Thr Met Val Tyr Pro Ser
                180                 185                 190

Asp Glu Ser Thr Lys Leu Lys Ser Ala Val Leu Thr Leu Lys Val Thr
                195                 200                 205

Gln Gly Tyr Tyr Gln Pro Tyr Thr Thr Met Ala Cys Cys Tyr Thr Thr
                210                 215                 220

Thr Thr His Thr Gln Thr Gln Ala Lys Lys Ser Ser Lys His Lys Ala
225                 230                 235                 240

Leu Lys Thr Thr Thr Thr Thr Gln Thr Thr Tyr Thr Gln Ser Gln Tyr
                245                 250                 255

Pro Tyr Asn Cys Thr Gln Gln Thr Gln Thr Ile Asp Ala Tyr Ala Met
                260                 265                 270

Phe Ile Ser Asn Cys Ala Val Ser Thr Asn Ile Asp Ile Cys Tyr Gln
                275                 280                 285

Thr Thr Gln Thr Thr Ala Tyr Tyr His Ser Cys Gln Asn Pro Thr Gln
                290                 295                 300

Tyr Thr Tyr Thr Gly Glu Arg Phe Arg Arg Asp Leu Val Lys Thr Leu
305                 310                 315                 320

Lys Asn Leu Gly Cys Ile Ser Gln Ala Gln Trp Val Ser Phe Thr Arg
                325                 330                 335

Arg Glu Gly Ser Leu Lys Leu Ser Ser Met Leu Leu Gly Thr Thr Ser
                340                 345                 350

Gly Ala Leu Ser Leu
                355

<210> SEQ ID NO 306
<211> LENGTH: 362
<212> TYPE: PRT
<213> ORGANISM: Unknown
<220> FEATURE:
<223> OTHER INFORMATION: Description of Unknown: Mammalian
      CCR-10 polypeptide

<400> SEQUENCE: 306

Met Gly Thr Glu Ala Thr Glu Gln Val Ser Trp Gly His Tyr Ser Gly
 1               5                  10                  15

Asp Glu Glu Asp Ala Tyr Ser Ala Glu Pro Leu Pro Glu Leu Cys Tyr
                 20                  25                  30

Lys Ala Asp Val Gln Ala Phe Ser Arg Ala Phe Gln Pro Ser Val Ser
                 35                  40                  45
```

Leu Thr Val Ala Ala Leu Gly Leu Ala Gly Asn Gly Leu Val Leu Ala
 50                  55                  60

Thr His Leu Ala Ala Arg Arg Ala Ala Arg Ser Pro Thr Ser Ala His
 65                  70                  75                  80

Leu Leu Gln Leu Ala Leu Ala Asp Leu Leu Leu Ala Leu Thr Leu Pro
                 85                  90                  95

Phe Ala Ala Ala Gly Ala Leu Gln Gly Trp Ser Leu Gly Ser Ala Thr
            100                 105                 110

Cys Arg Thr Ile Ser Gly Leu Tyr Ser Ala Ser Phe His Ala Gly Phe
        115                 120                 125

Leu Phe Leu Ala Cys Ile Ser Ala Asp Arg Tyr Val Ala Ile Ala Arg
130                 135                 140

Ala Leu Pro Ala Gly Pro Arg Pro Ser Thr Pro Gly Arg Ala His Leu
145                 150                 155                 160

Val Ser Val Ile Val Trp Leu Leu Ser Leu Leu Leu Ala Leu Pro Ala
                165                 170                 175

Leu Leu Phe Ser Gln Asp Gly Gln Arg Glu Gly Gln Arg Cys Arg
            180                 185                 190

Leu Ile Phe Pro Glu Gly Leu Thr Gln Thr Val Lys Gly Ala Ser Ala
        195                 200                 205

Val Ala Gln Val Ala Leu Gly Phe Ala Leu Pro Leu Gly Val Met Val
210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Val Ala Leu Val Ala Ala Phe
                245                 250                 255

Val Val Leu Gln Leu Pro Tyr Ser Leu Ala Leu Leu Leu Asp Thr Ala
            260                 265                 270

Asp Leu Leu Ala Ala Arg Glu Arg Ser Cys Pro Ala Ser Lys Arg Lys
        275                 280                 285

Asp Val Ala Leu Leu Val Thr Ser Gly Leu Ala Leu Ala Arg Cys Gly
290                 295                 300

Leu Asn Pro Val Leu Tyr Ala Phe Leu Gly Leu Arg Phe Arg Gln Asp
305                 310                 315                 320

Leu Arg Arg Leu Leu Arg Gly Gly Ser Cys Pro Ser Gly Pro Gln Pro
                325                 330                 335

Arg Arg Gly Cys Pro Arg Arg Pro Arg Leu Ser Ser Cys Ser Ala Pro
            340                 345                 350

Thr Glu Thr His Ser Leu Ser Trp Asp Asn
        355                 360

<210> SEQ ID NO 307
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Met Gly Thr Glu Ala Thr Glu Gln Val Ser Trp Gly His Tyr Ser Gly
  1               5                  10                  15

Asp Glu Glu Asp Ala Tyr Ser Ala Glu Pro Leu Pro Glu Leu Cys Tyr
                 20                  25                  30

Lys Ala Asp Val Gln Ala Phe Ser Arg Ala Phe Gln Pro Ser Thr Ser
             35                  40                  45

```
Gln Thr Thr Ala Ala Gln Gly Gln Ala Gly Asn Gly Gln Thr Gln Ala
    50                  55                  60

Thr His Gln Ala Ala Arg Arg Ala Ala Arg Ser Pro Thr Ser Ala His
65                  70                  75                  80

Gln Gln Gln Gln Ala Gln Ala Asp Gln Gln Ala Gln Thr Gln Pro
                85                  90                  95

Tyr Ala Ala Gly Ala Gln Gln Gly Trp Ser Leu Gly Ser Ala Thr
                100                 105                 110

Cys Arg Thr Ile Ser Gly Gln Tyr Ser Ala Ser Tyr His Ala Gly Tyr
                115                 120                 125

Gln Tyr Gln Ala Cys Thr Ser Ala Asp Arg Tyr Val Ala Ile Ala Arg
            130                 135                 140

Ala Leu Pro Ala Gly Pro Arg Pro Ser Thr Pro Gly Arg Ala His Gln
145                 150                 155                 160

Thr Ser Thr Thr Thr Trp Gln Gln Ser Gln Gln Ala Gln Pro Ala
                    165                 170                 175

Gln Gln Tyr Ser Gln Asp Gly Gln Arg Glu Gly Gln Arg Arg Cys Arg
            180                 185                 190

Leu Ile Phe Pro Glu Gly Leu Thr Gln Thr Val Lys Gly Ala Ser Ala
            195                 200                 205

Thr Ala Gln Thr Ala Gln Gly Tyr Ala Gln Pro Gln Gly Thr Met Thr
210                 215                 220

Ala Cys Tyr Ala Gln Gln Gly Arg Thr Leu Leu Ala Ala Arg Gly Pro
225                 230                 235                 240

Glu Arg Arg Arg Ala Leu Arg Thr Thr Thr Ala Gln Thr Ala Ala Tyr
                    245                 250                 255

Thr Thr Gln Gln Gln Pro Tyr Ser Gln Ala Gln Gln Gln Asp Thr Ala
                260                 265                 270

Asp Leu Leu Ala Ala Arg Glu Arg Ser Cys Pro Ala Ser Lys Arg Lys
            275                 280                 285

Asp Thr Ala Gln Gln Thr Thr Ser Gly Gln Ala Gln Ala Arg Cys Gly
            290                 295                 300

Gln Asn Pro Thr Gln Tyr Ala Tyr Gln Gly Leu Arg Phe Arg Gln Asp
305                 310                 315                 320

Leu Arg Arg Leu Leu Arg Gly Gly Ser Cys Pro Ser Gly Pro Gln Pro
                325                 330                 335

Arg Arg Gly Cys Pro Arg Arg Pro Arg Leu Ser Ser Cys Ser Ala Pro
                340                 345                 350

Thr Glu Thr His Ser Leu Ser Trp Asp Asn
                355                 360

<210> SEQ ID NO 308
<211> LENGTH: 350
<212> TYPE: PRT
<213> ORGANISM: Unknown
<220> FEATURE:
<223> OTHER INFORMATION: Description of Unknown: Mammalian
      CXCR1 polypeptide

<400> SEQUENCE: 308

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
                20                  25                  30

Glu Thr Glu Thr Leu Asn Lys Tyr Val Val Ile Ile Ala Tyr Ala Leu
```

```
                35                  40                  45
Val Phe Leu Leu Ser Leu Leu Gly Asn Ser Leu Val Met Leu Val Ile
 50                  55                  60

Leu Tyr Ser Arg Val Gly Arg Ser Val Thr Asp Val Tyr Leu Leu Asn
 65                  70                  75                  80

Leu Ala Leu Ala Asp Leu Leu Phe Ala Leu Thr Leu Pro Ile Trp Ala
                 85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

<210> SEQ ID NO 309
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Met Ser Asn Ile Thr Asp Pro Gln Met Trp Asp Phe Asp Asp Leu Asn
 1               5                  10                  15

Phe Thr Gly Met Pro Pro Ala Asp Glu Asp Tyr Ser Pro Cys Met Leu
                 20                  25                  30

Glu Thr Glu Thr Leu Asn Lys Tyr Thr Thr Thr Ala Tyr Ala Gln
             35                  40                  45
```

```
Thr Tyr Gln Gln Ser Gln Gln Gly Asn Ser Gln Thr Met Gln Thr Thr
    50                  55                  60

Gln Tyr Ser Arg Val Gly Arg Ser Val Thr Asp Thr Tyr Gln Gln Asn
 65                  70                  75                  80

Gln Ala Gln Ala Asp Gln Gln Tyr Ala Gln Thr Gln Pro Thr Trp Ala
                 85                  90                  95

Ala Ser Lys Val Asn Gly Trp Ile Phe Gly Thr Phe Leu Cys Lys Val
            100                 105                 110

Val Ser Leu Leu Lys Glu Val Asn Tyr Tyr Ser Gly Thr Gln Gln Gln
            115                 120                 125

Ala Cys Thr Ser Thr Asp Arg Tyr Gln Ala Thr Thr His Ala Thr Arg
        130                 135                 140

Thr Leu Thr Gln Lys Arg His Gln Thr Lys Tyr Thr Cys Gln Gly Cys
145                 150                 155                 160

Trp Gly Gln Ser Met Asn Gln Ser Gln Pro Tyr Tyr Gln Tyr Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
            195                 200                 205

Tyr Gly Tyr Thr Thr Pro Gln Tyr Thr Met Gln Tyr Cys Tyr Gly Tyr
        210                 215                 220

Thr Gln Arg Thr Gln Tyr Lys Ala His Met Gly Gln Lys His Arg Ala
225                 230                 235                 240

Met Arg Thr Thr Tyr Ala Thr Thr Gln Thr Tyr Gln Gln Cys Trp Gln
                245                 250                 255

Pro Tyr Asn Gln Thr Gln Leu Ala Asp Thr Leu Met Arg Thr Gln Val
            260                 265                 270

Ile Gln Glu Ser Cys Glu Arg Arg Asn Asn Ile Gly Arg Ala Leu Asp
            275                 280                 285

Ala Thr Glu Ile Gln Gly Tyr Gln His Ser Cys Gln Asn Pro Thr Thr
        290                 295                 300

Tyr Ala Tyr Thr Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Val Asn Val Ser Ser Asn Leu
            340                 345                 350

<210> SEQ ID NO 310
<211> LENGTH: 333
<212> TYPE: PRT
<213> ORGANISM: Unknown
<220> FEATURE:
<223> OTHER INFORMATION: Description of Unknown: Mammalian
      CXR polypeptide

<400> SEQUENCE: 310

Met Glu Ser Ser Gly Asn Pro Glu Ser Thr Thr Phe Phe Tyr Tyr Asp
  1               5                  10                  15

Leu Gln Ser Gln Pro Cys Glu Asn Gln Ala Trp Val Phe Ala Thr Leu
                 20                  25                  30

Ala Thr Thr Val Leu Tyr Cys Leu Val Phe Leu Leu Ser Leu Val Gly
             35                  40                  45

Asn Ser Leu Val Leu Trp Val Leu Val Lys Tyr Glu Ser Leu Glu Ser
 50                  55                  60
```

Leu Thr Asn Ile Phe Ile Leu Asn Leu Cys Leu Ser Asp Leu Val Phe
65                  70                  75                  80

Ala Cys Leu Leu Pro Val Trp Ile Ser Pro Tyr His Trp Gly Trp Val
                85                  90                  95

Leu Gly Asp Phe Leu Cys Lys Leu Leu Asn Met Ile Phe Ser Ile Ser
            100                 105                 110

Leu Tyr Ser Ser Ile Phe Phe Leu Thr Ile Met Thr Ile His Arg Tyr
            115                 120                 125

Leu Ser Val Val Ser Pro Leu Ser Thr Leu Arg Val Pro Thr Leu Arg
130                 135                 140

Cys Arg Val Leu Val Thr Met Ala Val Trp Val Ala Ser Ile Leu Ser
145                 150                 155                 160

Ser Ile Leu Asp Thr Ile Phe His Lys Val Leu Ser Ser Gly Cys Asp
                165                 170                 175

Tyr Ser Glu Leu Thr Trp Tyr Leu Thr Ser Val Tyr Gln His Asn Leu
            180                 185                 190

Phe Phe Leu Leu Ser Leu Gly Ile Ile Leu Phe Cys Tyr Val Glu Ile
            195                 200                 205

Leu Arg Thr Leu Phe Arg Ser Arg Ser Lys Arg His Arg Thr Val
210                 215                 220

Lys Leu Ile Phe Ala Ile Val Val Ala Tyr Phe Leu Ser Trp Gly Pro
225                 230                 235                 240

Tyr Asn Phe Thr Leu Phe Leu Gln Thr Leu Phe Arg Thr Gln Ile Ile
                245                 250                 255

Arg Ser Cys Glu Ala Lys Gln Gln Leu Glu Tyr Ala Leu Leu Ile Cys
            260                 265                 270

Arg Asn Leu Ala Phe Ser His Cys Cys Phe Asn Pro Val Leu Tyr Val
            275                 280                 285

Phe Val Gly Val Lys Phe Arg Thr His Leu Lys His Val Leu Arg Gln
290                 295                 300

Phe Trp Phe Cys Arg Leu Gln Ala Pro Ser Pro Ala Ser Ile Pro His
305                 310                 315                 320

Ser Pro Gly Ala Phe Ala Tyr Glu Gly Ala Ser Phe Tyr
                325                 330

<210> SEQ ID NO 311
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Glu Ser Ser Gly Asn Pro Glu Ser Thr Thr Phe Phe Tyr Tyr Asp
1               5                   10                  15

Leu Gln Ser Gln Pro Cys Glu Asn Gln Ala Trp Val Phe Ala Thr Leu
            20                  25                  30

Ala Thr Thr Thr Gln Tyr Cys Gln Thr Tyr Gln Gln Ser Gln Thr Gly
        35                  40                  45

Asn Ser Gln Thr Gln Trp Thr Gln Val Lys Tyr Glu Ser Leu Glu Ser
    50                  55                  60

Leu Thr Asn Thr Tyr Thr Gln Asn Gln Cys Gln Ser Asp Gln Thr Tyr
65                  70                  75                  80

Ala Cys Gln Gln Pro Thr Trp Thr Ser Pro Tyr His Trp Gly Trp Val

```
                85                  90                  95
Leu Gly Asp Phe Leu Cys Lys Leu Leu Asn Met Ile Phe Ser Thr Ser
            100                 105                 110
Gln Tyr Ser Ser Thr Tyr Tyr Gln Thr Thr Met Thr Thr His Arg Tyr
            115                 120                 125
Gln Ser Thr Thr Ser Pro Leu Ser Thr Leu Arg Val Pro Thr Leu Arg
            130                 135                 140
Cys Arg Thr Gln Thr Thr Met Ala Thr Trp Thr Ala Ser Thr Gln Ser
145                 150                 155                 160
Ser Thr Gln Asp Thr Thr Tyr His Lys Val Leu Ser Ser Gly Cys Asp
                165                 170                 175
Tyr Ser Glu Leu Thr Trp Tyr Leu Thr Ser Thr Tyr Gln His Asn Gln
            180                 185                 190
Tyr Tyr Gln Gln Ser Gln Gly Thr Thr Gln Tyr Cys Tyr Thr Glu Thr
            195                 200                 205
Gln Arg Thr Leu Phe Arg Ser Arg Ser Lys Arg Arg His Arg Thr Val
            210                 215                 220
Lys Gln Thr Tyr Ala Thr Thr Thr Ala Tyr Tyr Gln Ser Trp Gly Pro
225                 230                 235                 240
Tyr Asn Tyr Thr Gln Tyr Gln Gln Thr Leu Phe Arg Thr Gln Ile Ile
                245                 250                 255
Arg Ser Cys Glu Ala Lys Gln Gln Leu Glu Tyr Ala Gln Gln Thr Cys
            260                 265                 270
Arg Asn Gln Ala Tyr Ser His Cys Cys Tyr Asn Pro Thr Gln Tyr Thr
            275                 280                 285
Tyr Thr Gly Val Lys Phe Arg Thr His Leu Lys His Val Leu Arg Gln
            290                 295                 300
Phe Trp Phe Cys Arg Leu Gln Ala Pro Ser Pro Ala Ser Ile Pro His
305                 310                 315                 320
Ser Pro Gly Ala Phe Ala Tyr Glu Gly Ala Ser Phe Tyr
                325                 330

<210> SEQ ID NO 312
<211> LENGTH: 360
<212> TYPE: PRT
<213> ORGANISM: Unknown
<220> FEATURE:
<223> OTHER INFORMATION: Description of Unknown: Mammalian
      CXCR2 polypeptide

<400> SEQUENCE: 312

Met Glu Asp Phe Asn Met Glu Ser Asp Ser Phe Glu Asp Phe Trp Lys
1               5                   10                  15
Gly Glu Asp Leu Ser Asn Tyr Ser Tyr Ser Ser Thr Leu Pro Pro Phe
            20                  25                  30
Leu Leu Asp Ala Ala Pro Cys Glu Pro Glu Ser Leu Glu Ile Asn Lys
        35                  40                  45
Tyr Phe Val Val Ile Ile Tyr Ala Leu Val Phe Leu Leu Ser Leu Leu
    50                  55                  60
Gly Asn Ser Leu Val Met Leu Val Ile Leu Tyr Ser Arg Val Gly Arg
65                  70                  75                  80
Ser Val Thr Asp Val Tyr Leu Leu Asn Leu Ala Leu Ala Asp Leu Leu
                85                  90                  95
Phe Ala Leu Thr Leu Pro Ile Trp Ala Ala Ser Lys Val Asn Gly Trp
            100                 105                 110
```

```
Ile Phe Gly Thr Phe Leu Cys Lys Val Val Ser Leu Leu Lys Glu Val
            115                 120                 125

Asn Phe Tyr Ser Gly Ile Leu Leu Ala Cys Ile Ser Val Asp Arg
130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 313
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Thr Thr Thr Thr Tyr Ala Gln Thr Gln Gln Ser Gln Gln
    50                  55                  60

Gly Asn Ser Gln Thr Met Gln Thr Thr Leu Tyr Ser Arg Val Gly Arg
65                  70                  75                  80

Ser Val Thr Asp Thr Tyr Gln Gln Asn Gln Ala Gln Ala Asp Gln Gln
                85                  90                  95

Tyr Ala Gln Thr Gln Pro Thr Trp Ala Ala Ser Lys Val Asn Gly Trp
            100                 105                 110
```

```
Ile Phe Gly Thr Phe Leu Cys Lys Val Val Ser Leu Leu Lys Glu Thr
            115                 120                 125

Asn Tyr Tyr Ser Gly Thr Gln Gln Ala Cys Thr Ser Thr Asp Arg
    130                 135                 140

Tyr Gln Ala Thr Thr His Ala Thr Arg Thr Leu Thr Gln Lys Arg Tyr
145                 150                 155                 160

Gln Thr Lys Tyr Thr Cys Gln Ser Thr Trp Gly Ser Gln Gln Gln
                165                 170                 175

Ala Gln Pro Thr Gln Gln Tyr Arg Arg Thr Val Tyr Ser Ser Asn Val
            180                 185                 190

Ser Pro Ala Cys Tyr Glu Asp Met Gly Asn Asn Thr Ala Asn Trp Arg
            195                 200                 205

Met Leu Leu Arg Ile Leu Pro Gln Ser Tyr Gly Tyr Thr Thr Pro Gln
            210                 215                 220

Gln Thr Met Gln Tyr Cys Tyr Gly Tyr Thr Gln Arg Thr Gln Tyr Lys
225                 230                 235                 240

Ala His Met Gly Gln Lys His Arg Ala Met Arg Thr Thr Tyr Ala Thr
                245                 250                 255

Thr Gln Thr Tyr Gln Gln Cys Trp Gln Pro Tyr Asn Gln Thr Gln Leu
            260                 265                 270

Ala Asp Thr Leu Met Arg Thr Gln Val Ile Gln Glu Thr Cys Glu Arg
            275                 280                 285

Arg Asn His Ile Asp Arg Ala Leu Asp Ala Thr Glu Thr Gln Gly Thr
            290                 295                 300

Gln His Ser Cys Gln Asn Pro Gln Thr Tyr Ala Tyr Thr Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
            355                 360

<210> SEQ ID NO 314
<211> LENGTH: 372
<212> TYPE: PRT
<213> ORGANISM: Unknown
<220> FEATURE:
<223> OTHER INFORMATION: Description of Unknown: Mammalian
      CCR-10 polypeptide

<400> SEQUENCE: 314

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
                20                  25                  30

Val Glu Asn His Leu Cys Pro Ala Thr Glu Gly Pro Leu Met Ala Ser
            35                  40                  45

Phe Lys Ala Val Phe Val Pro Val Ala Tyr Ser Leu Ile Phe Leu Leu
        50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
```

```
                100                 105                 110
Val Gly Trp Val Leu Gly Thr Phe Leu Cys Lys Thr Val Ile Ala Leu
            115                 120                 125
His Lys Val Asn Phe Tyr Cys Ser Ser Leu Leu Ala Cys Ile Ala
    130                 135                 140
Val Asp Arg Tyr Leu Ala Ile Val His Ala Val His Ala Tyr Arg His
145                 150                 155                 160
Arg Arg Leu Leu Ser Ile His Ile Thr Cys Gly Thr Ile Trp Leu Val
                165                 170                 175
Gly Phe Leu Leu Ala Leu Pro Glu Ile Leu Phe Ala Lys Val Ser Gln
            180                 185                 190
Gly His His Asn Asn Ser Leu Pro Arg Cys Thr Phe Ser Gln Glu Asn
        195                 200                 205
Gln Ala Glu Thr His Ala Trp Phe Thr Ser Arg Phe Leu Tyr His Val
    210                 215                 220
Ala Gly Phe Leu Leu Pro Met Leu Val Met Gly Trp Cys Tyr Val Gly
225                 230                 235                 240
Val Val His Arg Leu Arg Gln Ala Gln Arg Arg Pro Gln Arg Gln Lys
                245                 250                 255
Ala Val Arg Val Ala Ile Leu Val Thr Ser Ile Phe Phe Leu Cys Trp
            260                 265                 270
Ser Pro Tyr His Ile Val Ile Phe Leu Asp Thr Leu Ala Arg Leu Lys
        275                 280                 285
Ala Val Asp Asn Thr Cys Lys Leu Asn Gly Ser Leu Pro Val Ala Ile
    290                 295                 300
Thr Met Cys Glu Phe Leu Gly Leu Ala His Cys Cys Leu Asn Pro Met
305                 310                 315                 320
Leu Tyr Thr Phe Ala Gly Val Lys Phe Arg Ser Asp Leu Ser Arg Leu
                325                 330                 335
Leu Thr Lys Leu Gly Cys Thr Gly Pro Ala Ser Leu Cys Gln Leu Phe
            340                 345                 350
Pro Ser Trp Arg Arg Ser Ser Leu Ser Glu Ser Glu Asn Ala Thr Ser
        355                 360                 365
Leu Thr Thr Phe
    370

<210> SEQ ID NO 315
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Met Asn Tyr Pro Leu Thr Leu Glu Met Asp Leu Glu Asn Leu Glu Asp
1               5                   10                  15
Leu Phe Trp Glu Leu Asp Arg Leu Asp Asn Tyr Asn Asp Thr Ser Leu
                20                  25                  30
Val Glu Asn His Leu Cys Pro Ala Thr Glu Gly Pro Leu Met Ala Ser
            35                  40                  45
Phe Lys Ala Val Phe Thr Pro Thr Ala Tyr Ser Gln Thr Tyr Gln Gln
        50                  55                  60
Gly Thr Thr Gly Asn Thr Gln Thr Gln Thr Gln Glu Arg His Arg
65                  70                  75                  80
```

-continued

Gln Thr Arg Ser Ser Thr Glu Thr Tyr Gln Tyr His Gln Ala Thr Ala
                85                  90                  95

Asp Gln Gln Gln Thr Tyr Thr Gln Pro Tyr Ala Thr Ala Glu Gly Ser
            100                 105                 110

Val Gly Trp Val Leu Gly Thr Phe Leu Cys Lys Thr Val Thr Ala Gln
        115                 120                 125

His Lys Thr Asn Tyr Tyr Cys Ser Ser Gln Gln Ala Cys Thr Ala
    130                 135                 140

Thr Asp Arg Tyr Leu Ala Ile Val His Ala Val His Ala Tyr Arg His
145                 150                 155                 160

Arg Arg Leu Leu Ser Thr His Thr Thr Cys Gly Thr Thr Trp Gln Thr
                165                 170                 175

Gly Tyr Gln Gln Ala Gln Pro Glu Thr Gln Tyr Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Tyr Gln Tyr His Thr
    210                 215                 220

Ala Gly Tyr Gln Gln Pro Met Gln Thr Met Gly Trp Cys Tyr Thr Gly
225                 230                 235                 240

Thr Thr His Arg Leu Arg Gln Ala Gln Arg Arg Pro Gln Arg Gln Lys
                245                 250                 255

Ala Thr Arg Thr Ala Thr Gln Thr Thr Ser Thr Tyr Tyr Gln Cys Trp
            260                 265                 270

Ser Pro Tyr His Thr Thr Thr Tyr Leu Asp Thr Leu Ala Arg Leu Lys
        275                 280                 285

Ala Val Asp Asn Thr Cys Lys Leu Asn Gly Ser Gln Pro Thr Ala Thr
    290                 295                 300

Thr Met Cys Glu Tyr Gln Gly Gln Ala His Cys Cys Gln Asn Pro Met
305                 310                 315                 320

Gln Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
        355                 360                 365

Leu Thr Thr Phe
    370

<210> SEQ ID NO 316
<211> LENGTH: 342
<212> TYPE: PRT
<213> ORGANISM: Unknown
<220> FEATURE:
<223> OTHER INFORMATION: Description of Unknown: Mammalian
      CXCR6 polypeptide

<400> SEQUENCE: 316

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

```
Leu Thr Asp Val Phe Leu Val Asn Leu Pro Leu Ala Asp Leu Val Phe
 65                  70                  75                  80

Val Cys Thr Leu Pro Phe Trp Ala Tyr Ala Gly Ile His Glu Trp Val
                 85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
            115                 120                 125

Ile Val Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
            195                 200                 205

Val Cys Tyr Ser Val Ile Ile Lys Thr Leu Leu His Ala Gly Gly Phe
210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
            275                 280                 285

Ala Phe Val Ser Leu Lys Phe Arg Lys Asn Phe Trp Lys Leu Val Lys
290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 317
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Ala Glu His Asp Tyr His Glu Asp Tyr Gly Phe Ser Ser Phe Asn
 1               5                  10                  15

Asp Ser Ser Gln Glu Glu His Gln Asp Phe Leu Gln Phe Ser Lys Val
                20                  25                  30

Phe Leu Pro Cys Met Tyr Gln Thr Tyr Thr Cys Gly Gln Thr Gly
             35                  40                  45

Asn Ser Gln Thr Gln Thr Thr Ser Thr Tyr Tyr His Lys Leu Gln Ser
50                  55                  60

Leu Thr Asp Thr Tyr Gln Thr Asn Gln Pro Gln Ala Asp Gln Thr Tyr
```

```
                65                  70                  75                  80
            Thr Cys Thr Gln Pro Tyr Trp Ala Tyr Ala Gly Ile His Glu Trp Val
                            85                  90                  95

Phe Gly Gln Val Met Cys Lys Ser Leu Leu Gly Ile Tyr Thr Thr Asn
                       100                 105                 110

Tyr Tyr Thr Ser Met Gln Thr Gln Thr Cys Thr Thr Asp Arg Tyr
                       115                 120                 125

Thr Thr Thr Thr Lys Ala Thr Lys Ala Tyr Asn Gln Gln Ala Lys Arg
            130                 135                 140

Met Thr Trp Gly Lys Val Thr Ser Gln Gln Thr Trp Thr Thr Ser Gln
            145                 150                 155                 160

Gln Thr Ser Gln Pro Gln Thr Thr Tyr Gly Asn Thr Tyr Asn Gln Asp
                       165                 170                 175

Lys Leu Ile Cys Gly Tyr His Asp Glu Ala Ile Ser Thr Thr Thr Gln
                       180                 185                 190

Ala Thr Gln Met Thr Gln Gly Tyr Tyr Gln Pro Gln Gln Thr Met Thr
                       195                 200                 205

Thr Cys Tyr Ser Val Ile Ile Lys Thr Leu Leu His Ala Gly Gly Phe
                       210                 215                 220

Gln Lys His Arg Ser Leu Lys Thr Thr Tyr Gln Thr Met Ala Thr Tyr
            225                 230                 235                 240

Gln Gln Thr Gln Met Pro Tyr Asn Gln Met Lys Tyr Thr Arg Ser Thr
                       245                 250                 255

His Trp Glu Tyr Tyr Ala Met Thr Ser Phe His Tyr Thr Thr Met Thr
                       260                 265                 270

Thr Glu Ala Thr Ala Tyr Gln Arg Ala Cys Gln Asn Pro Thr Gln Tyr
                       275                 280                 285

Ala Tyr Thr Ser Leu Lys Phe Arg Lys Asn Phe Trp Lys Leu Val Lys
                       290                 295                 300

Asp Ile Gly Cys Leu Pro Tyr Leu Gly Val Ser His Gln Trp Lys Ser
            305                 310                 315                 320

Ser Glu Asp Asn Ser Lys Thr Phe Ser Ala Ser His Asn Val Glu Ala
                       325                 330                 335

Thr Ser Met Phe Gln Leu
                       340

<210> SEQ ID NO 318
<211> LENGTH: 362
<212> TYPE: PRT
<213> ORGANISM: Unknown
<220> FEATURE:
<223> OTHER INFORMATION: Description of Unknown: Mammalian
      CXCR7 polypeptide

<400> SEQUENCE: 318

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
65                  70                  75                  80
```

```
Cys Tyr Ile Leu Asn Leu Ala Ile Ala Asp Leu Trp Val Val Leu Thr
                85                  90                  95
Ile Pro Val Trp Val Val Ser Leu Val Gln His Asn Gln Trp Pro Met
            100                 105                 110
Gly Glu Leu Thr Cys Lys Val Thr His Leu Ile Phe Ser Ile Asn Leu
        115                 120                 125
Phe Gly Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
            180                 185                 190
Glu Thr Tyr Cys Arg Ser Phe Tyr Pro Glu His Ser Ile Lys Glu Trp
        195                 200                 205
Leu Ile Gly Met Glu Leu Val Ser Val Val Leu Gly Phe Ala Val Pro
    210                 215                 220
Phe Ser Ile Ile Ala Val Phe Tyr Phe Leu Leu Ala Arg Ala Ile Ser
225                 230                 235                 240
Ala Ser Ser Asp Gln Glu Lys His Ser Ser Arg Lys Ile Ile Phe Ser
                245                 250                 255
Tyr Val Val Val Phe Leu Val Cys Trp Leu Pro Tyr His Val Ala Val
            260                 265                 270
Leu Leu Asp Ile Phe Ser Ile Leu His Tyr Ile Pro Phe Thr Cys Arg
        275                 280                 285
Leu Glu His Ala Leu Phe Thr Ala Leu His Val Thr Gln Cys Leu Ser
    290                 295                 300
Leu Val His Cys Cys Val Asn Pro Val Leu Tyr Ser Phe Ile Asn Arg
305                 310                 315                 320
Asn Tyr Arg Tyr Glu Leu Met Lys Ala Phe Ile Phe Lys Tyr Ser Ala
                325                 330                 335
Lys Thr Gly Leu Thr Lys Leu Ile Asp Ala Ser Arg Val Ser Glu Thr
            340                 345                 350
Glu Tyr Ser Ala Leu Glu Gln Ser Thr Lys
        355                 360

<210> SEQ ID NO 319
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Asp Leu His Leu Phe Asp Tyr Ser Glu Pro Gly Asn Phe Ser Asp
1               5                   10                  15
Ile Ser Trp Pro Cys Asn Ser Ser Asp Cys Ile Val Val Asp Thr Val
            20                  25                  30
Met Cys Pro Asn Met Pro Asn Lys Ser Val Leu Leu Tyr Thr Gln Ser
        35                  40                  45
Tyr Thr Tyr Thr Tyr Thr Tyr Thr Gly Met Thr Ala Asn Ser Thr
    50                  55                  60
Thr Thr Trp Thr Asn Ile Gln Ala Lys Thr Thr Gly Tyr Asp Thr His
65                  70                  75                  80
```

```
Cys Tyr Thr Gln Asn Gln Ala Thr Ala Asp Gln Trp Thr Thr Gln Thr
                85                  90                  95

Thr Pro Thr Trp Thr Thr Ser Gln Val Gln His Asn Gln Trp Pro Met
            100                 105                 110

Gly Glu Leu Thr Cys Lys Thr Thr His Gln Thr Tyr Ser Thr Asn Gln
        115                 120                 125

Tyr Gly Ser Thr Tyr Tyr Gln Thr Cys Met Ser Thr Asp Arg Tyr Leu
    130                 135                 140

Ser Ile Thr Tyr Phe Thr Asn Thr Pro Ser Ser Arg Lys Lys Met Thr
145                 150                 155                 160

Arg Arg Thr Thr Cys Thr Gln Thr Trp Gln Gln Ala Tyr Cys Thr Ser
                165                 170                 175

Gln Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Gln Thr Ser Thr Thr Gln Gly Tyr Ala Thr Pro
    210                 215                 220

Tyr Ser Thr Thr Ala Thr Tyr Tyr Gln Gln Ala Arg Ala Ile Ser
225                 230                 235                 240

Ala Ser Ser Asp Gln Glu Lys His Ser Ser Arg Lys Ile Ile Tyr Ser
                245                 250                 255

Tyr Thr Thr Thr Tyr Gln Thr Cys Trp Gln Pro Tyr His Thr Ala Thr
            260                 265                 270

Gln Gln Asp Thr Tyr Ser Ile Leu His Tyr Ile Pro Phe Thr Cys Arg
        275                 280                 285

Leu Glu His Ala Leu Phe Thr Ala Gln His Thr Thr Gln Cys Gln Ser
    290                 295                 300

Gln Thr His Cys Cys Thr Asn Pro Gln Tyr Ser Tyr Thr Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360
```

<210> SEQ ID NO 320
<211> LENGTH: 373
<212> TYPE: PRT
<213> ORGANISM: Unknown
<220> FEATURE:
<223> OTHER INFORMATION: Description of Unknown: Mammalian CLR-1a polypeptide

<400> SEQUENCE: 320

```
Met Arg Met Glu Asp Glu Asp Tyr Asn Thr Ser Ile Ser Tyr Gly Asp
1               5                   10                  15

Glu Tyr Pro Asp Tyr Leu Asp Ser Ile Val Val Leu Glu Asp Leu Ser
            20                  25                  30

Pro Leu Glu Ala Arg Val Thr Arg Ile Phe Leu Val Val Tyr Ser
        35                  40                  45

Ile Val Cys Phe Leu Gly Ile Leu Gly Asn Gly Leu Val Ile Ile Ile
    50                  55                  60

Ala Thr Phe Lys Met Lys Lys Thr Val Asn Met Val Trp Phe Leu Asn
```

```
                 65                  70                  75                  80
Leu Ala Val Ala Asp Phe Leu Phe Asn Val Phe Leu Pro Ile His Ile
                 85                  90                  95

Thr Tyr Ala Ala Met Asp Tyr His Trp Val Phe Gly Thr Ala Met Cys
                100                 105                 110

Lys Ile Ser Asn Phe Leu Leu Ile His Asn Met Phe Thr Ser Val Phe
                115                 120                 125

Leu Leu Thr Ile Ile Ser Ser Asp Arg Cys Ile Ser Val Leu Leu Pro
130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
                180                 185                 190

Phe Ser Leu Ser Thr Pro Gly Ser Ser Ser Trp Pro Thr His Ser Gln
                195                 200                 205

Met Asp Pro Val Gly Tyr Ser Arg His Met Val Val Thr Val Thr Arg
210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Ile Val Thr Ile Ile Thr Phe Phe Leu Cys
                260                 265                 270

Trp Cys Pro Tyr His Thr Leu Asn Leu Leu Glu Leu His His Thr Ala
                275                 280                 285

Met Pro Gly Ser Val Phe Ser Leu Gly Leu Pro Leu Ala Thr Ala Leu
290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
                340                 345                 350

Phe Thr Lys Met Ser Ser Met Asn Glu Arg Thr Ser Met Asn Glu Arg
                355                 360                 365

Glu Thr Gly Met Leu
                370

<210> SEQ ID NO 321
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Arg Met Glu Asp Glu Asp Tyr Asn Thr Ser Ile Ser Tyr Gly Asp
1               5                   10                  15

Glu Tyr Pro Asp Tyr Leu Asp Ser Ile Val Val Leu Glu Asp Leu Ser
                20                  25                  30

Pro Leu Glu Ala Arg Val Thr Arg Thr Tyr Gln Thr Thr Thr Tyr Ser
                35                  40                  45
```

Thr Thr Cys Tyr Gln Gly Thr Gln Gly Asn Gly Gln Thr Thr Thr Ile
 50                  55                  60

Ala Thr Phe Lys Met Lys Lys Thr Val Asn Met Thr Trp Tyr Gln Asn
 65                  70                  75                  80

Gln Ala Thr Ala Asp Tyr Gln Tyr Asn Thr Tyr Gln Pro Thr His Thr
                 85                  90                  95

Thr Tyr Ala Ala Met Asp Tyr His Trp Val Phe Gly Thr Ala Met Cys
            100                 105                 110

Lys Ile Ser Asn Phe Gln Gln Thr His Asn Met Tyr Thr Ser Thr Tyr
        115                 120                 125

Gln Gln Thr Thr Thr Ser Ser Asp Arg Cys Ile Ser Val Leu Leu Pro
130                 135                 140

Val Trp Ser Gln Asn His Arg Ser Val Arg Gln Ala Tyr Met Ala Cys
145                 150                 155                 160

Met Thr Thr Trp Thr Gln Ala Tyr Tyr Gln Ser Ser Pro Ser Gln Thr
                165                 170                 175

Tyr Arg Asp Thr Ala Asn Leu His Gly Lys Ile Ser Cys Phe Asn Asn
            180                 185                 190

Phe Ser Leu Ser Thr Pro Gly Ser Ser Ser Trp Pro Thr His Ser Gln
        195                 200                 205

Met Asp Pro Val Gly Tyr Ser Arg His Met Val Val Thr Val Thr Arg
210                 215                 220

Tyr Gln Cys Gly Tyr Gln Thr Pro Thr Gln Thr Thr Thr Ala Cys Tyr
225                 230                 235                 240

Gln Thr Thr Thr Cys Lys Gln Gln Arg Asn Arg Leu Ala Lys Thr Lys
                245                 250                 255

Lys Pro Tyr Lys Thr Thr Thr Thr Thr Thr Thr Tyr Tyr Gln Cys
            260                 265                 270

Trp Cys Pro Tyr His Thr Gln Asn Gln Leu Glu Leu His His Thr Ala
        275                 280                 285

Met Pro Gly Ser Val Phe Ser Gln Gly Gln Pro Gln Ala Thr Ala Gln
290                 295                 300

Ala Thr Ala Asn Ser Cys Met Asn Pro Thr Gln Tyr Thr Tyr Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
            340                 345                 350

Phe Thr Lys Met Ser Ser Met Asn Glu Arg Thr Ser Met Asn Glu Arg
        355                 360                 365

Glu Thr Gly Met Leu
    370

<210> SEQ ID NO 322
<211> LENGTH: 338
<212> TYPE: PRT
<213> ORGANISM: Unknown
<220> FEATURE:
<223> OTHER INFORMATION: Description of Unknown:
      DARIA Duffy antigen polypeptide

<400> SEQUENCE: 322

Met Ala Ser Ser Gly Tyr Val Leu Gln Ala Glu Leu Ser Pro Ser Thr
1               5                   10                  15

Glu Asn Ser Ser Gln Leu Asp Phe Glu Asp Val Trp Asn Ser Ser Tyr
            20                  25                  30

```
Gly Val Asn Asp Ser Phe Pro Asp Gly Asp Tyr Gly Ala Asn Leu Glu
            35                  40                  45

Ala Ala Ala Pro Cys His Ser Cys Asn Leu Leu Asp Asp Ser Ala Leu
 50                  55                  60

Pro Phe Phe Ile Leu Thr Ser Val Leu Gly Ile Leu Ala Ser Ser Thr
 65                  70                  75                  80

Val Leu Phe Met Leu Phe Arg Pro Leu Phe Arg Trp Gln Leu Cys Pro
                 85                  90                  95

Gly Trp Pro Val Leu Ala Gln Leu Ala Val Gly Ser Ala Leu Phe Ser
                100                 105                 110

Ile Val Val Pro Val Leu Ala Pro Gly Leu Gly Ser Thr Arg Ser Ser
            115                 120                 125

Ala Leu Cys Ser Leu Gly Tyr Cys Val Trp Tyr Gly Ser Ala Phe Ala
130                 135                 140

Gln Ala Leu Leu Leu Gly Cys His Ala Ser Leu Gly His Arg Leu Gly
145                 150                 155                 160

Ala Gly Gln Val Pro Gly Leu Thr Leu Gly Leu Thr Val Gly Ile Trp
                165                 170                 175

Gly Val Ala Ala Leu Leu Thr Leu Pro Val Thr Leu Ala Ser Gly Ala
            180                 185                 190

Ser Gly Gly Leu Cys Thr Leu Ile Tyr Ser Thr Glu Leu Lys Ala Leu
                195                 200                 205

Gln Ala Thr His Thr Val Ala Cys Leu Ala Ile Phe Val Leu Leu Pro
210                 215                 220

Leu Gly Leu Phe Gly Ala Lys Gly Leu Lys Lys Ala Leu Gly Met Gly
225                 230                 235                 240

Pro Gly Pro Trp Met Asn Ile Leu Trp Ala Trp Phe Ile Phe Trp Trp
                245                 250                 255

Pro His Gly Val Val Leu Gly Leu Asp Phe Leu Val Arg Ser Lys Leu
            260                 265                 270

Leu Leu Leu Ser Thr Cys Leu Ala Gln Gln Ala Leu Asp Leu Leu Leu
                275                 280                 285

Asn Leu Ala Glu Ala Leu Ala Ile Leu His Cys Val Ala Thr Pro Leu
            290                 295                 300

Leu Leu Ala Leu Phe Cys His Gln Ala Thr Arg Thr Leu Leu Pro Ser
305                 310                 315                 320

Leu Pro Leu Pro Glu Gly Trp Ser Ser His Leu Asp Thr Leu Gly Ser
                325                 330                 335

Lys Ser

<210> SEQ ID NO 323
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Met Ala Ser Ser Gly Tyr Val Leu Gln Ala Glu Leu Ser Pro Ser Thr
 1               5                  10                  15

Glu Asn Ser Ser Gln Leu Asp Phe Glu Asp Val Trp Asn Ser Ser Tyr
                20                  25                  30

Gly Val Asn Asp Ser Phe Pro Asp Gly Asp Tyr Gly Ala Asn Leu Glu
            35                  40                  45
```

```
Ala Ala Ala Pro Cys His Ser Cys Asn Leu Leu Asp Asp Ser Ala Gln
         50                  55                  60

Pro Tyr Tyr Thr Gln Thr Ser Thr Gln Gly Thr Gln Ala Ser Ser Thr
 65                  70                  75                  80

Thr Gln Tyr Met Gln Phe Arg Pro Leu Phe Arg Trp Gln Leu Cys Pro
                 85                  90                  95

Gly Trp Pro Thr Gln Ala Gln Gln Ala Thr Gly Ser Ala Gln Tyr Ser
            100                 105                 110

Thr Thr Thr Pro Thr Gln Ala Pro Gly Leu Gly Ser Thr Arg Ser Ser
            115                 120                 125

Ala Leu Cys Ser Leu Gly Tyr Cys Thr Trp Tyr Gly Ser Ala Tyr Ala
130                 135                 140

Gln Ala Gln Gln Gly Cys His Ala Ser Gln Gly His Arg Leu Gly
145                 150                 155                 160

Ala Gly Gln Val Pro Gly Leu Thr Gln Gly Gln Thr Gly Thr Trp
                165                 170                 175

Gly Thr Ala Ala Gln Gln Thr Gln Pro Thr Thr Gln Ala Ser Gly Ala
            180                 185                 190

Ser Gly Gly Leu Cys Thr Leu Ile Tyr Ser Thr Glu Leu Lys Ala Leu
195                 200                 205

Gln Ala Thr His Thr Thr Ala Cys Gln Ala Thr Tyr Thr Gln Gln Pro
210                 215                 220

Gln Gly Gln Tyr Gly Ala Lys Gly Gln Lys Ala Leu Gly Met Gly
225                 230                 235                 240

Pro Gly Pro Trp Met Asn Thr Gln Trp Ala Trp Tyr Thr Tyr Trp Trp
                245                 250                 255

Pro His Gly Thr Thr Gln Gly Gln Asp Tyr Gln Thr Arg Ser Lys Leu
            260                 265                 270

Leu Leu Leu Ser Thr Cys Leu Ala Gln Ala Leu Asp Leu Leu Gln
                275                 280                 285

Asn Gln Ala Glu Ala Gln Ala Thr Gln His Cys Thr Ala Thr Pro Gln
290                 295                 300

Gln Gln Ala Gln Tyr Cys His Gln Ala Thr Arg Thr Leu Leu Pro Ser
305                 310                 315                 320

Leu Pro Leu Pro Glu Gly Trp Ser Ser His Leu Asp Thr Leu Gly Ser
                325                 330                 335

Lys Ser

<210> SEQ ID NO 324
<211> LENGTH: 415
<212> TYPE: PRT
<213> ORGANISM: Unknown
<220> FEATURE:
<223> OTHER INFORMATION: Description of Unknown: Mammalian
      CXCR3 polypeptide

<400> SEQUENCE: 324

Met Glu Leu Arg Lys Tyr Gly Pro Gly Arg Leu Ala Gly Thr Val Ile
 1               5                  10                  15

Gly Gly Ala Ala Gln Ser Lys Ser Gln Thr Lys Ser Asp Ser Ile Thr
             20                  25                  30

Lys Glu Phe Leu Pro Gly Leu Tyr Thr Ala Pro Ser Ser Pro Phe Pro
             35                  40                  45

Pro Ser Gln Val Ser Asp His Gln Val Leu Asn Asp Ala Glu Val Ala
 50                  55                  60
```

Ala Leu Leu Glu Asn Phe Ser Ser Tyr Asp Tyr Gly Glu Asn Glu
 65                  70                  75                  80

Ser Asp Ser Cys Cys Thr Ser Pro Pro Cys Pro Gln Asp Phe Ser Leu
             85                  90                  95

Asn Phe Asp Arg Ala Phe Leu Pro Ala Leu Tyr Ser Leu Leu Phe Leu
            100                 105                 110

Leu Gly Leu Leu Gly Asn Gly Ala Val Ala Ala Val Leu Leu Ser Arg
            115                 120                 125

Arg Thr Ala Leu Ser Ser Thr Asp Thr Phe Leu Leu His Leu Ala Val
            130                 135                 140

Ala Asp Thr Leu Leu Val Leu Thr Leu Pro Leu Trp Ala Val Asp Ala
145                 150                 155                 160

Ala Val Gln Trp Val Phe Gly Ser Gly Leu Cys Lys Val Ala Gly Ala
                165                 170                 175

Leu Phe Asn Ile Asn Phe Tyr Ala Gly Ala Leu Leu Leu Ala Cys Ile
            180                 185                 190

Ser Phe Asp Arg Tyr Leu Asn Ile Val His Ala Thr Gln Leu Tyr Arg
            195                 200                 205

Arg Gly Pro Pro Ala Arg Val Thr Leu Thr Cys Leu Ala Val Trp Gly
210                 215                 220

Leu Cys Leu Leu Phe Ala Leu Pro Asp Phe Ile Phe Leu Ser Ala His
225                 230                 235                 240

His Asp Glu Arg Leu Asn Ala Thr His Cys Gln Tyr Asn Phe Pro Gln
            245                 250                 255

Val Gly Arg Thr Ala Leu Arg Val Leu Gln Leu Val Ala Gly Phe Leu
            260                 265                 270

Leu Pro Leu Leu Val Met Ala Tyr Cys Tyr Ala His Ile Leu Ala Val
            275                 280                 285

Leu Leu Val Ser Arg Gly Gln Arg Arg Leu Arg Ala Met Arg Leu Val
290                 295                 300

Val Val Val Val Val Ala Phe Ala Leu Cys Trp Thr Pro Tyr His Leu
305                 310                 315                 320

Val Val Leu Val Asp Ile Leu Met Asp Leu Gly Ala Leu Ala Arg Asn
            325                 330                 335

Cys Gly Arg Glu Ser Arg Val Asp Val Ala Lys Ser Val Thr Ser Gly
            340                 345                 350

Leu Gly Tyr Met His Cys Cys Leu Asn Pro Leu Leu Tyr Ala Phe Val
            355                 360                 365

Gly Val Lys Phe Arg Glu Arg Met Trp Met Leu Leu Leu Arg Leu Gly
            370                 375                 380

Cys Pro Asn Gln Arg Gly Leu Gln Arg Gln Pro Ser Ser Ser Arg Arg
385                 390                 395                 400

Asp Ser Ser Trp Ser Glu Thr Ser Glu Ala Ser Tyr Ser Gly Leu
                405                 410                 415

<210> SEQ ID NO 325
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Met Glu Leu Arg Lys Tyr Gly Pro Gly Arg Leu Ala Gly Thr Val Ile

```
              1               5                      10                     15
            Gly Gly Ala Ala Gln Ser Lys Ser Gln Thr Lys Ser Asp Ser Ile Thr
                              20                     25                     30
            Lys Glu Phe Leu Pro Gly Leu Tyr Thr Ala Pro Ser Ser Pro Phe Pro
                              35                     40                     45
            Pro Ser Gln Val Ser Asp His Gln Val Leu Asn Asp Ala Glu Val Ala
             50                              55                     60
            Ala Leu Leu Glu Asn Phe Ser Ser Tyr Asp Tyr Gly Glu Asn Glu
             65                     70                     75                     80
            Ser Asp Ser Cys Cys Thr Ser Pro Cys Pro Gln Asp Phe Ser Leu
                                   85                     90                     95
            Asn Phe Asp Arg Ala Phe Leu Pro Ala Gln Tyr Ser Gln Gln Tyr Gln
                                  100                    105                    110
            Gln Gly Gln Gln Gly Asn Gly Ala Thr Ala Ala Thr Gln Gln Ser Arg
                                  115                    120                    125
            Arg Thr Ala Leu Ser Ser Thr Asp Thr Tyr Gln Gln His Gln Ala Thr
                                  130                    135                    140
            Ala Asp Thr Gln Gln Thr Gln Thr Gln Pro Gln Trp Ala Thr Asp Ala
             145                              150                    155                    160
            Ala Val Gln Trp Val Phe Gly Ser Gly Leu Cys Lys Val Ala Gly Ala
                                  165                    170                    175
            Gln Tyr Asn Thr Asn Tyr Tyr Ala Gly Ala Gln Gln Ala Cys Thr
                                  180                    185                    190
            Ser Tyr Asp Arg Tyr Leu Asn Ile Val His Ala Thr Gln Leu Tyr Arg
                                  195                    200                    205
            Arg Gly Pro Pro Ala Arg Thr Thr Gln Thr Cys Gln Ala Thr Trp Gly
                              210                    215                    220
            Gln Cys Gln Gln Tyr Ala Gln Pro Asp Tyr Thr Tyr Gln Ser Ala His
             225                              230                    235                    240
            His Asp Glu Arg Leu Asn Ala Thr His Cys Gln Tyr Asn Phe Pro Gln
                                  245                    250                    255
            Val Gly Arg Thr Ala Leu Arg Val Leu Gln Leu Thr Ala Gly Tyr Gln
                                  260                    265                    270
            Gln Pro Gln Gln Thr Met Ala Tyr Cys Tyr Ala His Thr Gln Ala Thr
                                  275                    280                    285
            Gln Gln Val Ser Arg Gly Gln Arg Arg Leu Arg Ala Met Arg Gln Thr
                              290                    295                    300
            Thr Thr Thr Thr Thr Ala Tyr Ala Gln Cys Trp Thr Pro Tyr His Gln
             305                              310                    315                    320
            Thr Thr Leu Val Asp Ile Leu Met Asp Leu Gly Ala Leu Ala Arg Asn
                                  325                    330                    335
            Cys Gly Arg Glu Ser Arg Val Asp Ala Lys Ser Val Thr Ser Gly
                              340                    345                    350
            Gln Gly Tyr Met His Cys Cys Gln Asn Pro Gln Gln Tyr Ala Tyr Thr
                              355                    360                    365
            Gly Thr Lys Phe Arg Glu Arg Met Trp Met Leu Leu Leu Arg Leu Gly
                              370                    375                    380
            Cys Pro Asn Gln Arg Gly Leu Gln Arg Gln Pro Ser Ser Ser Arg Arg
             385                              390                    395                    400
            Asp Ser Ser Trp Ser Glu Thr Ser Glu Ala Ser Tyr Ser Gly Leu
                                  405                    410                    415

<210> SEQ ID NO 326
```

```
<211> LENGTH: 21
<212> TYPE: PRT
<213> ORGANISM: Unknown
<220> FEATURE:
<223> OTHER INFORMATION: Description of Unknown: Mammalian
      CD81 polypeptide

<400> SEQUENCE: 326

Leu Phe Val Phe Asn Phe Val Phe Trp Leu Ala Gly Gly Val Ile Leu
1               5                   10                  15

Gly Val Ala Leu Trp
            20

<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln Tyr Thr Tyr Asn Tyr Thr Tyr Trp Gln Ala Gly Gly Thr Thr Gln
1               5                   10                  15

Gly Thr Ala Gln Trp
            20

<210> SEQ ID NO 328
<211> LENGTH: 21
<212> TYPE: PRT
<213> ORGANISM: Unknown
<220> FEATURE:
<223> OTHER INFORMATION: Description of Unknown: Mammalian
      CD81 peptide

<400> SEQUENCE: 328

Leu Ile Ala Val Gly Ala Val Met Met Phe Val Gly Phe Leu Gly Cys
1               5                   10                  15

Tyr Gly Ala Ile Gln
            20

<210> SEQ ID NO 329
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gln Thr Ala Thr Gly Ala Thr Met Met Tyr Thr Gly Tyr Gln Gly Cys
1               5                   10                  15

Tyr Gly Ala Thr Gln
            20

<210> SEQ ID NO 330
<211> LENGTH: 23
<212> TYPE: PRT
<213> ORGANISM: Unknown
<220> FEATURE:
<223> OTHER INFORMATION: Description of Unknown: Mammalian
      CD81 peptide

<400> SEQUENCE: 330

Leu Gly Thr Phe Phe Thr Cys Leu Val Ile Leu Phe Ala Cys Glu Val
1               5                   10                  15
```

Ala Ala Gly Ile Trp Gly Phe
            20

<210> SEQ ID NO 331
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Gly Thr Tyr Tyr Thr Cys Gln Thr Thr Gln Tyr Ala Cys Glu Thr
1               5                   10                  15

Ala Ala Gly Thr Trp Gly Phe
            20

<210> SEQ ID NO 332
<211> LENGTH: 23
<212> TYPE: PRT
<213> ORGANISM: Unknown
<220> FEATURE:
<223> OTHER INFORMATION: Description of Unknown: Mammalian
      CD81 peptide

<400> SEQUENCE: 332

Tyr Leu Ile Gly Ile Ala Ala Ile Val Val Ala Val Ile Met Ile Phe
1               5                   10                  15

Glu Met Ile Leu Ser Met Val
            20

<210> SEQ ID NO 333
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Tyr Gln Thr Gly Thr Ala Ala Thr Thr Thr Ala Thr Thr Met Thr Tyr
1               5                   10                  15

Glu Met Thr Gln Ser Met Val
            20

<210> SEQ ID NO 334
<211> LENGTH: 236
<212> TYPE: PRT
<213> ORGANISM: Unknown
<220> FEATURE:
<223> OTHER INFORMATION: Description of Unknown:
      CD81 polypeptide

<400> SEQUENCE: 334

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys

```
                65                  70                  75                  80

Tyr Gly Ala Ile Gln Glu Ser Gln Cys Leu Leu Gly Thr Phe Phe Thr
                    85                  90                  95

Cys Leu Val Ile Leu Phe Ala Cys Glu Val Ala Ala Gly Ile Trp Gly
                100                 105                 110

Phe Val Asn Lys Asp Gln Ile Ala Lys Asp Val Lys Gln Phe Tyr Asp
                115                 120                 125

Gln Ala Leu Gln Gln Ala Val Val Asp Asp Ala Asn Asn Ala Lys
130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
                180                 185                 190

Lys Ile Asp Asp Leu Phe Ser Gly Lys Leu Tyr Leu Ile Gly Ile Ala
                195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235

<210> SEQ ID NO 335
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Met Gly Val Glu Gly Cys Thr Lys Cys Ile Lys Tyr Gln Gln Tyr Thr
1               5                   10                  15

Tyr Asn Tyr Thr Tyr Trp Gln Ala Gly Gly Thr Thr Gln Gly Thr Ala
                20                  25                  30

Gln Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Thr
        50                  55                  60

Gln Thr Ala Thr Gly Ala Thr Met Met Tyr Thr Gly Tyr Gln Gly Cys
65                  70                  75                  80

Tyr Gly Ala Thr Gln Glu Ser Gln Cys Gln Gln Gly Thr Tyr Tyr Thr
                85                  90                  95

Cys Gln Thr Thr Gln Tyr Ala Cys Glu Thr Ala Ala Gly Thr Trp Gly
                100                 105                 110

Phe Val Asn Lys Asp Gln Ile Ala Lys Asp Val Lys Gln Phe Tyr Asp
                115                 120                 125

Gln Ala Leu Gln Gln Ala Val Val Asp Asp Ala Asn Asn Ala Lys
130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
                180                 185                 190
```

```
Lys Ile Asp Asp Leu Phe Ser Gly Lys Gln Tyr Gln Thr Gly Thr Ala
        195                 200                 205

Ala Thr Thr Thr Ala Thr Thr Met Thr Tyr Glu Met Thr Gln Ser Met
    210                 215                 220

Val Leu Cys Cys Gly Ile Arg Asn Ser Ser Val Tyr
225                 230                 235

<210> SEQ ID NO 336
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Trp Thr Ser Thr Thr Glu Ala Gln Ala Tyr Tyr His Cys Cys Gln Asn
1               5                   10                  15

Pro Thr Gln Tyr
            20

<210> SEQ ID NO 337
<211> LENGTH: 53
<212> TYPE: PRT
<213> ORGANISM: Unknown
<220> FEATURE:
<223> OTHER INFORMATION: Description of Unknown: Mammalian
      CXCR3 polypeptide

<400> SEQUENCE: 337

Met Val Leu Glu Val Ser Asp His Gln Val Leu Asn Asp Ala Glu Val
1               5                   10                  15

Ala Ala Leu Leu Glu Asn Phe Ser Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg
    50

<210> SEQ ID NO 338
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Thr Tyr Thr Thr Met Thr Thr Tyr Tyr Gly Tyr Trp Ala Pro Tyr
1               5                   10                  15

Asn Thr Thr Gln Gln Gln Asn Thr Tyr
            20                  25

<210> SEQ ID NO 339
<211> LENGTH: 352
<212> TYPE: PRT
<213> ORGANISM: Unknown
<220> FEATURE:
<223> OTHER INFORMATION: Description of Unknown: Mammalian
      CXCR4 polypeptide

<400> SEQUENCE: 339

Met Glu Gly Ile Ser Ile Tyr Thr Ser Asp Asn Tyr Thr Glu Glu Met
1               5                   10                  15
```

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Val Ser Thr Glu Ser Glu Ser Ser Ser Phe His Ser Ser
            340                 345                 350

<210> SEQ ID NO 340
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu 20                  25                  30
Asn Ala Asn Phe Asn Lys Ile Phe Gln Pro Thr Thr Tyr Ser Thr Thr
                35                  40                  45

Phe Gln Thr Gly Thr Thr Gly Asn Gly Gln Val Thr Gln Thr Met Gly
            50                  55                  60

Tyr Gln Lys Lys Leu Arg Ser Met Thr Asp Lys Tyr Arg Leu His Leu
 65                  70                  75                  80

Ser Thr Ala Asp Gln Gln Phe Thr Thr Gln Pro Phe Trp Ala Val
                85                  90                  95

Asp Ala Val Ala Asn Trp Tyr Phe Gly Asn Phe Leu Cys Lys Ala Val
                100                 105                 110

His Thr Thr Tyr Thr Val Asn Gln Tyr Ser Ser Thr Gln Thr Gln Ala
                115                 120                 125

Tyr Thr Ser Leu Asp Arg Tyr Leu Ala Ile Val His Ala Thr Asn Ser
                130                 135                 140

Gln Arg Pro Arg Lys Leu Leu Ala Glu Lys Thr Thr Tyr Thr Gly Thr
145                 150                 155                 160

Trp Ile Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Phe Gln Tyr Gln His Thr Met Thr Gly Gln
                195                 200                 205

Thr Gln Pro Gly Thr Thr Thr Gln Ser Cys Tyr Cys Ile Ile Ile Ser
                210                 215                 220

Lys Leu Ser His Ser Lys Gly His Gln Lys Arg Lys Ala Leu Lys Thr
225                 230                 235                 240

Thr Val Ile Gln Thr Gln Ala Tyr Phe Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Thr Thr Glu
                275                 280                 285

Ala Gln Ala Phe Phe His Cys Cys Leu Asn Pro Ile Gln Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
                340                 345                 350

<210> SEQ ID NO 341
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

```
Asn Ala Asn Phe Asn Lys Ile Phe Gln Pro Thr Thr Tyr Ser Thr Thr
            35                  40                  45

Tyr Gln Thr Gly Thr Thr Gly Asn Gly Gln Thr Thr Gln Thr Met Gly
 50                  55                  60

Tyr Gln Lys Lys Leu Arg Ser Met Thr Asp Lys Tyr Arg Leu His Leu
 65                  70                  75                  80

Ser Thr Ala Asp Gln Gln Phe Thr Thr Gln Pro Phe Trp Ala Val
                85                  90                  95

Asp Ala Val Ala Asn Trp Tyr Phe Gly Asn Phe Leu Cys Lys Ala Thr
                100                 105                 110

His Thr Thr Tyr Thr Thr Asn Gln Tyr Ser Ser Val Gln Thr Gln Ala
            115                 120                 125

Phe Thr Ser Leu Asp Arg Tyr Leu Ala Ile Val His Ala Thr Asn Ser
130                 135                 140

Gln Arg Pro Arg Lys Leu Leu Ala Glu Lys Thr Thr Tyr Val Gly Thr
145                 150                 155                 160

Trp Thr Pro Ala Gln Gln Gln Thr Pro Asp Tyr Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Thr Met Thr Gly Gln
            195                 200                 205

Thr Gln Pro Gly Thr Thr Thr Gln Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Thr Ser Thr Thr Glu
                275                 280                 285

Ala Gln Ala Tyr Tyr His Cys Cys Gln Asn Pro Thr Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 342
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45
```

Tyr Gln Thr Gly Thr Thr Gly Asn Gly Gln Val Thr Gln Val Met Gly
            50                  55                  60

Tyr Gln Lys Lys Leu Arg Ser Met Thr Asp Lys Tyr Arg Leu His Gln
 65                  70                  75                  80

Ser Val Ala Asp Gln Gln Tyr Val Thr Thr Gln Pro Phe Trp Ala Thr
                85                  90                  95

Asp Ala Thr Ala Asn Trp Tyr Phe Gly Asn Phe Leu Cys Lys Ala Val
            100                 105                 110

His Thr Thr Tyr Thr Val Asn Gln Tyr Ser Ser Val Gln Thr Gln Ala
            115                 120                 125

Phe Thr Ser Leu Asp Arg Tyr Leu Ala Ile Val His Ala Thr Asn Ser
            130                 135                 140

Gln Arg Pro Arg Lys Leu Leu Ala Glu Lys Thr Thr Tyr Thr Gly Thr
145                 150                 155                 160

Trp Thr Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Thr Met Val Gly Gln
            195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Ile Ser Thr Thr Glu
            275                 280                 285

Ala Leu Ala Phe Tyr His Cys Cys Gln Asn Pro Thr Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 343
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Thr Tyr Ser Thr Thr
            35                  40                  45

Phe Gln Thr Gly Thr Thr Gly Asn Gly Gln Val Thr Gln Val Met Gly

```
                50                  55                  60
Tyr Gln Lys Lys Leu Arg Ser Met Thr Asp Lys Tyr Arg Leu His Leu
 65                  70                  75                  80

Ser Thr Ala Asp Gln Gln Phe Thr Thr Thr Gln Pro Phe Trp Ala Val
                 85                  90                  95

Asp Ala Val Ala Asn Trp Tyr Phe Gly Asn Phe Leu Cys Lys Ala Thr
                100                 105                 110

His Thr Thr Tyr Thr Thr Asn Gln Tyr Ser Ser Val Gln Thr Gln Ala
                115                 120                 125

Phe Thr Ser Leu Asp Arg Tyr Leu Ala Ile Val His Ala Thr Asn Ser
                130                 135                 140

Gln Arg Pro Arg Lys Leu Leu Ala Glu Lys Val Thr Tyr Thr Gly Val
145                 150                 155                 160

Trp Thr Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Tyr Gln His Thr Met Thr Gly Gln
                195                 200                 205

Thr Gln Pro Gly Thr Thr Thr Gln Ser Cys Tyr Cys Ile Ile Ile Ser
                210                 215                 220

Lys Leu Ser His Ser Lys Gly His Gln Lys Arg Lys Ala Leu Lys Thr
225                 230                 235                 240

Thr Val Ile Gln Thr Gln Ala Tyr Phe Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Thr Thr Glu
                275                 280                 285

Ala Leu Ala Phe Tyr His Cys Cys Gln Asn Pro Thr Gln Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 344
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
                35                  40                  45

Tyr Gln Thr Gly Thr Thr Gly Asn Gly Gln Thr Thr Gln Thr Met Gly
                50                  55                  60
```

```
Tyr Gln Lys Lys Leu Arg Ser Met Thr Asp Lys Tyr Arg Leu His Leu
 65                  70                  75                  80

Ser Thr Ala Asp Gln Gln Phe Thr Thr Gln Pro Phe Trp Ala Val
                 85                  90                  95

Asp Ala Val Ala Asn Trp Tyr Phe Gly Asn Phe Leu Cys Lys Ala Thr
            100                 105                 110

His Thr Thr Tyr Thr Thr Asn Gln Tyr Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Thr Gly Val
145                 150                 155                 160

Trp Thr Pro Ala Gln Gln Gln Thr Thr Pro Asp Tyr Thr Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Thr Met Thr Gly Gln
        195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Thr Gln Ile Gln Ala Phe Phe Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Thr Ser Thr Thr Glu
        275                 280                 285

Ala Gln Ala Tyr Tyr His Cys Cys Gln Asn Pro Thr Gln Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 345
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Met Glu Gly Ile Ser Ile Tyr Thr Ser Asp Asn Tyr Thr Glu Glu Met
  1               5                  10                  15

Gly Ser Gly Asp Tyr Asp Ser Met Lys Glu Pro Cys Phe Arg Glu Glu
                 20                  25                  30

Asn Ala Asn Phe Asn Lys Ile Phe Gln Pro Thr Thr Tyr Ser Thr Thr
             35                  40                  45

Phe Gln Thr Gly Thr Thr Gly Asn Gly Gln Val Thr Gln Val Met Gly
     50                  55                  60

Tyr Gln Lys Lys Leu Arg Ser Met Thr Asp Lys Tyr Arg Leu His Gln
 65                  70                  75                  80
```

```
Ser Val Ala Asp Gln Gln Tyr Val Thr Thr Gln Pro Phe Trp Ala Thr
                85                  90                  95

Asp Ala Thr Ala Asn Trp Tyr Phe Gly Asn Phe Leu Cys Lys Ala Val
            100                 105                 110

His Thr Thr Tyr Thr Val Asn Gln Tyr Ser Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Val Thr Tyr Thr Gly Val
145                 150                 155                 160

Trp Thr Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Thr Met Thr Gly Gln
        195                 200                 205

Thr Gln Pro Gly Thr Thr Thr Gln Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Ile Ser Thr Thr Glu
        275                 280                 285

Ala Leu Ala Phe Tyr His Cys Cys Gln Asn Pro Thr Gln Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 346
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Phe Gln Thr Gly Thr Thr Gly Asn Gly Gln Val Thr Gln Thr Met Gly
        50                  55                  60

Tyr Gln Lys Lys Leu Arg Ser Met Thr Asp Lys Tyr Arg Leu His Leu
65                  70                  75                  80

Ser Thr Ala Asp Gln Gln Phe Thr Thr Thr Gln Pro Phe Trp Ala Val
```

```
                    85                  90                  95

Asp Ala Val Ala Asn Trp Tyr Phe Gly Asn Phe Leu Cys Lys Ala Thr
                100                 105                 110

His Thr Thr Tyr Thr Val Asn Gln Tyr Ser Ser Val Gln Thr Gln Ala
                115                 120                 125

Phe Thr Ser Leu Asp Arg Tyr Leu Ala Ile Val His Ala Thr Asn Ser
        130                 135                 140

Gln Arg Pro Arg Lys Leu Leu Ala Glu Lys Thr Thr Tyr Thr Gly Thr
145                 150                 155                 160

Trp Thr Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Tyr Gln Tyr Gln His Thr Met Thr Gly Gln
        195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Thr Gln Ile Gln Ala Phe Tyr Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Leu Ala Tyr Phe His Cys Cys Gln Asn Pro Thr Gln Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 347
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Phe Gln Thr Gly Thr Thr Gly Asn Gly Gln Val Thr Gln Val Met Gly
        50                  55                  60

Tyr Gln Lys Lys Leu Arg Ser Met Thr Asp Lys Tyr Arg Gln His Gln
65                  70                  75                  80

Ser Val Ala Asp Gln Gln Phe Thr Thr Gln Pro Phe Pro Trp Ala Thr
                85                  90                  95
```

```
Asp Ala Thr Ala Asn Trp Tyr Phe Gly Asn Phe Leu Cys Lys Ala Thr
                100                 105                 110

His Thr Thr Tyr Thr Thr Asn Gln Tyr Ser Ser Val Gln Thr Gln Ala
            115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Thr Gly Thr
145                 150                 155                 160

Trp Thr Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Thr Met Thr Gly Gln
    195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Thr Gln Ile Gln Ala Phe Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Thr Ser Thr Thr Glu
    275                 280                 285

Ala Gln Ala Tyr Tyr His Cys Cys Gln Asn Pro Thr Gln Tyr Ala Phe
290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 348
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Tyr Gln Thr Gly Thr Thr Gly Asn Gly Gln Thr Ile Gln Thr Met Gly
    50                  55                  60

Tyr Gln Lys Lys Leu Arg Ser Met Thr Asp Lys Tyr Arg Leu His Leu
65                  70                  75                  80

Ser Val Ala Asp Gln Gln Tyr Thr Thr Thr Gln Pro Phe Trp Ala Thr
                85                  90                  95

Asp Ala Val Ala Asn Trp Tyr Phe Gly Asn Phe Leu Cys Lys Ala Val
                100                 105                 110
```

His Thr Thr Tyr Thr Val Asn Gln Tyr Ser Ser Val Gln Thr Gln Ala
            115                 120                 125

Phe Thr Ser Leu Asp Arg Tyr Leu Ala Ile Val His Ala Thr Asn Ser
        130                 135                 140

Gln Arg Pro Arg Lys Leu Leu Ala Glu Lys Thr Thr Tyr Thr Gly Thr
145                 150                 155                 160

Trp Ile Pro Ala Gln Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Tyr Gln His Thr Met Thr Gly Gln
        195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Ile Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Thr Ser Thr Glu
        275                 280                 285

Ala Gln Ala Phe Tyr His Cys Cys Leu Asn Pro Ile Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 349
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Gln Pro Thr Thr Tyr Ser Thr Thr
        35                  40                  45

Tyr Gln Thr Gly Thr Thr Gly Asn Gly Gln Thr Thr Gln Thr Met Gly
    50                  55                  60

Tyr Gln Lys Lys Leu Arg Ser Met Thr Asp Lys Tyr Arg Gln His Leu
65                  70                  75                  80

Ser Val Ala Asp Gln Gln Tyr Thr Ile Thr Gln Pro Tyr Trp Ala Thr
                85                  90                  95

Asp Ala Thr Ala Asn Trp Tyr Phe Gly Asn Phe Leu Cys Lys Ala Thr
            100                 105                 110

His Thr Thr Tyr Thr Thr Asn Gln Tyr Ser Ser Val Gln Thr Gln Ala

-continued

```
                115                 120                 125
Phe Thr Ser Leu Asp Arg Tyr Leu Ala Ile Val His Ala Thr Asn Ser
        130                 135                 140
Gln Arg Pro Arg Lys Leu Leu Ala Glu Lys Thr Thr Tyr Val Gly Thr
145                 150                 155                 160
Trp Thr Pro Ala Gln Gln Thr Thr Pro Asp Tyr Ile Phe Ala Asn
                165                 170                 175
Val Ser Glu Ala Asp Asp Arg Tyr Ile Cys Asp Arg Phe Tyr Pro Asn
                180                 185                 190
Asp Leu Trp Val Val Thr Phe Gln Tyr Gln His Thr Met Thr Gly Gln
            195                 200                 205
Thr Gln Pro Gly Thr Thr Thr Gln Ser Cys Tyr Cys Ile Ile Ile Ser
        210                 215                 220
Lys Leu Ser His Ser Lys Gly His Gln Lys Arg Lys Ala Leu Lys Thr
225                 230                 235                 240
Thr Thr Thr Gln Thr Gln Ala Tyr Tyr Ala Cys Trp Gln Pro Tyr Tyr
                245                 250                 255
Thr Gly Thr Ser Thr Asp Ser Phe Ile Leu Glu Ile Ile Lys Gln
            260                 265                 270
Gly Cys Glu Phe Glu Asn Thr Val His Lys Trp Ile Ser Thr Thr Glu
        275                 280                 285
Ala Leu Ala Tyr Tyr His Cys Cys Gln Asn Pro Thr Gln Tyr Ala Phe
        290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Ser Phe His Ser Ser
                340                 345                 350

<210> SEQ ID NO 350
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Met Glu Gly Ile Ser Ile Tyr Thr Ser Asp Asn Tyr Thr Glu Glu Met
1               5                   10                  15
Gly Ser Gly Asp Tyr Asp Ser Met Lys Glu Pro Cys Phe Arg Glu Glu
                20                  25                  30
Asn Ala Asn Phe Asn Lys Ile Phe Gln Pro Thr Thr Tyr Ser Thr Thr
            35                  40                  45
Phe Gln Thr Gly Thr Thr Gly Asn Gly Gln Val Thr Gln Val Met Gly
        50                  55                  60
Tyr Gln Lys Lys Leu Arg Ser Met Thr Asp Lys Tyr Arg Leu His Leu
65                  70                  75                  80
Ser Thr Ala Asp Gln Gln Phe Thr Thr Gln Pro Phe Trp Ala Val
                85                  90                  95
Asp Ala Val Ala Asn Trp Tyr Phe Gly Asn Phe Leu Cys Lys Ala Val
                100                 105                 110
His Thr Thr Tyr Thr Val Asn Gln Tyr Ser Ser Val Gln Thr Gln Ala
            115                 120                 125
```

```
Phe Thr Ser Leu Asp Arg Tyr Leu Ala Ile Val His Ala Thr Asn Ser
        130                 135                 140

Gln Arg Pro Arg Lys Leu Leu Ala Glu Lys Thr Thr Tyr Thr Gly Thr
145                 150                 155                 160

Trp Thr Pro Ala Gln Gln Thr Ile Pro Asp Phe Ile Tyr Ala Asn
                165                 170                 175

Val Ser Glu Ala Asp Asp Arg Tyr Ile Cys Asp Arg Phe Tyr Pro Asn
                180                 185                 190

Asp Leu Trp Val Val Phe Gln Tyr Gln His Thr Met Thr Gly Gln
        195                 200                 205

Thr Gln Pro Gly Thr Thr Thr Gln Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Thr Gln Ile Gln Ala Phe Phe Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Gln Ala Tyr Phe His Cys Cys Gln Asn Pro Thr Leu Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 351
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Tyr Gln Thr Gly Thr Thr Gly Asn Gly Gln Val Thr Gln Thr Met Gly
        50                  55                  60

Tyr Gln Lys Lys Leu Arg Ser Met Thr Asp Lys Tyr Arg Leu His Leu
65                  70                  75                  80

Ser Thr Ala Asp Gln Gln Phe Thr Thr Thr Gln Pro Phe Trp Ala Val
                85                  90                  95

Asp Ala Val Ala Asn Trp Tyr Phe Gly Asn Phe Leu Cys Lys Ala Thr
                100                 105                 110

His Thr Thr Tyr Thr Thr Asn Gln Tyr Ser Ser Val Gln Thr Gln Ala
            115                 120                 125

Phe Thr Ser Leu Asp Arg Tyr Leu Ala Ile Val His Ala Thr Asn Ser
        130                 135                 140
```

Gln Arg Pro Arg Lys Leu Leu Ala Glu Lys Val Thr Tyr Thr Gly Val
145                 150                 155                 160

Trp Thr Pro Ala Gln Gln Thr Ile Pro Asp Phe Ile Phe Ala Asn
            165                 170                 175

Val Ser Glu Ala Asp Asp Arg Tyr Ile Cys Asp Arg Phe Tyr Pro Asn
        180                 185                 190

Asp Leu Trp Val Val Phe Gln Tyr Gln His Thr Met Thr Gly Gln
            195                 200                 205

Thr Gln Pro Gly Thr Thr Thr Gln Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Thr Gln Ile Gln Ala Phe Tyr Ala Cys Trp Gln Pro Tyr Tyr
                245                 250                 255

Thr Gly Thr Ser Thr Asp Ser Phe Ile Leu Glu Ile Ile Lys Gln
            260                 265                 270

Gly Cys Glu Phe Glu Asn Thr Val His Lys Trp Ile Ser Thr Thr Glu
            275                 280                 285

Ala Leu Ala Tyr Tyr His Cys Cys Gln Asn Pro Thr Gln Tyr Ala Phe
290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 352
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Gln Pro Thr Thr Tyr Ser Thr Thr
        35                  40                  45

Tyr Gln Thr Gly Thr Thr Gly Asn Gly Gln Val Thr Gln Val Met Gly
    50                  55                  60

Tyr Gln Lys Lys Leu Arg Ser Met Thr Asp Lys Tyr Arg Leu His Gln
65                  70                  75                  80

Ser Val Ala Asp Gln Gln Tyr Val Thr Thr Gln Pro Phe Trp Ala Thr
                85                  90                  95

Asp Ala Thr Ala Asn Trp Tyr Phe Gly Asn Phe Leu Cys Lys Ala Val
            100                 105                 110

His Thr Thr Tyr Thr Val Asn Gln Tyr Ser Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Val Gly Thr

```
145                 150                 155                 160
Trp Thr Pro Ala Gln Gln Thr Thr Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Tyr Gln His Thr Met Thr Gly Gln
                195                 200                 205

Thr Gln Pro Gly Thr Thr Thr Gln Ser Cys Tyr Cys Ile Ile Ile Ser
            210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Ile Ser Thr Thr Glu
                275                 280                 285

Ala Leu Ala Tyr Phe His Cys Cys Gln Asn Pro Thr Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 353
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Thr Tyr Gln Pro Thr Thr Tyr Ser Thr Thr
        35                  40                  45

Tyr Gln Thr Gly Thr Thr Gly Asn Gly Gln Thr Thr Gln Thr Met Gly
    50                  55                  60

Tyr Gln Lys Lys Leu Arg Ser Met Thr Asp Lys Tyr Arg Gln His Gln
65                  70                  75                  80

Ser Thr Ala Asp Gln Gln Tyr Thr Thr Thr Gln Pro Tyr Trp Ala Thr
                85                  90                  95

Asp Ala Thr Ala Asn Trp Tyr Phe Gly Asn Phe Leu Cys Lys Ala Val
            100                 105                 110

His Thr Thr Tyr Thr Val Asn Gln Tyr Ser Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Thr Gly Thr
145                 150                 155                 160
```

Trp Thr Pro Ala Gln Gln Thr Ile Pro Asp Phe Ile Tyr Ala Asn
            165                 170                 175

Val Ser Glu Ala Asp Asp Arg Tyr Ile Cys Asp Arg Phe Tyr Pro Asn
        180                 185                 190

Asp Leu Trp Val Val Phe Gln Tyr Gln His Thr Met Thr Gly Gln
        195                 200                 205

Thr Gln Pro Gly Thr Thr Thr Gln Ser Cys Tyr Cys Ile Ile Ser
    210                 215                 220

Lys Leu Ser His Ser Lys Gly His Gln Lys Arg Lys Ala Leu Lys Thr
225                 230                 235                 240

Thr Val Thr Gln Ile Gln Ala Phe Tyr Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Ile Thr Glu
            275                 280                 285

Ala Gln Ala Tyr Phe His Cys Cys Gln Asn Pro Thr Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 354
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Tyr Gln Thr Gly Thr Thr Gly Asn Gly Gln Val Thr Gln Thr Met Gly
    50                  55                  60

Tyr Gln Lys Lys Leu Arg Ser Met Thr Asp Lys Tyr Arg Leu His Leu
65              70                  75                  80

Ser Val Ala Asp Gln Gln Phe Thr Thr Gln Pro Phe Trp Ala Val
                85                  90                  95

Asp Ala Val Ala Asn Trp Tyr Phe Gly Asn Phe Leu Cys Lys Ala Val
            100                 105                 110

His Thr Thr Tyr Thr Val Asn Gln Tyr Ser Ser Val Gln Ile Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Thr Gly Thr
145                 150                 155                 160

Trp Thr Pro Ala Gln Gln Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Thr Phe Gln Tyr Gln His Thr Met Thr Gly Gln
        195                 200                 205

Thr Gln Pro Gly Thr Thr Gln Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Tyr Tyr His Cys Cys Gln Asn Pro Thr Gln Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 355
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Gln Pro Thr Thr Tyr Ser Thr Thr
        35                  40                  45

Phe Gln Thr Gly Thr Thr Gly Asn Gly Gln Val Thr Gln Val Met Gly
    50                  55                  60

Tyr Gln Lys Lys Leu Arg Ser Met Thr Asp Lys Tyr Arg Leu His Gln
65                  70                  75                  80

Ser Val Ala Asp Gln Gln Tyr Val Thr Thr Gln Pro Phe Trp Ala Thr
                85                  90                  95

Asp Ala Thr Ala Asn Trp Tyr Phe Gly Asn Phe Leu Cys Lys Ala Thr
            100                 105                 110

His Thr Thr Tyr Thr Thr Asn Gln Tyr Ser Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Val Gly Thr
145                 150                 155                 160

Trp Thr Pro Ala Gln Gln Gln Thr Thr Pro Asp Phe Ile Phe Ala Asn
                165                 170                 175

Val Ser Glu Ala Asp Asp Arg Tyr Ile Cys Asp Arg Phe Tyr Pro Asn

```
                    180                 185                 190
Asp Leu Trp Val Val Tyr Gln Tyr Gln His Thr Met Thr Gly Gln
            195                 200                 205

Thr Gln Pro Gly Thr Thr Thr Gln Ser Cys Tyr Cys Ile Ile Ser
    210                 215                 220

Lys Leu Ser His Ser Lys Gly His Gln Lys Arg Lys Ala Leu Lys Thr
225                 230                 235                 240

Thr Val Ile Gln Thr Gln Ala Tyr Tyr Ala Cys Trp Gln Pro Tyr Tyr
                    245                 250                 255

Thr Gly Thr Ser Thr Asp Ser Phe Ile Leu Glu Ile Ile Lys Gln
            260                 265                 270

Gly Cys Glu Phe Glu Asn Thr Val His Lys Trp Ile Ser Ile Thr Glu
                275                 280                 285

Ala Gln Ala Phe Phe His Cys Cys Leu Asn Pro Ile Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                    325                 330                 335

His Ser Ser Val Ser Thr Glu Ser Glu Ser Ser Phe His Ser Ser
            340                 345                 350

<210> SEQ ID NO 356
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Phe Gln Thr Gly Thr Thr Gly Asn Gly Gln Val Thr Gln Val Met Gly
        50                  55                  60

Tyr Gln Lys Lys Leu Arg Ser Met Thr Asp Lys Tyr Arg Gln His Gln
65                  70                  75                  80

Ser Val Ala Asp Gln Gln Phe Thr Thr Gln Pro Phe Trp Ala Thr
                    85                  90                  95

Asp Ala Thr Ala Asn Trp Tyr Phe Gly Asn Phe Leu Cys Lys Ala Val
                100                 105                 110

His Thr Thr Tyr Thr Val Asn Gln Tyr Ser Ser Val Gln Thr Gln Ala
            115                 120                 125

Phe Thr Ser Leu Asp Arg Tyr Leu Ala Ile Val His Ala Thr Asn Ser
        130                 135                 140

Gln Arg Pro Arg Lys Leu Leu Ala Glu Lys Thr Thr Tyr Thr Gly Thr
145                 150                 155                 160

Trp Ile Pro Ala Gln Gln Gln Thr Ile Pro Asp Phe Ile Phe Ala Asn
                    165                 170                 175

Val Ser Glu Ala Asp Asp Arg Tyr Ile Cys Asp Arg Phe Tyr Pro Asn
                180                 185                 190
```

Asp Leu Trp Thr Val Val Phe Gln Tyr Gln His Thr Met Thr Gly Gln
            195                 200                 205

Thr Gln Pro Gly Thr Thr Thr Gln Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
            245                 250                 255

Thr Gly Thr Ser Thr Asp Ser Phe Ile Leu Leu Glu Ile Ile Lys Gln
        260                 265                 270

Gly Cys Glu Phe Glu Asn Thr Val His Lys Trp Ile Ser Ile Thr Glu
275                 280                 285

Ala Gln Ala Phe Tyr His Cys Cys Leu Asn Pro Ile Gln Tyr Ala Phe
            290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
            325                 330                 335

His Ser Ser Val Ser Thr Glu Ser Glu Ser Ser Ser Phe His Ser Ser
            340                 345                 350

<210> SEQ ID NO 357
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Thr Tyr Gln Pro Thr Thr Tyr Ser Thr Thr
        35                  40                  45

Tyr Gln Thr Gly Thr Thr Gly Asn Gly Gln Thr Thr Gln Thr Met Gly
    50                  55                  60

Tyr Gln Lys Lys Leu Arg Ser Met Thr Asp Lys Tyr Arg Leu His Gln
65                  70                  75                  80

Ser Val Ala Asp Gln Gln Tyr Val Thr Gln Pro Phe Trp Ala Thr
            85                  90                  95

Asp Ala Thr Ala Asn Trp Tyr Phe Gly Asn Phe Leu Cys Lys Ala Val
            100                 105                 110

His Thr Thr Tyr Thr Val Asn Gln Tyr Ser Ser Val Gln Thr Gln Ala
        115                 120                 125

Phe Thr Ser Leu Asp Arg Tyr Leu Ala Ile Val His Ala Thr Asn Ser
    130                 135                 140

Gln Arg Pro Arg Lys Leu Leu Ala Glu Lys Thr Thr Tyr Thr Gly Thr
145                 150                 155                 160

Trp Thr Pro Ala Gln Gln Gln Thr Ile Pro Asp Phe Ile Phe Ala Asn
            165                 170                 175

Val Ser Glu Ala Asp Asp Arg Tyr Ile Cys Asp Arg Phe Tyr Pro Asn
        180                 185                 190

Asp Leu Trp Thr Val Val Phe Gln Tyr Gln His Thr Met Thr Gly Gln
    195                 200                 205

```
Thr Gln Pro Gly Thr Thr Thr Gln Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Thr Thr Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Ile Ser Thr Thr Glu
            275                 280                 285

Ala Leu Ala Tyr Phe His Cys Cys Gln Asn Pro Thr Gln Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 358
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Gln Pro Thr Thr Tyr Ser Thr Thr
            35                  40                  45

Phe Gln Thr Gly Thr Thr Gly Asn Gly Gln Val Thr Gln Thr Met Gly
        50                  55                  60

Tyr Gln Lys Lys Leu Arg Ser Met Thr Asp Lys Tyr Arg Gln His Leu
65                  70                  75                  80

Ser Thr Ala Asp Gln Gln Tyr Val Thr Thr Gln Pro Tyr Trp Ala Thr
                85                  90                  95

Asp Ala Thr Ala Asn Trp Tyr Phe Gly Asn Phe Leu Cys Lys Ala Thr
            100                 105                 110

His Thr Thr Tyr Thr Thr Asn Gln Tyr Ser Ser Val Gln Thr Gln Ala
        115                 120                 125

Phe Thr Ser Leu Asp Arg Tyr Leu Ala Ile Val His Ala Thr Asn Ser
130                 135                 140

Gln Arg Pro Arg Lys Leu Leu Ala Glu Lys Thr Thr Tyr Val Gly Thr
145                 150                 155                 160

Trp Thr Pro Ala Gln Gln Gln Thr Thr Pro Asp Tyr Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Thr Met Thr Gly Gln
        195                 200                 205

Thr Gln Pro Gly Thr Thr Thr Gln Ser Cys Tyr Cys Ile Ile Ile Ser
```

```
                210                 215                 220

Lys Leu Ser His Ser Lys Gly His Gln Lys Arg Lys Ala Leu Lys Thr
225                 230                 235                 240

Thr Val Ile Gln Thr Gln Ala Tyr Tyr Ala Cys Trp Gln Pro Tyr Tyr
                245                 250                 255

Thr Gly Thr Ser Thr Asp Ser Phe Ile Leu Leu Glu Ile Ile Lys Gln
                260                 265                 270

Gly Cys Glu Phe Glu Asn Thr Val His Lys Trp Thr Ser Thr Thr Glu
                275                 280                 285

Ala Gln Ala Tyr Tyr His Cys Cys Gln Asn Pro Thr Gln Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 359
<211> LENGTH: 355
<212> TYPE: PRT
<213> ORGANISM: Unknown
<220> FEATURE:
<223> OTHER INFORMATION: Description of Unknown: Mammalian
      CXCR3 polypeptide

<400> SEQUENCE: 359

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
                20                  25                  30

Phe Leu Ser Ile Phe Tyr Ser Val Ile Phe Ala Ile Gly Leu Val Gly
                35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
                100                 105                 110

Phe Phe Gly Ser Ile Phe Phe Ile Thr Val Ile Ser Ile Asp Arg Tyr
                115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
                180                 185                 190

Val Glu Thr Asn Phe Leu Gly Phe Leu Leu Pro Leu Leu Ile Met Ser
                195                 200                 205

Tyr Cys Tyr Phe Arg Ile Ile Gln Thr Leu Phe Ser Cys Lys Asn His
    210                 215                 220
```

```
Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
            245                 250                 255

Lys Leu Tyr Asp Phe Phe Pro Ser Cys Asp Met Arg Lys Asp Leu Arg
        260                 265                 270

Leu Ala Leu Ser Val Thr Glu Thr Val Ala Phe Ser His Cys Cys Leu
    275                 280                 285

Asn Pro Leu Ile Tyr Ala Phe Ala Gly Leu Lys Phe Arg Arg Tyr Leu
290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 360
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
            20                  25                  30

Tyr Gln Ser Thr Tyr Tyr Ser Thr Thr Tyr Ala Thr Gly Gln Val Gly
        35                  40                  45

Asn Gln Gln Val Val Phe Ala Leu Thr Asn Ser Lys Lys Pro Lys Ser
50                  55                  60

Val Thr Asp Ile Tyr Leu Leu Asn Gln Ala Gln Ser Asp Gln Gln Phe
65                  70                  75                  80

Thr Ala Thr Gln Pro Tyr Trp Thr His Tyr Leu Ile Asn Glu Lys Gly
                85                  90                  95

Leu His Asn Ala Met Cys Lys Tyr Thr Thr Ala Tyr Tyr Tyr Thr Gly
            100                 105                 110

Tyr Tyr Gly Ser Thr Tyr Tyr Thr Thr Thr Ser Thr Asp Arg Tyr
        115                 120                 125

Leu Ala Ile Val Leu Ala Ala Asn Ser Met Asn Asn Arg Thr Val Gln
130                 135                 140

His Gly Thr Thr Thr Ser Gln Gly Thr Trp Ala Ala Ala Thr Gln Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Gln Gly Phe Leu Gln Pro Gln Gln Thr Met Ser
        195                 200                 205

Tyr Cys Tyr Tyr Arg Ile Thr Gln Thr Leu Phe Ser Cys Lys Asn His
210                 215                 220
```

```
Lys Lys Ala Lys Ala Ile Lys Gln Ile Gln Gln Thr Thr Thr Phe
225                 230                 235                 240

Tyr Gln Tyr Trp Thr Pro Tyr Asn Thr Met Thr Tyr Gln Glu Thr Gln
            245                 250                 255

Lys Leu Tyr Asp Phe Phe Pro Ser Cys Asp Met Arg Lys Asp Leu Arg
            260                 265                 270

Leu Ala Gln Ser Val Thr Glu Thr Thr Ala Tyr Ser His Cys Cys Gln
            275                 280                 285

Asn Pro Gln Thr Tyr Ala Tyr Ala Gly Glu Lys Phe Arg Arg Tyr Leu
            290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
            325                 330                 335

Val Leu Ser Ser Asn Phe Thr Tyr His Thr Ser Asp Gly Asp Ala Leu
            340                 345                 350

Leu Leu Leu
        355

<210> SEQ ID NO 361
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
            20                  25                  30

Tyr Gln Ser Thr Tyr Tyr Ser Thr Thr Tyr Ala Thr Gly Gln Thr Gly
        35                  40                  45

Asn Gln Gln Thr Thr Tyr Ala Gln Thr Asn Ser Lys Lys Pro Lys Ser
    50                  55                  60

Val Thr Asp Ile Tyr Leu Leu Asn Gln Ala Gln Ser Asp Gln Phe
65                  70                  75                  80

Val Ala Thr Gln Pro Phe Trp Thr His Tyr Leu Ile Asn Glu Lys Gly
                85                  90                  95

Leu His Asn Ala Met Cys Lys Tyr Thr Thr Ala Tyr Tyr Tyr Thr Gly
            100                 105                 110

Tyr Tyr Gly Ser Thr Tyr Tyr Thr Thr Thr Ser Thr Asp Arg Tyr
        115                 120                 125

Leu Ala Ile Val Leu Ala Ala Asn Ser Met Asn Asn Arg Thr Val Gln
    130                 135                 140

His Gly Thr Thr Thr Ser Gln Gly Thr Trp Ala Ala Thr Gln Thr
145                 150                 155                 160

Ala Ala Pro Gln Phe Met Tyr Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Gln Gly Tyr Leu Gln Pro Gln Gln Thr Met Ser
        195                 200                 205

Tyr Cys Tyr Phe Arg Thr Thr Gln Thr Leu Phe Ser Cys Lys Asn His
```

-continued

```
            210                 215                 220
Lys Lys Ala Lys Ala Ile Lys Leu Thr Gln Gln Thr Thr Thr Tyr
225                 230                 235                 240

Tyr Gln Phe Trp Thr Pro Tyr Asn Thr Met Thr Phe Gln Glu Thr Gln
                245                 250                 255

Lys Leu Tyr Asp Phe Phe Pro Ser Cys Asp Met Arg Lys Asp Leu Arg
                260                 265                 270

Leu Ala Leu Ser Val Thr Glu Thr Val Ala Phe Ser His Cys Cys Gln
            275                 280                 285

Asn Pro Gln Thr Tyr Ala Tyr Ala Gly Glu Lys Phe Arg Arg Tyr Leu
            290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 362
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
                20                  25                  30

Tyr Gln Ser Thr Tyr Tyr Ser Thr Thr Tyr Ala Thr Gly Gln Thr Gly
            35                  40                  45

Asn Leu Gln Val Thr Phe Ala Gln Thr Asn Ser Lys Lys Pro Lys Ser
        50                  55                  60

Val Thr Asp Ile Tyr Leu Leu Asn Gln Ala Gln Ser Asp Gln Leu Phe
65                  70                  75                  80

Val Ala Thr Gln Pro Phe Trp Thr His Tyr Leu Ile Asn Glu Lys Gly
                85                  90                  95

Leu His Asn Ala Met Cys Lys Tyr Thr Thr Ala Tyr Tyr Thr Gly
                100                 105                 110

Tyr Tyr Gly Ser Thr Tyr Tyr Thr Thr Thr Ser Thr Asp Arg Tyr
            115                 120                 125

Leu Ala Ile Val Leu Ala Ala Asn Ser Met Asn Asn Arg Thr Val Gln
130                 135                 140

His Gly Thr Thr Thr Ser Gln Gly Val Trp Ala Ala Thr Gln Thr
145                 150                 155                 160

Ala Ala Pro Gln Phe Met Tyr Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Tyr Gln Gly Tyr Gln Gln Pro Gln Gln Thr Met Ser
        195                 200                 205
```

```
Tyr Cys Tyr Phe Arg Ile Thr Gln Thr Leu Phe Ser Cys Lys Asn His
210                 215                 220

Lys Lys Ala Lys Ala Ile Lys Gln Ile Gln Gln Thr Thr Thr Thr Phe
225                 230                 235                 240

Phe Gln Tyr Trp Thr Pro Tyr Asn Thr Met Thr Tyr Gln Glu Thr Gln
                245                 250                 255

Lys Leu Tyr Asp Phe Phe Pro Ser Cys Asp Met Arg Lys Asp Leu Arg
                260                 265                 270

Leu Ala Gln Ser Val Thr Glu Thr Ala Phe Ser His Cys Cys Gln
                275                 280                 285

Asn Pro Gln Ile Tyr Ala Tyr Ala Gly Glu Lys Phe Arg Arg Tyr Leu
290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
                340                 345                 350

Leu Leu Leu
        355

<210> SEQ ID NO 363
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
                20                  25                  30

Tyr Gln Ser Thr Tyr Tyr Ser Thr Thr Tyr Ala Thr Gly Gln Thr Gly
            35                  40                  45

Asn Leu Gln Val Thr Phe Ala Gln Thr Asn Ser Lys Lys Pro Lys Ser
50                  55                  60

Val Thr Asp Ile Tyr Leu Gln Asn Leu Ala Gln Ser Asp Gln Gln Tyr
65                  70                  75                  80

Thr Ala Thr Gln Pro Phe Trp Thr His Tyr Leu Ile Asn Glu Lys Gly
                85                  90                  95

Leu His Asn Ala Met Cys Lys Tyr Thr Thr Ala Tyr Tyr Tyr Thr Gly
                100                 105                 110

Tyr Tyr Gly Ser Thr Tyr Tyr Thr Thr Thr Ser Thr Asp Arg Tyr
            115                 120                 125

Leu Ala Ile Val Leu Ala Ala Asn Ser Met Asn Asn Arg Thr Val Gln
130                 135                 140

His Gly Val Thr Thr Ser Gln Gly Thr Trp Ala Ala Ala Thr Gln Thr
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
                180                 185                 190

Val Glu Thr Asn Phe Gln Gly Phe Leu Gln Pro Gln Gln Thr Met Ser
                195                 200                 205
```

```
Tyr Cys Tyr Phe Arg Thr Thr Gln Thr Leu Phe Ser Cys Lys Asn His
        210                 215                 220

Lys Lys Ala Lys Ala Ile Lys Leu Ile Gln Gln Thr Thr Thr Thr Phe
225                 230                 235                 240

Tyr Gln Tyr Trp Thr Pro Tyr Asn Val Met Thr Phe Gln Glu Thr Gln
                245                 250                 255

Lys Leu Tyr Asp Phe Phe Pro Ser Cys Asp Met Arg Lys Asp Leu Arg
            260                 265                 270

Leu Ala Leu Ser Thr Thr Glu Thr Thr Ala Tyr Ser His Cys Cys Gln
        275                 280                 285

Asn Pro Gln Thr Tyr Ala Tyr Ala Gly Glu Lys Phe Arg Arg Tyr Leu
290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
        340                 345                 350

Leu Leu Leu
        355

<210> SEQ ID NO 364
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
            20                  25                  30

Tyr Gln Ser Thr Tyr Tyr Ser Thr Thr Tyr Ala Thr Gly Gln Thr Gly
        35                  40                  45

Asn Leu Gln Val Thr Phe Ala Gln Thr Asn Ser Lys Lys Pro Lys Ser
50                  55                  60

Val Thr Asp Ile Tyr Gln Gln Asn Gln Ala Gln Ser Asp Gln Gln Tyr
65                  70                  75                  80

Thr Ala Thr Gln Pro Tyr Trp Thr His Tyr Leu Ile Asn Glu Lys Gly
                85                  90                  95

Leu His Asn Ala Met Cys Lys Tyr Thr Thr Ala Tyr Tyr Tyr Thr Gly
            100                 105                 110

Tyr Tyr Gly Ser Thr Tyr Tyr Thr Thr Thr Ser Thr Asp Arg Tyr
        115                 120                 125

Leu Ala Ile Val Leu Ala Ala Asn Ser Met Asn Asn Arg Thr Val Gln
130                 135                 140

His Gly Thr Thr Thr Ser Gln Gly Val Trp Ala Ala Ala Thr Gln Thr
145                 150                 155                 160

Ala Ala Pro Gln Phe Met Tyr Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Gln Gly Phe Leu Gln Pro Gln Gln Thr Met Ser
```

```
              195                 200                 205
Tyr Cys Tyr Phe Arg Ile Thr Gln Thr Leu Phe Ser Cys Lys Asn His
    210                 215                 220

Lys Lys Ala Lys Ala Ile Lys Leu Ile Gln Gln Thr Thr Thr Phe
225                 230                 235                 240

Tyr Gln Phe Trp Thr Pro Tyr Asn Thr Met Thr Phe Gln Glu Thr Leu
                245                 250                 255

Lys Leu Tyr Asp Phe Phe Pro Ser Cys Asp Met Arg Lys Asp Leu Arg
            260                 265                 270

Leu Ala Gln Ser Thr Thr Glu Thr Thr Ala Tyr Ser His Cys Cys Gln
                275                 280                 285

Asn Pro Gln Thr Tyr Ala Tyr Ala Gly Glu Lys Phe Arg Arg Tyr Leu
            290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
                340                 345                 350

Leu Leu Leu
        355

<210> SEQ ID NO 365
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
                20                  25                  30

Tyr Gln Ser Thr Tyr Tyr Ser Thr Tyr Ala Thr Gly Gln Val Gly
            35                  40                  45

Asn Gln Gln Val Val Phe Ala Leu Thr Asn Ser Lys Lys Pro Lys Ser
    50                  55                  60

Val Thr Asp Ile Tyr Gln Gln Asn Leu Ala Gln Ser Asp Gln Gln Phe
65                  70                  75                  80

Thr Ala Thr Gln Pro Tyr Trp Thr His Tyr Leu Ile Asn Glu Lys Gly
                85                  90                  95

Leu His Asn Ala Met Cys Lys Tyr Thr Thr Ala Tyr Tyr Tyr Thr Gly
            100                 105                 110

Tyr Tyr Gly Ser Thr Tyr Thr Thr Thr Ser Thr Asp Arg Tyr
            115                 120                 125

Leu Ala Ile Val Leu Ala Ala Asn Ser Met Asn Asn Arg Thr Val Gln
            130                 135                 140

His Gly Thr Thr Ser Gln Gly Thr Trp Ala Ala Ala Thr Gln Thr
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190
```

Val Glu Thr Asn Tyr Gln Gly Tyr Gln Gln Pro Gln Gln Thr Met Ser
195                 200                 205

Tyr Cys Tyr Tyr Arg Thr Thr Gln Thr Leu Phe Ser Cys Lys Asn His
210                 215                 220

Lys Lys Ala Lys Ala Ile Lys Leu Ile Gln Gln Thr Thr Thr Thr Phe
225                 230                 235                 240

Tyr Gln Phe Trp Thr Pro Tyr Asn Thr Met Thr Phe Gln Glu Thr Leu
                245                 250                 255

Lys Leu Tyr Asp Phe Phe Pro Ser Cys Asp Met Arg Lys Asp Leu Arg
                260                 265                 270

Leu Ala Leu Ser Val Thr Glu Thr Val Ala Phe Ser His Cys Cys Gln
                275                 280                 285

Asn Pro Gln Ile Tyr Ala Tyr Ala Gly Glu Lys Phe Arg Arg Tyr Leu
                290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
                340                 345                 350

Leu Leu Leu
        355

<210> SEQ ID NO 366
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Thr
                20                  25                  30

Tyr Gln Ser Thr Tyr Tyr Ser Thr Thr Tyr Ala Thr Gly Gln Val Gly
            35                  40                  45

Asn Gln Gln Val Val Phe Ala Leu Thr Asn Ser Lys Lys Pro Lys Ser
        50                  55                  60

Val Thr Asp Ile Tyr Leu Leu Asn Gln Ala Gln Ser Asp Gln Gln Phe
65                  70                  75                  80

Thr Ala Thr Gln Pro Tyr Trp Thr His Tyr Leu Ile Asn Glu Lys Gly
                85                  90                  95

Leu His Asn Ala Met Cys Lys Tyr Thr Thr Ala Tyr Tyr Tyr Thr Gly
                100                 105                 110

Tyr Tyr Gly Ser Thr Tyr Tyr Thr Thr Thr Ser Thr Asp Arg Tyr
            115                 120                 125

Leu Ala Ile Val Leu Ala Ala Asn Ser Met Asn Asn Arg Thr Val Gln
        130                 135                 140

His Gly Thr Thr Thr Ser Gln Gly Thr Trp Ala Ala Thr Gln Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
                180                 185                 190

-continued

Val Glu Thr Asn Phe Gln Gly Phe Leu Gln Pro Gln Gln Thr Met Ser
           195                 200                 205

Tyr Cys Tyr Tyr Arg Ile Thr Gln Thr Leu Phe Ser Cys Lys Asn His
210             215                 220

Lys Lys Ala Lys Ala Ile Lys Gln Ile Gln Gln Thr Thr Thr Thr Phe
225                 230                 235                 240

Tyr Gln Tyr Trp Thr Pro Tyr Asn Thr Met Thr Tyr Gln Glu Thr Gln
           245                 250                 255

Lys Leu Tyr Asp Phe Phe Pro Ser Cys Asp Met Arg Lys Asp Leu Arg
           260                 265                 270

Leu Ala Gln Ser Val Thr Glu Thr Thr Ala Tyr Ser His Cys Cys Gln
           275                 280                 285

Asn Pro Gln Thr Tyr Ala Tyr Ala Gly Glu Lys Phe Arg Arg Tyr Leu
           290                 295                 300

Tyr His Leu Tyr Gly Lys Cys Leu Ala Val Leu Cys Gly Arg Ser Val
305             310                 315                 320

His Val Asp Phe Ser Ser Ser Glu Ser Gln Arg Ser Arg His Gly Ser
               325                 330                 335

Val Leu Ser Ser Asn Phe Thr Tyr His Thr Ser Asp Gly Asp Ala Leu
           340                 345                 350

Leu Leu Leu
       355

<210> SEQ ID NO 367
<211> LENGTH: 355
<212> TYPE: PRT
<213> ORGANISM: Unknown
<220> FEATURE:
<223> OTHER INFORMATION: Description of Unknown: Mammalian
      CCR3 polypeptide

<400> SEQUENCE: 367

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
               20                  25                  30

Met Ala Gln Phe Val Pro Pro Leu Tyr Ser Leu Val Phe Thr Val Gly
           35                  40                  45

Leu Leu Gly Asn Val Val Val Val Met Ile Leu Ile Lys Tyr Arg Arg
50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
               85                  90                  95

His Asn Trp Val Phe Gly His Gly Met Cys Lys Leu Leu Ser Gly Phe
               100                 105                 110

Tyr His Thr Gly Leu Tyr Ser Glu Ile Phe Phe Ile Ile Leu Leu Thr
           115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
               165                 170                 175

Leu Phe Glu Glu Thr Leu Cys Ser Ala Leu Tyr Pro Glu Asp Thr Val

```
                    180                 185                 190
Tyr Ser Trp Arg His Phe His Thr Leu Arg Met Thr Ile Phe Cys Leu
            195                 200                 205

Val Leu Pro Leu Leu Val Met Ala Ile Cys Tyr Thr Gly Ile Ile Lys
        210                 215                 220

Thr Leu Leu Arg Cys Pro Ser Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
        275                 280                 285

Ile Ala Tyr Ser His Cys Cys Met Asn Pro Val Ile Tyr Ala Phe Val
        290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 368
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Gln Tyr Ser Gln Thr Tyr Thr Thr Gly
        35                  40                  45

Gln Gln Gly Asn Thr Thr Val Thr Met Thr Gln Ile Lys Tyr Arg Arg
    50                  55                  60

Leu Arg Ile Met Thr Asn Ile Tyr Gln Gln Asn Gln Ala Ile Ser Asp
65                  70                  75                  80

Gln Gln Tyr Gln Val Thr Gln Pro Tyr Trp Thr His Tyr Val Arg Gly
                85                  90                  95

His Asn Trp Val Phe Gly His Gly Met Cys Lys Gln Leu Ser Gly Tyr
            100                 105                 110

Tyr His Thr Gly Gln Tyr Ser Glu Thr Tyr Tyr Thr Thr Gln Gln Thr
        115                 120                 125

Thr Asp Arg Tyr Leu Ala Ile Val His Ala Val Phe Ala Leu Arg Ala
    130                 135                 140

Arg Thr Thr Thr Phe Gly Thr Thr Ser Thr Val Thr Trp Gly Gln
145                 150                 155                 160

Ala Val Gln Ala Ala Gln Pro Glu Phe Ile Phe Tyr Glu Thr Glu Glu
                165                 170                 175
```

```
Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Tyr Cys Gln
            195                 200                 205

Val Gln Pro Gln Gln Val Met Ala Thr Cys Tyr Thr Gly Thr Thr Lys
        210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Thr Met Gln Thr Thr Glu Thr
                275                 280                 285

Thr Ala Tyr Ser His Cys Cys Met Asn Pro Thr Thr Tyr Ala Tyr Val
            290                 295                 300

Gly Glu Arg Phe Arg Met Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 369
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Thr Pro Pro Gln Tyr Ser Gln Thr Phe Thr Thr Gly
        35                  40                  45

Gln Gln Gly Asn Thr Thr Val Thr Met Thr Gln Ile Lys Tyr Arg Arg
    50                  55                  60

Leu Arg Ile Met Thr Asn Ile Tyr Leu Gln Asn Gln Ala Ile Ser Asp
65                  70                  75                  80

Gln Leu Phe Gln Thr Thr Gln Pro Tyr Trp Thr His Tyr Val Arg Gly
                85                  90                  95

His Asn Trp Val Phe Gly His Gly Met Cys Lys Gln Leu Ser Gly Phe
            100                 105                 110

Tyr His Thr Gly Gln Tyr Ser Glu Thr Phe Tyr Thr Thr Gln Gln Thr
        115                 120                 125

Thr Asp Arg Tyr Leu Ala Ile Val His Ala Val Phe Ala Leu Arg Ala
    130                 135                 140

Arg Thr Thr Thr Tyr Gly Thr Thr Ser Thr Thr Thr Trp Gly Gln
145                 150                 155                 160

Ala Thr Gln Ala Ala Gln Pro Glu Phe Ile Tyr Tyr Glu Thr Glu Glu
                165                 170                 175
```

```
Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Tyr Cys Gln
        195                 200                 205

Val Gln Pro Gln Gln Val Met Ala Thr Cys Tyr Thr Gly Thr Thr Lys
    210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
            260                 265                 270

Cys Glu Arg Ser Lys His Leu Asp Leu Val Met Gln Val Thr Glu Thr
        275                 280                 285

Thr Ala Tyr Ser His Cys Cys Met Asn Pro Val Thr Tyr Ala Tyr Thr
    290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 370
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Thr Pro Pro Gln Tyr Ser Gln Thr Tyr Thr Thr Gly
        35                  40                  45

Gln Gln Gly Asn Thr Thr Val Thr Met Thr Gln Ile Lys Tyr Arg Arg
    50                  55                  60

Leu Arg Ile Met Thr Asn Ile Tyr Gln Gln Asn Leu Ala Ile Ser Asp
65                  70                  75                  80

Gln Gln Phe Gln Thr Thr Gln Pro Phe Trp Thr His Tyr Val Arg Gly
                85                  90                  95

His Asn Trp Val Phe Gly His Gly Met Cys Lys Gln Gln Ser Gly Phe
            100                 105                 110

Tyr His Thr Gly Gln Tyr Ser Glu Thr Phe Phe Thr Thr Gln Gln Thr
        115                 120                 125

Thr Asp Arg Tyr Leu Ala Ile Val His Ala Val Phe Ala Leu Arg Ala
    130                 135                 140

Arg Thr Thr Thr Tyr Gly Thr Thr Thr Ser Thr Thr Thr Trp Gly Gln
145                 150                 155                 160

Ala Thr Gln Ala Ala Gln Pro Glu Phe Ile Tyr Tyr Glu Thr Glu Glu
```

```
                165                 170                 175
Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Thr Tyr Cys Gln
            195                 200                 205

Thr Gln Pro Gln Gln Thr Met Ala Thr Cys Tyr Thr Gly Thr Thr Lys
            210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Val Met Gln Val Thr Glu Thr
                275                 280                 285

Thr Ala Tyr Ser His Cys Cys Met Asn Pro Thr Thr Tyr Ala Phe Thr
                290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 371
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Met Thr Thr Ser Leu Asp Thr Val Glu Thr Phe Gly Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Thr Pro Pro Gln Tyr Ser Gln Thr Tyr Thr Thr Gly
            35                  40                  45

Gln Gln Gly Asn Val Thr Val Thr Met Thr Gln Ile Lys Tyr Arg Arg
        50                  55                  60

Leu Arg Ile Met Thr Asn Ile Tyr Leu Gln Asn Gln Ala Ile Ser Asp
65                  70                  75                  80

Gln Leu Phe Gln Thr Thr Gln Pro Phe Trp Thr His Tyr Val Arg Gly
                85                  90                  95

His Asn Trp Val Phe Gly His Gly Met Cys Lys Gln Ser Gly Phe
            100                 105                 110

Tyr His Thr Gly Gln Tyr Ser Glu Thr Phe Tyr Thr Thr Gln Gln Thr
        115                 120                 125

Thr Asp Arg Tyr Leu Ala Ile Val His Ala Val Phe Ala Leu Arg Ala
    130                 135                 140

Arg Thr Thr Thr Tyr Gly Thr Thr Thr Ser Thr Thr Thr Trp Gly Gln
145                 150                 155                 160
```

Ala Val Gln Ala Ala Gln Pro Glu Phe Thr Phe Tyr Glu Thr Glu
          165                 170                 175

Leu Phe Glu Glu Thr Leu Cys Ser Ala Leu Tyr Pro Glu Asp Thr Val
        180                 185                 190

Tyr Ser Trp Arg His Phe His Thr Leu Arg Met Thr Ile Phe Cys Gln
        195                 200                 205

Thr Gln Pro Gln Gln Thr Met Ala Thr Cys Tyr Thr Gly Ile Thr Lys
        210                 215                 220

Thr Leu Leu Arg Cys Pro Ser Lys Lys Lys Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Thr Met Gln Thr Thr Glu Thr
                275                 280                 285

Thr Ala Tyr Ser His Cys Cys Met Asn Pro Thr Thr Tyr Ala Tyr Thr
                290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 372
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Thr Pro Pro Gln Tyr Ser Gln Thr Phe Thr Thr Gly
            35                  40                  45

Gln Gln Gly Asn Thr Thr Val Thr Met Thr Gln Ile Lys Tyr Arg Arg
        50                  55                  60

Leu Arg Ile Met Thr Asn Ile Tyr Leu Gln Asn Gln Ala Ile Ser Asp
65                  70                  75                  80

Gln Leu Phe Gln Thr Thr Gln Pro Tyr Trp Thr His Tyr Val Arg Gly
                85                  90                  95

His Asn Trp Val Phe Gly His Gly Met Cys Lys Gln Gln Ser Gly Phe
                100                 105                 110

Tyr His Thr Gly Gln Tyr Ser Glu Thr Phe Phe Thr Gln Gln Thr
            115                 120                 125

Thr Asp Arg Tyr Leu Ala Ile Val His Ala Val Phe Ala Leu Arg Ala
        130                 135                 140

Arg Thr Thr Thr Tyr Gly Thr Thr Thr Ser Thr Thr Thr Trp Gly Gln
145                 150                 155                 160

```
Ala Val Gln Ala Ala Gln Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Thr Tyr Cys Gln
        195                 200                 205

Thr Gln Pro Gln Gln Thr Met Ala Thr Cys Tyr Thr Gly Thr Thr Lys
    210                 215                 220

Thr Leu Leu Arg Cys Pro Ser Lys Lys Tyr Glu Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
            260                 265                 270

Cys Glu Arg Ser Lys His Leu Asp Leu Thr Met Gln Val Thr Glu Thr
        275                 280                 285

Ile Ala Tyr Ser His Cys Cys Met Asn Pro Thr Thr Tyr Ala Phe Thr
    290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 373
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Gln Tyr Ser Gln Thr Tyr Thr Thr Gly
        35                  40                  45

Gln Gln Gly Asn Thr Thr Val Thr Met Thr Gln Ile Lys Tyr Arg Arg
    50                  55                  60

Leu Arg Ile Met Thr Asn Ile Tyr Gln Gln Asn Leu Ala Ile Ser Asp
65                  70                  75                  80

Gln Gln Tyr Gln Val Thr Gln Pro Tyr Trp Thr His Tyr Val Arg Gly
                85                  90                  95

His Asn Trp Val Phe Gly His Gly Met Cys Lys Gln Leu Ser Gly Phe
            100                 105                 110

Tyr His Thr Gly Gln Tyr Ser Glu Thr Phe Phe Thr Gln Gln Thr
        115                 120                 125

Thr Asp Arg Tyr Leu Ala Ile Val His Ala Val Phe Ala Leu Arg Ala
    130                 135                 140

Arg Thr Thr Thr Tyr Gly Thr Thr Ser Thr Thr Thr Trp Gly Gln
```

```
            145                 150                 155                 160
Ala Thr Gln Ala Ala Gln Pro Glu Phe Ile Tyr Tyr Glu Thr Glu Glu
                165                 170                 175

Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Phe Cys Gln
                195                 200                 205

Thr Gln Pro Gln Gln Thr Met Ala Thr Cys Tyr Thr Gly Thr Ile Lys
                210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Val Met Gln Thr Thr Glu Thr
                275                 280                 285

Ile Ala Tyr Ser His Cys Cys Met Asn Pro Thr Thr Tyr Ala Tyr Thr
                290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 374
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Val Pro Pro Gln Tyr Ser Gln Thr Phe Thr Thr Gly
                35                  40                  45

Gln Gln Gly Asn Thr Thr Val Thr Met Thr Gln Ile Lys Tyr Arg Arg
        50                  55                  60

Leu Arg Ile Met Thr Asn Ile Tyr Gln Gln Asn Leu Ala Ile Ser Asp
65                  70                  75                  80

Gln Gln Tyr Gln Val Thr Gln Pro Phe Trp Ile His Tyr Val Arg Gly
                85                  90                  95

His Asn Trp Val Phe Gly His Gly Met Cys Lys Gln Leu Ser Gly Tyr
                100                 105                 110

Tyr His Thr Gly Gln Tyr Ser Glu Thr Phe Phe Thr Gln Gln Thr
        115                 120                 125

Thr Asp Arg Tyr Leu Ala Ile Val His Ala Val Phe Ala Leu Arg Ala
        130                 135                 140
```

```
Arg Thr Thr Thr Phe Gly Thr Thr Ser Thr Thr Trp Gly Gln
145                 150                 155                 160

Ala Val Gln Ala Ala Gln Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Tyr Cys Gln
            195                 200                 205

Val Gln Pro Gln Gln Val Met Ala Thr Cys Tyr Thr Gly Thr Thr Lys
        210                 215                 220

Thr Pro Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Thr Met Gln Val Thr Glu Thr
            275                 280                 285

Ile Ala Tyr Ser His Cys Cys Met Asn Pro Thr Thr Tyr Ala Tyr Thr
        290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 375
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Met Thr Thr Ser Leu Asp Thr Val Glu Thr Phe Gly Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Thr Pro Pro Gln Tyr Ser Gln Thr Tyr Thr Thr Gly
            35                  40                  45

Gln Gln Gly Asn Thr Val Thr Thr Met Thr Gln Ile Lys Tyr Arg Arg
    50                  55                  60

Leu Arg Ile Met Thr Asn Ile Tyr Gln Gln Asn Leu Ala Ile Ser Asp
65                  70                  75                  80

Gln Gln Phe Gln Thr Thr Gln Pro Phe Trp Thr His Tyr Val Arg Gly
                85                  90                  95

His Asn Trp Val Phe Gly His Gly Met Cys Lys Gln Leu Ser Gly Tyr
                100                 105                 110

Tyr His Thr Gly Gln Tyr Ser Glu Thr Phe Phe Thr Thr Gln Gln Thr
            115                 120                 125

Thr Asp Arg Tyr Leu Ala Ile Val His Ala Val Phe Ala Leu Arg Ala
        130                 135                 140
```

```
Arg Thr Thr Thr Tyr Gly Thr Thr Ser Thr Thr Trp Gly Gln
145                 150                 155                 160

Ala Thr Gln Ala Ala Gln Pro Glu Phe Ile Phe Tyr Glu Thr Glu Glu
            165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Gln
        195                 200                 205

Thr Gln Pro Gln Gln Thr Met Ala Thr Cys Tyr Thr Gly Thr Thr Lys
        210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Val Met Leu Thr Thr Glu Val
            275                 280                 285

Thr Ala Tyr Ser His Cys Cys Met Asn Pro Thr Thr Tyr Ala Phe Thr
            290                 295                 300

Gly Gly Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
            340                 345                 350

Ile Val Phe
        355

<210> SEQ ID NO 376
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Thr Pro Pro Gln Tyr Ser Gln Thr Tyr Thr Thr Gly
        35                  40                  45

Gln Gln Gly Asn Thr Thr Thr Met Thr Gln Thr Lys Tyr Arg Arg
    50                  55                  60

Leu Arg Ile Met Thr Asn Ile Tyr Leu Gln Asn Gln Ala Thr Ser Asp
65                  70                  75                  80

Gln Leu Phe Gln Thr Thr Gln Pro Tyr Trp Thr His Tyr Val Arg Gly
            85                  90                  95

His Asn Trp Val Phe Gly His Gly Met Cys Lys Gln Gln Ser Gly Phe
            100                 105                 110

Tyr His Thr Gly Gln Tyr Ser Glu Thr Phe Phe Thr Thr Gln Gln Thr
        115                 120                 125

Thr Asp Arg Tyr Leu Ala Ile Val His Ala Val Phe Ala Leu Arg Ala
```

```
                    130                 135                 140
Arg Thr Thr Thr Phe Gly Thr Thr Ser Thr Thr Thr Trp Gly Gln
145                 150                 155                 160

Ala Thr Gln Ala Ala Gln Pro Glu Tyr Thr Tyr Tyr Glu Thr Glu
                165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Phe Cys Gln
            195                 200                 205

Val Gln Pro Gln Gln Thr Met Ala Thr Cys Tyr Thr Gly Thr Thr Lys
            210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Trp Thr Pro Tyr Asn
                245                 250                 255

Thr Ala Thr Gln Gln Ser Ser Tyr Gln Ser Ile Leu Phe Gly Asn Asp
            260                 265                 270

Cys Glu Arg Ser Lys His Leu Asp Leu Thr Met Gln Val Thr Glu Thr
            275                 280                 285

Ile Ala Tyr Ser His Cys Cys Met Asn Pro Thr Thr Tyr Ala Tyr Thr
290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355

<210> SEQ ID NO 377
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Thr Pro Pro Gln Tyr Ser Gln Thr Tyr Thr Thr Gly
            35                  40                  45

Gln Gln Gly Asn Thr Thr Thr Met Thr Gln Ile Lys Tyr Arg Arg
        50                  55                  60

Leu Arg Ile Met Thr Asn Ile Tyr Gln Gln Asn Gln Ala Thr Ser Asp
65                  70                  75                  80

Gln Gln Tyr Gln Thr Thr Gln Pro Tyr Trp Thr His Tyr Val Arg Gly
                85                  90                  95

His Asn Trp Val Phe Gly His Gly Met Cys Lys Gln Gln Ser Gly Phe
            100                 105                 110

Tyr His Thr Gly Gln Tyr Ser Glu Thr Tyr Tyr Thr Thr Gln Gln Thr
        115                 120                 125
```

Thr Asp Arg Tyr Leu Ala Ile Val His Ala Val Phe Ala Leu Arg Ala
130                 135                 140

Arg Thr Thr Thr Phe Gly Thr Thr Ser Thr Val Thr Trp Gly Gln
145                 150                 155                 160

Ala Val Gln Ala Ala Gln Pro Glu Phe Thr Phe Tyr Glu Thr Glu Glu
                165                 170                 175

Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Phe Cys Gln
                195                 200                 205

Thr Gln Pro Gln Gln Thr Met Ala Thr Cys Tyr Thr Gly Thr Thr Lys
210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
                245                 250                 255

Thr Ala Thr Gln Gln Ser Ser Tyr Gln Ser Ile Leu Phe Gly Asn Asp
                260                 265                 270

Cys Glu Arg Ser Lys His Leu Asp Leu Thr Met Gln Val Thr Glu Thr
                275                 280                 285

Ile Ala Tyr Ser His Cys Cys Met Asn Pro Thr Thr Tyr Ala Phe Thr
290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
355

<210> SEQ ID NO 378
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Thr Pro Pro Gln Tyr Ser Gln Thr Tyr Thr Thr Gly
                35                  40                  45

Gln Gln Gly Asn Thr Val Thr Thr Met Thr Gln Ile Lys Tyr Arg Arg
50                  55                  60

Leu Arg Ile Met Thr Asn Ile Tyr Leu Leu Asn Gln Ala Thr Ser Asp
65                  70                  75                  80

Gln Gln Phe Gln Val Thr Gln Pro Phe Trp Ile His Tyr Val Arg Gly
                85                  90                  95

His Asn Trp Val Phe Gly His Gly Met Cys Lys Gln Gln Ser Gly Phe
                100                 105                 110

Tyr His Thr Gly Gln Tyr Ser Glu Thr Phe Tyr Thr Thr Gln Gln Thr
                115                 120                 125

-continued

```
Thr Asp Arg Tyr Leu Ala Ile Val His Ala Val Phe Ala Leu Arg Ala
            130                 135                 140

Arg Thr Thr Thr Tyr Gly Thr Thr Ser Thr Thr Thr Trp Gly Gln
145                 150                 155                 160

Ala Thr Gln Ala Ala Gln Pro Glu Phe Ile Tyr Tyr Glu Thr Glu
            165                 170                 175

Leu Phe Glu Glu Thr Leu Cys Ser Ala Leu Tyr Pro Glu Asp Thr Val
            180                 185                 190

Tyr Ser Trp Arg His Phe His Thr Leu Arg Met Thr Ile Tyr Cys Gln
            195                 200                 205

Val Gln Pro Gln Gln Val Met Ala Thr Cys Tyr Thr Gly Thr Thr Lys
            210                 215                 220

Thr Leu Leu Arg Cys Pro Ser Lys Lys Tyr Lys Ala Ile Arg Gln
225                 230                 235                 240

Thr Tyr Thr Thr Met Ala Thr Tyr Tyr Thr Tyr Trp Thr Pro Tyr Asn
            245                 250                 255

Thr Ala Thr Gln Gln Ser Ser Tyr Gln Ser Ile Leu Phe Gly Asn Asp
            260                 265                 270

Cys Glu Arg Ser Lys His Leu Asp Leu Thr Met Gln Thr Thr Glu Thr
            275                 280                 285

Thr Ala Tyr Ser His Cys Cys Met Asn Pro Thr Thr Tyr Ala Tyr Thr
            290                 295                 300

Gly Glu Arg Phe Arg Lys Tyr Leu Arg His Phe His Arg His Leu
305                 310                 315                 320

Leu Met His Leu Gly Arg Tyr Ile Pro Phe Leu Pro Ser Glu Lys Leu
            325                 330                 335

Glu Arg Thr Ser Ser Val Ser Pro Ser Thr Ala Glu Pro Glu Leu Ser
            340                 345                 350

Ile Val Phe
355

<210> SEQ ID NO 379
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Gln Pro Pro Gln Tyr Ser Gln Thr Phe Thr Phe Gly Phe Thr Gly Asn
            35                  40                  45

Met Gln Val Thr Gln Thr Gln Ile Asn Cys Lys Arg Leu Lys Ser Met
            50                  55                  60

Thr Asp Ile Tyr Leu Gln Asn Gln Ala Ile Ser Asp Gln Phe Phe Gln
65                  70                  75                  80

Gln Thr Thr Pro Tyr Trp Ala His Tyr Ala Ala Ala Gln Trp Asp Phe
            85                  90                  95

Gly Asn Thr Met Cys Gln Gln Gln Thr Gly Gln Tyr Phe Thr Gly Tyr
            100                 105                 110

Tyr Ser Gly Thr Tyr Tyr Thr Thr Gln Gln Thr Thr Asp Arg Tyr Leu
```

-continued

```
            115                 120                 125
Ala Val Val His Ala Val Phe Ala Leu Lys Ala Arg Thr Thr Thr Tyr
        130                 135                 140

Gly Thr Thr Thr Ser Thr Thr Thr Trp Thr Thr Ala Thr Tyr Ala Ser
145                 150                 155                 160

Gln Pro Gly Thr Thr Tyr Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Gln Gly Gln Val Gln Pro Gln Gln
        195                 200                 205

Thr Met Thr Thr Cys Tyr Ser Gly Ile Gln Lys Thr Leu Leu Arg Cys
    210                 215                 220

Arg Asn Glu Lys Lys Arg His Arg Ala Val Arg Gln Thr Tyr Thr Thr
225                 230                 235                 240

Met Thr Thr Tyr Tyr Gln Tyr Trp Ala Pro Tyr Asn Thr Val Gln Gln
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Gln Gly Met Thr
        275                 280                 285

His Cys Cys Ile Asn Pro Thr Ile Tyr Ala Tyr Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

WATER-SOLUBLE TRANS-MEMBRANE PROTEINS AND METHODS FOR THE PREPARATION AND USE THEREOF

REFERENCE TO RELATED APPLICATIONS

This application is a Continuation-in-Part of U.S. patent application Ser. No. 14/669,753 and a Continuation-in-Part of International Application No. PCT/US2015/022780, both filed on Mar. 26, 2015; and both of which claim the benefit of the filing dates under 35 U.S.C. § 119(e) of U.S. Provisional Application No. 62/117,550 filed on Feb. 18, 2015, U.S. Provisional Application No. 61/993,783 filed on May 15, 2014, and U.S. Provisional Application No. 61/971,388 filed on Mar. 27, 2014.

This application also claims the benefit of the filing date under 35 U.S.C. § 119(e) to U.S. Provisional Application No. 62/117,550 filed on Feb. 18, 2015, U.S. Provisional Application No. 61/993,783 filed on May 15, 2014, and U.S. Provisional Application No. 61/971,388 filed on Mar. 27, 2014.

The entire contents of each of the above referenced applications, including all drawings and sequence listings, are incorporated herein by reference.

STATEMENT OF FEDERALLY SPONSORED RESEARCH

This invention was made with Government support under Contract No. N66001-10-1-4062 awarded by the Space and Naval Warfare Systems Center and under Grant No. HR0011-12-1-0003 awarded by the Defense Advanced Research Projects Agency. The Government has certain rights in the invention.

BACKGROUND OF THE INVENTION

Membrane proteins play vital roles in all living systems. Approximately ~30% of all genes in almost all sequenced genomes code for membrane proteins. However, our detailed understanding of their structure and function lags far behind that of soluble proteins. As of March 2015, there are over 100,000 structures in the Protein Data Bank. However, there are only 945 membrane protein structures with 530 unique structures including 28 G-protein coupled receptors and no tetraspanin membrane proteins.

There are several bottlenecks in elucidating the structure and function of membrane receptors and their recognition and ligand-binding properties although they are of great interest. The most critical and challenging task is that it is extremely difficult to produce milligram quantities of soluble and stable receptors. Inexpensive large-scale production methods are desperately needed, and have thus been the focus of extensive research. It is only possible to conduct detailed structural studies once these preliminary obstacles have been surmounted.

Zhang et al. (U.S. Pat. No. 8,637,452), incorporated herein by reference, describes an improved process for water solubilizing GPCRs wherein certain hydrophobic amino acids located in the transmembrane regions were substituted by polar amino acids. However, the process is labor-intensive. Further, while the modified transmembrane regions met the water-soluble criteria, improvements in water solubility and ligand binding are desired. Therefore, there is a need in the art for improved methods of studying G-protein coupled receptors.

SUMMARY OF THE INVENTION

The present invention is directed to a method of designing, selecting and/or producing water-soluble membrane proteins and peptides, peptides (and transmembrane domains) designed, selected or produced therefrom, compositions comprising said peptides, and methods of use thereof. In particular, the method relates to a process for designing a library of water soluble membrane peptides, such as GPCR variants and tetraspanin membrane proteins, using the "QTY Principle," changing the water-insoluble amino acids (Leu, Ile, Val and Phe, or the simple letter code L, I, V, F) into water-soluble, non-ionic amino acids (Gln, Thr and Tyr, or the simple letter code Q, T, Y). Furthermore, two additional non-ionic amino acids Asn (N) and Ser (S) may also be used for the substitution for L, I and V but not for F. In the embodiments discussed below, it is to be understood that Asn (N) and Ser (S) are envisioned as being substitutable for Q and T (as a variant is described) or L, I or V (as a native protein is described). For the purposes of brevity, however, the application does not further elaborate the details of these alternative embodiments as these are known to those skilled in the art as a result of the teaching herein.

The invention encompasses a modified, synthetic, and/or non-naturally occurring, α-helical domain(s) and water-soluble polypeptide (e.g., "sGPCR") comprising such modified α-helical domain(s), wherein the modified α-helical domain(s) comprise an amino acid sequence in which a plurality of hydrophobic amino acid residues (L, I V, F) within a α-helical domain of a native membrane protein are replaced with hydrophilic, non-ionic amino acid residues (Q, T, T, Y, respectively, or "Q, T, Y") and/or N and S. The invention also encompasses a method of preparing a water-soluble polypeptide comprising replacing a plurality of hydrophobic amino acid residues (L, I, V, F) within the α-helical domain(s) of a native membrane protein with hydrophilic, non-ionic amino acid residues (Q/N/S, T/N/S, Y). The invention additionally encompasses a polypeptide prepared by replacing a plurality of hydrophobic amino acid residues (L, I, V, F) within the α-helical domain of a native membrane protein with hydrophilic, non-ionic amino acid residues (Q/N/S, T/N/S, Y, respectively). The variant can be characterized by the name of the parent or native protein (e.g., CXCR4) followed by the abbreviation "QTY" (e.g., CXCR4-QTY).

Thus one aspect of the invention provides a computer implemented method for executing a procedure to select a water-soluble variant of a membrane protein (e.g., a G Protein-Coupled Receptor (GPCR)), the method comprising: (1) entering a sequence of the membrane protein (e.g., GPCR) for analysis; (2) obtaining a variant of the membrane protein (e.g., GPCR), wherein a plurality of hydrophobic amino acids in the transmembrane TM domain alpha-helical segments ("TM regions") of the membrane protein (e.g., GPCR) are substituted, wherein: (a) said hydrophobic amino acids are selected from the group consisting of Leucine (L), Isoleucine (I), Valine (V), and Phenylalanine (F); (b) each said Leucine (L) is independently substituted by Glutamine (Q), Asparagine (N), or Serine (S); (c) each said Isoleucine (I) and said Valine (V) are independently substituted by Threonine (T), Asparagine (N), or Serine (S); and, (d) each said Phenylalanine is substituted by Tyrosine (Y); and, subsequently, (3) obtaining an α-helical secondary structure result for the variant to verify maintenance of α-helical secondary structures in the variant; (4) obtaining a transmembrane region result for the variant to verify water solubility of the variant, thereby designing the water-soluble variant of the membrane protein (e.g., GPCR).

In certain embodiments, step (3) is performed prior to, concurrently with, or after step (4). Additional steps, as described herein, can be incorporated into the above processing sequence. Processing preferably uses computational steps preformed by a data processing system. The system utilizes automated computational systems and methods to select protein variants.

In certain embodiments, in step (2), one subset of said plurality of hydrophobic amino acids in one and the same TM region of the GPCR are substituted to generate one member of a library of potential variants, and one or more different subsets of said plurality of hydrophobic amino acids are substituted to generate additional members of the library. In certain embodiments, the method may further comprising ranking all members of said library based on a combined score, wherein the combined score is a weighed combination of the α-helical secondary structure prediction result and the trans-membrane region prediction result. In certain embodiments, the method further comprises ranking the variant using a ranking function. In certain embodiments, the ranking function may include a secondary structure component and a water solubility component. For example, the ranking function may include a weighting value for the secondary structure component and/or the water solubility component. In certain embodiments, the method further comprises performing the method with a data processor, which may further comprise a memory connected thereto.

In certain embodiments, the method may further comprising selecting N members with the highest combined scores to form a first library of potential variants for said TM region, wherein N is a pre-determined integer (e.g., 3, 4, 5, 6, 7, 8, 9, 10, 11, 12, 13, 14, 15, 16, 17, 18, 19, 20 or more). In certain embodiments, the method may further comprising generating one library of potential variants for 1, 2, 3, 4, 5, or all 6 other TM regions of the GPCR. In certain embodiments, the method may further comprising replacing two or more TM regions of the GPCR with corresponding TM regions from the libraries of potential variants, to create a library of combinatory variants. In certain embodiments, the method further comprises producing/expressing said combinatory variants. In certain embodiments, the method further comprises testing said combinatory variants for ligand binding (e.g., in yeast two-hybrid system), wherein those having substantially the same ligand binding compared to that of the GPCR are selected. In certain embodiments, the method further comprises testing said combinatory variants for a biological function of the GPCR, wherein those having substantially the same biological function compared to that of the GPCR are selected.

Certain water-soluble polypeptides of the invention possess the ability to bind the ligand which normally binds to the wild type or native membrane protein (e.g., GPCR). In certain embodiments, the amino acids within potential ligand binding sites of the native membrane protein (e.g., GPCRs) are not replaced and/or the sequences of the extracellular and/or intracellular domains of the native membrane proteins (e.g., GPCRs) are identical.

The (non-ionic) hydrophilic residues (which replace one or more hydrophobic residues in the α-helical domain of a native membrane protein) are selected from the group consisting of: glutamine (Q), threonine (T), tyrosine (Y), Asparagine (N), and serine (S), and any combinations thereof. In additional aspects, the hydrophobic residues selected from leucine (L), isoleucine (I), valine (V), and phenylalanine (F) are replaced. In certain embodiments, the phenylalanine residues of the α-helical domain of the protein are replaced with tyrosine; each of the isoleucine and/or valine residues of the α-helical domain of the protein are independently replaced with threonine (or S or N); and/or each of the leucine residues of the α-helical domain of the protein are independently replaced with glutamine (or S or N).

In certain embodiments, substantially all (e.g., 96%, 97%, 98%, 99%, or 100%), or 30%, 40%, 50%, 60%, 70%, 75%, 80%, 85%, 90%, 95% of said leucines are substituted by glutamines. In certain embodiments, substantially all (e.g., 96%, 97%, 98%, 99%, or 100%), or 30%, 40%, 50%, 60%, 70%, 75%, 80%, 85%, 90%, 95% of said isoleucines are substituted by threonines. In certain embodiments, substantially all (e.g., 96%, 97%, 98%, 99%, or 100%), or 30%, 40%, 50%, 60%, 70%, 75%, 80%, 85%, 90%, 95% of said valines are substituted by threonines. In certain embodiments, substantially all (e.g., 96%, 97%, 98%, 99%, or 100%), or 30%, 40%, 50%, 60%, 70%, 75%, 80%, 85%, 90%, 95% of said phenylalanines are substituted by tyrosines. In certain embodiments, one or more (e.g., 1, 2, or 3) said leucines are not substituted. In certain embodiments, one or more (e.g., 1, 2, or 3) said isoleucines are not substituted. In certain embodiments, one or more (e.g., 1, 2, or 3) said valines are not substituted. In certain embodiments, one or more (e.g., 1, 2, or 3) said phenylalanines are not substituted.

In certain embodiments, the library of combinatory variants comprises less than about 2 million members. In certain embodiments, the sequence of the GPCR comprises information about the TM regions of the GPCR. In certain embodiments, the sequence of the GPCR is obtained from a protein structure database (e.g., PDB, UniProt). In certain embodiments, the TM regions of the GPCR are predicted based on the sequence of the GPCR. For example, the TM regions of the GPCR can be predicted using TMHMM 2.0 (TransMembrane prediction using Hidden Markov Models) software module/package. In certain embodiments, the TMHMM 2.0 software module/package utilizes a dynamic baseline for peak searching.

In certain embodiments, the method further comprises providing a polynucleotide sequence for each variants of the GPCR. The polynucleotide sequence may be codon optimized for expression in a host (e.g., a bacterium such as *E. coli*, a yeast such as *S. cerevisae* or *S. pombe*, an insect cell such as Sf9 cell, a non-human mammalian cell, or a human cell).

In certain embodiments, the scripted procedure can comprise VBA scripts. In certain embodiments, the scripted procedure is operable in a Linux system (e.g., Ubuntu 12.04 LTS), a Unix system, a Microsoft Windows operating system, an Android operating system, or an Apple iOS operating system. Different programming language including $C^{++T}$ Java Script, MATLAB, etc. can be used in conjunction with implementations of the present invention. Coded instructions can be stored on a memory device, such as a non-transitory computer readable medium, that can be used with a computer system known to those skilled in the art.

In certain embodiments, the α-helical domain is one of 7-transmembrane α-helical domains in a native membrane protein is a G-protein coupled receptor (GPCR). In some embodiments, the GPCR is selected from the group consisting of: purinergic receptors ($P2Y_1$, $P2Y_2$, $P2Y_4$, $P2Y_6$), $M_1$ and $M_3$ muscarinic acetylcholine receptors, receptors for thrombin (protease-activated receptor (PAR)-1, PAR-2), thromboxane ($TXA_2$), sphingosine 1-phosphate ($S1P_2$, S1P$_3$, S1P$_4$ and S1P$_5$), lysophosphatidic acid (LPA$_1$, LPA$_2$, LPA$_3$), angiotensin II (AT$_1$), serotonin (5-HT$_{2c}$ and 5-HT$_4$), somatostatin (sst$_5$), endothelin (ET$_A$ and ET$_B$), cholecystokinin (CCK$_1$), V$_{1a}$ vasopressin receptors, D$_5$ dopamine receptors, fMLP formyl peptide receptors, GAL$_2$ galanin receptors, EP$_3$ prostanoid receptors, A$_1$ adenosine receptors, α$_1$ adrenergic receptors, BB$_2$ bombesin receptors, B$_2$ bradykinin receptors, calcium-sensing receptors, chemokine receptors, KSHV-ORF74 chemokine receptors, NK$_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4.

In other embodiments, the native membrane protein or membrane protein is an integral membrane protein. In a further aspect, the native membrane protein is a mammalian protein. The proteins of the invention are preferably human. In certain embodiments, references to specific GPCR proteins (e.g., CXCR4) refer to mammalian GPCRs, such as non-human mammalian GPCRs, or human GPCRs.

In some embodiments, the α-helical domain is one of 7-transmembrane α-helical domains in a G-protein coupled receptor (GPCR) variant modified, for example, in the extracellular or intracellular loops to improve or alter ligand binding, as described elsewhere in the literature. For the purposes of this invention, the word "native" or "wild type" is intended to refer to the protein (or α-helical domain) prior to water solubilization in accordance with the methods described herein.

In certain embodiments, the membrane protein can be a tetraspanin membrane protein characterized by 4 transmembrane alpha-helices. Approximately 54 human tetraspanin membrane proteins have been reviewed and annotated. Many are known to mediate cellular signal transduction events that play a critical role in regulation of cell development, activation, growth and motility. For example, CD81 receptor plays a critical role as the receptor for Hepatitis C virus entry and plasmodium infection. CD81 gene is localized in the tumor-suppressor gene region and can be a candidate for mediating cancer malignancies. CD151 is involved in enhanced cell motility, invasion and metastasis of cancer cells. Expression of CD63 correlates with the invasiveness of ovarian cancer. A characteristic of a tetraspanin membrane protein is a Cysteine-cysteine-glycine motif in the second, or large, extracellular loop.

Another aspect of the invention provides a water-soluble variant of a G Protein-Coupled Receptor (GPCR), wherein: (1) a plurality of hydrophobic amino acids in the transmembrane TM domain alpha-helical segments ("TM regions") of the GPCR are substituted, wherein: (a) said hydrophobic amino acids are selected from the group consisting of Leucine (L), Isoleucine (I), Valine (V), and Phenylalanine (F); (b) each said Leucine (L) is independently substituted by Glutamine (Q), Asparagine (N), or Serine (S); (c) each said Isoleucine (I) and said Valine (V) are independently substituted by Threonine (T), Asparagine (N), or Serine (S); and, (d) each said Phenylalanine is substituted by Tyrosine (Y); and, subsequently, (2) all seven TM regions of the variant maintains α-helical secondary structures; and, (3) there is no predicted trans-membrane region.

In certain embodiments, the water-soluble variant comprises one or more amino acid sequences selected from the group consisting of SEQ ID NOs: 4-11, 13-20, 22-29, 31-38, 40-47, 49-56, and 58-64. It may further comprise one or more amino acid sequences selected from the group consisting of SEQ ID NOs: 3, 12, 21, 30, 39, 48, and 57. In certain embodiments, the water-soluble variant binds to a CXCR4 ligand.

In certain embodiments, the water-soluble variant comprises one or more amino acid sequences selected from the group consisting of SEQ ID NOs: 69-76, 78-85, 87, 89-96, 98-105, 107-114 and 116-123. It may further comprise one or more amino acid sequences selected from the group consisting of SEQ ID NOs: 68, 77, 86, 88, 97, 106, 115 and 124. In certain embodiments, the water-soluble variant binds to a CX3CR1 ligand.

In certain embodiments, the water-soluble variant comprises one or more amino acid sequences selected from the group consisting of SEQ ID NOs: 128-135, 137-144, 146-153, 155-162, 164-171, 173 and 175-182. It may further comprise one or more amino acid sequences selected from the group consisting of SEQ ID NOs: 127, 136, 145, 154, 163, 172, 174 and 183. In certain embodiments, the water-soluble variant binds to a CCR3 ligand.

In certain embodiments, the water-soluble variant comprises one or more amino acid sequences selected from the group consisting of SEQ ID NOs: 187-194, 196-203, 205-206, 208, 210-217, 219-225, 227-234. It may further comprise one or more amino acid sequences selected from the group consisting of SEQ ID NOs: 186, 195, 204, 207, 209, 218, 226, and 235. In certain embodiments, the water-soluble variant binds to a CCR5 ligand.

In certain embodiments, the water-soluble variant comprises one or more amino acid sequences selected from the group consisting of SEQ ID NOs: 236-243, 245-252, 254-261, 263-270, 272, 274-281, and 283-290. It may further comprise one or more amino acid sequences selected from the group consisting of SEQ ID NOs: 235, 244, 253, 262, 271, 273, 282 and 291. In certain embodiments, the water-soluble variant binds to a CXCR3 ligand.

In certain embodiments, the water-soluble variant comprises one or more transmembrane domains as set forth in any one of SEQ ID NOs: 2, 67, 126, 185, 327, 293, 295, 297, 299, 301, 303, 305, 307, 309, 311, 313, 315, 317, 319, 321, 323 or 325. In certain embodiments, the variant is water soluble and binds a ligand of a homologous native transmembrane protein.

Another aspect of the invention provides a method of producing a protein in a bacterium (e.g., an E. coli), comprising: (a) culturing the bacterium in a growth medium under a condition suitable for protein production; (b) fractioning a lysate of the bacterium to produce a soluble fraction and the insoluble pellet fraction; and, (c) isolating the protein from the soluble fraction; wherein: (1) the protein is a variant G-protein couple receptor (GPCR) of the invention; and, (2) the yield of the protein is at least 20 mg/L (e.g., 30 mg/L, 40 mg/L, 50 mg/L or more) of growth medium.

In certain embodiments, the bacterium is E. coli BL21, and the growth medium is LB medium. In certain embodiments, the protein is encoded by a plasmid in the bacterium. In certain embodiments, expression of the protein is under the control of an inducible promoter, such as an inducible promoter inducible by IPTG. In certain embodiments, the lysate is produced by sonication. In certain embodiments, the soluble fraction is produced by centrifuging the lysate at 14,500×g or more.

Another aspect of the invention provides a method of treatment for a disorder or disease that is mediated by the activity a membrane protein in a subject in need thereof, comprising administering to said subject an effective amount of a water-soluble polypeptide described herein.

In certain embodiments, the water-soluble polypeptide retains the ligand-binding activity of the membrane protein. Examples of disorders and diseases that can be treated by administering a water-soluble peptide of the invention include, but are not limited to, cancer (such as, small cell lung cancer, melanoma, triple negative breast cancer), Parkinson's disease, cardiovascular disease, hypertension, and bronchial asthma.

Another aspect of the invention provides a pharmaceutical composition comprising a therapeutically effective amount of a water-soluble polypeptide of the invention and pharmaceutically acceptable carrier or diluent.

In yet another aspect, the invention provides a cell transfected with a subject water-soluble peptide comprising a modified α-helical domain. In certain embodiments, the cell is an animal cell (e.g., human, non-human mammalian, insect, avian, fish, reptile, amphibian, or other cell), yeast or a bacterial cell.

The invention also includes a computer implemented method performed on a computer system, the method comprising one or more of the methods (or steps thereof) as described herein. Computer systems including a non-transient computer readable medium having computer-executable instructions stored thereon, the computer-executable instructions when executed by the computer system causing the computer system to perform the methods the computer-executable instructions when executed by the computer system causing the computer system to perform the methods contemplated herein. Additionally, computer systems comprising at least one memory to store sequence data and quantitative results described herein and at least one processor coupled to the memory, the processor being configured to perform the methods described herein are contemplated. A user interface, such as a graphical user interface (GUI) in conjunction with an electronic display device can be used to select processing parameters that are operative to control the selection process, including computational methods described herein.

Another aspect of the invention provides a non-transitory computer readable medium having stored thereon a sequence of instructions to perform any of the methods of the invention.

A further aspect of the invention provides a data processing system operative to select a water-soluble variant of a G Protein-Coupled Receptor comprising: a data processor operative to perform substitution of amino acids as in any of the methods of the invention, wherein the system ranks a protein variant with a ranking function.

It should be understood that all embodiments of the invention, including those described only under one aspect of the invention (e.g., screening method), are to be construed to be applicable to all aspects of the invention (e.g., water-soluble proteins or methods of use), and are to be construed to be combinable with any one or more additional embodiments of the invention unless explicitly disclaimed or otherwise improper, as should be readily understood by one of skill in the art.

BRIEF DESCRIPTION OF THE DRAWINGS

The foregoing and other objects, features and advantages of the invention will be apparent from the following more particular description of the representative embodiments of the invention, as illustrated in the accompanying drawings in which like reference characters refer to the same parts throughout the different views. The drawings are not necessarily to scale, emphasis instead being placed upon illustrating the principles of the invention.

FIG. 1B is a side view of an alpha helix. After applying the QTY Code of systematic amino acid changes, the alpha helix become water-soluble. FIG. 1C is a top view of an alpha helix before and after QTY Code substitution: the helix on the left is the natural membrane helix with mostly hydrophobic amino acids, the helix on the right is the same helix after applying QTY Code substitution. The helix now has most hydrophilic amino acids (FIG. 1D). Before QTY Code, the GPCR membrane proteins are surrounded by hydrophobic lipid molecules to embed them inside the lipid membrane (left portion of FIG. 1D). After applying QTY Code, the GPCR membrane proteins become water-soluble and no long need detergent to surround it for stabilization (right portion of FIG. 1D).

FIG. 4 is an illustration of the potential variants in each of the seven TM regions of a GPCR CXCR4.

FIGS. 11A and 11B are schematic illustration of flowcharts setting forth processing steps of certain preferred embodiments of the invention.

DETAILED DESCRIPTION OF THE INVENTION

Figure 1A:
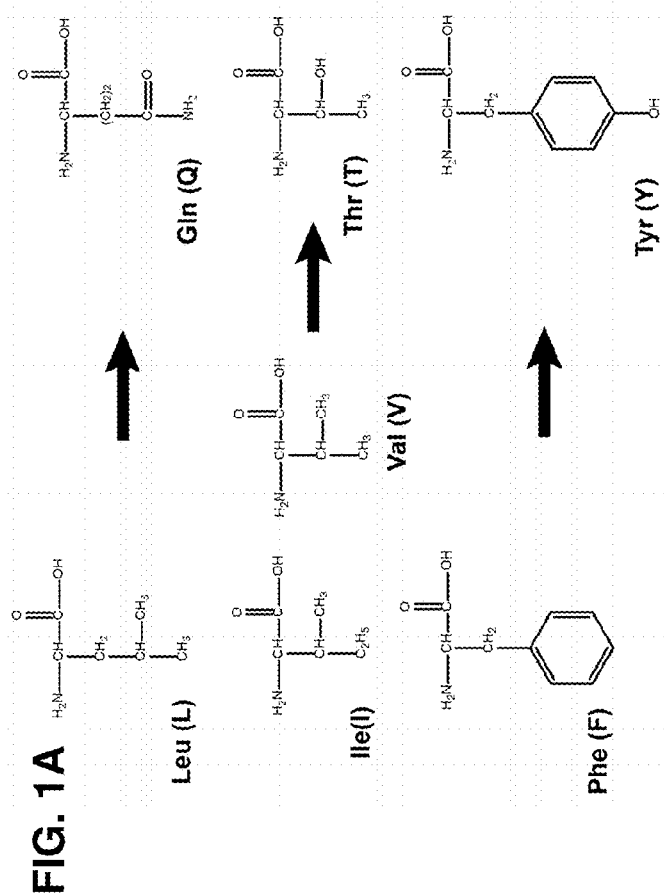
FIGS. 1A-1D is the general illustration for the QTY Code that systematically substitutes the hydrophobic amino acids L, I, V and F to Q, T, T, Y, respectively (FIG. 1A). The molecular shapes of amino acids leucine and glutamine are similar; likewise, molecular shapes of isoleucine and valine are similar to threonine; and molecular shapes of phenylalanine and tyrosine are similar. Leucine, isoleucine, valine and phenylalanine are hydrophobic and cannot bind with water molecules. In contrast, glutamine can bind with 4 water molecules, 2 hydrogen donors, and 2 hydrogen acceptors; the —OH group on threonine and tyrosine can bind to 3 water molecules, 1 hydrogen donor and 2 acceptors.
Figure 1B:
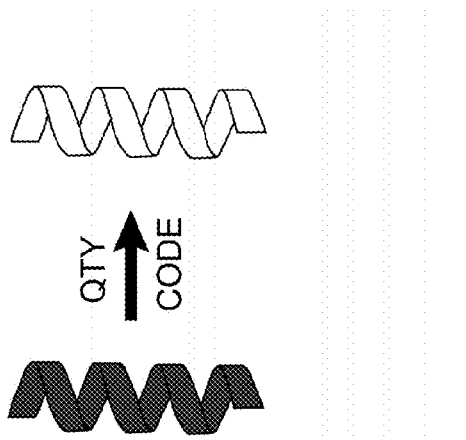
Figure 1C:
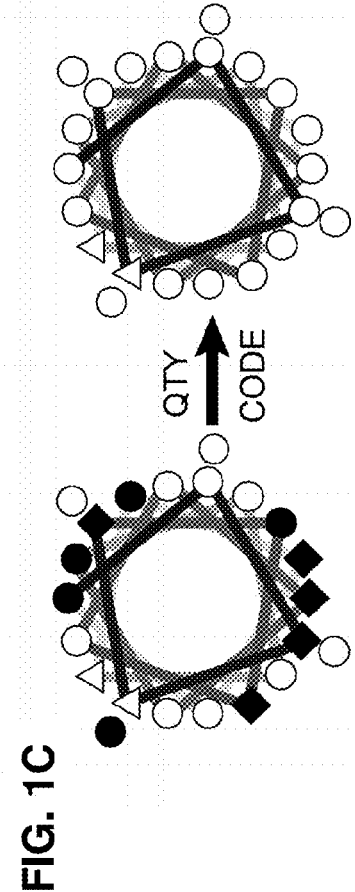
Figure 1D:
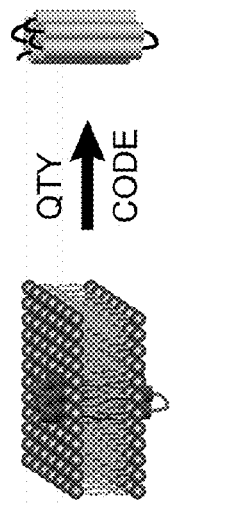
Figure 2:
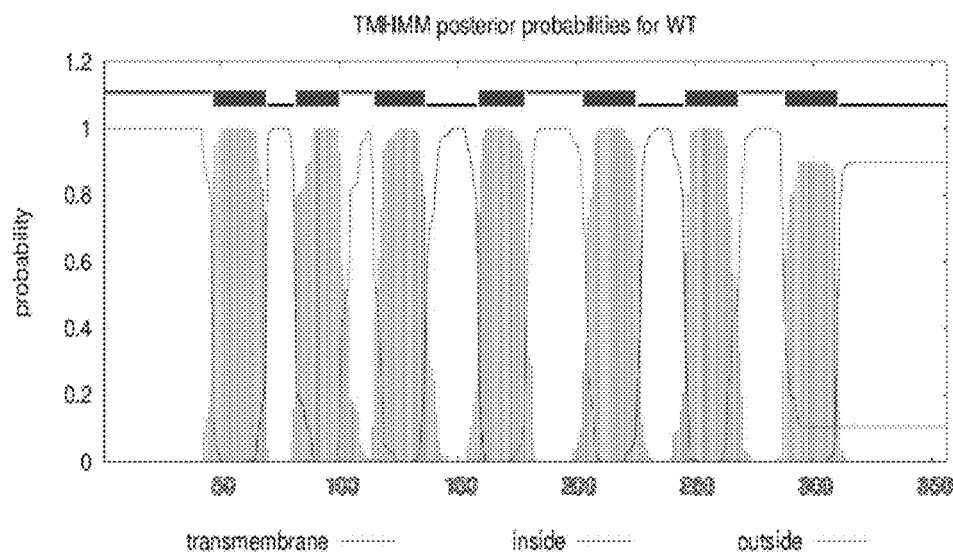
FIG. 2 is a TMHMM prediction for the transmembrane domain regions for CXCR4. The prediction shows 7 distinctive hydrophobic transmembrane segments. In contrast, in a TMHMM prediction for a variant of CXCR4 subject to the QTY substitution method of the invention (CXCR4-QTY), there are no distinctive 7 hydrophobic transmembrane segments visible anymore.

A description of preferred embodiments of the invention follows. The words "a" or "an" are meant to encompass one or more, unless otherwise specified.

In some aspects, the invention is directed to the use of the QTY (Glutamine, threonine and tyrosine) replacement (or "QTY Code") method (or "principle") to change the 7-trans-membrane α-helix hydrophobic residues leucine (L), isoleucine (I), valine (V), and phenylalanine (F) of a native protein to the hydrophilic residues glutamine (Q), threonine (T) and tyrosine (Y). In certain embodiments, as described above, Asn (N) and Ser (S) can also be used as substitute residues for L, I and/or V, but not F. This invention can convert a water insoluble, native membrane protein to a more water-soluble counterpart that still maintains some or substantially all functions of the native protein.

The invention includes a process for designing water-soluble peptides. The process is described in terms of GPCR proteins as an illustrative example, with specificity in the first instance to human CCR3, CCR5, CXCR4, and CX3CR1. However, the general principle of the invention also applies to other proteins with transmembrane (α-helical) regions.

GPCRs typically have 7-transmembrane alpha-helices (7TM) and 8 loops (8NTM) connected by the seven TM regions. These transmembrane segments may be referred to as TM1, TM2, TM3, TM4, TM5, TM6 and TM7. The 8 non-transmembrane loops are divided into 4 extracellular loops EL1, EL2, EL3, and EL4, and 4 intracellular loops, IL1, IL2, IL3, and IL4, thus a total of 8 loops (including the N- and C-terminal loops that are each only connected to one TM region, and each has a free end). Thus a 7TM GPCR protein can be divided into 15 fragments based on the transmembrane and non-transmembrane features.

One aspect of the invention provides a process of operating a computer program to execute a scripted procedure to select, or make a water-soluble variant of a membrane protein (e.g., a G Protein-Coupled Receptor (GPCR)), the method comprising:

(1) entering a sequence of the membrane protein (e.g., GPCR) for analysis;
(2) obtaining a variant of the membrane protein (e.g., GPCR), wherein a plurality of hydrophobic amino acids in the transmembrane TM domain alpha-helical segments ("TM regions") of the membrane protein (e.g., GPCR) are substituted, wherein:
   (a) said hydrophobic amino acids are selected from the group consisting of Leucine (L), Isoleucine (I), Valine (V), and Phenylalanine (F);
   (b) each said Leucine (L) is independently substituted by Glutamine (Q), Asparagine (N), or Serine (S);
   (c) each said Isoleucine (I) and said Valine (V) are independently substituted by Threonine (T), Asparagine (N), or Serine (S); and,
   (d) each said Phenylalanine is substituted by Tyrosine (Y); and, subsequently,
(3) obtaining an α-helical secondary structure result for the variant to verify maintenance of α-helical secondary structures in the variant;
(4) obtaining a trans-membrane region result for the variant to verify water solubility of the variant, thereby selecting the water-soluble variant of the membrane protein (e.g., GPCR). As used herein, "water-soluble variant of the (trans)membrane protein" or "water-soluble (trans)membrane variant" may be used interchangeably.

The exact sequence of carrying out the steps of the invention may be variable. For example, in certain embodiments, step (3) is performed prior to step (4). In certain embodiments, step (3) is performed concurrently with step (4). In certain embodiments, step (3) is performed after step (4).

In certain embodiments, the plurality of hydrophobic amino acids are randomly selected from all potential hydrophobic amino acids L, I, V, and F located on all TM regions of the protein. In certain embodiments, the plurality of hydrophobic amino acids is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 50%, 55%, 60%, 65%, 70%, 75%, 80%, 85%, 90%, 91%, 92%, 93%, 94%, 95%, 96%, 97%, 98%, 99%, or 100% of all the potential hydrophobic amino acids L, I, V, and F located on all TM regions of the protein. In certain embodiments, the plurality of hydrophobic amino acids is no less than about 10%, 15%, 20%, 25%, 30%, 35%, 40%, 45%, 50% of all the potential hydrophobic amino acids L, I, V, and F located on all TM regions of the protein. In certain embodiments, the plurality of hydrophobic amino acids is no more than about 95%, 90%, 85%, 80%, 75%, 70%, 65%, 60%, or 50% of all the potential hydrophobic amino acids L, I, V, and F located on all TM regions of the protein. In certain embodiments, the randomly selected hydrophobic amino acids L, I, V, and F may be roughly evenly distributed on all TM regions, or may be preferentially or exclusively distributed on 1, 2, 3, 4, 5, or 6 TM regions.

In certain embodiments, every potential hydrophobic amino acids L, I, V, and F on all TM regions of the protein are substituted. For example, all L are independently substituted by Q (or S or N); and/or all I and V are independently substituted by T (or S or N); and/or all F are substituted by Y. In certain embodiments, all L are substituted by Q, all I and V are substituted by T, and all F are substituted by Y.

In certain embodiments, instead of randomly substituting selected hydrophobic amino acids L, I, V, and F in all TM regions, all substitutions can first be limited to any one of the TM regions (such as the most N-terminal or C-terminal TM region), and only desired substitution variants are selected as members of a library of potential variants. All members of the library differ in the substitutions in the chosen TM region, either due to the positions substituted (e.g., the $3^{rd}$ vs. the $10^{th}$ residue in the TM region is substituted), or due to the identity of the substituent residues (e.g., S vs. T for an I or V substitution), or both. The desired substitution variants are selected based on a pre-determined criteria, such as a scoring system that takes into consideration the α-helical secondary structure prediction result and/or the trans-membrane region prediction result.

This process can be repeated for 1, 2, 3, 4, 5, 6 additional TM regions of the protein, or all the remaining TM regions of the protein, each iteration creates a library of potential variants that can be stored in an electronic memory or database. Within the same library, all variants differ in the substitutions in the chosen TM region (see above), but are otherwise the same in the remaining TM regions and non-TM regions.

Domain swapping or shuffling using sequences from two or more such libraries creates combinatory variants having hydrophobic amino acids L, I, V, F substitutions in two or more TM regions. Depending on the number of members in each library, the total possible combinations of combinatory variants can approach millions with just a few members in each library. For example, for a GPCR having 7 TM regions, if there are 8 members in each of the seven libraries, the total number of combinatory variants based on the libraries will be $8^7$ or about 2.1 million. In certain embodiments, the library of combinatory variants comprises less than about 5, 4, 3, 2, 1, or 0.5 million members.

Thus in certain embodiments, in step (2), one subset of said plurality of hydrophobic amino acids in one and the same TM region of the protein (e.g., GPCR) are substituted to generate one member of a library of potential variants, and one or more different subsets of said plurality of hydrophobic amino acids are substituted to generate additional members of the library.

In certain embodiments, the method further comprises ranking all members of said library based on a combined score, wherein the combined score is a weighed combination of the α-helical secondary structure prediction result and the trans-membrane region prediction result.

As one of ordinary skill in the art would appreciate, the domains having different sequences will likely predict different water solubilities and propensities for alpha helical formation. One can assign "a score" to a specific predicted water solubility or range of solubilities, propensity to form alpha helical structure or range of propensities. The score can be quantitative (0,1) where 0 can represent, for example, a domain with an unacceptable predicted water solubility and 1 can represent, for example, a domain with an acceptable predicted water solubility. This score can be based on a threshold value, for example. Or, the score can be assessed on a scale, for example, between 1 and 10 establishing characterizing increasing degrees of water solubility. Or, the score can be quantitative, such as in describing the predicted solubility in terms of mg/mL. Upon assessing a score to each domain, the domain variants can be readily compared (or ranked) by one or, preferably, both of the scores to select domain variants that are both water soluble and form alpha helices. Thus, preferred embodiments can utilize a ranking function that can be used to compute the ranking data. Note also that water soluble proteins made based on the currently described system can be analyzed and characterized to provide input to the system such that those combinations of substitution that are not effective to achieve a given biological function can be used to constrain the computational model, thereby enabling a more efficient processing of the information.

For example, using the methods of the invention, one or more variants can be designed and produced in vitro and/or in vivo, and one or more biological functions of the variants can be determined based on any of many art-recognized methods. For GPCR, for example, ligand binding and/or downstream signal transduction by the variants can be compared to that of the wild-type GPCR, and the patterns of QTY substitution used to generate a specific variant can be associated with an enhanced, maintained, or diminished biological activity. Such structural-functional relationship information obtained based on one or more variants can be used for machine learning or impart additional constrain on the computational model of the invention, to more efficiently rank the variants created by the methods of the invention. Thus new potential variants having substitution patterns more closely matching that of a known successful variant can be ranked higher that another potential variant having substitution patterns less closely matching that of the known successful variant, or more closely matching that of a known unsuccessful variant.

The TMHMM program, when run as a standalone version of the software module/package (e.g., one for the Linux system), produces a score of between 0 and 1 that can be used to predict the propensity of forming transmembrane regions/proteins. The score can be used as a quantitative prediction for water solubility in the methods of the invention.

Thus in certain embodiment, the α-helical secondary structure component of a ranking function can be a quantitative score, such as 0.5 or 1 for having no predicted α-helical secondary structures, and 0 for having maintained predicted α-helical secondary structures. In certain embodiments, the trans-membrane region result can be provided by a TM region prediction program, such as TMHMM 2.0, which provides a numeric value between 0 and 1, with 0 being no predicted TM region, and 1 being the strongest propensity of forming TM region(s). Thus the two scores can be combined, either directly or with weighing, such that the combined score represents an overall assessment of maintained secondary structure as well as predicted water solubility (as measured by propensity to form TM regions). For example, a combined score of 0 indicates that the variant has no predicted TM region, while having maintained predicted α-helical secondary structures, and is thus a desired variant. Meanwhile, a variant has strong propensity to form TM region (due to the presence of large number of hydrophobic residues, for example), tends to have a larger combined score and thus undesirable under this scoring scheme.

In certain embodiments, the method includes eliminating variants having an α-helical secondary structure prediction result tending to show that the α-helical secondary structures are destroyed or disrupted. In certain embodiments, the method includes eliminating variants having trans-membrane region prediction result tending to show strong propensity to form TM regions. Thus the system can include a beaming module in which variants can be excluded from further selection processing.

In certain embodiments, the ranking function can be selected to include a weighing scheme that assigns 5%, 10%, 20%, 25%, 30%, 40%, 50%, 60%, 70%, 80%, 90% or 95% weight to the α-helical secondary structure prediction result, and the remaining to the trans-membrane region prediction result. The user can either manually select the weighting features, or the software can automatically select the weighting features depending on the desired characteristics such as biological function.

In certain embodiments, the method further comprises selecting N members with the highest combined scores to form a first library of potential variants for said TM region, wherein N is a pre-determined integer (e.g., 3, 4, 5, 6, 7, 8, 9, 10, 11, 12, 13, 14, 15, 16, 17, 18, 19, 20 or more).

In certain embodiments, the method further comprises generating one library of potential variants for 1, 2, 3, 4, 5, 6, or all the remaining TM regions of the protein (e.g., GPCR). Each entry in the library can include fields used to define attributes of that entry, including the ranking data generated by one or more ranking functions.

In certain embodiments, the method further comprises replacing two or more (e.g., all) TM regions of the protein (e.g., GPCR) with corresponding TM regions from the libraries of potential variants, to create a library of combinatory variants. As used herein, "corresponding TM regions" refer to the TM regions in the libraries of potential variants that are the same or homologous to the TM regions of the protein (e.g., GPCR) that are being combined. For example, if the $2^{nd}$ and $3^{rd}$ TM regions from the N-terminal of a GPCR are to be substituted, TM region sequences from the library having substitutions only in the $2^{nd}$ TM regions, and TM region sequences from the library having substitutions only in the $3^{rd}$ TM regions, are imported/pasted/transferred into the $2^{nd}$ and $3^{rd}$ TM regions of the GPCR to create combinatory variants.

In certain embodiments, substantially all (e.g., 96%, 97%, 98%, 99%, or 100%), or 30%, 40%, 50%, 60%, 70%, 75%, 80%, 85%, 90%, 95% of said leucines are substituted by glutamines. In certain embodiments, substantially all (e.g., 96%, 97%, 98%, 99%, or 100%), or 30%, 40%, 50%, 60%, 70%, 75%, 80%, 85%, 90%, 95% of said isoleucines are substituted by threonines. In certain embodiments, substantially all (e.g., 96%, 97%, 98%, 99%, or 100%), or 30%, 40%, 50%, 60%, 70%, 75%, 80%, 85%, 90%, 95% of said valines are substituted by threonines. In certain embodiments, wherein substantially all (e.g., 96%, 97%, 98%, 99%, or 100%), or 30%, 40%, 50%, 60%, 70%, 75%, 80%, 85%, 90%, 95% of said phenylalanines are substituted by tyrosines. In certain embodiments, one or more (e.g., 1, 2, or 3) said leucines are not substituted. In certain embodiments, one or more (e.g., 1, 2, or 3) said isoleucines are not substituted. In certain embodiments, one or more (e.g., 1, 2, or 3) said valines are not substituted. In certain embodiments, one or more (e.g., 1, 2, or 3) said phenylalanines are not substituted.

In certain embodiments, the method further comprises producing/expressing said combinatory variants. In certain embodiments, the method further comprises testing said combinatory variants for ligand binding (e.g., in vitro, or in a biological system such as yeast two-hybrid system), wherein those having substantially the same ligand binding compared to that of the GPCR are selected. In certain embodiments, the method further comprises testing said combinatory variants for a biological function of the GPCR, wherein those having substantially the same biological function compared to that of the GPCR are selected.

In certain embodiments, the sequence of the TM protein (e.g., GPCR) contains information about the TM regions of the protein, e.g., the location of one or more transmembrane regions of the TM protein, such as the location of all TM regions. Such sequences may belong to proteins having resolved crystal structure with defined TM regions. Such sequences may also belong to proteins having annotated TM region information based on prior research, and such information is readily available from a public or proprietary database, such as PDB, UniProt, GenBank, EMBL, DBJ, etc.

The Protein Data Bank (PDB) is a weekly updated repository for the three-dimensional structural data of large biological molecules, such as proteins and nucleic acids. The data, typically obtained by X-ray crystallography or NMR spectroscopy and submitted by biologists and biochemists from around the world, are freely accessible on the Internet via the websites of its member organizations (PDBe, PDBj, and RCSB). The PDB is overseen by the Worldwide Protein Data Bank, wwPDB. The PDB is a key resource in areas of structural biology, such as structural genomics, and most major scientific journals, and some funding agencies, now require scientists to submit their structure data to the PDB.

If the contents of the PDB are thought of as primary data, then there are hundreds of derived (i.e., secondary) databases that categorize the data differently. For example, both SCOP and CATH categorize structures according to type of structure and assumed evolutionary relations; GO categorize structures based on genes; while crystallographic database store information about the 3D structure of the proteins. All such publically available database may be used to provide input sequence information, including information about the existence and position of transmembrane regions.

Another publically available database that can provide sequence information for use in the methods of the invention is UniProt. UniProt is a comprehensive, high-quality and freely accessible database of protein sequence and functional information, many entries being derived from genome sequencing projects. It contains a large amount of information about the biological function of proteins derived from the research literature. UniProt provides four core databases: UniProtKB (with sub-parts Swiss-Prot and TrEMBL), UniParc, UniRef, and UniMes. Among them, UniProtKB/Swiss-Prot is a manually annotated, non-redundant protein sequence database that combines information extracted from scientific literature and biocurator-evaluated computational analysis. The aim of UniProtKB/Swiss-Prot is to provide all known relevant information about a particular protein. Annotation is regularly reviewed to keep up with current scientific findings. The manual annotation of an entry involves detailed analysis of the protein sequence and of the scientific literature. Sequences from the same gene and the same species are merged into the same database entry. Differences between sequences are identified, and their cause documented (e.g., alternative splicing, natural variation, etc.). Computer-predictions are manually evaluated, and relevant results selected for inclusion in the entry. These predictions include post-translational modifications, transmembrane domains and topology, signal peptides, domain identification, and protein family classification, all may be used to provide useful sequence information pertaining to the TM regions used in the methods of the invention.

In certain embodiments, the sequence of the TM protein (e.g., GPCR) does not contain information about the location of one or more (e.g., any) transmembrane regions. However, the TM region(s) can be predicted based on sequence homology with a related protein having known TM regions. For example, the related protein may be a homologous protein in a different species.

In certain embodiments, the sequence of the TM protein (e.g., GPCR) does not contain information about the location of one or more (e.g., any) transmembrane regions, and such information is not readily available based on known information. In this embodiment, the invention provides computation of TM regions using art-recognized methods, such as the TMHMM 2.0 (TransMembrane prediction using Hidden Markov Models) program, developed by Center for Biological Sequence Analysis. See further details regarding this below.

In certain embodiments, the method further comprises providing a polynucleotide sequence for each variants of the protein (e.g., GPCR). Such polynucleotide sequence can be readily generated based on the protein sequence of the protein (e.g., GPCR), and the known genetic code. In certain embodiments, the polynucleotide sequence is codon optimized for expression in a host. The host may be a bacterium such as E. coli, a yeast such as S. cerevisae or S. pombe, an insect cell such as Sf9 cell, a non-human mammalian cell, or a human cell.

In certain embodiments, the protein is a GPCR, such as one selected from the group consisting of: purinergic receptors ($P2Y_1$, $P2Y_2$, $P2Y_4$, $P2Y_6$), $M_1$ and $M_3$ muscarinic acetylcholine receptors, receptors for thrombin (protease-activated receptor (PAR)-1, PAR-2), thromboxane ($TXA_2$), sphingosine 1-phosphate ($S1P_2$, $S1P_3$, $S1P_4$ and $S1P_5$), lysophosphatidic acid ($LPA_1$, $LPA_2$, $LPA_3$), angiotensin II ($AT_1$), serotonin ($5\text{-}HT_{2c}$ and $5\text{-}HT_4$), somatostatin ($sst_5$), endothelin ($ET_A$ and $ET_B$), cholecystokinin ($CCK_1$), $V_{1a}$ vasopressin receptors, $D_5$ dopamine receptors, fMLP formyl peptide receptors, $GAL_2$ galanin receptors, $EP_3$ prostanoid receptors, $A_1$ adenosine receptors, $\alpha_1$ adrenergic receptors, $BB_2$ bombesin receptors, $B_2$ bradykinin receptors, calcium-sensing receptors, chemokine receptors, KSHV-ORF74 chemokine receptors, $NK_1$ tachykinin receptors, thyroid-stimulating hormone (TSH) receptors, protease-activated receptors, neuropeptide receptors, adenosine A2B receptors, P2Y purinoceptors, metabolic glutamate receptors, GRK5, GPCR-30, and CXCR4.

In certain embodiments, the scripted procedure of the method comprises VBA scripts.

In certain embodiments, the scripted procedure is operable in a Linux system (e.g., Ubuntu 12.04 LTS), a Microsoft Windows operative system, or an Apple iOS operative system.

In certain embodiments, the process comprises all, or substantially all, of the following steps:
(1) identifying a first transmembrane region of a (trans) membrane protein, if necessary, by predicting an alpha-helical structure of the protein (e.g., a GPCR);
(2) modifying a plurality of hydrophobic amino acids via the QTY Code, as defined herein to obtain a modified first transmembrane sequence;
(3) scoring the propensity of the alpha-helical structure of the first modified transmembrane sequence of (2) (e.g., in the context of a modified (trans)membrane protein having the first modified transmembrane sequence) to arrive at a structure score;
(4) scoring the water solubility prediction of the first modified transmembrane sequence of (2) (e.g., in the context of a modified (trans)membrane protein having the first modified transmembrane sequence) to arrive at a solubility score;
(5) repeating steps (2) through (4) to arrive at a first library of putative water soluble first modified transmembrane variants;
(6) comparing the structure scores and solubility scores of each putative water soluble first modified transmembrane variants in the first library and, preferably ranking the putative water soluble first modified transmembrane variants using said structure scores and solubility scores;
(7) selecting a plurality of putative water soluble first modified transmembrane variants (wherein the plurality is the integer, H, or preferably less than 10, 9, 8, 7, 6, 5 or 4) to arrive at a second library of putative water soluble first modified transmembrane variants;
(8) repeating steps (1) through (7) for a second, third, fourth, fifth, sixth, seventh or, preferably, all transmembrane regions of the protein (the sum of the transmembrane regions modified by the method being an integer n);
(9) identifying the amino acid sequences of the protein which are not included in any transmembrane region modified in steps (1) through (8), and including any extracellular or intracellular domain of the protein;
(10) generating combinatorial variants of putative water soluble modified transmembrane protein (see above); and,
(11) optionally, identifying a nucleic acid sequence for each putative water soluble modified transmembrane variant.

Using the nucleic acid sequences identified in the above process, nucleic acid sequences for each putative water-soluble modified transmembrane variant and each non-transmembrane domains (including the extracellular and intracellular domains) can be generated and combinatorially expressed to create a library of up to $H^n$ putative water-soluble transmembrane protein variants. For example, where H is 8 and n is 7, a library of approximately 2 million water-soluble protein variants can be designed.

Another aspect of the invention pertains to the expression of the water-soluble variant proteins (e.g., GPCR) designed based on the methods of the invention. This aspect of the invention is partly based on the surprising finding that the water-soluble variant proteins (e.g., GPCR) designed based on the methods of the invention can achieve high levels of expression in both in vitro cell-free expression system and expression in commonly used cell-based expression systems, such as E. coli. In addition, the expressed proteins are highly soluble, and can be easily purified from the soluble fraction of the expression system, such as the soluble fraction from the lysate of an E. coli culture, as opposed to the insoluble aggregates or pellets in which most membrane proteins are typically found.

Thus one aspect of the invention provides a method of producing a protein in a bacterium (e.g., an E. coli), comprising:
(a) culturing the bacterium in a growth medium under a condition suitable for protein production;
(b) fractioning a lysate of the bacterium to produce a soluble fraction and the insoluble pellet fraction; and,
(c) isolating the protein from the soluble fraction;
wherein:
(1) the protein is a subject variant protein (e.g., G-protein couple receptor (GPCR)) of the invention; and,
(2) the yield of the protein is at least 20 mg/L (e.g., 30 mg/L, 40 mg/L, 50 mg/L or more) of growth medium.

In certain embodiments, the bacterium is E. coli BL21, and the growth medium is LB medium. In certain embodiments, the protein is encoded by a plasmid in the bacterium. In certain embodiments, expression of the protein is under the control of an inducible promoter. For example, the inducible promoter may be inducible by IPTG. In certain embodiments, the lysate is produced by sonication. In certain embodiments, the soluble fraction is produced by centrifuging the lysate at 14,500× g or more.

With the general aspects of the inventions described above, certain features or specific embodiments of the invention are further described below.

Transmembrane Region Prediction

Certain methods of the invention comprise a step of predicting a transmembrane region of a protein, such as GPCR. There are many programs and software known in the art relating to the TM region, and any of which may be used individually or in combination in the methods of the invention where a TM region prediction step is called for. These programs usually have a very simple user interface, typically requiring the user to provide an input sequence of a specified format (such as FASTA or plain text), and provides prediction results using text or graphics or both. Some programs also offer more advanced features, such as allowing the user to specify certain parameters to fine tune the prediction results. All such programs can be used in the methods of the invention.

One exemplary TM region prediction program is TMHMM (hosted by Center for Biological Sequence Analysis, Technical University of Denmark), which method predicts 97-98% TM region helices correctly. It predicts transmembrane helices in proteins using the Hidden Markov Model. The input protein sequence can be the FASTA format, and the output can be presented as an html page with an image of predicted locations for the TM regions. In a study by Moller et al., entitled "Evaluation of Methods for the Prediction of Membrane Spanning Regions," Bioinformatics 17(7):646-653, 2001, TMHMM was determined to be the best performing transmembrane prediction program at the time of evaluation.

The programs compared in that study include the following, all can be used to predict TM region in the methods of the invention: TMHMM 1.0, 2.0, and a retrained version of 2.0 (Sonnhammer et al., *Int. Conf Intell. Syst. Mol. Biol.* AAAI Press, Montreal, Canada, pp. 176-182, 1998; Krogh et al., *J Mol Biol.* 305(3):567-80, 2001); MEMSAT 1.5 (Jones et al., *Biochemistry* 33:3038-3049, 1994); Eisenberg (Eisenberg et al., *Nature* 299:371-374, 1982); Kyte/Doolittle (Kyte and Doolittle, *J. Mol. Biol.* 157:105-132, 1982); TMAP (Persson and Argos, *J. Protein Chem.* 16:453-457, 1997); DAS (Cserzo et al., *Protein Eng.* 10:673-676, 1997); HMMTOP (Tusnady and Simon, *J. Mol. Biol.* 283:489-506, 1998); SOSUI (Hirokawa et al., *Bioinformatics* 14:378-379, 1998); PHD (Rost et al., *Int. Conf. Intell. Syst. Mol. Biol.* AAAI Press, St. Louis, USA, pp. 192-200, 1996); TMpred (Hofmann and Stoffel, *Biol. Chem. Hoppe-Seyler* 374:166, 1993); KKD (Klein et al., *Biochim. Biophys. Acta.* 815:468-476, 1985); ALOM2 (Nakai and Kanehisa, *Genomics* 14:489-911, 1992); and Toppred 2 (Claros and Heijne, *Comput. Appl. Biosci.* 10:685-686, 1994). All references cited are incorporated herein by reference.

The principals of TMHMM is described in Krogh et al., Predicting transmembrane protein topology with a hidden Markov model: Application to complete genomes. *Journal of Molecular Biology*, 305(3):567-580, January 2001 (incorporated by reference); and Sonnhammer et al., A hidden Markov model for predicting transmembrane helices in protein sequences. In J. Glasgow, T. Littlejohn, F. Major, R. Lathrop, D. Sankoff, and C. Sensen, editors, *Proceedings of the Sixth International Conference on Intelligent Systems for Molecular Biology*, pages 175-182, Menlo Park, Calif., 1998, AAAI Press (incorporated by reference).

DAS (Dense Alignment Surface, Cserzo et al., "Prediction of transmembrane alpha-helices in procariotic membrane proteins: the Dense Alignment Surface method," *Prot. Eng.* 10(6): 673-676, 1997, Stockholm University, Sweden) predicts transmembrane regions using the Dense Alignment Surface method. DAS is based on low-stringency dot-plots of the query sequence against a set of library sequences—non-homologous membrane proteins—using a previously derived, special scoring matrix. The method provides a high precision hyrdophobicity profile for the query from which the location of the potential transmembrane segments can be obtained. The novelty of the DAS-TMfilter algorithm is a second prediction cycle to predict TM segments in the sequences of the TM-library. To use the DAS server, user enters a protein sequence at www dot sbc dot su dot se slash~miklos slash DAS, and the DA server will predict a TM region of the input sequence.

HMMTOP (Hungarian Academy of Sciences, Budapest) is an automatic server for predicting transmembrane helices and topology of proteins using Hidden Markov Model, developed by G. E. Tusnády, at the Institute of Enzymology. The method used by this prediction server is described in G. E Tusnády and I. Simon (1998) "Principles Governing Amino Acid Composition of Integral Membrane Proteins: Applications to Topology Prediction." *J. Mol. Biol.* 283: 489-506 (incorporated by reference). The new features of HMMTOP 2.0 version is described in 'G. E Tusnády and I. Simon (2001) "The HMMTOP transmembrane topology prediction server," *Bioinformatics* 17: 849-850 (incorporated by reference).

MEMSAT2 Transmembrane Prediction Page (www dot sacs dot ucsf dot edu slash cgi-bin slash memsat dot py) predicts transmembrane segments in a protein using FASTA format or plain text as input. A related program, the MEMSAT (1.5) software, is copyrighted by Dr. David Jones (Jones et al., *Biochemistry* 33:3038-3049, 1994). The latest version of MEMSTAT, MEMSAT V3, is a widely used all-helical membrane protein prediction method MEMSAT. The method was benchmarked on a test set of transmembrane proteins of known topology. From sequence data MEMSAT was estimated to have an accuracy of over 78% at predicting the structure of all-helical transmembrane proteins and the location of their constituent helical elements within a membrane. MEMSATSVM is highly accurate predictor of transmembrane helix topology. It is capable of discriminating signal peptides and identifying the cytosolic and extra-cellular loops. MEMSAT3 and MEMSATSVM are both parts of the PSIPRED Protein Sequence Analysis Workbench, which aggregates several structure prediction methods into one location at the University College London.

The Phobius server (phobius dot sbc dot su dot se) is for prediction of transmembrane topology and signal peptides from the amino acid sequence of a protein in FASTA format. Phobius is described in Lukas et al., "A Combined Transmembrane Topology and Signal Peptide Prediction Method," *Journal of Molecular Biology* 338(5):1027-1036, 2004). PoyPhobius is described in: Lukas et al., "An HMM posterior decoder for sequence feature prediction that includes homology information," *Bioinformatics,* 21 (Suppl 1):i251-i257, 2005. And the Phobius webserver is described in: Lukas et al., "Advantages of combined transmembrane topology and signal peptide prediction—the Phobius web server," *Nucleic Acids Res.* 35:W429-32, 2007 (all cited art incorporated by reference).

SOSUI is for the discrimination of membrane proteins and soluble ones together with the prediction of transmembrane helices. SOSUI predicts transmembrane regions using Hydrophobicity Analysis for Topology and Probe Helix Method for Tertial Structure. The accuracy of the classification of proteins is said to be as high as 99%, and the corresponding value for the transmembrane helix prediction is said to be about 97%. The system SOSUI is available through internet access www dot tuat dot ac dot jp slash mitaku slash sosui.

TMPred (European Molecular Biology Network, Swiss node) predicts transmembrane regions and protein orientation in a query sequence. Specifically, the TMPred algorithm is based on the statistical analysis of TMbase, a database of naturally occurring transmembrane proteins. The prediction is made using a combination of several weight-matrices for scoring. See Hofmann & Stoffel (1993) "TMbase—A database of membrane spanning proteins segments," *Biol. Chem. Hoppe-Seyler,* 374:166.

The SPLIT 4.0 server is a membrane protein secondary structure prediction server (split dot pmfst dot hr slash split slash 4) that predicts the transmembrane TM secondary structures of membrane proteins in SWISS-PROT format, using the method of preference functions. See Juretic et al., "Basic charge clusters and predictions of membrane protein topology," *J. Chem. Inf. Comput. Sci.,* 42:620-632, 2002 (incorporated by reference).

PRED-TMR predicts transmembrane domains in proteins using solely the protein sequence itself. The algorithm refines a standard hydrophobicity analysis with a detection of potential termini ("edges," starts and ends) of transmembrane regions. This allows both to discard highly hydrophobic regions not delimited by clear start and end configurations and to confirm putative transmembrane segments not distinguishable by their hydrophobic composition. The accuracy obtained on a test set of 101 non-homologous transmembrane proteins with reliable topologies compares well with that of other popular existing methods. Only a slight decrease in prediction accuracy was observed when the algorithm was applied to all transmembrane proteins of the SwissProt database (release 35). See Pasquier et al., "A novel method for predicting transmembrane segments in proteins based on a statistical analysis of the SwissProt database: the PRED-TMR algorithm," *Protein Eng.,* 12(5): 381-385, 1999 (incorporated by reference).

In the related PRED-TMR2, the application has been extended with a pre-processing stage represented by an artificial neural network which is able to discriminate with a high accuracy transmembrane proteins from soluble or fibrous ones. Applied on several test sets of transmembrane proteins, the system gives a perfect prediction rating of 100% by classifying all the sequences in the transmembrane class. Applied on 995 non-transmembrane protein extracted from the PDB SELECT database, the neural network predicts falsely 23 of them to be transmembrane (97.7% of correct assignment). See Pasquier and Hamodrakas, "An hierarchical artificial neural network system for the classification of transmembrane proteins," *Protein Eng.*, 12(8): 631-634, 1999 (incorporated by reference).

Protein Alpha Helical Secondary Structure Prediction

Certain methods of the invention comprise a step of predicting alpha helical secondary structure of a protein, such as GPCR. There are many such programs and software known in the art, and any of which may be used individually or in combination in the methods of the invention where alpha helical secondary structure prediction step is called for. All such programs can be used in the methods of the invention.

Early methods of secondary-structure prediction were restricted to predicting the three predominate states: helix, sheet, or random coil. These methods were based on the helix- or sheet-forming propensities of individual amino acids, sometimes coupled with rules for estimating the free energy of forming secondary structure elements. Such methods were typically ~60% accurate in predicting which of the three states (helix/sheet/coil) a residue adopts. The first widely used technique to predict protein secondary structure from the amino acid sequence was the Chou-Fasman method.

A significant increase in accuracy (to nearly ~80%) was made by taking advantage of information provided by multiple sequence alignment; knowing the full distribution of amino acids that occur at a position (and in its vicinity, typically ~7 residues on either side) throughout evolution provides a much better picture of the structural tendencies near that position. For example, a given protein might have a glycine at a given position, which by itself might suggest a random coil. However, multiple sequence alignment might reveal that helix-favoring amino acids occur at that position (and nearby positions) in 95% of homologous proteins throughout evolution. Moreover, by examining the average hydrophobicity at that and nearby positions, the same alignment might also suggest a pattern of residue solvent accessibility consistent with an α-helix. Taken together, these factors would suggest that the glycine of the original protein adopts α-helical structure, rather than random coil. Thus in the methods of the invention, the alpha helical secondary structure prediction program may combine all the available data to form a 3-state prediction, including neural networks, hidden Markov models and support vector machines. Such prediction methods also provide a confidence score for their predictions at every position.

Secondary-structure prediction methods are continuously benchmarked, e.g., EVA (benchmark). EVA is a continuously running benchmark project for assessing the quality of protein structure prediction and secondary structure prediction methods. Methods for predicting both secondary structure and tertiary structure—including homology modeling, protein threading, and contact order prediction—are compared to results from each weeks newly solved protein structures deposited in the Protein Data Bank (PDB). The project aims to determine the prediction accuracy that would be expected for non-expert users of common, publicly available prediction webservers.

Based on these tests, the most accurate methods at present are Psipred, SAM (Karplus, "SAM-T08, HMM-based protein structure prediction," *Nucleic Acids Res.* (2009) 37 (Web Server issue): W492-497. doi:10.1093/nar/gkp403); PORTER (Pollastri & McLysaght, "Porter: a new, accurate server for protein secondary structure prediction," *Bioinformatics* 21 (8):1719-1720, 2005); PROF (Yachdav et al. (2014). "PredictProtein—an open resource for online prediction of protein structural and functional features," *Nucleic Acids Res.* 42 (Web Server issue): W337-343. doi:10.1093/nar/gku366); and SABLE (Adamczak et al. (2005) "Combining prediction of secondary structure and solvent accessibility in proteins," *Proteins* 59 (3): 467-475. doi:10.1002/prot.20441). In addition, the standard method for assigning secondary-structure classes (helix/strand/coil) to PDB structures is DSSP (Kabsch W and Sander (1983) "Dictionary of protein secondary structure: pattern recognition of hydrogen-bonded and geometrical features," *Biopolymers* 22 (12): 2577-2637. doi:10.1002/bip.360221211), against which the predictions are benchmarked. All incorporated by reference and all can be used in the methods of the invention.

The DSSP algorithm is the standard method for assigning secondary structure to the amino acids of a protein, given the atomic-resolution coordinates of the protein. DSSP begins by identifying the intra-backbone hydrogen bonds of the protein using a purely electrostatic definition, assuming partial charges of −0.42 e and +0.20 e to the carbonyl oxygen and amide hydrogen respectively, their opposites assigned to the carbonyl carbon and amide nitrogen. A hydrogen bond is identified if E in the following equation is less than −0.5 kcal/mol:

$$E = 0.084 \left\{ \frac{1}{r_{ON}} + \frac{1}{r_{CH}} - \frac{1}{r_{OH}} - \frac{1}{r_{CN}} \right\} \cdot 332 \text{ kcal/mol}$$

Based on this, eight types of secondary structure are assigned. The $3_{10}$ helix, α helix and π helix have symbols G, H and I and are recognized by having a repetitive sequence of hydrogen bonds in which the residues are three, four, or five residues apart respectively. Two types of beta sheet structures exist; a beta bridge has symbol B while longer sets of hydrogen bonds and beta bulges have symbol E. T is used for turns, featuring hydrogen bonds typical of helices, S is used for regions of high curvature (where the angle between

and

is less than 70°), and a blank (or space) is used if no other rule applies, referring to loops. These eight types are usually grouped into three larger classes: helix (G, H and I), strand (E and B) and loop (all others).

PSIPRED (Psi-blast based secondary structure prediction) is a technique used to investigate protein structure. It employs neural network, machine learning methods in its algorithm. It is a server-side program, featuring a website serving as a front-end interface, which can predict a protein's secondary structure (beta sheets, alpha helices and coils) from the primary sequence. See bioinf dot cs dot ucl dot ac dot uk slash psipred. The idea of this method is a machine learning method that uses the information of the evolutionarily related proteins to predict the secondary structure of a new amino acid sequence. Specifically, PSIBLAST is used to find related sequences and to build a position-specific scoring matrix. This matrix is processed by a neural network, which was constructed and trained to predict the secondary structure of the input sequence. The prediction method or algorithm is split into three stages: Generation of a sequence profile, Prediction of initial secondary structure, and Filtering of the predicted structure. PSIPRED works to normalize the sequence profile generated by PSIBLAST. Then, by using neural networking, initial secondary structure is predicted. For each amino acid in the sequence the neural network is fed with a window of 15 acids. There is additional information attached, indicating if the window spans the N or C terminus of the chain. This results in a final input layer of 315 input units, divided into 15 groups of 21 units. The network has a single hidden layer of 75 units and 3 output nodes (one for each secondary structure element: helix, sheet, coil). A second neural network is used for filtering the predicted structure of the first network. This network is also fed with a window of 15 positions. The indicator on the possible position of the window at a chain terminus is also forwarded. This results in 60 input units, divided into 15 groups of four. The network has a single hidden layer of 60 units and results in three output nodes (one for each secondary structure element: helix, sheet, coil). The three final output nodes deliver a score for each secondary structure element for the central position of the window. Using the secondary structure with the highest score, PSIPRED generates the protein prediction. The Q3 value is the fraction of residues predicted correctly in the secondary structure states, namely helix, strand and coil.

Step-by-Step Description of an Exemplary Embodiment:

With the invention generally described above, certain non-limiting but illustrative embodiments are described below with reference to representative flow charts in the figures.

Figure 9A:
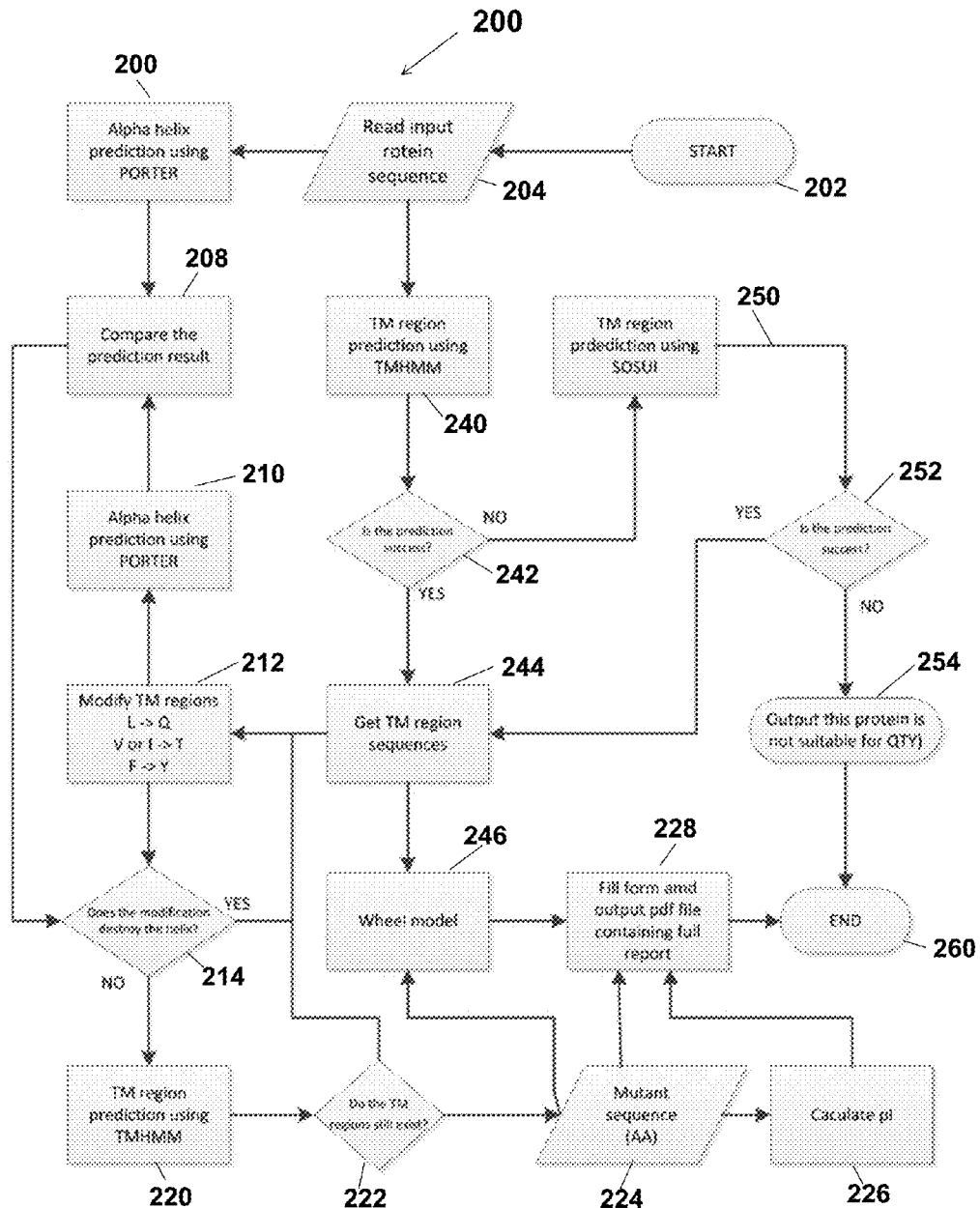
FIG. 9A is a flowchart of a representative embodiment of the process.
Figure 9B:
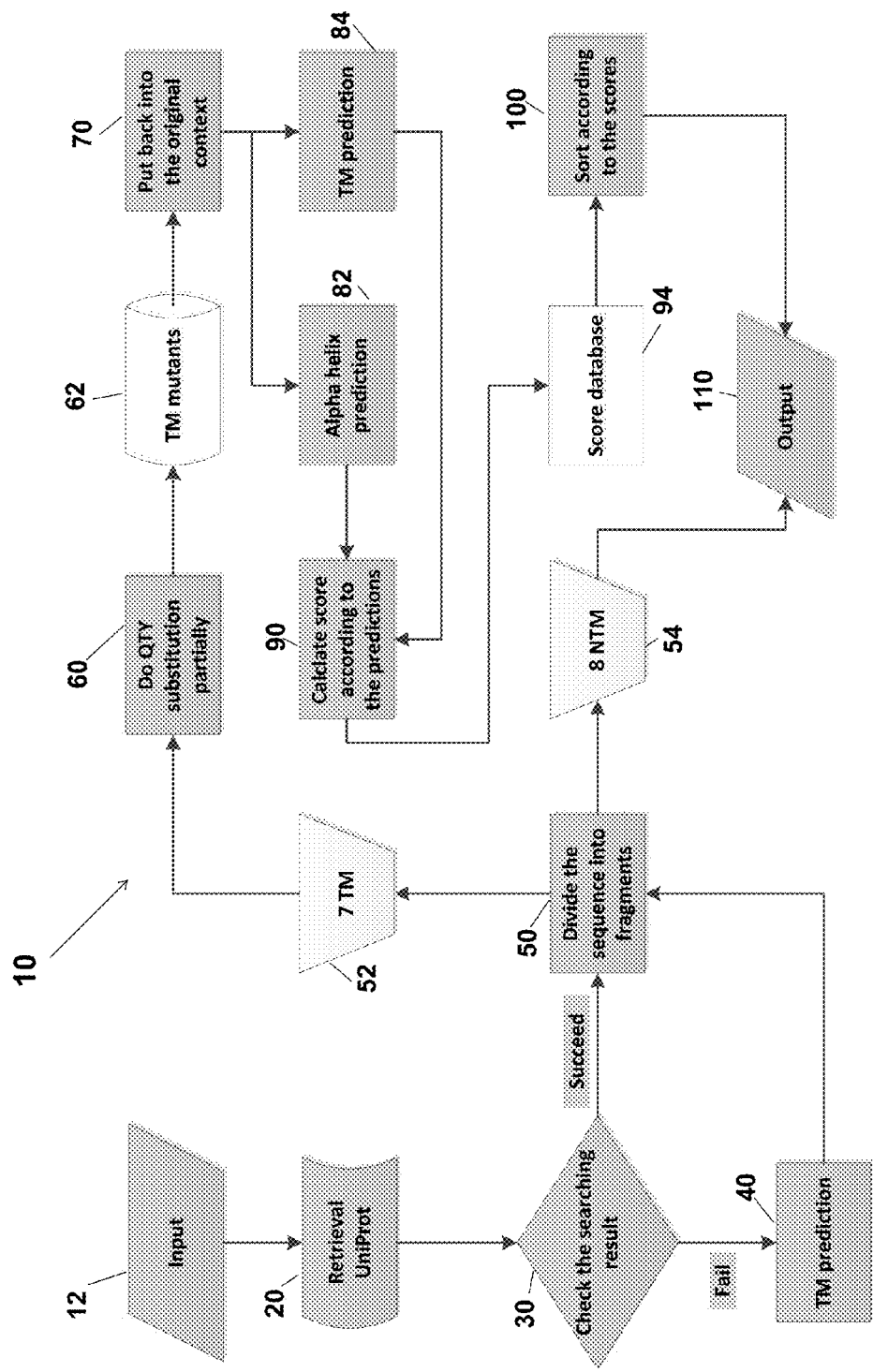
FIG. 9B is another flowchart of a representative embodiment of the process.

FIG. 9A illustrates one embodiment of the invention that is non-limiting. It generally illustrates a method 200 of the invention in which selected hydrophobic amino acids L, I, V, and F in the TM region of the proteins (e.g., GPCR) are replaced according to the "QTY Code" of the invention, without limiting the substitutions in any particular TM region/domain.

In that specific embodiment, the process starts 202 by acquiring or reading 204 an input of a protein sequence which may or may not be a transmembrane protein. The protein sequence can then be subject to TM region prediction 206 (if such information is not already available from the input protein sequence) and alpha-helical secondary structure prediction based on any of art-recognized methods. The TM region prediction, for example, can be performed using a program 240 such as the TMHMM program. If the prediction does not yield any TM region at 242, it may be possible that one or more different TM region prediction programs 250, such as SOSUI, can be used to predict the presence/absence of TM region. If no TM region is predicted based on such programs at 252, it is likely that no TM region exists in the protein 254, and the process will terminate 260.

On the other hand, if one or more TM region(s) are predicted by any of the suitable programs at 242, the TM region protein sequences are obtained 244, and the QTY Code of the invention can be applied to the hydrophobic amino acids L, I, V, and F within such TM region(s). More specifically, according to the QTY code, each leucine in the TM regions can be independently substituted 212 by glutamine (Q), serine (S), or asparagine (N), or remain unsubstituted; each isoleucine and valine in the TM regions can be independently substituted by threonine (T), serine (S), or asparagine (N), or remain unsubstituted; and each phenylalanine in the TM regions can be substituted by tyrosine (Y), or remain unsubstituted. The result of such QTY substitution produces one or more putative water-soluble variants of the original transmembrane protein. Note that the number of substitutions made for each amino acid in a region can be selected as a parameter.

Next, the alpha-helical secondary structures in each putative water-soluble variant can be predicted using any art-recognized programs, such as PORTER 210. The result can be compared to that of the original protein 208, preferably predicted using the same program (e.g., PORTER). Note that the alpha-helical secondary structure of the original protein can be predicted using any art-recognized program, wither before, concurrently, or after the TM region prediction step of the original protein.

If the result of the alpha-helical secondary structure prediction shows that the potential water-soluble variant has maintained or largely maintained the same alpha-helical secondary structure as the original protein at 214, it suggests that the specific pattern of QTY substitution in that variant does not or does not significantly affect the alpha-helical secondary structure in the original protein. The TM regions' prediction can then be conducted 220, verified 222, and the mutant sequence generated 224. Optionally, if the result shows that one or more of the alpha-helical secondary structure(s) in the original protein is destroyed at 214, the variant can be discarded at this step as undesirable, thus terminating the process.

On the other hand, the method of the invention also requires the predicted QTY variant to show less or no propensity to form TM region, as compared to the original protein. Thus the putative water-soluble variant can be subject to TM region prediction, such as using the same TM region prediction program used for the initial TM region prediction (if necessary) in the original protein. If the result shows that significant TM region still exist, the variant may be discarded. On the other hand, if the result shows that no TM region exists, or the propensity of forming TM regions is low, the variant can be selected as the desired variant having enhanced water-solubility over the original protein, while having maintained the alpha-helical secondary structure and hence likely the function of the original protein.

If desired, additional steps can be performed to provide further characterization of the resulting water-soluble variant. Such additional characterization may include calculating 226 the pI of the variant and compare it to that of the original protein. The pI should have no change or very little change (i.e. less than 30 percent, or preferably less than 20 percent or more preferably less than 10 percent). Other additional characterization may include creating a helical wheel model 246 (such as the one shown in FIG. 3) to show the location and any clustering of the QTY substitutions on any particular TM regions.

Another illustrative embodiment of the invention for designing the transmembrane regions of a protein (e.g., a GPCR) by the QTY Code of the invention can be performed on a computer system, using the representative process 10 described in FIG. 9B, some of the detailed steps are further described below. Many of the steps are optional or can be combined according to the methods of the invention.

1: In step 1, a computer interface of a computer system receives a protein sequence, selected for analysis, and data descriptive of the protein (e.g., the sequence) entered, uploaded or inputted 12 through a computer interface of a computer system. The data entered can be a protein name, a database reference, or a protein sequence. For example, the protein sequence can be uploaded through a computer interface.

2: In step 2, additional data about the protein can be identified, determined, obtained and/or entered, including its name or sequence and entered via the computer interface. One source to obtain 20 protein data is a database named UniProt (www dot uniprot dot org). Alternatively, the method of the invention can store data relating to the protein, or related sequences to the protein, for later retrieval by the user in this step. In embodiments, the program can prompt the user to select a database or file for retrieving additional data (e.g., sequence data) relating to the protein selected for analysis.

3: In step 3, the user can enter, upload, or obtain data identifying the transmembrane regions. For example, the user can be prompted to obtain the data from a public source, such as from UniProt. The information can be verified 30 and collected from the database for use in Step 5.

4: Alternatively or additionally, if the TM region information is not readily available from the input protein sequence, the transmembrane region can nevertheless be established 40 by any art recognized methods. Transmembrane regions are generally characterized by an alpha helical conformation. Transmembrane helix prediction can be predicted, for example, using a software module/package named TMHMM 2.0 (TransMembrane prediction using Hidden Markov Models), developed by Center for Biological Sequence Analysis (www dot cbs dot dtu dot dk slash services slash TMHMM). A version of the software may have problems on peak finding and sometimes fails to find 7-TM regions for a GPCR. Therefore, a modified version of the program may be used when necessary, wherein the peak searching method executed by the computer system introduces a dynamic baseline. Here, for example, in the case of a GPCR, if all seven TM regions using the initial baseline value are not found, the baseline can be changed to a lower value. For example, the default baseline may be set at 0.2. To identify a missing seventh transmembrane region, one can set the baseline value to 0.1. If more than seven TM regions are found, the baseline can be changed to a higher value, such as 0.15, to eliminate spurious TM prediction. For example, when the CCR-2 amino acid sequence was subjected to the TMHMM 2.0 software, only 6 transmembrane regions were initially identified. When the TMHMM 2.0 baseline value was set to 0.07, however, a correct total of 7 transmembrane regions were identified. The result of the TM region prediction is then provided to step 5.

5: in step 5, after identifying the TM data either through de novo prediction or through obtaining such information through the initial sequence input, the sequence of a GPCR is divided 50 into a total of 15 fragments (i.e., 7-transmembrane segments (7TM) 52 and 8 non-transmembrane segments (8NTM)) 54 according to the TM region information. That is, there should be 7TM and 8 NTM fragments for each typical GPCR.

It is understood that the system can execute one or more, such as all of the steps described above, using a computer interface for input by a user. It is also understood that the system can omit one or more of the steps described above, or combine two or more steps.

6: In step 6, QTY substitution 60 is performed partially, on a selected subsets of hydrophobic amino acids L, I, V, and F within a given TM region of the protein. Specifically, a first transmembrane region (typically, but not necessarily, the transmembrane region which is most proximal to the N-terminal of the protein) is first selected for variation. Some or all of the hydrophobic amino acids (L, I, V, and F) in the first transmembrane region are then substituted with the corresponding non-ionic hydrophilic amino acids (Q/S/N, T/S/N, T/S/N, or Y). It is understood that the amino acid is not actually substituted into the protein in this context. Rather, the amino acid designation is substituted in the sequence for modeling. Thus, the term "sequence" is intended to include "sequence data." Typically, most or all of the hydrophobic amino acids are selected for substitution. If less than all amino acids are selected, it may be desirable to select the internal hydrophobic amino acids leaving one or more N and/or C terminal amino acids of the transmembrane regions hydrophobic. Additionally or alternatively, it may be desirable to select to replace all of the leucines (L) in a transmembrane region. Additionally or alternatively, it may be desirable to select and replace all of the isoleucines (I) in a transmembrane region. Additionally or alternatively, it may be desirable to select to replace all of the valines (V) in a transmembrane region. Additionally or alternatively, it may be desirable to select to replace all of the phenylalanines (F) in a transmembrane region. Additionally or alternatively, it can be beneficial to retain one or more phenylalanines in the transmembrane region. Additionally or alternatively, it can be beneficial to retain one or more valines in the transmembrane region. Additionally or alternatively, it can be beneficial to retain one or more leucines in the transmembrane region. Additionally or alternatively, it can be beneficial to retain one or more isoleucines in the transmembrane region. Additionally or alternatively, it can be beneficial to retain one or more hydrophobic amino acids in the transmembrane region where the wild type sequence is characterized by three or more contiguous hydrophobic amino acids.

7: In step 7, the transmembrane region so designed is put back into the context of the original protein. That is, the mutated or re-designed TM region 62 with the QTY substitutions is swapped into the corresponding TM region of the original protein, to create the transmembrane variants 70 or "putative variants," since each sets of substitution creates one specific putative variant for that TM region. Together, these related putative variants form a first library of putative variants.

8: In steps 82 and 84, each putative variant is then subjected to the transmembrane region prediction process (84), as discussed herein (e.g., loss of predicted TM region). The variant is also assessed a score for the sequence's propensity to form an alpha helix (82). The variant is also subjected to a water solubility prediction process, as discussed herein. For example, the variant is assessed a score for the sequence's propensity to be water soluble. Such score may be based on a predicted propensity to form TM regions, with strong propensity to form TM regions being associated with poor water solubility, and low or now propensity to form TM regions being associated with high water solubility. Of course, complete water solubility at all concentrations is not required for most commercial purposes. Water solubility is preferably determined to be that required for functionality at the predicted conditions of use (e.g., in a ligand binding assay).

9: In step 9, putative variants that predict loss of alpha helical structure and/or "water insolubility" (predicted at the expected conditions of use) are discarded. Putative variants that predict alpha helical structure and water solubility can be selected, such as by using the combined score or rank 90 that is a weighted combination based on a ranking function of the alpha-helical secondary structure prediction result and the TM region/water solubility prediction result. For example, one can select transmembrane variants that are highly water soluble, or are characterized by 0, 1, 2, or 3 hydrophobic amino acids (e.g., higher weight for the water solubility prediction result), with a possible expectation that alpha helical structure can be compromised. Alternatively or additionally, one can select highly alpha-helical structures (e.g., higher weight for the alpha helical secondary structure prediction result), characterized by 3, 4, 5 or 6 hydrophobic amino acids.

10: In step 10, the putative variants in the same library 94 can be sorted or ranked 100 based on the score calculation scheme outlined above. Then a pre-determined number of putative variants can be selected as the final members in the first putative variant library. For example, in the combined score described above, a score of 0 means no propensity to form TM region, and complete maintenance of the original alpha helical secondary structure, and is thus the most desired putative variant. A slightly higher score may indicate a slight propensity to form TM region (or a less propensity of being water soluble). Thus the putative variant is less desirable but may still be selected based on its superior combined score compared to the other putative variants in the library.

In certain embodiments, a pre-determined number of desired putative variants can be selected, such as 10, 9, 8, 7, 6, 5, 4, 3, 2, or 1.

These steps (e.g., steps 6-10) can be repeated for a second, third, fourth, fifth, sixth and/or seventh (or more) transmembrane region or domain to create one putative variant library for each such TM regions or domains.

11: In step 11, one can select 110 a combination of the TM regions or domains with the putative variants and the unsubstituted non-TM regions. For example, one, two, three or four domains with putative variants possessing high alpha-helical structure scores and one, two, three, four, five, or six domains with putative variants possessing high water solubility scores can be combined. In another example, one can combine a domain/TM region that is characterized by all hydrophobic amino acids being substituted by a hydrophilic amino acid, thus maximizing the water solubility score, and a second domain/TM region that retains 3, 4, or 5 hydrophobic amino acids in a plurality of variant selections. Such selected putative variants can be "shuffled," as is known in the art, with the extracellular and intracellular domains to create an initial combinatorial library of putative water-soluble protein variants.

In certain embodiments, all or a fraction of the putative water soluble protein variants of the initial combinatorial library designed as described herein can be made (produced or expressed in vitro or in a host cell) and screened for water solubility and/or ligand binding, preferably in a high through-put screen. Amplification of the library, for example, can result in less than 100% of the putative water-soluble protein combinatorial variants from being expressed. A reporter system can be used to screen ligand binding, as is well known in the art. Using the methods of the invention, one can rapidly identify a library of putative water soluble modified transmembrane combinatorial variants that contain functionally combined extracellular and intracellular domains, and generate water soluble protein variants possessing the proper 3 dimensional structure of the wild type protein, and retaining ligand binding function (including binding affinity), or other functions. The software can include a learning module in which verified functionality of protein variants is used to eliminate certain variants or rank them differently.

In certain embodiments, to be practical experimentally, the initial combinatorial library has about 2 million potentially water-soluble GPCR, or CXCR4, variants. Of course, a library of more or less variants can be designed as well. Smaller libraries may be preferred in certain embodiments since they can be optimized based on analysis of the research results as described herein. Analysis of research results is likely to establish trends to optimize the number of domain variants to shuffle and the assumptions for selecting domain variants.

In certain embodiments, certain hydrophobic amino acids in the TM region of the transmembrane proteins are selected for modification based on the helical forming propensity also known as "the helix prediction score" (see www dot proteopedia dot org slash wiki slash index dot php slash Main_Page). The varied fragments are randomly assembled to form about 2M ($8^7$) variants of full-length GPCR genes. The predicted number of variants can generally be characterized by the formula $H^n$, where n=the number of transmembrane regions modified and/or varied by the method (in the example of GPCR, n=7) and H=the number of putative variants in each transmembrane region available for generating the combinatorial variants.

Once the initial combinatorial library, or selection of the domain variants to be shuffled, is selected, nucleic acid molecules, or DNA or cDNA molecules, encoding the proteins in the initial combinatorial library can be designed. The nucleic acid molecules are preferably designed to provide codon optimization and intron deletions for the expression systems selected to produce a library of coding sequences. For example, if the expression system is *E. coli*, codons optimized for *E. coli* expression can be selected. See www dot dna20 dot com slash resources slash gene designer. In addition, a promoter region, such as a promoter suitable for expression in the expression system (e.g., *E. coli*) is selected and operatively connected to the coding sequences in the library of coding sequences.

The initial library of coding sequences, or a portion thereof, is then expressed to produce a library of putative water soluble GPCRs. The library is then subjected to a ligand binding assay. In the binding assay, the putative water soluble GPCRs are contacted with the ligand, preferably in an aqueous medium and ligand binding is detected.

The invention includes transmembrane domain variants, and nucleic acid molecules encoding same, obtained, or obtainable, from the methods described herein.

The invention also contemplates water soluble GPCR variants ("sGPCRs") characterized by a plurality of transmembrane domains independently characterized by at least 50%, preferably at least about 60%, more preferably at least about 70% or 80%, such as at least about 90%) of the hydrophobic amino acid residues (L, I, V, and F) of a native transmembrane protein (e.g., GPCR) substituted by a Q, T, T, or Y, respectively). The sGPCRs of the invention are characterized by water solubility and ligand binding. In particular, the sGPCR binds the same natural ligand as the corresponding native GPCR.

The invention further encompasses a method of treatment for a disorder or disease that is mediated by the activity of a membrane protein, comprising the use of a water-soluble polypeptide to treat said disorders and diseases, wherein said water-soluble polypeptide comprises a modified α-helical domain, and wherein said water-soluble polypeptide retains the ligand-binding activity of the native membrane protein. Examples of such disorders and diseases include, but are not limited to, cancer, small cell lung cancer, melanoma, breast cancer, Parkinson's disease, cardiovascular disease, hypertension, and asthma.

As described herein, the water-soluble peptides described herein can be used for the treatment of conditions or diseases mediated by the activity of a membrane protein. In certain aspects, the water-soluble peptides can act as "decoys" for the membrane receptor and bind to the ligand that otherwise activates the membrane receptor. As such, the water-soluble peptides described herein can be used to reduce the activity of a membrane protein. These water-soluble peptides can remain in the circulation and competitively bind to specific ligands, thereby reducing the activity of membrane bound receptors. For example, the GPCR CXCR4 is over-expressed in small cell lung cancer and facilitates metastasis of tumor cells. Binding of this ligand by a water-soluble peptide such as that described herein may significantly reduce metastasis.

The chemokine receptor, CXCR4, is known in viral research as a major coreceptor for the entry of T cell line-tropic HIV (Feng et al. (1996) *Science* 272: 872-877; Davis et al. (1997) *J Exp Med* 186: 1793-1798; Zaitseva et al. (1997) *Nat Med* 3: 1369-1375; Sanchez et al. (1997) *J Biol Chem* 272: 27529-27531). Stromal cell derived factor 1 (SDF-1) is a chemokine that interacts specifically with CXCR4. When SDF-1 binds to CXCR4, CXCR4 activates Gαi protein-mediated signaling (pertussis toxin-sensitive) (Chen et al. (1998) *Mol Pharmacol* 53: 177-181), including downstream kinase pathways such as Ras/MAP Kinases and phosphatidylinositol 3-kinase (PI3K)/Akt in lymphocyte, megakaryocytes, and hematopoietic stem cells (Bleul et al. (1996) *Nature* 382: 829-833; Deng et al. (1997) *Nature* 388: 296-300; Kijowski et al. (2001) *Stem Cells* 19: 453-466; Majka et al. (2001) *Folia. Histochem. Cytobiol.* 39: 235-244; Sotsios et al. (1999) *J. Immunol.* 163: 5954-5963; Vlahakis et al. (2002) *J. Immunol.* 169: 5546-5554). In mice transplanted with human lymph nodes, SDF-1 induces CXCR4-positive cell migration into the transplanted lymph node (Blades et al. (2002) *J. Immunol.* 168: 4308-4317).

Recently, studies have shown that CXCR4 interactions may regulate the migration of metastatic cells. Hypoxia, a reduction in partial oxygen pressure, is a microenvironmental change that occurs in most solid tumors and is a major inducer of tumor angiogenesis and therapeutic resistance. Hypoxia increases CXCR4 levels (Staller et al. (2003) *Nature* 425: 307-311). Microarray analysis on a sub-population of cells from a bone metastatic model with elevated metastatic activity showed that one of the genes increased in the metastatic phenotype was CXCR4. Furthermore, overexpression CXCR4 in isolated cells significantly increased the metastatic activity (Kang et al. (2003) *Cancer Cell* 3: 537-549). In samples collected from various breast cancer patients, Muller et al. (Muller et al. (2001) *Nature* 410: 50-56) found that CXCR4 expression level is higher in primary tumors relative to normal mammary gland or epithelial cells. Moreover, CXCR4 antibody treatment has been shown to inhibit metastasis to regional lymph nodes when compared to control isotypes that all metastasized to lymph nodes and lungs (Muller et al. (2001). As such a decoy therapy model is suitable for treating CXCR4 mediated diseases and disorders.

In another embodiment of the invention relates to the treatment of a disease or disorder involving CXCR4-dependent chemotaxis, wherein the disease is associated with aberrant leukocyte recruitment or activation. The disease is selected from the group consisting of arthritis, psoriasis, multiple sclerosis, ulcerative colitis, Crohn's disease, allergy, asthma, AIDS associated encephalitis, AIDS related maculopapular skin eruption, AIDS related interstitial pneumonia, AIDS related enteropathy, AIDS related periportal hepatic inflammation and AIDS related glomerulo nephritis.

In another aspect, the invention relates to the treatment of a disease or disorder selected from arthritis, lymphoma, non-small lung cancer, lung cancer, breast cancer, prostate cancer, multiple sclerosis, central nervous system developmental disease, dementia, Parkinson's disease, Alzheimer's disease, tumor, fibroma, astrocytoma, myeloma, glioblastoma, an inflammatory disease, an organ transplantation rejection, AIDS, HIV-infection or angiogenesis.

The invention also encompasses a pharmaceutical composition comprising said water-soluble polypeptide and a pharmaceutically acceptable carrier or diluent.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above. Langer, *Science* 249: 1527, 1990; and Hanes, *Advanced Drug Delivery Reviews* 28: 97-119, 1997. The compositions and pharmacologic agents described herein can be administered in the form of a depot injection or implant preparation which can be formulated in such a manner as to permit a sustained or pulsatile release of the active ingredient.

Transdermal administration includes percutaneous absorption of the composition through the skin. Transdermal formulations include patches, ointments, creams, gels, salves and the like. Transdermal delivery can be achieved using a skin patch or using transferosomes. See Paul et al., *Eur. J. Immunol.* 25: 3521-24, 1995; and Cevc et al., *Biochem. Biophys. Acta* 1368: 201-15, 1998.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment.

An "effective amount" refers to that amount of the therapeutic agent that is sufficient to ameliorate one or more symptoms of a disorder and/or prevent advancement of a disorder, cause regression of the disorder and/or to achieve a desired effect.

Computer System

Various aspects and functions described herein may be implemented as specialized hardware or software components executing in one or more computer systems. There are many examples of computer systems that are currently in use. These examples include, among others, network appliances, personal computers, workstations, mainframes, networked clients, servers, media servers, application servers, database servers, and web servers. Other examples of computer systems may include mobile computing devices, such as cellular phones and personal digital assistants, and network equipment, such as load balancers, routers, and switches. Further, aspects may be located on a single computer system or may be distributed among a plurality of computer systems connected to one or more communications networks.

For example, various aspects, functions, and processes may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, embodiments are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Figure 10:
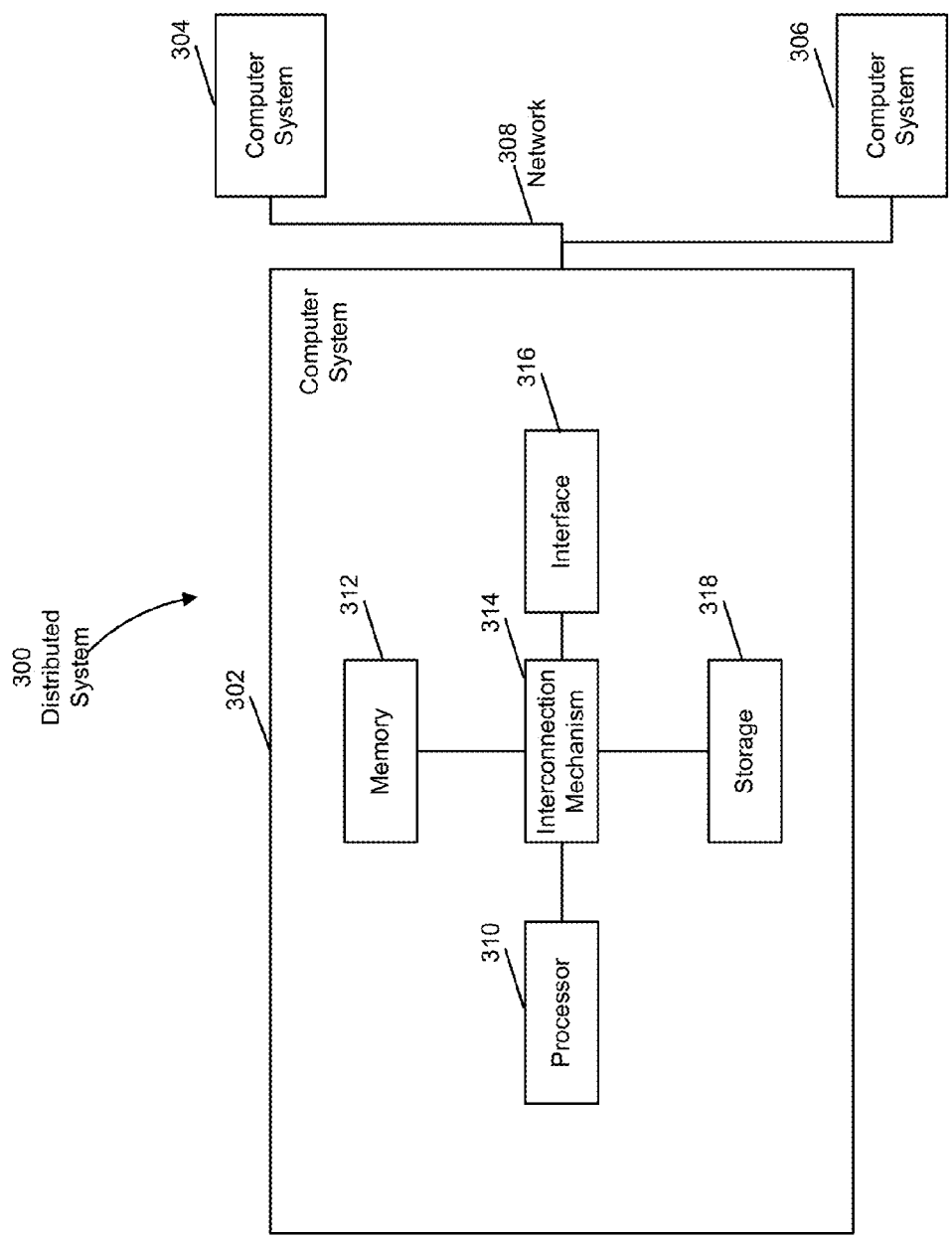
FIG. 10 is an illustration of the computer systems of the invention.

Referring to FIG. 10, there is illustrated a block diagram of a distributed computer system 300, in which various aspects and functions are practiced. As shown, the distributed computer system 300 includes one or more computer systems that exchange information. More specifically, the distributed computer system 300 includes computer systems 302, 304, and 306. As shown, the computer systems 302, 304, and 306 are interconnected by, and may exchange data through, a communication network 308. The network 308 may include any communication network through which computer systems may exchange data. To exchange data using the network 308, the computer systems 302, 304, and 306 and the network 308 may use various methods, protocols and standards. Examples of these protocols and standards include NAS, Web, storage and other data movement protocols suitable for use in a big data environment. To ensure data transfer is secure, the computer systems 302, 304, and 306 may transmit data via the network 308 using a variety of security measures including, for example, SSL or VPN technologies. While the distributed computer system 300 illustrates three networked computer systems, the distributed computer system 300 is not so limited and may include any number of computer systems and computing devices, networked using any medium and communication protocol.

As illustrated in FIG. 10, the computer system 302 includes a processor 310, a memory 312, an interconnection element 314, an interface 316 and data storage element 318. To implement at least some of the aspects, functions, and processes disclosed herein, the processor 310 performs a series of instructions that result in manipulated data. The processor 310 may be any type of processor, multiprocessor or controller. Example processors may include a commercially available processor such as an Intel Xeon, Itanium, Core, Celeron, or Pentium processor; an AMD Opteron processor; an Apple A4 or A5 processor; a Sun UltraSPARC processor; an IBM Power5+ processor; an IBM mainframe chip; or a quantum computer. The processor 310 is connected to other system components, including one or more memory devices 312, by the interconnection element 314.

The memory 312 stores programs (e.g., sequences of instructions coded to be executable by the processor 310) and data during operation of the computer system 302. Thus, the memory 312 may be a relatively high performance, volatile, random access memory such as a dynamic random access memory ("DRAM") or static memory ("SRAM"). However, the memory 312 may include any device for storing data, such as a disk drive or other nonvolatile storage device. Various examples may organize the memory 312 into particularized and, in some cases, unique structures to perform the functions disclosed herein. These data structures may be sized and organized to store values for particular data and types of data.

Components of the computer system 302 are coupled by an interconnection element such as the interconnection element 314. The interconnection element 314 may include any communication coupling between system components such as one or more physical busses in conformance with specialized or standard computing bus technologies such as IDE, SCSI, PCI and InfiniBand. The interconnection element 314 enables communications, including instructions and data, to be exchanged between system components of the computer system 302.

The computer system 302 also includes one or more interface devices 316 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 302 to exchange information and to communicate with external entities, such as users and other systems.

The data storage element 318 includes a computer readable and writeable nonvolatile, or non-transitory, data storage medium in which instructions are stored that define a program or other object that is executed by the processor 310. The data storage element 318 also may include information that is recorded, on or in, the medium, and that is processed by the processor 310 during execution of the program. More specifically, the information may be stored in one or more data structures specifically configured to conserve storage space or increase data exchange performance. The instructions may be persistently stored as encoded signals, and the instructions may cause the processor 310 to perform any of the functions described herein. The medium may, for example, be optical disk, magnetic disk or flash memory, among others. In operation, the processor 310 or some other controller causes data to be read from the nonvolatile recording medium into another memory, such as the memory 312, that allows for faster access to the information by the processor 310 than does the storage medium included in the data storage element 318. The memory may be located in the data storage element 318 or in the memory 312, however, the processor 310 manipulates the data within the memory, and then copies the data to the storage medium associated with the data storage element 318 after processing is completed. A variety of components may manage data movement between the storage medium and other memory elements and examples are not limited to particular data management components. Further, examples are not limited to a particular memory system or data storage system.

Although the computer system 302 is shown by way of example as one type of computer system upon which various aspects and functions may be practiced, aspects and functions are not limited to being implemented on the computer system 302 as shown in FIG. 10. Various aspects and functions may be practiced on one or more computers having a different architectures or components than that shown in FIG. 10. For instance, the computer system 302 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 302 may be a computer system including an operating system that manages at least a portion of the hardware elements included in the computer system 302. In some examples, a processor or controller, such as the processor 310, executes an operating system. Examples of a particular operating system that may be executed include a Windows-based operating system, such as, Windows NT, Windows 2000 (Windows ME), Windows XP, Windows Vista or Windows 7 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Oracle Corporation, or a UNIX operating systems available from various sources. Many other operating systems may be used, and examples are not limited to any particular operating system.

The processor 310 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, $C^{++}$, Ada, C# (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in $C^{++}$. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user space application) or in a commonly shared data structure (such as an application registry that is defined by an operating system). In addition, some examples provide for both system and user interfaces that allow external entities to modify the parameters and thereby configure the behavior of the components.

Figure 11B:
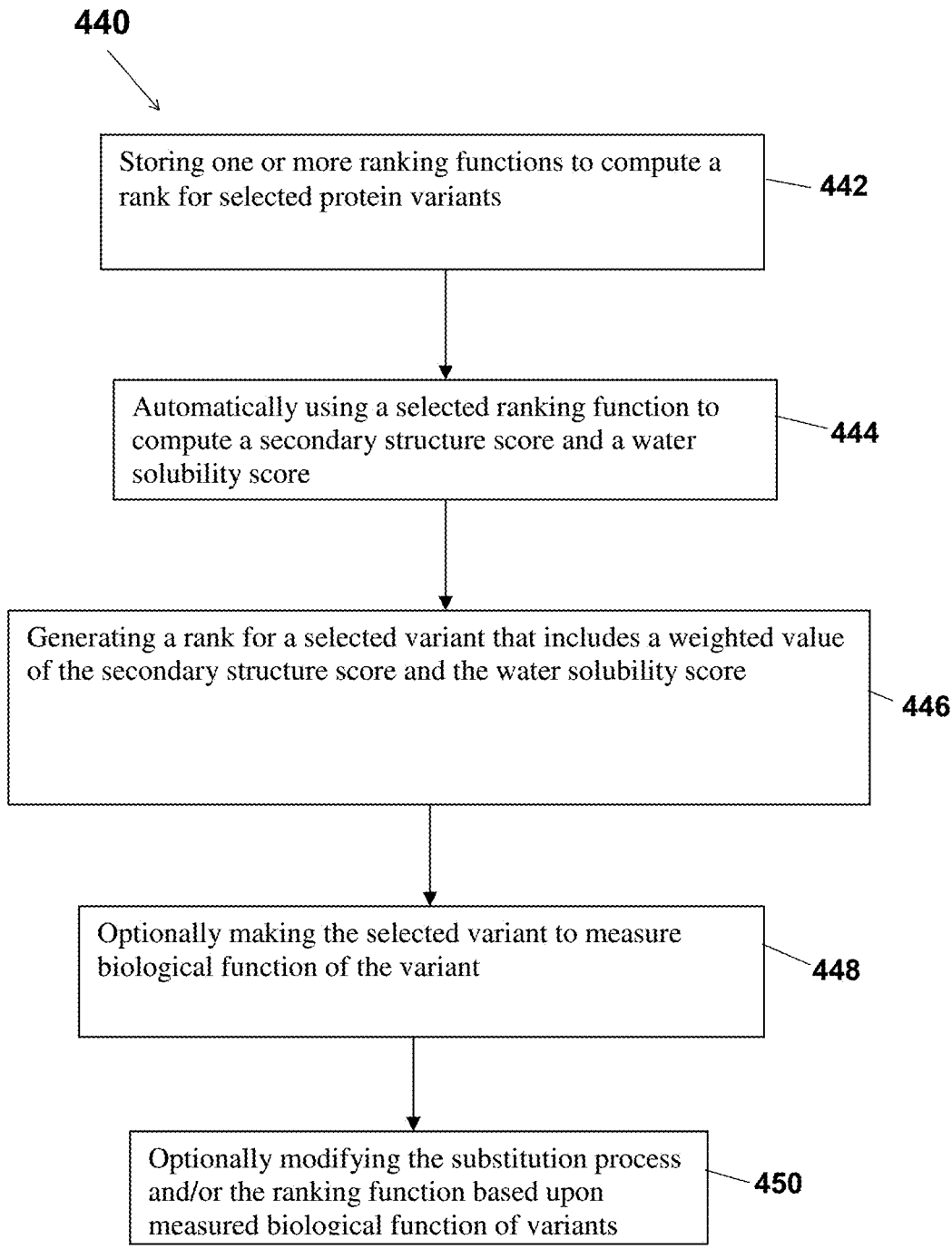

The software is generally depicted in FIG. 11A to perform a computational method in which the user selects operating parameters to execute a procedure on a computer 402, as previously described herein, where one or more sequences are entered 404, and substitutions are performed 408. The system is operative to verify secondary structures 408 and verify water solubility for the one or more variants. As shown in FIG. 11B, the program can include additional processing options in addition to those previously described, wherein one or more ranking functions 442 can be stored, the user can select or the system can automatically select 444 the ranking function to be used. The system can then generate a rank 446 as described herein, and then a user can make 448 a selected variant to measure function 448, and subsequently enter functional data to modify the processing sequence 450 based thereon.

The invention will be better understood in connection with the following example, which is intended as an illustration only and not limiting of the scope of the invention. Various changes and modifications to the disclosed embodiments will be apparent to those skilled in the art and such changes and may be made without departing from the spirit of the invention and the scope of the appended claims.

EXAMPLES

Example 1: CXC Chemokine Receptor Type 4 Isoform a (CXCR4)

CXCR4 is a chemokine receptor 356 amino acids in length. It has a pI of about 8.61 and a Molecular Weight of 40221.19 Da. The sequence for CXCR4, as published in the literature, is:

(SEQ ID NO. 1)
MSIPLPLLQIYTSDNYTEEMGSGDYDSMKEPCFREENANFNKIFLPTIYS

IIFLTGIVGNGLVILVMGYQKKLRSMTDKYRLHLSVADLLFVITLPFWAV

DAVANWYFGNFLCKAVHVIYTVNLYSSVLILAFISLDRYLAIVHATNSQR

PRKLLAEKVVYVGVWIPALLLTIPDFIFANVSEADDRYICDRFYPNDLWV

VVFQFQHIMVGLILPGIVILSCYCIIISKLSHSKGHQKRKALKTTVILIL

AFFACWLPYYIGISIDSFILLEIIKQGCEFENTVHKWISITEALAFFHCC

LNPILYAFLGAKFKTSAQHALTSVSRGSSLKILSKGKRGGHSSVSTESES

SSFHSS.

Figure 3:
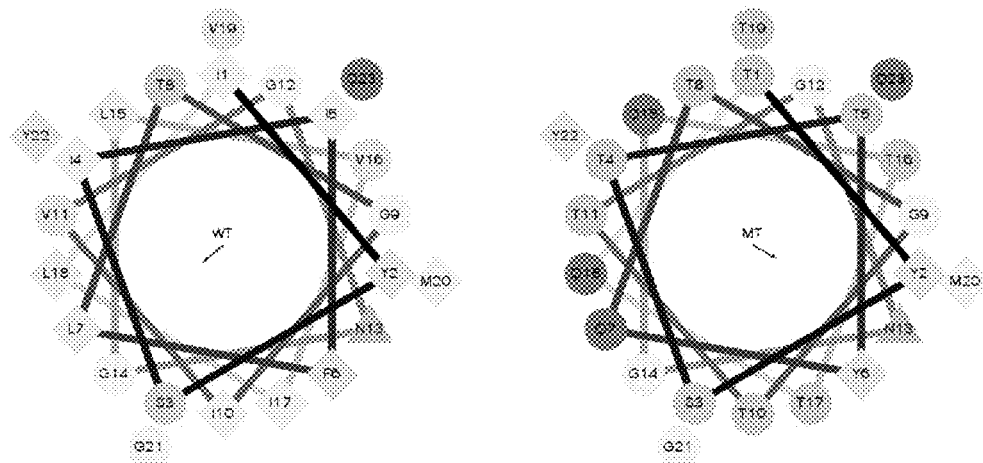
FIG. 3 illustrates the predicted alpha helical wheel structure of the fully QTY Code modified TM1 domain of CXCR4.

Subjecting the sequence to TMHMM results in the identification of the transmembrane domains as depicted in FIG. 3.

Replacing all or substantially all of the hydrophobic amino acids, L, I V, and F, with Q, T and Y (respectively) results in the following sequence:

-continued (SEQ ID NO. 5)

IFQPTTYSTTFQTGTTGNGQVTQVM (SEQ ID NO. 6)

IFQPTTYSTTFQTGTTGNGQVTQTM (SEQ ID NO. 7)

IFQPTTYSTTYQTGTTGNGQVTQTM (SEQ ID NO. 8)

IFQPTTYSTTYQTGTTGNGQTTQVM (SEQ ID NO. 9)

IFQPTTYSTTYQTGTTGNGQTIQTM (SEQ ID NO. 10)

IFQPTTYSTTYQTGTTGNGQTTQTM (SEQ ID NO. 11)

TYQPTTYSTTYQTGTTGNGQTTQTM (SEQ ID NO: 2)

1 MSIPLPLLQIYTSDNYTEEMGSGDYDSMKEPCFREENANFNKIFLPTTYSTTYQTGTTGN
61 GQTTQTMGYQKKLRSMTDKYRQHQSTADQQYTTTQPYWATDAVANWYFGNFLCKATHTTY
121 TTNQYSSTQTQAYTSQDRYLAIVHATNSQRPRKLLAEKTTYTGTWTPAQQQTTPDYTYAN
181 VSEADDRYICDRFYPNDLWVVVYQYQHTMTGQTQPGTTTQSCYCTIISKLSHSKGHQKRK
241 ALKTTTTQTQAYYACWQPYYTGTSTDSYILLEIIKQGCEFENTVHKWTSTTEAQAYYHCC
301 QNPTQYAYQGAKFKTSAQHALTSVSRGSSLKILSKGKRGGHSSVSTESESSSFHSS.

The predicted pI of the protein is 8.54 and the Molecular Weight is 40551.64 Da. Each of the predicted transmembrane regions has been underlined and exemplified a fully modified domain of the invention. Thus, for example, the invention includes a transmembrane domain comprising Amino Acids 47-70 of SEQ ID NO: 2 (TM1), and proteins comprising the same. As an example, FIG. 3 represents the alpha-helical prediction of the TM1 sequence. Preferably the protein comprising TM1 herein includes one or more (e.g., all) of the extracellular and intracellular loop sequences of SEQ ID NO: 2 (the sequences which have not been underlined). In addition or alternatively, the protein comprising the TM1 herein includes one or more additional transmembrane regions (the underlined sequences) in SEQ ID NO: 2 or homologous sequences retaining one, two, three or, possibly four or more of the native L, I V and F amino acids, as set forth in SEQ ID NO: 1.

The native protein sequence for CXCR4 (differing in the N-terminal amino acids) was subjected to the method a second time. The program output divided the native sequence into the extracellular and intracellular regions and selected 8 transmembrane domain variants for each transmembrane domain. The results are illustrated in FIG. 4 and in the following table:

(SEQ ID NO. 3; EC1)

MEGISIYTSDNYTEEMGSGDYDSMKEPCFREENANFNK

TM 1 Variants:

(SEQ ID NO. 4)

IFLPTTYSTTFQTGTTGNGQVTQVM

-continued (SEQ ID NO. 12; IC1)

GYQKKLRSMTDKYR

TM 2 Variants:

(SEQ ID NO. 13)

LHLSTADQQFTTTQPFWAVDAV (SEQ ID NO. 14)

LHLSVADQQYTTTQPFWATDAV (SEQ ID NO. 15)

LHQSVADQQYVTTQPFWATDAT (SEQ ID NO. 16)

QHQSVADQQFTTTQPFWATDAT (SEQ ID NO. 17)

LHQSVADQQYTITQPYWATDAT (SEQ ID NO. 18)

QHLSVADQQYTITQPYWATDAT (SEQ ID NO. 19)

QHLSTADQQYVTTQPYWATDAT (SEQ ID NO. 20)

QHQSTADQQYTTTQPYWATDAT (SEQ ID NO. 21; EC2)

ANWYFGNFLCK

TM 3 Variants:

(SEQ ID NO. 22)

AVHVTYTVNQYSSVQIQAFT (SEQ ID NO. 23)

AVHTTYTVNQYSSVQIQAFT

-continued

AVHTTYTVNQYSSVQTQAFT (SEQ ID NO. 24)

ATHTTYTVNQYSSVQTQAFT (SEQ ID NO. 25)

ATHTIYTTNQYSSVQTQAFT (SEQ ID NO. 26)

AVHTTYTTNQYSSVQTQAFT (SEQ ID NO. 27)

ATHTTYTTNQYSSVQTQAFT (SEQ ID NO. 28)

ATHTTYTTNQYSSTQTQAYT (SEQ ID NO. 29)

SLDRYLAIVHATNSQRPRKLLAEK (SEQ ID NO. 30; IC2)

TM 4 Variants:

VTYTGVWTPAQQQTIPDFIF (SEQ ID NO. 31)

TTYTGTWIPAQQQTIPDFIF (SEQ ID NO. 32)

TTYTGTWTPAQQQTIPDFIF (SEQ ID NO. 33)

TTYTGTWTPAQQQTIPDFIY (SEQ ID NO. 34)

TTYVGTWTPAQQQTTPDYIF (SEQ ID NO. 35)

TTYVGTWTPAQQQTTPDFIY (SEQ ID NO. 36)

TTYTGVWTPAQQQTTPDYTF (SEQ ID NO. 37)

TTYTGTWTPAQQQTTPDYTY (SEQ ID NO. 38)

ANVSEADDRYICDRFYPNDLW (SEQ ID NO. 39; EC3)

TM 5 Variants:

VVVFQFQHTMVGQTQPGTTTQ (SEQ ID NO. 40)

VVVFQFQHTMTGQTQPGTTTQ (SEQ ID NO. 41)

VVVFQYQHTMTGQTQPGTTTQ (SEQ ID NO. 42)

VVVYQYQHTMTGQTQPGTTTQ (SEQ ID NO. 43)

TVVFQYQHTMTGQTQPGTTTQ (SEQ ID NO. 44)

VVTFQYQHTMTGQTQPGTTTQ (SEQ ID NO. 45)

TVVYQYQHTMTGQTQPGTTTQ (SEQ ID NO. 46)

TTTYQYQHTMTGQTQPGTTTQ (SEQ ID NO. 47)

SCYCIIISKLSHSKGHQKRKALKTT (SEQ ID NO. 48; IC3)

TM 6 Variants:

VTQIQAFFACWQPYYTGTST (SEQ ID NO. 49)

VIQIQAYFACWQPYYTGTST (SEQ ID NO. 50)

VIQIQAYYACWQPYYTGTST (SEQ ID NO. 51)

VIQTQAFYACWQPYYTGTST (SEQ ID NO. 52)

VIQTQAYFACWQPYYTGTST (SEQ ID NO. 53)

VTQIQAFYACWQPYYTGTST (SEQ ID NO. 54)

VIQTQAYYACWQPYYTGTST (SEQ ID NO. 55)

TTQTQAYYACWQPYYTGTST (SEQ ID NO. 56)

DSFILLEIIKQGCEFENTVHK (SEQ ID NO. 57; EC4)

TM 7 Variants

WISITEAQAFFHCCLNPIQY (SEQ ID NO. 58)

WISITEAQAFYHCCLNPIQY (SEQ ID NO. 59)

WISITEAQAYFHCCQNPTLY (SEQ ID NO. 60)

WISTTEALAFYHCCQNPTQY (SEQ ID NO. 61)

WISTTEALAYFHCCQNPTQY (SEQ ID NO. 62)

WISITEALAYYHCCQNPTQY (SEQ ID NO. 63)

WISTTEALAYYHCCQNPTQY
WTSTTEAQAYYHCCQNPTQY (SEQ ID NO. 64)

AFLGAKFKTSAQHALTSVSRGSSLKILSKGKRGGHSSVSTESESSSF (SEQ ID NO. 65; IC4)
HSS.

It is believed that it is clear from the above, that the sequences (SEQ ID NOs: 3, 12, 21, 30, 39, 48, 57 and 65) before, between and after each list of transmembrane domain variants are the N', intermediary and C' extracellular and intracellular regions, respectively.

The sequences above were then used to generate coding sequences, as is known in the art, suitable for expression in the expression system, in this case yeast. The coding sequences were then shuffled and expressed to produce a library comprising a plurality of proteins each having SEQ ID NOs: 3, 12, 21, 30, 39, 48, 57 and 65 with one transmembrane domain variant from each variant list in between the respective intracellular and extracellular domain.

Figure 5:
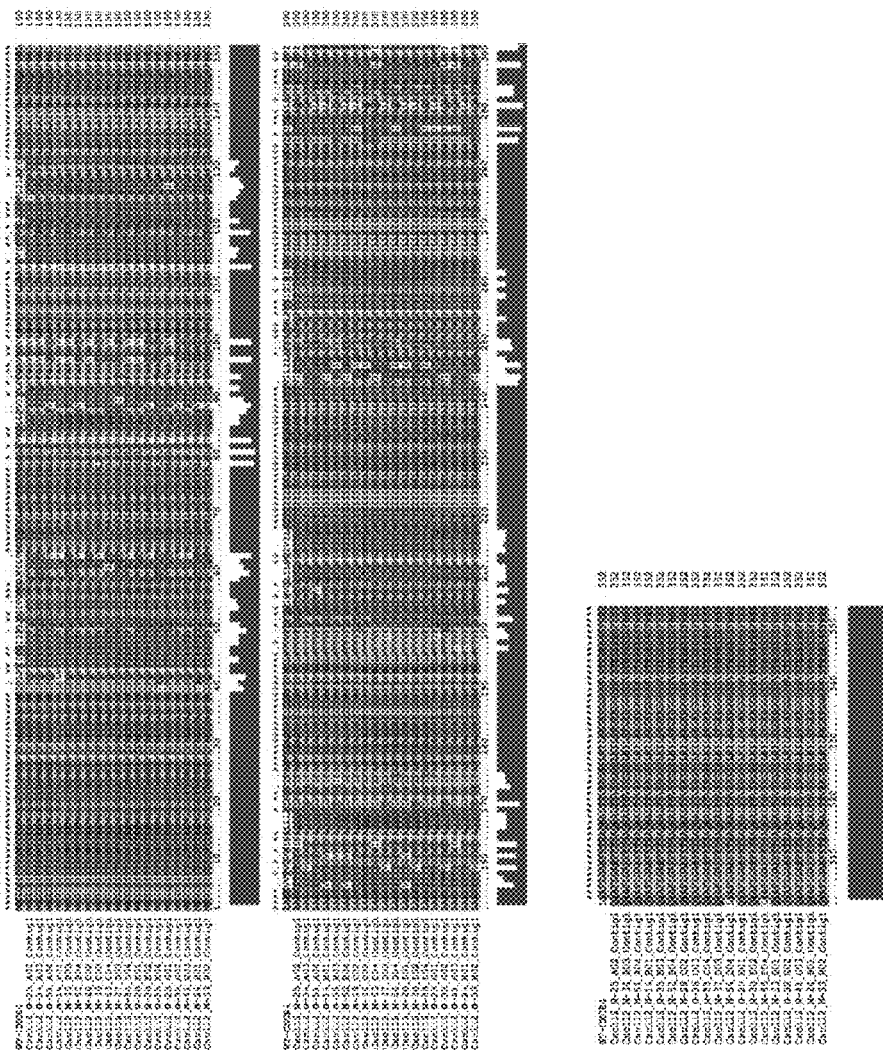
FIGS. 5, 6, 7, and 8 are sequence alignments of the wild type proteins and QTY variants of CXCR4, CXCR3, CCR3 and CCR5, respectively. QTY Code is only applied to the 7 hydrophobic transmembrane segments, but not the extracellular and intracellular segments.

The library so produced was then assayed for CXCR4 cognate ligand, SDF1a (or CCL12) on a plasmid expressed in yeast binding inside living yeast cells. Ligand binding was detected by gene activation from the yeast 2-hybrid system and samples were then sequenced. Nineteen CXCR4 variants were sequenced. The results are shown in FIG. 5.

Example 2: CXC Chemokine Receptor Type 3 Isoform b (CX3CR1)

CX3CR1 is a chemokine receptor 355 amino acids in length. It has a pI of about 6.74 and a Molecular Weight of 40396.4 Da. The subjecting of the sequence to TMHMM results in the identification of the transmembrane domains. Replacing all or substantially all of the hydrophobic amino acids, L, I V, and F, with Q, T and Y (respectively) within the transmembrane domains results in the following sequence (lower line), aligned with the wild type (top line):

```
MDQFPESVTENFEYDDLAEACYIGDIVVFGTVFLSIFYSVIFAIGLVGNLLVVFALTNSK (SEQ ID NO. 66)
||||||||||||||||||||||||||||||||*|**||***|*|**||*****|*||||
MDQFPESVTENFEYDDLAEACYIGDIVVFGTVFQSTYYSTTYATGQTGNQQTTYAQTNSK (SEQ ID NO. 67)

KPKSVTDIYLLNLALSDLLFVATLPFWTHYLINEKGLHNAMCKFTTAFFFIGFFGSIFFI
|||||||*|**|*|*||****||*|*||||*|||||||||||||||||||****|**||****
KPKSVTDTYQQNQAQSDQQYTATQPYWTHYQINEKGLHNAMCKFTTAYYYTGYYGSTYYT

TVISIDRYLAIVLAANSMNNRTVQHGVTISLGVWAAAILVAAPQFMFTKQKENECLGDYP
|**|*||||||||||||||||||||*|*|*|*|||***||||*|*||||||||||||||
TTTSTDRYLAIVLAANSMNNRTVQHGTTTSQGTWAAATQTAAPQYMYTKQKENECLGDYP

EVLQEIWPVLRNVETNFLGFLLPLLIMSYCYFRIIQTLFSCKNHKKAKAIKLILLVVIVF
||||||||||||||**|***|***||||*|**||**||||||||||||*********
EVLQEIWPVLRNVETNYQGYQQPQQTMSYCYYRTTQTQYSCKNHKKAKAIKQTQQTTTTY

FLFWTPYNVMIFLETLKLYDFFPSCDMRKDLRLALSVTETVAFSHCCLNPLIYAFAGEKF
***|||||*|***||||||||||||||||||||||*|*||*|*|||||*|**|*|||||
YQYWTPYNTMTYQETLKLYDFFPSCDMRKDLRLAQSTTETTAYSHCCQNPQTYAYAGEKF

RRYLYHLYGKCLAVLCGRSVHVDFSSSESQRSRHGSVLSSNFTYHTSDGDALLLL
||||||||||||||||||||||||||||||||||||||||||||||||||||||
RRYLYHLYGKCLAVLCGRSVHVDFSSSESQRSRHGSVLSSNFTYHTSDGDALLLL.
```

The predicted pI of the protein variant is 6.74 and the Molecular Weight is 41027.17 Da. Each of the predicted transmembrane regions has been underlined and exemplified a fully modified domain of the invention. Thus, for example, the invention includes a transmembrane domain comprising the underlined Amino Acids of SEQ ID NO: 67. Preferably the protein comprising TM1 herein includes one or more (e.g., all) of the extracellular and intracellular loop sequences of SEQ ID NO: 66 (the sequences which have not been underlined). In addition or alternatively, the protein comprising the TM1 herein includes one or more additional transmembrane regions (the underlined sequences) in SEQ ID NO: 67 or homologous sequences retaining one, two, three or, possibly four or more of the native V, L, I and F amino acids, as set forth in SEQ ID NO: 66.

The native protein sequence for CX3CR1 was subjected to the method a second time. The program output divided the native sequence into the extracellular and intracellular regions and selected 8 transmembrane domain variants for each transmembrane domain. The results are illustrated in the following table:

```
                                          (SEQ ID NO. 68)
MDQFPESVTENFEYDDLAEACYIGDIVVFGT

TM 1 Variants:
                                          (SEQ ID NO. 69)
TYQSTYYSTTFATGQVGNQQVVFALTNS (SEQ ID NO. 70)
TYQSTYYSTTYATGQVGNQQVVFALTNS (SEQ ID NO. 71)
TYQSTYYSTTYATGQVGNQQVVFAQTNS (SEQ ID NO. 72)
TYQSTYYSTTYATGQTGNLQVTFAQTNS (SEQ ID NO. 73)
TYQSTYYSTTYATGQTGNQLVTFAQTNS (SEQ ID NO. 74)
TYQSTYYSTTYATGQTGNQQVVFAQTNS (SEQ ID NO. 75)
TYQSTYYSTTYATGQTGNLQVTYAQTNS (SEQ ID NO. 76)
TYQSTYYSTTYATGQTGNQQTTYAQTNS (SEQ ID NO. 77)
KKPKSVTDIY TM 2 Variants
                                          (SEQ ID NO. 78)
LLNQAQSDQLFVATQPFWTHY (SEQ ID NO. 79)
LLNQAQSDQQFVATQPFWTHY (SEQ ID NO. 80)
QQNLAQSDQQFVATQPFWTHY (SEQ ID NO. 81)
LQNLAQSDQQYTATQPFWTHY (SEQ ID NO. 82)
QLNLAQSDQQYTATQPFWTHY (SEQ ID NO. 83)
LLNQAQSDQQFTATQPYWTHY (SEQ ID NO. 84)
QQNLAQSDQQFTATQPYWTHY (SEQ ID NO. 85)
QQNQAQSDQQYTATQPYWTHY (SEQ ID NO. 86)
LINEKGLHNAMCK TM3 Variant
                                          (SEQ ID NO. 87)
YTTAYYYTGYYGSTYYTTTTST
```

-continued

```
                                     (SEQ ID NO. 88)
DRYLAIVLAANSMNNRT

TM4 Variants:
                                     (SEQ ID NO. 89)
VQHGTTTSQGTWAAATQVAAPQFMF (SEQ ID NO. 90)
VQHGVTTSQGTWAAATQTAAPQFMF (SEQ ID NO. 91)
VQHGTTTSQGVWAAATQTAAPQFMY (SEQ ID NO. 92)
VQHGTTTSQGTWAAAIQTAAPQFMY (SEQ ID NO. 93)
VQHGTTTSQGTWAAATQTAAPQFMF (SEQ ID NO. 94)
VQHGTTISQGTWAAATQTAAPQYMF (SEQ ID NO. 95)
VQHGTTTSQGTWAAATQTAAPQFMY (SEQ ID NO. 96)
TQHGTTTSQGTWAAATQTAAPQYMY (SEQ ID NO. 97)
TKQKENECLGDYPEVLQEIWPVLRNVET TM5 Variants:
                                     (SEQ ID NO. 98)
NFLGFQQPQQIMSYCYFRIT (SEQ ID NO. 99)
NFQGFLQPQQTMSYCYFRIT (SEQ ID NO. 100)
NFQGFLQPQQTMSYCYFRTT (SEQ ID NO. 101)
NFQGFQQPQQTMSYCYYRIT (SEQ ID NO. 102)
NFQGFLQPQQTMSYCYYRTT (SEQ ID NO. 103)
NFQGYLQPQQTMSYCYFRTT (SEQ ID NO. 104)
NYQGFQQPQQTMSYCYFRTT (SEQ ID NO. 105)
NYQGYQQPQQTMSYCYYRTT (SEQ ID NO. 106)
QTLFSCKNHKKAKAIK TM6 Variants:
                                     (SEQ ID NO. 107)
LIQQTTTTFYQFWTPYNTMTFQETL (SEQ ID NO. 108)
LIQQTTTTFYQYWTPYNVMTFQETQ (SEQ ID NO. 109)
LIQQTTTTYYQFWTPYNTMTFQETQ (SEQ ID NO. 110)
QIQQTTTTFYQYWTPYNTMTFQETQ (SEQ ID NO. 111)
LTQQTTTTYYQFWTPYNTMTFQETQ (SEQ ID NO. 112)
QIQQTTTTFFQYWTPYNTMTYQETQ (SEQ ID NO. 113)
QIQQTTTTFYQYWTPYNTMTYQETQ (SEQ ID NO. 114)
QTQQTTTTYYQYWTPYNTMTYQETQ (SEQ ID NO. 115)
KLYDFFPSCDMRKDLRL TM7 Variants:
                                     (SEQ ID NO. 116)
ALSVTETVAFSHCCQNPQIYAFAG (SEQ ID NO. 117)
AQSVTETTAFSHCCQNPLIYAFAG (SEQ ID NO. 118)
ALSVTETVAFSHCCQNPQTYAYAG (SEQ ID NO. 119)
AQSVTETTAFSHCCQNPQIYAYAG (SEQ ID NO. 120)
ALSVTETTAFSHCCQNPQTYAYAG (SEQ ID NO. 121)
ALSTTETTAYSHCCQNPQIYAFAG (SEQ ID NO. 122)
ALSVTETTAYSHCCQNPQTYAYAG (SEQ ID NO. 123)
AQSTTETTAYSHCCQNPQTYAYAG (SEQ ID NO. 124)
EKFRRYLYHLYGKCLAVLCGRSVHVDFSSS

ESQRSRHGSVLSSNFTYHTSDGDALLLL.
```

As in Example 1 above, that the sequences before, between and after each list of transmembrane domain variants are the N', intermediary and C' intra or extracellular regions, respectively.

The sequences above were then used to generate coding sequences, as is known in the art, suitable for expression in the expression system, in this case yeast. The coding sequences were then shuffled and expressed to produce a library comprising a plurality of proteins each having SEQ ID NOs: 68, 77, 86, 88, 97, 106, and 115 with one transmembrane domain variant from each variant list in between the respective intracellular and extracellular domain.

Figure 6:
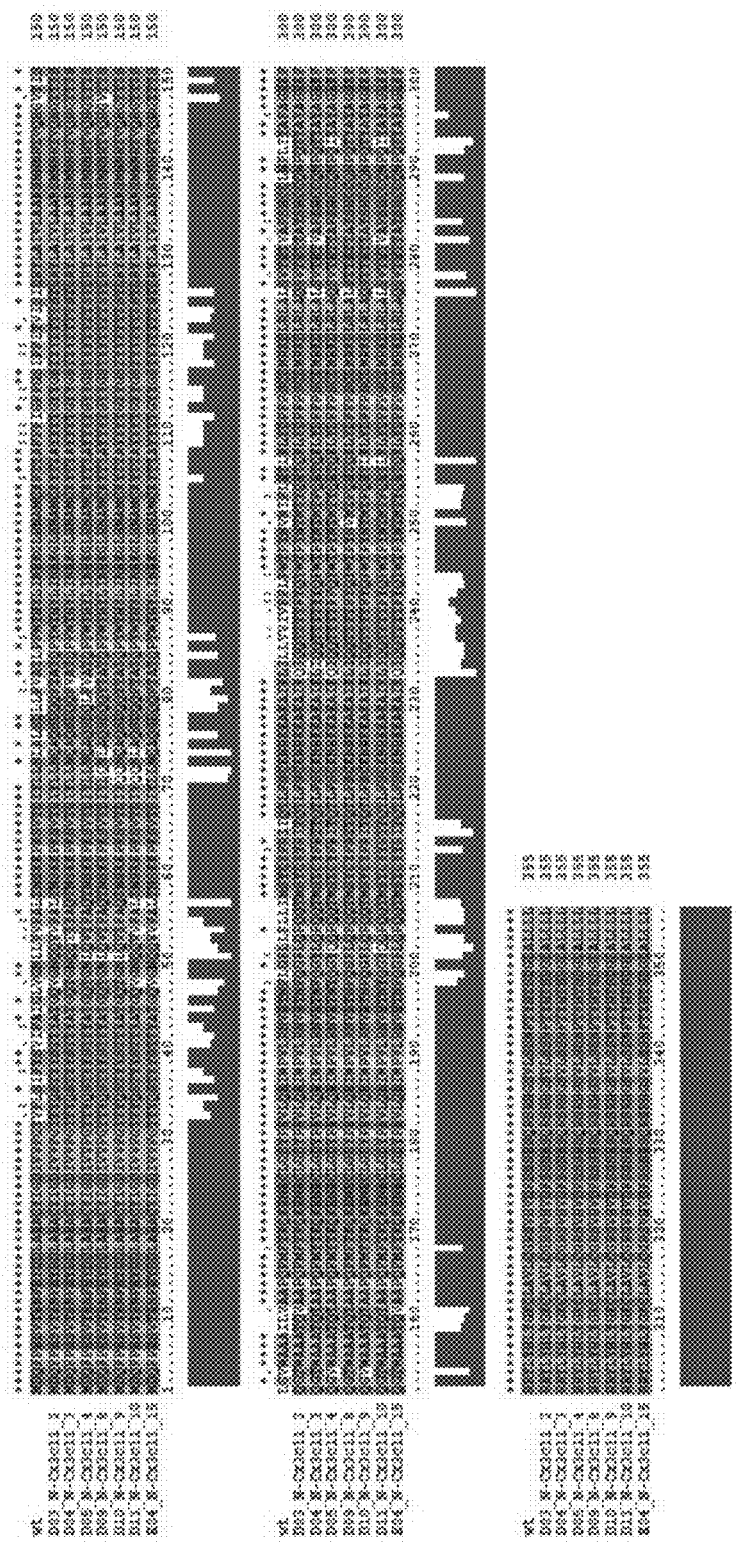

The library so produced was then assayed for CX3CR1 cognate ligand (CXCL1) binding in an aqueous medium, as described in Example 1. Ligand binding was detected and samples were then sequenced. Seven variants were sequenced. The results are shown in FIG. 6.

Example 3: CCR3 Variants

The method of Example 1 was repeated for Chemokine Receptor Type 3 isoform 3.

| Name | pI   | MW (Da)  |
|------|------|----------|
| WT   | 8.87 | 43122.3  |
| MT   | 8.78 | 43531.64 |

Replacing all or substantially all of the hydrophobic amino acids, L, I V, and F, with Q, T and Y (respectively) within the transmembrane domains results in the following sequence (lower line), aligned with the wild type (top line):

```
MPFGIRMLLRAHKPGRSEMTTSLDTVETFGTTSYYDDVGLLCEKADTRALMAQFVPPLYS  (SEQ ID NO. 125)
|||||||||||||||||||||||||||||||||||||||||||||||||||||||*||
MPFGIRMLLRAHKPGRSEMTTSLDTVETFGTTSYYDDVGLLCEKADTRALMAQFVPPQYS  (SEQ ID NO. 126)

LVFTVGLLGNVVVVMILIKYRRLRIMTNIYLLNLAISDLLFLVTLPFWIHYVRGHNWVFG
***|*|**||****|***|||||||||*|**|*|*||*****|*|*|*||||||||||
QTYTTGQQGNTTTTMTQTKYRRLRIMTNTYQQNQATSDQQYQTTQPYWTHYVRGHNWVFG

HGMCKLLSGFYHTGLYSEIFFIILLTIDRYLAIVHAVFALRARTVTFGVITSIVTWGLAV
|||||||||||||||||*******|*|||*|**||**|*|||||||**||**|||*|*
HGMCKLLSGFYHTGLYSETYYTTQQTTDRYQATTHATYAQRARTVTFGTTTSTTTWGQAT

LAALPEFIFYETEELFEETLCSALYPEDTVYSWRHFHTLRMTIFCLVLPLLVMAICYTGI
*||*||***|||||||||||||||||||||||||||||||||**|***|**||*||||*
QAAQPEYTYYETEELFEETLCSALYPEDTVYSWRHFHTLRMTTYCQTQPQQTMATCYTGT

IKTLLRCPSKKKYKAIRLIFVIMAVFFIFWTPYNVAILLSSYQSILFGNDCERSKHLDLV
*|||||||||||||||*****||*****||||*|***||||||||||||||||||||**
TKTLLRCPSKKKYKAIRQTYTTMATYYTYWTPYNTATQQSSYQSILFGNDCERSKHLDQT

MLVTEVIAYSHCCMNPVIYAFVGERFRKYLRHFFHRHLLMHLGRYIPFLPSEKLERTSSV
|**||**|||||||**||**||||||||||||||||||||||||||||||||||||||
MQTTETTAYSHCCMNPTTYAYTGERFRKYLRHFFHRHLLMHLGRYIPFLPSEKLERTSSV

SPSTAEPELSIVF
|||||||||||||
SPSTAEPELSIVF
```

Each of the predicted transmembrane regions have been underlined and exemplify a fully modified domain of the invention. Thus, for example, the invention includes a transmembrane domain comprising the underlined Amino Acids of SEQ ID NO: 126. Preferably the protein comprising TM1 herein includes one or more (e.g., all) of the extracellular and intracellular loop sequences of SEQ ID NO: 126 (the sequences which have not been underlined). In addition or alternatively, the protein comprising the TM1 herein includes one or more additional transmembrane regions (the underlined sequences) in SEQ ID NO: 126 or homologous sequences retaining one, two, three or, possibly four or more of the native V, L I and F amino acids, as set forth in SEQ ID NO: 125.

The native protein sequence for CCR3 was subjected to the method a second time (noting a difference in the N terminal sequence). The program output divided the native sequence into the extracellular and intracellular regions and selected 8 transmembrane domain variants for each transmembrane domain. The results are illustrated in the following table:

```
                                  (SEQ ID NO. 127)
MTTSLDTVETFGTTSYYDDVGLLCEKADTRALMA

TM1 Variants:
                                  (SEQ ID NO. 128)
QFVPPQYSQTFTTGQQGNVTVTMTQIKY (SEQ ID NO. 129)
QFVPPQYSQTFTTGQQGNTTVTMTQIKY (SEQ ID NO. 130)
QFVPPQYSQTYTTGQQGNTTVTMTQIKY (SEQ ID NO. 131)
QFTPPQYSQTYTTGQQGNVTTTMTQIKY (SEQ ID NO. 132)
QFTPPQYSQTYTTGQQGNTVTTMTQIKY (SEQ ID NO. 133)
QFTPPQYSQTYTTGQQGNTTVTMTQIKY (SEQ ID NO. 134)
QFTPPQYSQTYTTGQQGNTTTTMTQIKY (SEQ ID NO. 135)
QYTPPQYSQTYTTGQQGNTTTTMTQTKY (SEQ ID NO. 136)
RRLRIMTNIY TM2 Variants:
                                  (SEQ ID NO. 137)
LLNQATSDQQFQVTQPFWIHY (SEQ ID NO. 138)
LQNQAISDQLFQTTQPFWTHY (SEQ ID NO. 139)
QQNLAISDQQFQTTQPFWTHY (SEQ ID NO. 140)
QLNQAISDQQFQTTQPYWTHY (SEQ ID NO. 141)
QQNLAISDQQYQVTQPYWTHY (SEQ ID NO. 142)
LQNQATSDQLFQTTQPYWTHY (SEQ ID NO. 143)
QQNQAISDQQYQVTQPYWTHY (SEQ ID NO. 144)
QQNQATSDQQYQTTQPYWTHY (SEQ ID NO. 145)
VRGHNWVFGHGMCK TM3 Variants:
                                  (SEQ ID NO. 146)
LQSGFYHTGQYSETFFTTQQTT (SEQ ID NO. 147)
QLSGFYHTGQYSETFFTTQQTT (SEQ ID NO. 148)
QLSGFYHTGQYSETFYTTQQTT (SEQ ID NO. 149)
QLSGFYHTGQYSETYFTTQQTT
```

-continued (SEQ ID NO. 150)
QLSGYYHTGQYSETFFTTQQTT (SEQ ID NO. 151)
QQSGFYHTGQYSETFFTTQQTT (SEQ ID NO. 152)
QQSGFYHTGQYSETFYTTQQTT (SEQ ID NO. 153)
QQSGYYHTGQYSETYYTTQQTT (SEQ ID NO. 154)
DRYLAIVHAVFALRART TM4 Variants:

(SEQ ID NO. 155)
TTFGTTTSTVTWGQAVQAAQPEFIF (SEQ ID NO. 156)
TTFGTTTSTTTWGQAVQAAQPEFIF (SEQ ID NO. 157)
TTYGTTTSTTTWGQAVQAAQPEFIF (SEQ ID NO. 158)
TTYGTTTSTTTWGQAVQAAQPEFTF (SEQ ID NO. 159)
TTYGTTTSTTTWGQATQAAQPEFIF (SEQ ID NO. 160)
TTFGTTTSTTTWGQATQAAQPEFIY (SEQ ID NO. 161)
TTYGTTTSTTTWGQATQAAQPEFIY (SEQ ID NO. 162)
TTYGTTTSTTTWGQATQAAQPEYTY (SEQ ID NO. 163)
YETEELFEETLCSALYPEDTVYSWRHFHTLRM

TM5 Variants:

(SEQ ID NO. 164)
TIFCQVQPQQTMATCYTGTT (SEQ ID NO. 165)
TIFCQTQPQQVMATCYTGTT (SEQ ID NO. 166)
TIFCQTQPQQTMATCYTGIT (SEQ ID NO. 167)
TIFCQTQPQQTMATCYTGTI (SEQ ID NO. 168)
TTFCQVQPQQVMATCYTGTT (SEQ ID NO. 169)
TIYCQVQPQQVMATCYTGTT (SEQ ID NO. 170)
TIFCQTQPQQTMATCYTGTT (SEQ ID NO. 171)
TTYCQTQPQQTMATCYTGTT (SEQ ID NO. 172)
KTLLRCPSKKKYKAIR

TM 6 Variant:

(SEQ ID NO. 173)
QTYTTMATYYYTYWTPYNTATQQSSY (SEQ ID NO. 174)
QSILFGNDCERSKHLDL

-continued

TM7 Variants:

(SEQ ID NO. 175)
VMQVTEVTAYSHCCMNPVTYAFTG (SEQ ID NO. 176)
VMQVTEVTAYSHCCMNPTTYAYVG (SEQ ID NO. 177)
VMLTTEVTAYSHCCMNPTTYAFTG (SEQ ID NO. 178)
VMQVTETTAYSHCCMNPVTYAYTG (SEQ ID NO. 179)
TMQVTETIAYSHCCMNPTTYAFTG (SEQ ID NO. 180)
TMQVTETTAYSHCCMNPTTYAFVG (SEQ ID NO. 181)
VMQTTETIAYSHCCMNPTTYAYTG (SEQ ID NO. 182)
TMQTTETTAYSHCCMNPTTYAYTG (SEQ ID NO: 183)
ERFRKYLRHFFHRHLLMHLGRYIPFLPSEKLERTSSVSPSTAEPELS

IVF.

As in Example 1 above, the sequences before, between and after each list of transmembrane domain variants are the N', intermediary and C' intra or extracellular regions, respectively.

The sequences above were then used to generate coding sequences, as is known in the art, suitable for expression in the expression system, in this case yeast. The coding sequences were then shuffled and expressed to produce a library comprising a plurality of proteins each having SEQ ID NOs: 127, 136, 145, 154, 163, 172, 174 and 183 with one transmembrane domain variant from each variant list in between the respective intracellular and extracellular domain.

Figure 7:
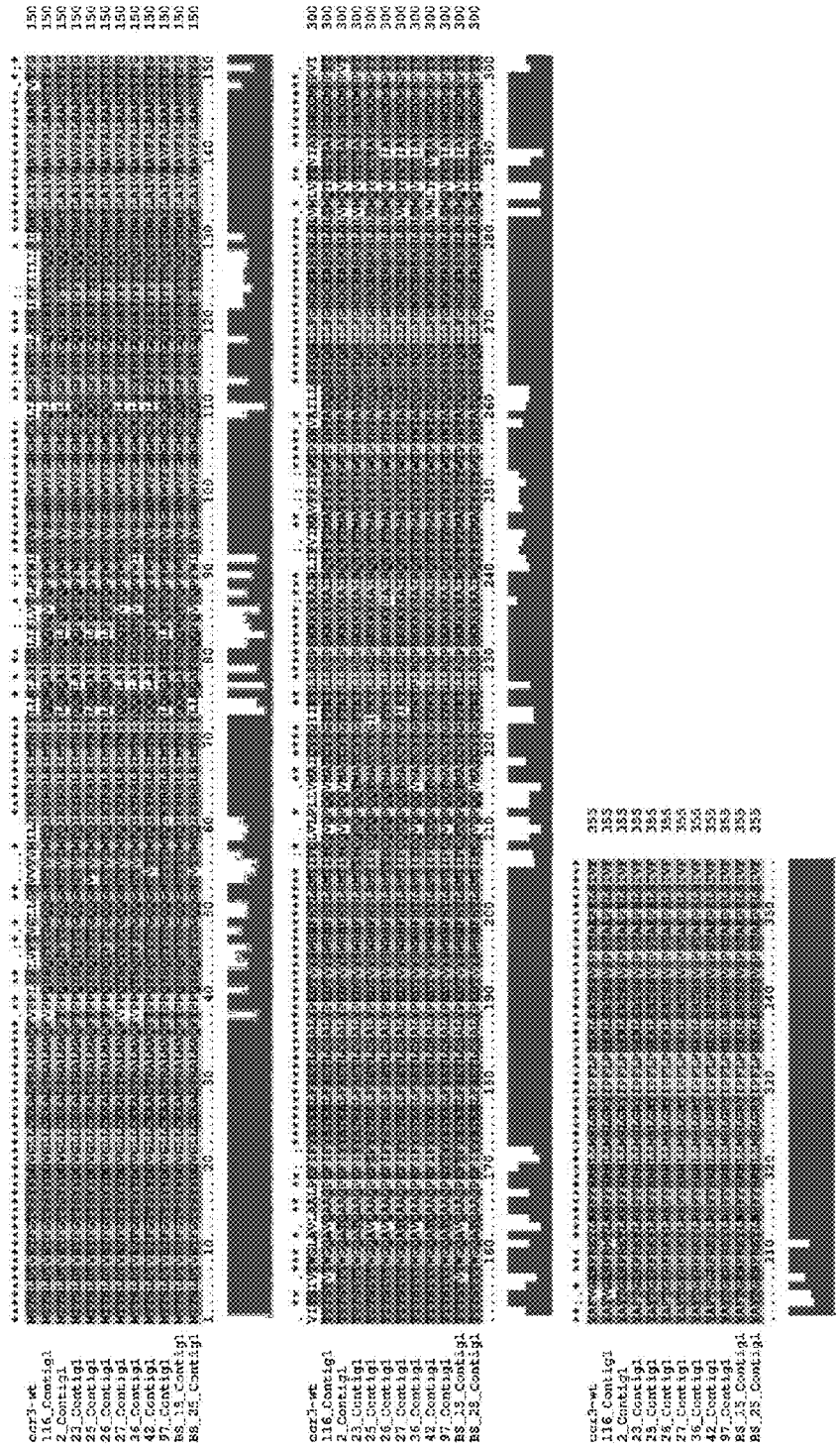

The library so produced was then assayed for CCR3 cognate ligand, CCL3, binding in an aqueous medium, as described in Example 1. Ligand binding was detected and samples were then sequenced. Eleven variants were sequenced. The results are shown in FIG. 7.

Example 4: CCR5 Variants

The method of Example 1 was repeated for Chemokine Receptor Type 5 isoform 3.

| Name | pI | MW (Da) |
|---|---|---|
| WT | 9.21 | 40524.05 |
| MT | 9.06 | 41058.3 |

Replacing all or substantially all of the hydrophobic amino acids, L, I V, and F, with Q, T and Y (respectively) within the transmembrane domains results in the following sequence (lower line), aligned with the wild type (top line):

```
MDYQVSSPIYDINYYTSEPCQKINVKQIAARLLPPLYSLVFIFGFVGNMLVILILINCKR  (SEQ ID NO. 184)
|||||||||||||||||||||||||||||||||*||*****|**|||*******||||
MDYQVSSPIYDINYYTSEPCQKINVKQIAARLLPPQYSQTYTYGYTGNMQTTQTQTNCKR  (SEQ ID NO. 185)

LKSMTDIYLLNLAISDLFFLLTVPFWAHYAAAQWDFGNTMCQLLTGLYFIGFFSGIFFII
||||||*|**|*|*||*****|*|*|||||||||||||||**||*|**|**||*****
LKSMTDTYQQNQATSDQYYQQTTPYWAHYAAAQWDFGNTMCQQQTGQYYTGYYSGTYYTT

LLTIDRYLAVVHAVFALKARTVTFGVVTSVITWVVAVFASLPGIIFTRSQKEGLHYTCSS
**|*|||||||||||||||||*|**|**|**|**||*|***|||||||||||||||||
QQTTDRYLAVVHAVFALKARTVTYGTTTSTTTWTTATYASQPGTTYTRSQKEGLHYTCSS

HFPYSQYQFWKNFQTLKIVILGLVLPLLVMVICYSGILKTLLRCRNEKKRHRAVRLIFTI
|||||||||||||||||****|***|***|**||||**||*||||||||||||||***|*
HFPYSQYQFWKNFQTLKTTTQGQTQPQQTMTTCYSGTQKTQLRCRNEKKRHRAVRQTYTT

MIVYFLFWAPYNIVLLLNTFQEFFGLNNCSSSNRLDQAMQVTETLGMTHCCINPIIYAFV
|**|***||||*****||||||||||||||||||||||||||||||||||*||**||**
MTTYYQYWAPYNTTQQQNTFQEFFGLNNCSSSNRLDQAMQVTETLGMTHCCTNPTTYAYT

GEKFRNYLLVFFQKHIAKRFCKCCSIFQQEAPERASSVYTRSTGEQEISVGL
|||*|||*****||||||||||||||||||||||||||||||||||||||||
GEKYRNYQQTYYQKHIAKRFCKCCSIFQQEAPERASSVYTRSTGEQEISVGL.
```

Each of the predicted transmembrane regions has been underlined and exemplified a fully modified domain of the invention. Thus, for example, the invention includes a transmembrane domain comprising the underlined Amino Acids of SEQ ID NO: 185. Preferably the protein comprising TM1 herein includes one or more (e.g., all) of the extracellular and intracellular loop sequences of SEQ ID NO: 185 (the sequences which have not been underlined). In addition or alternatively, the protein comprising the TM1 herein includes one or more additional transmembrane regions (the underlined sequences) in SEQ ID NO: 185 or homologous sequences retaining one, two, three or, possibly four or more of the native V, L I and F amino acids, as set forth in SEQ ID NO: 184.

The native protein sequence for CCR5 was subjected to the method a second time (noting a difference in the N terminal sequence). The program output divided the native sequence into the extracellular and intracellular regions and selected 8 transmembrane domain variants for each transmembrane domain. The results are illustrated in the following table:

```
                                        (SEQ ID NO. 186)
MDYQVSSPIYDINYYTSEPCQKINVKQIAA

TM1 Variants:
                                        (SEQ ID NO. 187)
RLQPPQYSQTFTFGFTGNMQVTQTQINC (SEQ ID NO. 188)
RLQPPQYSQTFTFGYTGNMQVTQTQINC (SEQ ID NO. 189)
RQQPPQYSQTFTFGFTGNMQTTQTQINC (SEQ ID NO. 190)
RQQPPQYSQTFTYGFTGNMQTTQTQINC (SEQ ID NO. 191)
RQQPPQYSQTYTFGFTGNMQTTQTQINC (SEQ ID NO. 192)
RQQPPQYSQTFTFGYTGNMQTTQTQINC (SEQ ID NO. 193)
RQQPPQYSQTYTFGYTGNMQTTQTQINC (SEQ ID NO. 194)
RQQPPQYSQTYTYGYTGNMQTTQTQTNC (SEQ ID NO. 195)
KRLKSMTDIY TM2 Variants:
                                        (SEQ ID NO. 196)
LQNQAISDQFFQQTVPFWAHY (SEQ ID NO. 197)
LQNQAISDQFFQQTTPFWAHY (SEQ ID NO. 198)
LQNQAISDQFFQQTTPYWAHY (SEQ ID NO. 199)
LQNQAISDQFYQQTTPYWAHY (SEQ ID NO. 200)
LQNQAISDQYFQQTTPYWAHY (SEQ ID NO. 201)
LQNQATSDQFFQQTTPYWAHY (SEQ ID NO. 202)
LQNQAISDQYYQQTTPYWAHY (SEQ ID NO. 203)
QQNQATSDQYYQQTTPYWAHY (SEQ ID NO. 204)
AAAQWDFGNTMCQ TM3 Variants:
                                        (SEQ ID NO. 205)
QQTGQYFTGYYSGTYYTTQQTT (SEQ ID NO. 206)
QQTGQYYTGYYSGTYYTTQQTT (SEQ ID NO. 207)
DRYLAVVHAVFALKART TM4 Variant:
                                        (SEQ ID NO. 208)
TTYGTTTSTTTWTTATYASQPGTTY (SEQ ID NO. 209)
TRSQKEGLHYTCSSHFPYSQYQFWKNFQTLKI TM5 Variants:
                                        (SEQ ID NO. 210)
VIQGQVQPQQVMVTCYSGIQ
```

-continued (SEQ ID NO. 211)
VIQGQVQPQQVMTTCYSGIQ (SEQ ID NO. 212)
VIQGQVQPQQTMTTCYSGIQ (SEQ ID NO. 213)
VTQGQVQPQQTMVTCYSGTQ (SEQ ID NO. 214)
TIQGQVQPQQVMTTCYSGTQ (SEQ ID NO. 215)
TIQGQVQPQQTMVTCYSGTQ (SEQ ID NO. 216)
TTQGQVQPQQVMTTCYSGTQ (SEQ ID NO. 217)
TTQGQTQPQQTMTTCYSGTQ (SEQ ID NO. 218)
KTLLRCRNEKKRHRAVR TM6 Variants:

(SEQ ID NO. 219)
QTFTTMTTYYQFWAPYNIVQQLNTF (SEQ ID NO. 220)
QTFTTMTTYYQFWAPYNTVQQLNTF (SEQ ID NO. 221)
QTFTTMTTYYQYWAPYNTVQQLNTF (SEQ ID NO. 222)
QTFTTMTTYYQYWAPYNTVQQQNTF (SEQ ID NO. 223)
QTYTTMTTYYQYWAPYNTVQQLNTF (SEQ ID NO. 224)
QTFTTMTTYYQYWAPYNTTQQLNTF (SEQ ID NO. 225)
QTYTTMTTYYQYWAPYNTVQQQNTF (SEQ ID NO. 225)
QTYTTMTTYYQYWAPYNTTQQQNTY (SEQ ID NO. 226)
QEFFGLNNCSSSNRLDQ

TM7 Variants:

(SEQ ID NO. 227)
AMQVTETQGMTHCCINPIIYAFVG (SEQ ID NO. 228)

-continued

AMQVTETLGMTHCCTNPIIYAFTG (SEQ ID NO. 229)
AMQVTETQGMTHCCINPTIYAYVG (SEQ ID NO. 230)
AMQTTETQGMTHCCINPITYAFTG (SEQ ID NO. 231)
AMQTTETQGMTHCCINPTIYAFTG (SEQ ID NO. 232)
AMQVTETQGMTHCCTNPTIYAYVG (SEQ ID NO. 233)
AMQTTETQGMTHCCINPTTYAYVG (SEQ ID NO. 234)
AMQTTETQGMTHCCTNPTTYAYTG (SEQ ID NO. 235)
EKFRNYLLVFFQKHIAKRFCKCCSIFQQEAPERASSVYTRSTGEQE

ISVGL.

As in Example 1 above, the sequences before, between and after each list of transmembrane domain variants are the N', intermediary and C' intra or extracellular regions, respectively.

The sequences above were then used to generate coding sequences, as is known in the art, suitable for expression in the expression system, in this case yeast. The coding sequences were then shuffled and expressed to produce a library comprising a plurality of proteins each having SEQ ID NO:s, 186, 195, 204, 207, 209, 218, 226, and 235 with one transmembrane domain variant from each variant list in between the respective intracellular and extracellular domain.

Figure 8:
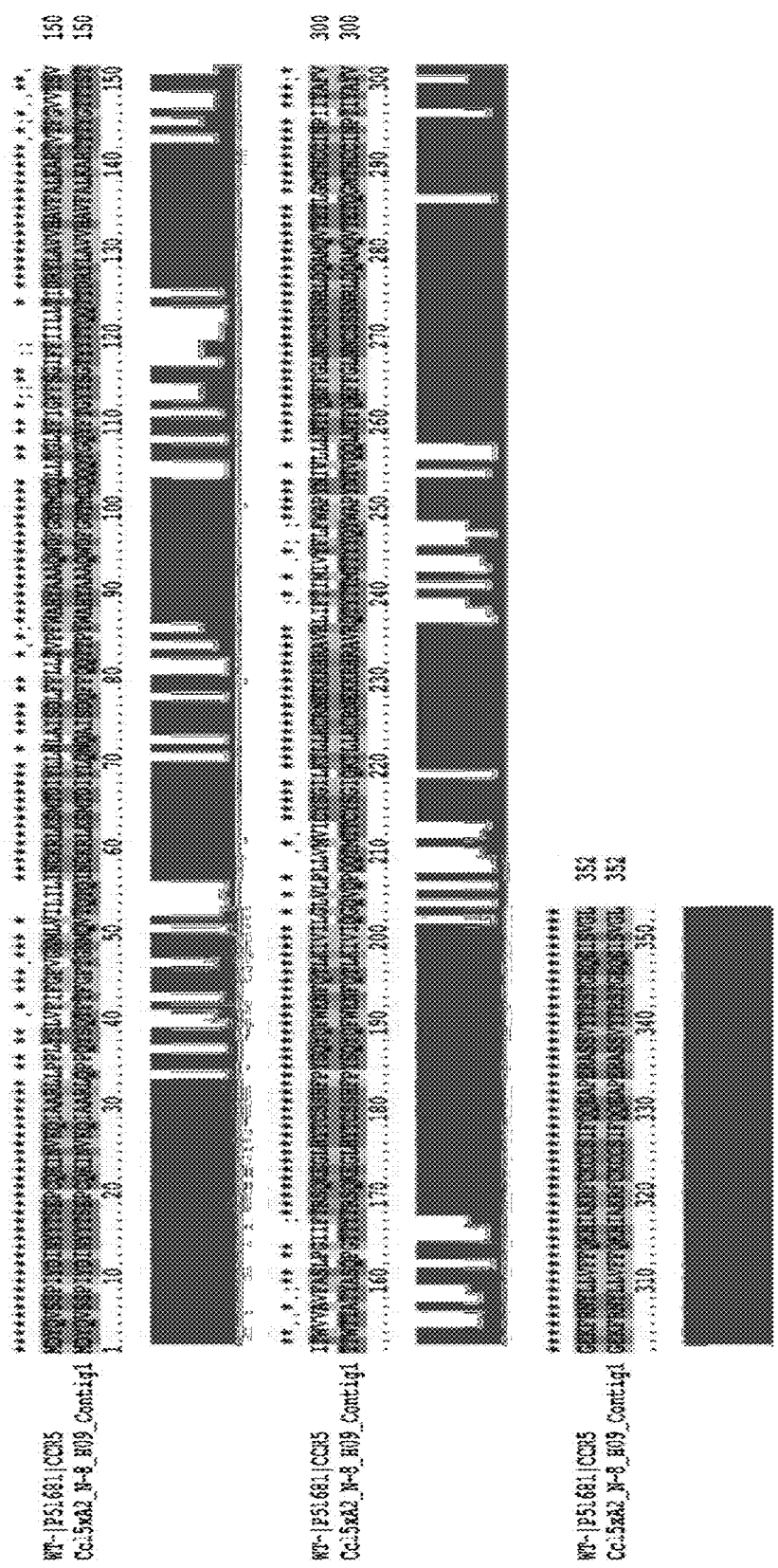

The library so produced was then assayed for CCR5 cognate ligand, CCLS, binding in an aqueous medium, as described in Example 1. Ligand binding was detected and samples were then sequenced. One variant was sequenced. The results are shown in FIG. 8.

Example 5: CXCR3 Variants

The method of Example 1 was repeated for the CXC chemokine receptor type 3 isoform 2. Replacing all or substantially all of the hydrophobic amino acids, L, I V, and F, with Q, T and Y (respectively) within the transmembrane domains results in the following sequence (SEQ ID NO: 325, lower line), aligned with the wild type (SEQ ID NO: 324, top line):

```
MELRKYGPGRLAGTVIGGAAQSKSQTKSDSITKEFLPGLYTAPSSPFPPSQVSDHQVLND
||||||||||||||||||||||||||||||||||||||||||||||||||||||||||||
MELRKYGPGRLAGTVIGGAAQSKSQTKSDSITKEFLPGLYTAPSSPFPPSQVSDHQVLND

AEVAALLENFSSSYDYGENESDSCCTSPPCPQDFSLNFDRAFLPALYSLLFLLGLLGNGA
|||||||||||||||||||||||||||||||||||||||||||||*||*****|**||||
AEVAALLENFSSSYDYGENESDSCCTSPPCPQDFSLNFDRAFLPAQYSQQYQQGQQGNGA

VAAVLLSRRTALSSTDTFLLHLAVADTLLVLTLPLWAVDAAVQWVFGSGLCKVAGALFNI
*||***|||||||||||***|*|*|||****|*|*||*||||||||||||||||||**|*
TAATQQSRRTALSSTDTYQQHQATADTQQTQTQPQWATDAAVQWVFGSGLCKVAGAQYNT

NFYAGALLLACISFDRYLNIVHATQLYRRGPPARVTLTCLAVWGLCLLFALPDFIFLSAH
|*||||***||*|*|||||||||||||||||||||*|*||*|*||*|***|*||****|||
NYYAGAQQQACTSYDRYLNIVHATQLYRRGPPARTTQTCQATWGQCQQYAQPDYTYQSAH

HDERLNATHCQYNFPQVGRTALRVLQLVAGFLLPLLVMAYCYAHILAVLLVSRGQRRLRA
|||||||||||||||||||||||||||*||***|***|||||||**|***|||||||||
HDERLNATHCQYNFPQVGRTALRVLQLTAGYQQPQQTMAYCYAHTQATQQVSRGQRRLRA
```

```
MRLVVVVVVAFALCWTPYHLVVLVDILMDLGALARNCGRESRVDVAKSVTSGLGYMHCCL
||*******|*|*|||||***||||||||||||||||||||||||||*||||||*
MRQTTTTTTAYAQCWTPYHQTTLVDILMDLGALARNCGRESRVDVAKSVTSGQGYMHCCQ

NPLLYAFVGVKFRERMWMLLLRLGCPNQRGLQRQPSSSRRDSSWSETSEASYSGL
||**||**|*|||||||||||||||||||||||||||||||||||||||||||||
NPQQYAYTGTKFRERMWMLLLRLGCPNQRGLQRQPSSSRRDSSWSETSEASYSGL
```

Each of the predicted transmembrane regions has been underlined and exemplified a fully modified domain of the invention. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in SEQ ID NO: 325 or homologous sequences retaining one, two, three or, possibly four or more of the native V, L I and F amino acids, as set forth in SEQ ID NO: 324.

As discussed above, the native protein sequence for CXCR3 was subjected to the method. The program output divided the native sequence into the extracellular and intracellular regions and selected 8 transmembrane domain variants for each transmembrane domain. The results are illustrated in the following table:

MVLEVSDHQVLNDAEVAALLENFSSSYDYGENESDSCCTSPP (SEQ ID NO. 235)

CPQDFSLNFDR

TM 1 Variants:

AFLPALYSQQFQQGQQGNGAVAATQLS (SEQ ID NO. 236)

AFQPALYSQQFQQGQQGNGAVAAVQQS (SEQ ID NO. 237)

AFQPAQYSQQFLQGQQGNGAVAATQQS (SEQ ID NO. 238)

AYQPALYSLQYQQGQQGNGATAAVQQS (SEQ ID NO. 239)

AYQPALYSQLFQQGQQGNGATAATQQS (SEQ ID NO. 240)

AFQPALYSLQYQQGQQGNGATAATQQS (SEQ ID NO. 241)

AYQPAQYSLQYQQGQQGNGATAAVQQS (SEQ ID NO. 242)

AYQPAQYSQQYQQGQQGNGATAATQQS (SEQ ID NO. 243)

RRTALSSTD (SEQ ID NO. 244)

TM 2 Variants:

TFLQHLAVADTQQVQTLPQWA (SEQ ID NO. 245)

TFLQHQAVADTQLVQTQPQWA (SEQ ID NO.: 246)

TFQQHLAVADTQQVQTQPQWA (SEQ ID NO.: 247)

TYLQHQAVADTQQVQTQPQWA (SEQ ID NO.: 248)

TYQLHQAVADTQQVQTQPQWA (SEQ ID NO.: 249)

TYQQHLAVADTQQVQTQPQWA (SEQ ID NO.: 250)

TYQQHQAVADTQQVQTQPQWA (SEQ ID NO.: 251)

TYQQHQATADTQQTQTQPQWA (SEQ ID NO.: 252)

VDAAVQWVFGSGLCK (SEQ ID NO.: 253)

TM 3 Variants:

TAGAQYNTNFYAGAQQQACISF (SEQ ID NO.: 254)

TAGAQYNTNFYAGAQLQACTSF (SEQ ID NO.: 255)

TAGAQYNTNFYAGAQQLACTSF (SEQ ID NO.: 256)

TAGAQFNTNYYAGAQQQACISF (SEQ ID NO.: 257)

TAGAQYNTNYYAGAQQQACISF (SEQ ID NO.: 258)

TAGAQYNTNYYAGAQLQACTSF (SEQ ID NO.: 259)

TAGAQYNTNYYAGAQQLACTSF (SEQ ID NO.: 260)

TAGAQYNTNYYAGAQQQACTSY (SEQ ID NO.: 261)

DRYLNIVHATQLYRRGPPARVT (SEQ ID NO.: 262)

TM 4 Variants:

LTCQAVWGQCQQFAQPDFIF (SEQ ID NO.: 263)

QTCQAVWGQCQQFAQPDFIF (SEQ ID NO.: 264)

QTCQATWGQCQQFAQPDFIF (SEQ ID NO.: 265)

QTCQATWGQCQQYAQPDFIF (SEQ ID NO.: 266)

QTCQATWGQCQQFAQPDFTF (SEQ ID NO.: 267)

QTCQATWGQCQQFAQPDYIF (SEQ ID NO.: 268)

QTCQATWGQCQQYAQPDYIF (SEQ ID NO.: 269)

QTCQATWGQCQQYAQPDYTY (SEQ ID NO.: 270)

LSAHHDERLNATHCQYNFPQVGR

TM 5 Variant:

(SEQ ID NO.: 272)
TAQRTQQQTAGYQQPQQTMAY (SEQ ID NO.: 273)
CYAHILAVLLVSRGQRRLRAMR

TM 6 Variants:

(SEQ ID NO.: 274)
QVTTTTVAFAQCWTPYHQVVQV (SEQ ID NO.: 275)
QVTTTTVAFAQCWTPYHQTVQV (SEQ ID NO.: 276)
QVTTTTTAFAQCWTPYHQTVQV (SEQ ID NO.: 277)
QVTTTTTAYAQCWTPYHQTVQV (SEQ ID NO.: 278)
QVTTTTTAFAQCWTPYHQTTQV (SEQ ID NO.: 279)
QTTTTTVAFAQCWTPYHQTTQV (SEQ ID NO.: 280)
QVTTTTTAYAQCWTPYHQTTQV (SEQ ID NO.: 281)
QTTTTTTAYAQCWTPYHQTTQT (SEQ ID NO.: 282)
DILMDLGALARNCGRESRVDV

TM 7 Variants:

(SEQ ID NO.: 283)
AKSVTSGQGYMHCCLNPLQYAFV (SEQ ID NO.: 284)
AKSVTSGQGYMHCCLNPQLYAFT (SEQ ID NO.: 285)
AKSVTSGQGYMHCCLNPLQYAFT (SEQ ID NO.: 286)
AKSTTSGQGYMHCCLNPQQYAFV (SEQ ID NO.: 287)
AKSTTSGQGYMHCCQNPLQYAFV (SEQ ID NO.: 288)
AKSTTSGQGYMHCCQNPQLYAFV (SEQ ID NO.: 289)
AKSTTSGQGYMHCCQNPLQYAFT (SEQ ID NO.: 290)
AKSTTSGQGYMHCCQNPQQYAYT (SEQ ID NO.: 291)
GVKFRERMWMLLLRLGCPNQRGLQRQPSSSRRDSSWSETSEASYSGL.

The sequences above can be used to generate coding sequences, as is known in the art, suitable for expression in the expression system, in this case yeast. The coding sequences were then shuffled and expressed to produce a library comprising a plurality of proteins each having the intracellular and extracellular loops with one transmembrane domain variant from each variant list in between the respective intracellular and extracellular domain.

The library so produced can then be assayed for cognate ligand binding in an aqueous medium, as described in Example 1.

Example 6: CCR-1 C-C Chemokine Receptor Type 1

Example 1 was repeated for the title protein.

| Name | pI | MW (Da) |
| --- | --- | --- |
| WT | 8.38 | 41172.64 |
| MT | 8.31 | 41583.78 |

Replacing all or substantially all of the hydrophobic amino acids, L, I V, and F, with Q, T and Y (respectively) within the transmembrane domains results in the following sequence (lower line SEQ ID NO: 293), aligned with the wild type (top line SEQ ID NO: 292):

```
METPNTTEDYDTTTEFDYGDATPCQKVNERAFGAQLLPPLYSLVFVIGLVGNILVVLVLV
||||||||||||||||||||||||||||||||||||||*||*||*****|**||*******|
METPNTTEDYDTTTEFDYGDATPCQKVNERAFGAQLQPPQYSQTYTTGQTGNTQTTQTQV

QYKRLKNMTSIYLLNLAISDLLFLFTLPFWIDYKLKDDWVFGDAMCKILSGFYYTGLYSE
||||||||||*|**|*|*|******|*|*||||||||||||||||||**||*||||*|||
QYKRLKNMTSTYQQNQATSDQQYQYTQPYWTDYKLKDDWVFGDAMCKTQSGYYYTGQYSE

IFFIILLTIDRYLAIVHAVFALRARTVTFGVITSIIIWALAILASMPGLYFSKTQWEFTH
*******|||||||||||||||||||*|*|**|***||**|**||||*|||||||||||
TYYTTQQTIDRYLAIVHAVFALRARTTTYGTTTSTTTWAQATQASMPGQYFSKTQWEFTH

HTCSLHFPHESLREWKLFQALKLNLFGLVLPLLVMIICYTGIIKILLRRPNEKKSKAVRL
||||||||||||||||||||||||||**|***|***|**|||**|***|||||||||||*
HTCSLHFPHESLREWKLFQALKLNQYGQTQPQQTMTTCYTGTTKTQQRRPNEKKSKAVRQ

IFVIMIIFFLFWTPYNLTILISVFQDFLFTHECEQSRHLDLAVQVTEVIAYTHCCVNPVI
****|******||||*|||*|||||||||||||||||||||||*|*|**||||||*||**
TYTTMTTYYQYWTPYNQTTQTSVFQDFLFTHECEQSRHLDLATQTTETTAYTHCCTNPTT

YAFVGERFRKYLRQLFHRRVAVHLVKWLPFLSVDRLERVSSTSPSTGEHELSAGF
||**||||||||||||||||||||||||||||||||||||||||||||||||||
YAYTGERFRKYLRQLFHRRVAVHLVKWLPFLSVDRLERVSSTSPSTGEHELSAGF
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native V, L I and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 7: CCR-2 C-C Chemokine Receptor Type 2 Isoform A

Example 1 was repeated for the title protein. Replacing each of the hydrophobic amino acids, L, I V, and F, with Q, T and Y (respectively) within the transmembrane domains results in the following sequence (lower line SEQ ID NO: 295), aligned with the wild type (top line SEQ ID NO: 294):

invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native V, L I and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 8: CCR-4 C-C Chemokine Receptor Type 4

Example 1 was repeated for the title protein. Replacing all or substantially all of the hydrophobic amino acids, L, I V, and F, with Q, T and Y (respectively) within the transmembrane domains results in the following sequence (lower line

```
MLSTSRSRFIRNTNESGEEVTTFFDYDYGAPCHKFDVKQIGAQLLPPLYSLVFIFGFVGN
||||||||||||||||||||||||||||||||||||||||*||*||*****|**||
MLSTSRSRFIRNTNESGEEVTTFFDYDYGAPCHKFDVKQIGAQLQPPQYSQTYTYGYTGN

MLVVLILINCKKLKCLTDIYLLNLAISDLLFLITLPLWAHSAANEWVFGNAMCKLFTGLY
|******|||||||||||**|*|*||*****|*|*|||||||||||||||||||||*|
MQTTQTQINCKKLKCLTDIYQQNQATSDQQYQTTQPQWAHSAANEWVFGNAMCKLFTGQY

HIGYFGGIFFIILLTIDRYLAIVHAVFALKARTVTFGVVTSVITWLVAVFASVPGIIFTK
|*||*||*******|*|||||||||||||||||*|**|**||**|**||*||***||
HTGYYGGTYYTTQQTTDRYLAIVHAVFALKARTVTYGTTTSTTTWQTATYASTPGTTYTK

CQKEDSVYVCGPYFPRGWNNFHTIMRNILGLVLPLLIMVICYSGILKTLLRCRNEKKRHR
|||||||||||||||||||||||||||**|***|***|**|||**||**|||||||||
CQKEDSVYVCGPYFPRGWNNFHTIMRNTQGQTQPQQTMTTCYSGTQKTQQRCRNEKKRHR

AVRVIFTIMIVYFLFWTPYNIVILLNTFQEFFGLSNCESTSQLDQATQVTETLGMTHCCI
|*|***|*|**|***||||****||||||||||||||||||||||||||||*||||||*
TRTTYTTMTTYYQYWTPYNTTTQLNTFQEFFGLSNCESTSQLDQATQVTETQGMTHCCT

NPIIYAFVGEKFRSLFHIALGCRIAPLQKPVCGGPGVRPGKNVKVTTQGLLDGRGKGKSI
||**||**|||||||||||||||||||||||||||||||||||||||||||||||||||
NPTTYAYTGEKFRSLFHIALGCRIAPLQKPVCGGPGVRPGKNVKVTTQGLLDGRGKGKSI

GRAPEASLQDKEGA
||||||||||||||
GRAPEASLQDKEGA
```

Each of the predicted transmembrane regions has been underlined and exemplified a fully modified domain of the SEQ ID NO: 297), aligned with the wild type (top line SEQ ID NO: 296):

```
MNPTDIADTTLDESIYSNYYLYESIPKPCTKEGIKAFGELFLPPLYSLVFVFGLLGNSVV
|||||||||||||||||||||||||||||||||||||||||||||||*****|**|||**
MNPTDIADTTLDESIYSNYYLYESIPKPCTKEGIKAFGELFLPPLYSQTYTYGQQGNSTT

VLVLFKYKRLRSMTDVYLLNLAISDLLFVFSLPFWGYYAADQWVFGLGLCKMISNMYLVG
*****|||||||||*|**|*|*||*****|*|*|||||||||||||||||*|||**|
TQTQYKYKRLRSMTDTYQQNQATSDQQYTYSQPYWGYYAADQWVFGLGLCKMTSWMYQTG

FYSGIFFVMLSIDRYLAIVHAVFSLRARTLTYGVITSLATWSVAVFASLPGFLFSTCYT
*|||****|*|||||||||||||||||*|||**||*|||*|**||*||***|||||
YYSGTYYTMQMSIDRYLAIVHAVFSLRARTQTYGTTTSQATWSTATYASQPGYQYSTCYT
```

```
ERNHTYCKTKYSLNSTTWKVLSSLEINILGLVIPLGIMLFCYSMIIRTLQHCKNEKKNKA
||||||||||||||||||||||||*|**|***|*|*|**||||**|||||||||||||
ERNHTYCKTKYSLNSTTWKVLSSLETNTQGQTTPQGTMQYCYSMTTRTLQHCKNEKKNKA

VKMIFAVVVLFLGFWTPYNIVLFLETLVELEVLQDCTFERYLDYAIQATETLAFVHCCLN
|||**|******|*|||||*****|||||||||||||||||||||||*|**|||*|
VKMTYATTTQYQGYWTPYNTTQYQETLVELEVLQDCTFERYLDYAIQATETQAYTHCCQN

PIIYFFLGEKFRKYILQLFKTCRGLFVLCQYCGLLQTYSADTPSSSYTQSTMDHDLHDAL
|**|***||||||||||||||||||||||||||||||||||||||||||||||||||
PTTYYYQGEKFRKYILQLFKTCRGLFVLCQYCGLLQTYSADTPSSSYTQSTMDHDLHDAL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native V, L I and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 9: CCR-6 C-C Chemokine Receptor Type 6

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 299), aligned with the wild type (top line SEQ ID NO: 298):

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I, V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 10: CCR-7 C-C Chemokine Receptor Type 7 Precursor

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 301), aligned with the wild type (top line SEQ ID NO: 300):

```
MSGESMNFSDVFDSSEDYFVSVNTSYYSVDSEMLLCSLQEVRQFSRLFVPIAYSLICVFG
||||||||||||||||||||||||||||||||||||||||||||||||*|||**|**|
MSGESMNFSDVFDSSEDYFVSVNTSYYSVDSEMLLCSLQEVRQFSRLFVPTAYSQTCTYG

LLGNILVVITFAFYKKARSMTDVYLLNMAIADILFVLTLPFWAVSHATGAWVFSNATCKL
**||*****|*|*||||||||||**|||*|*****|*|*||*||||||||||||||||
QQGNTQTTTTYAYYKKARSMTDVYQQNMATADTQYTQTQPYWATSHATGAWVFSNATCKL

LKGIYAINFNCGMLLLTCISMDRYIAIVQATKSFRLRSRTLPRSKIICLVVWGLSVIISS
|||*||*|*|||***||*|||||*||||||||||||||||||||**|***||*|***||
LKGTYATNYNCGMQQQTCTSMDRYTAIVQATKSFRLRSRTLPRSKTTCQTTWGQSTTTSS

STFVFNQKYNTQGSDVCEPKYQTVSEPIRWKLLMLGLELLFGFFIPLMFMIFCYTFIVKT
||***|||||||||||||||||||||||||||||||||**|***|*|*|**|||***||
STYTYNQKYNTQGSDVCEPKYQTVSEPIRWKLLMLGLELQYGYYTPQMYMTYCYTYTTKT

LVQAQNSKRHKAIRVIIAVVLVFLACQIPHNMVLLVTAANLGKMNRSCQSEKLIGYTKTV
**||||||||||||***|******|||*||||****||||||||||||||||||||||
QTQAQNSKRHKAIRTTTATTQTYQACQTPHNMTQQTTAANLGKMNRSCQSEKLIGYTKTV

TEVLAFLHCCLNPVLYAFIGQKFRNYFLKILKDLWCVRRKYKSSGFSCAGRYSENISRQT
||**|**|||*|**||**||||||||||||||||||||||||||||||||||||||||
TETQAYQHCCQNPTQYAYTGQKFRNYFLKILKDLWCVRRKYKSSGFSCAGRYSENISRQT

SETADNDNASSFTM
||||||||||||||
SETADNDNASSFTM
```

```
MDLGKPMKSVLVVALLVIFQVCLCQDEVTDDYIGDNTTVDYTLFESLCSKKDVRNFKAWF
||||||||||||||||||||||||||||||||||||||||||||||||||||||||||||
MDLGKPMKSVLVVALLVIFQVCLCQDEVTDDYIGDNTTVDYTLFESLCSKKDVRNFKAWF

LPIMYSIICFVGLLGNGLVVLTYIYFKRLKTMTDTYLLNLAVADILFLLTLPFWAYSAAK
||*|||**|**|**|||****||*||||||||||**|*|*|*****|*|*||||||||
LPTMYSTTCYTGQQGNGQTTQTYTYFKRLKTMTDTYQQNQATADTQYQQTQPYWAYSAAK

SWVFGVHFCKLIFAIYKMSFFSGMLLLLCISIDRYVAIVQAVSAHRHRARVLLISKLSCV
||||||||||***|*||||**|||****|*|||||||||||||||||||****||*||*
SWVFGVHFCKQTYATYKMSYYSGMQQQQCTSIDRYVAIVQAVSAHRHRARTQQTSKQSCT

GIWILATVLSIPELLYSDLQRSSSEQAMRCSLITEHVEAFITIQVAQMVIGFLVPLLAMS
|*|**||**|*|||||||||||||||||||||||||||||||||||**|***|**|||
GTWTQATTQSTPELLYSDLQRSSSEQAMRCSLITEHVEAFITIQVAQMTTGYQTPQQAMS

FCYLVIIRTLLQARNFERNKAIKVIIAVVVVFIVFQLPYNGVVLAQTVANFNITSSTCEL
*||****||**|||||||||||***|********|*|||***||||||||||||||||
YCYQTTTRTQQQARNFERNKAIKTTTATTTYTTYQQPYNGTTQAQTVANFNITSSTCEL

SKQLNIAYDVTYSLACVRCCVNPFLYAFIGVKFRNDLFKLFKDLGCLSQEQLRQWSSCRH
||||||||*|||*||*|||*||**|*||||||||||||||||||||||||||||||||
SKQLNIAYDTTYSQACTRCCTNPYQYAYIGVKFRNDLFKLFKDLGCLSQEQLRQWSSCRH

IRRSSMSVEAETTTTFSP
||||||||||||||||||
IRRSSMSVEAETTTTFSP
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V, and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 11: CCR-8 C-C Chemokine Receptor Type 8

Example 1 was repeated for the title protein. Replacing all or substantially all of the hydrophobic amino acids, L, I V, and F, with Q, T and Y (respectively) within the transmembrane domains results in the following sequence (lower line SEQ ID NO.:303), aligned with the wild type (top line SEQ ID NO. 302):

```
MDYTLDLSVTTVTDYYYPDIFSSPCDAELIQTNGKLLLLAVFYCLLFVFSLLGNSLVILVL
|||||||||||||||||||||||||||||||||||||**||*****|**|||*******
MDYTLDLSVTTVTDYYYPDIFSSPCDAELIQTNGKLLLATYYCQQYTYSQQGNSQTTQTQ

VVCKKLRSITDVYLLNLALSDLLFVFSFPFQTYYLLDQWVFGTVMCKVVSGFYYIGFYSS
**||||||||||**|*|||*****|*|****|*||||**||||||||||||||*|*|*|||
TTCKKLRSITDVYQQNQAQSDQQYTYSYPYQTYYQQDQWVFGTVMCKVVSGYYYTGYYSS

MFFITLMSVDRYLAVVHAVYALKVRTIRMGTTLCLAVWLTAIMATIPLLVFYQVASEDGV
|***|*||*|||||||||||||||||||||||*|*|*|*|||*|****||*|||||
MYYTTQMSTDRYLAVVHAVYALKVRTIRMGTTLCQATWQTATMATTPQQTYYQTASEDGV

LQCYSFYNQQTLKWKIFTNFKMNILGLLIPFTIFMFCYIKILHQLKRCQNHNKTKAIRLV
|||||||||||||||**||*|||**|***|*||*|||||||||||||||||||||||**
LQCYSFYNQQTLKWKTYTNYKMNTQGQQTPYTTYMYCYIKILHQLKRCQNHNKTKAIRQT

LIVVIASLLFWVPFNVVLFLTSLHSMHILDGCSISQQLTYATHVTEIISFTHCCVNPVIY
*****||***|*|*****|||||||||||||||||||||||||||**|*||||*||**|
QTTTTASQQYWTPYNTTQYQTSLHSMHILDGCSISQQLTYATHVTETTSYTHCCTNPTTY

AFVGEKFKKHLSEIFQKSCSQIFNYLGRQMPRESCEKSSSCQQHSSRSSSVDYIL
|**|||||||||||||||||||||||||||||||||||||||||||||||||||
AYTGEKFKKHLSEIFQKSCSQIFNYLGRQMPRESCEKSSSCQQHSSRSSSVDYIL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V, and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 12: CCR-9 C-C Chemokine Receptor Type 9 Isoform B

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 305), aligned with the wild type (top line SEQ ID NO: 304):

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V, and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 13: CCR-10 C-C Chemokine Receptor Type 10

Example 1 was repeated for the title protein. Replacing each of the hydrophobic amino acids, L, I V, and F, with Q, T and Y (respectively) within the transmembrane domains results in the following sequence (lower line SEQ ID NO: 307), aligned with the wild type (top line SEQ ID NO: 306):

```
MADDYGSESTSSMEDYVNFNFTDFYCEKNNVRQFASHFLPPLYWLVFIVGALGNSLVILV
||||||||||||||||||||||||||||||||||||||||||*||*****||*|||*****
MADDYGSESTSSMEDYVNFNFTDFYCEKNNVRQFASHFLPPQYWQTYTTGAQGNSQTTQT

YWYCTRVKTMTDMFLLNLAIADLLFLVTLPFWAIAAADQWKFQTFMCKVVNSMYKMNFYS
|||||||||||||***|*|*||*****|*|*||*||||||||||||||||||||||*||
YWYCTRVKTMTDMYQQNQATADQQYQTTQPYWATAAADQWKFQTFMCKVVNSMYKMNYYS

CVLLIMCISVDRYIATAQAMRAHTWREKRLLYSKMVCFTINVLAAALCIPEILYSQIKEE
|****||*|*|||*|||||||||||||||**||||*|*|**|||*|*||||||||||||
CTQQTMCTSTDRYTATAQAMRAHTWREKRQQYSKMTCYTTWTQAAAQCTPEILYSQIKEE

SGIAICTMVYPSDESTKLKSAVLTLKVILGFFLPFVVMACCYTIIIHTLIQAKKSSKHKA
|||||||||||||||||||||||||||**|***|***||||||***||**|||||||||
SGIAICTMVYPSDESTKLKSAVLTLKVTQGYYQPYTTMACCYTTTTHTQTQAKKSSKHKA

LKVTITVLTVFVLSQFPYNCILLVQTIDAYAMFISNCAVSTNIDICFQVTQTIAFFHSCL
||*|*|**|****||*|||****|||||||||||||||||||||||*|*||*|**|||*
LKTTTTTQTTYTQSQYPYNCTQQTQTIDAYAMFISNCAVSTNIDICYQTTQTTAYYHSCQ

NPVLYVFVGERFRRDLVKTLKNLGCISQAQWVSFTRREGSLKLSSMLLETTSGALSL
||**|***||||||||||||||||||||||||||||||||||||||||||||||||
NPTQYTYTGERFRRDLVKTLKNLGCISQAQWVSFTRREGSLKLSSMLLETTSGALSL
```

```
MGTEATEQVSWGHYSGDEEDAYSAEPLPELCYKADVQAFSRAFQPSVSLTVAALGLAGNG
|||||||||||||||||||||||||||||||||||||||||||||*|*|*||*|*||||
MGTEATEQVSWGHYSGDEEDAYSAEPLPELCYKADVQAFSRAFQPSTSQTTAAQGQAGNG

LVLATHLAARRAARSPTSAHLLQLALADLLLALTLPFAAAGALQGWSLGSATCRTISGLY
***|||*|||||||||||||**|*|*|***|*|*||||*|||||||||||||||||||*|
QTQATHQAARRAARSPTSAHQQQQAQADQQQAQTQPYAAAGAQQGWSLGSATCRTISGQY

SASFHAGFLFLACISADRYVAIARALPAGPRPSTPGRAHLVSVIVWLLSLLLALPALLFS
|||*|||****|*|||||||||||||||||||||||||**|***|**|***|*||***|
SASYHAGYQYQACTSADRYVAIARALPAGPRPSTPGRAHQTSTTTWQQSQQQAQPAQQYS

QDGQREGQRRCRLIFPEGLTQTVKGASAVAQVALGFALPLGVMVACYALLGRTLLAARGP
|||||||||||||||||||||||||||*|*|*|*|*|*|*|**||||||||||||||||
QDGQREGQRRCRLIFPEGLTQTVKGASATAQTAQGYAQPQGTMTACYAQQGRTLLAARGP
```

```
ERRRALRVVVALVAAFVVLQLPYSLALLLDTADLLAARERSCPASKRKDVALLVTSGLAL
||||||||***|**||****|*|||*|***|||||||||||||||||||*|***|||*|*
ERRRALRTTTAQTAAYTTQQQPYSQAQQQDTADLLAARERSCPASKRKDTAQQTTSGQAQ

ARCGLNPVLYAFLGLRFRQDLRRLLRGGSCPSGPQPRRGCPRRPRLSSCSAPTETHSLSW
||||*||**||**||||||||||||||||||||||||||||||||||||||||||||||
ARCGQNPTQYAYQGLRFRQDLRRLLRGGSCPSGPQPRRGCPRRPRLSSCSAPTETHSLSW

DN
||
DN
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence. The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 14: CXCR1 Chemokine Receptor Type 1

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 309), aligned with the wild type (top line SEQ ID NO: 308):

```
MSNITDPQMWDFDDLNFTGMPPADEDYSPCMLETETLNKYVVIIAYALVFLLSLLGNSLV
|||||||||||||||||||||||||||||||||||||||****|||*****|**|||**
MSNITDPQMWDFDDLNFTGMPPADEDYSPCMLETETLNKYTTTTAYAQTYQQSQQGNSQT

MLVILYSRVGRSVTDVYLLNLALADLLFALTLPIWAASKVNGWIFGTFLCKVVSLLKEVN
|****|||||||||*|**|*|*|***|*|*|*|||||||||||||||||||||||||||
MQTTQYSRVGRSVTDTYQQNQAQADQQYAQTQPTWAASKVNGWIFGTFLCKVVSLLKEVN

FYSGILLLACISVDRYLAIVHATRTLTQKRHLVKFVCLGCWGLSMNLSLPFFLFRQAYHP
*|||****||*|*|||*|**|||||||||||**|**|*|||*|*|*|****|||||
YYSGTQQQACTSTDRYQATTHATRTLTQKRHQTKYTCQGCWGQSMNQSQPYYQYRQAYHP

NNSSPVCYEVLGNDTAKWRMVLRILPHTFGPIVPLFVMLFCYGFTLRTLFKAHMGQKHRA
|||||||||||||||||||||||||||*|***|***|**|||*|*|**|||||||||
NNSSPVCYEVLGNDTAKWRMVLRILPHTYGYTTPQYTMQYCYGYTQRTQYKAHMGQKHRA

MRVIFAVVLIFLLCWLPYNLVLLADTLMRTQVIQESCERRNNIGRALDATEILGFLHSCL
||***|*******||*|||***|||||||||||||||||||||||||||*|**|||*
MRTTYATTQTYQQCWQPYNQTQLADTLMRTQVIQESCERRNNIGRALDATEIQGYQHSCQ

NPIIYAFIGQNFRHGFLKILAMHGLVSKEFLARHRVTSYTSSSVNVSSNL
||**||**||||||||||||||||||||||||||||||||||||||||||
NPTTYAYTGQNFRHGFLKILAMHGLVSKEFLARHRVTSYTSSSVNVSSNL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 15: CXR Chemokine Receptor 1 CXR1

Example 1 was repeated for the title protein. Replacing each of the hydrophobic amino acids, L, I V, and F, with Q, T and Y (respectively) within the transmembrane domains results in the following sequence (lower line SEQ ID NO: 311), aligned with the wild type (top line SEQ ID NO: 310):

```
MESSGNPESTTFFYYDLQSQPCENQAWVFATLATTVLYCLVFLLSLVGNSLVLWVLVKYE
|||||||||||||||||||||||||||||||||||**||*****|**|||***|**||||
MESSGNPESTTFFYYDLQSQPCENQAWVFATLATTTQYCQTYQQSQTGNSQTQWTQVKYE
```

-continued

```
SLESLTNIFILNLCLSDLVFACLLPVWISPYHWGWVLGDFLCKLLNMIFSISLYSSIFFL
||||||****|*|**|||***||**|*|*|||||||||||||||||||||*|*|||****
SLESLTNYTQNQCQSDQTYACQQPTWTSPYHWGWVLGDFLCKLLNMIFSTSQYSSTYYQ

TIMTIHRYLSVVSPLSTLRVPTLRCRVLVTMAVWVASILSSILDTIFHKVLSSGCDYSEL
|*|*|||*|**||||||||||||***|||*|*||**||**|**|||||||||||||
TTMTTHRYQSTTSPLSTLRVPTLRCRTQTTMATWTASTQSSTQDTTYHKVLSSGCDYSEL

TWYLTSVYQHNLFFLLSLGIILFCYVEILRTLFRSRSKRRHRTVKLIFAIVVAYFLSWGP
||||||*|||*****|*|****|||*|**||||||||||||||***|***||**||||
TWYLTSTYQHNQYYQQSQGTTQYCYTETQRTLFRSRSKRRHRTVKQTYATTTAYYQSWGP

YNFTLFLQTLFRTQIIRSCEAKQQLEYALLICRNLAFSHCCFNPVLYVFVGVKFRTHLKH
|||*|***||||||||||||||||||||***|||*|*|||*|**|***||||||||||
YNYTQYQQTLFRTQIIRSCEAKQQLEYAQQTCRNQAYSHCCYNPTQYTYTGVKFRTHLKH

VLRQFWFCRLQAPSPASIPHSPGAFAYEGASFY
|||||||||||||||||||||||||||||||||
VLRQFWFCRLQAPSPASIPHSPGAFAYEGASFY
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native V, L I and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 16: CXCR2 Chemokine Receptor Type 2

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 313), aligned with the wild type (top line SEQ ID NO: 312):

```
MEDFNMESDSFEDFWKGEDLSNYSYSSTLPPFLLDAAPCEPESLEINKYFVVIIYALVFL
|||||||||||||||||||||||||||||||||||||||||||||||||||****||****
MEDFNMESDSFEDFWKGEDLSNYSYSSTLPPFLLDAAPCEPESLEINKYFTTTTYAQTYQ

LSLLGNSLVMLVILYSRVGRSVTDVYLLNLALADLLFALTLPIWAASKVNGWIFGTFLCK
*|**|||**|***||||||||||*|**|*|*|***|*|*|*|||||||||||||||||
QSQQGNSQTMQTTLYSRVGRSVTDTYQQNQAQADQQYAQTQPTWAASKVNGWIFGTFLCK

VVSLLKEVNFYSGILLLACISVDRYLAIVHATRTLTQKRYLVKFICLSIWGLSLLLALPV
||||||*|*|||****||*|*|||*|**||||||||||**|**|*|*||*|***|*|*
VVSLLKETNYYSGTQQQACTSTDRYQATTHATRTLTQKRYQTKYTCQSTWGQSQQQAQPT

LLFRRTVYSSNVSPACYEDMGNNTANWRMLLRILPQSFGFIVPLLIMLFCYGFTLRTLFK
***|||||||||||||||||||||||||||||||||*|***|***|**|||*|*||**|
QQYRRTVYSSNVSPACYEDMGNNTANWRMLLRILPQSYGYTTPQQTMQYCYGYTQRTQYK

AHMGQKHRAMRVIFAVVLIFLLCWLPYNLVLLADTLMRTQVIQETCERRNHIDRALDATE
||||||||||***|*******||*|||***||||||||||||||||||||||||||||
AHMGQKHRAMRTTYATTQTYQQCWQPYNQTQLADTLMRTQVIQETCERRNHIDRALDATE

ILGILHSCLNPLIYAFIGQKFRHGLLKILAIHGLISKDSLPKDSRPSFVGSSSGHTSTTL
**|**|||*|**||**||||||||||||||||||||||||||||||||||||||||||
TQGTQHSCQNPQTYAYTGQKFRHGLLKILAIHGLISKDSLPKDSRPSFVGSSSGHTSTTL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 17: CCR-10 C-C Chemokine Receptor Type 10

Example 1 was repeated for the title protein. Replacing each of the hydrophobic amino acids, L, I V, and F, with Q, T and Y (respectively) within the transmembrane domains results in the following sequence (lower line SEQ ID NO: 315), aligned with the wild type (top line SEQ ID NO: 314):

be designed, shuffled and proteins expressed. The expressed proteins can be assayed for ligand binding, as described herein.

```
MNYPLTLEMDLENLEDLFWELDRLDNYNDTSLVENHLCPATEGPLMASFKAVFVPVAYSL
||||||||||||||||||||||||||||||||||||||||||||||||*|*|||*
MNYPLTLEMDLENLEDLFWELDRLDNYNDTSLVENHLCPATEGPLMASFKAVFTPTAYSQ

IFLLGVIGNVLVLVILERHRQTRSSTETFLFHLAVADLLLVFILPFAVAEGSVGWVLGTF
****|**||*******|||||||||||***|*|*||*******|*|*|||||||||||
TYQQGTTGNTQTQTTQERHRQTRSSTETYQYHQATADQQQTYTQPYATAEGSVGWVLGTF

LCKTVIALHKVNFYCSSLLLACIAVDRYLAIVHAVHAYRHRRLLSIHITCGTINLVGFLL
||||*|*||*|*||||***||*|*|||||||||||||||||||*|*||||*|**|***
LCKTVTAQHKTNYYCSSQQQACTATDRYLAIVHAVHAYRHRRLLSTHTTCGTTWQTGYQQ

ALPEILFAKVSQGHHNNSLPRCTFSQENQAETHAWFTSRFLYHVAGFLLPMLVMGWCYVG
|*||***|||||||||||||||||||||||||||||||**||*||***||**||||*|
AQPETQYAKVSQGHHNNSLPRCTFSQENQAETHAWFTSRYQYHTAGYQQPMQTMGWCYTG

VVHRLRQAQRRPQRQKAVRVAILVTSIFFLCWSPYHIVIFLDTLARLKAVDNTCKLNGSL
**||||||||||||||*|*|***||****|||||****||||||||||||||||||||*
TTHRLRQAQRRPQRQKATRTATQTTSTYYQCWSPYHTTTYLDTLARLKAVDNTCKLNGSQ

PVAITMCEFLGLAHCCLNPMLYTFAGVKFRSDLSRLLTKLGCTGPASLCQLFPSWRRSSL
|*|*|||**|*|||*|||*||||||||||||||||||||||||||||||||||||||||
PTATTMCEYQGQAHCCQNPMQYTFAGVKFRSDLSRLLTKLGCTGPASLCQLFPSWRRSSL

SESENATSLTTF
||||||||||||
SESENATSLTTF
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can Example 18: CXCR6 Chemokine Receptor Type 6

Example 1 was repeated for the title protein. Replacing each of the hydrophobic amino acids, L, I V, and F, with Q, T and Y (respectively) within the transmembrane domains results in the following sequence (lower line SEQ ID NO: 317), aligned with the wild type (top line SEQ ID NO: 316):

```
MAEHDYHEDYGFSSFNDSSQEEHQDFLQFSKVFLPCMYLVVFVCGLVGNSLVLVISIFYH
||||||||||||||||||||||||||||||||||||*****||**||*****|**||
MAEHDYHEDYGFSSFNDSSQEEHQDFLQFSKVFLPCMYQTTYTCGQTGNSQTQTTSTYYH

KLQSLTDVFLVNLPLADLVFVCTLPFWAYAGTHEWVFGQVMCKSLLGIYTINFYTSMLIL
||||||****|*|*|****||*|*||||||||||||||||||||||||*|*|||***
KLQSLTDTYQTNQPQADQTYTCTQPYWAYAGIHEWVFGQVMCKSLLGIYTTNYYTSMQTQ

TCITVDRFIVVVKATKAYNQQAKRMTWGKVTSLLIWVISLLVSLPQIIYGNVFNLDKLIC
||*|*||*****||||||||||||||||||***|**|***|*||**||**|*|||||
TCTTTDRYTTTTKATKAYNQQAKRMTWGKVTSQQTWTTSQQTSQPQTTYGNTYNQDKLIC

GYHDEAISTVVLATQMTLGFFLPLLTMIVCYSVIIKTLLHAGGFQKHRSLKIIFLVMAVF
|||||||***||||*|***|**||**||||||||||||||||||||||||*****||**
GYHDEAISTTTQATQMTQGYYQPQQTMTTCYSVIIKTLLHAGGFQKHRSLKTTYQTMATY

LLTQMPFNLMKFIRSTHWEYYAMTSFHYTIMVTEAIAYLRACLNPVLYAFVSLKFRKNFW
**|||*|*|**|||||||||||||||||*|*|||*|*|||*||**||**||||||||
QQTQMPYNQMKYTRSTHWEYYAMTSFHYTTMTTEATAYQRACQNPTQYAYTSLKFRKNFW

KLVKDIGCLPYLGVSHQWKSSEDNSKTFSASHNVEATSMFQL
||||||||||||||||||||||||||||||||||||||||||
KLVKDIGCLPYLGVSHQWKSSEDNSKTFSASHNVEATSMFQL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 19: CXCR7 Chemokine Receptor Type 7

Example 1 was repeated for the title protein. Replacing all or substantially all of the hydrophobic amino acids, L, I V, and F, with Q, T and Y (respectively) within the transmembrane domains results in the following sequence (lower line SEQ ID NO: 319), aligned with the wild type (top line SEQ ID NO: 318):

domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 20: CLR-1 a Chemokine Like Receptor 1 Isoform A

Example 1 was repeated for the title protein. Replacing all or substantially all of the hydrophobic amino acids, L, I V,

```
MDLHLFDYSEPGNFSDISWPCNSSDCIVVDTVMCPNMPNKSVLLYTLSFIYIFIFVIGMI
|||||||||||||||||||||||||||||||||||||||||||*|**|******||*
MDLHLFDYSEPGNFSDISWPCNSSDCIVVDTVMCPNMPNKSVLLYTQSYTYTYTYTTGMT

ANSVVVWVNIQAKTTGYDTHCYILNLAIADLWVVLTIPVWVVSLVQHNQWPMGELTCKVT
|||***|*||||||||||||**|*|*|*|***|*|**|*|||||||||||||||||*|
ANSTTTWTNIQAKTTGYDTHCYTQNQATADQWTTQTTPTWTTSQVQHNQWPMGELTCKTT

HLIFSINLFGSIFFLTCMSVDRYLSITYFTNTPSSRKKMVRRVVCILVWLLAFCVSLPDT
|***|**||****||||*|||||||||||||||||||||*|**|***|**|*|*|||
HQTYSTNQYGSTYYQTCMSTDRYLSITYFTNTPSSRKKMTRRTTCTQTWQQAYCTSQPDT

YYLKTVTSASNNETYCRSFYPEHSIKEWLIGMELVSVVLGFAVPFSIIAVFYFLLARAIS
||||||||||||||||||||||||||||||**|***|*|*|**|**|***||||
YYLKTVTSASNNETYCRSFYPEHSIKEWLIGMEQTSTTQGYATPYSTTATYYYQQARAIS

ASSDQEKHSSRKIIFSYVVVFLVCWLPYHVAVLLDIFSILHYIPFTCRLEHALFTALHVT
|||||||||||*||******||*|||*|||**|||||||||||||||||||||*|*|
ASSDQEKHSSRKIIYSYTTTYQTCWQPYHTATQQDTYSILHYIPFTCRLEHALFTAQHTT

QCLSLVHCCVNPVLYSFINRNYRYELMKAFIFKYSAKTGLTKLIDASRVSETEYSALEQS
||*|**|||*|**||**||||||||||||||||||||||||||||||||||||||||||
QCQSQTHCCTNPTQYSYTNRNYRYELMKAFIFKYSAKTGLTKLIDASRVSETEYSALEQS

TK
||
TK
```

Each of the predicted transmembrane regions has been underlined and exemplified a fully modified domain of the invention. Thus, for example, the invention includes a transmembrane domain comprising each underlined and F, with Q, T and Y (respectively) within the transmembrane domains results in the following sequence (lower line SEQ ID NO: 321), aligned with the wild type (top line SEQ ID NO: 320):

```
MRMEDEDYNTSISYGDEYPDYLDSIVVLEDLSPLEARVTRIFLVVVYSIVCFLGILGNGL
|||||||||||||||||||||||||||||||||||||||******||**|**|**|||*
MRMEDEDYNTSISYGDEYPDYLDSIVVLEDLSPLEARVTRTYQTTTYSTTCYQGTQGNGQ

VIIIATFKMKKTVNMVWFLNLAVADFLFNVFLPTHITYAAMDYHWVFGTAMCKISNFLLI
***|||||||||||*|**|*|*|||***|***|*|||||||||||||||||||||||***
TTTIATFKMKKTVNMTWYQNQATADYQYNTYQPTHTTYAAMDYHWVFGTAMCKISNFQQT

HNMFTSVFLLTIISSDRCISVLLPVWSQNHRSVRLAYMACMVIWVLAFFLSSPSLVFRDT
|||*||****|**|||||||||||||||||||||*|||**|**|***|||*||***|||
HNMYTSTYQQTTTSSDRCISVLLPVWSQNHRSVRQAYMACMTTWTQAYYQSSPSQTYRDT

ANLHGKISCFNNFSLSTPGSSSNPTHSQMDPVGYSRHMVVTVTRFLCGFLVPVLIITACY
|||||||||||||||||||||||*||||||||||||||||||||**|***|****|||
ANLHGKISCFNNFSLSTPGSSSWPTHSQMDPVGYSRHMVVTVTRYQCGYQTPTQTTTACY

LTIVCKLQRNRLAKTKKPFKIIVTIIITFFLCWCPYHTLNLLELHHTAMPGSVFSLGLPL
*|**||*|||||||||||*|***|***|***||||||*|*|||||||||||||||*|*|*
QTTTCKQQRNRLAKTKKPYKTTTTTTTTYYQCWCPYHTQNQLELHHTAMPGSVFSQGQPQ
```

```
ATALAIANSCMNPILYVFMGQDFKKFKVALFSRLVNALSEDTGHSSYPSHRSFTKMSSMN
|||*|*||||||||**|**||||||||||||||||||||||||||||||||||||||||
ATAQATANSCMNPTQYTYMGQDFKKFKVALFSRLVNALSEDTGHSSYPSHRSFTKMSSMN

ERTSMNERETGML
|||||||||||||
ERTSMNERETGML
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 21: DARIA Duffy Antigen/Chemokine Receptor Isoform A

Example 1 was repeated for the title protein. Replacing each of the hydrophobic amino acids, L, I V, and F, with Q, T and Y (respectively) within the transmembrane domains results in the following sequence (lower line SEQ ID NO: 323), aligned with the wild type (top line SEQ ID NO: 322):

```
MASSGYVLQAELSPSTENSSQLDFEDVWNSSYGVNDSFPDGDYGANLEAAAPCHSCNLLD
||||||||||||||||||||||||||||||||||||||||||||||||||||||||||||
MASSGYVLQAELSPSTENSSQLDFEDVWNSSYGVNDSFPDGDYGANLEAAAPCHSCNLLD

DSALPFFILTSVLGILASSTVLFMLFRPLFRWQLCPGWPVLAQLAVGSALFSIVVPVLAP
|||*|****||**|**||||***|*||||||||||||||**||*|*|||**|***|**||
DSAQPYYTQTSTQGTQASSTTQYMQFRPLFRWQLCPGWPTQAQQATGSAQYSTTTPTQAP

GLGSTRSSALCSLGYCVWYGSAFAQALLLGCHASLGHRLGAGQVPGLTLGLTVGIWGVAA
||||||||||||||||*|||||*|||***|||||*|||||||||||||*|*|*|*||*||
GLGSTRSSALCSLGYCTWYGSAYAQAQQQGCHASQGHRLGAGQVPGLTQGQTTGTWGTAA

LLTLPVTLASGASGGLCTLIYSTELKALQATHTVACLAIFVLLPLGLFGAKGLKKALGMG
**|*|*|*|||||||||||||||||||||||||*||*|*****|*|**||||*|||||||
QQTQPTTQASGASGGLCTLIYSTELKALQATHTTACQATYTQQPQGQYGAKGQKKALGMG

PGPWMNILWAWFIFWWPHGVVLGLDFLVRSKLLLLSTCLAQQALDLLLNLAEALAILHCV
||||||**|||***|||||***|*|***|||||||||||||||||||*|*|||*|**||*
PGPWMNTQWAWYTYWWPHGTTQGQDYQTRSKLLLLSTCLAQQALDLLQNQAEAQATQHCT

ATPLLLALFCHQATRTLLPSLPLPEGWSSHLDTLGSKS
|||***|**|||||||||||||||||||||||||||||
ATPQQQAQYCHQATRTLLPSLPLPEGWSSHLDTLGSKS
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I, V and F amino acids, as set forth in the wild type sequence. The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 22: CD81 Antigen

CD81 may play an important role in the regulation of lymphoma cell growth and interacts with a 16 kDa Leu-13 protein to form a complex possibly involved in signal transduction. CD81 may act as a viral receptor for HCV.

Example 1 was repeated for the title protein. Replacing each of the hydrophobic amino acids, L, I V, and F, with Q, T and Y (respectively) within the transmembrane domains results in the following sequence (lower line SEQ ID NO: 325), aligned with the wild type (top line SEQ ID NO: 324):

```
WT:  1 MGVEGCTKCIKYLLFVFNFVFWLAGGVILGVALWLRHDPQTTNLLYLELGDKPAPNTFYV
       ||||||||||||*****|***|*|||***|*|*|||||||||||||||||||||||||||
MT:  1 MGVEGCTKCIKYQQYTYNYTYWQAGGTTQGTAQWLRHDPQTTNLLYLELGDKPAPNTFYV

WT: 61 GIYILIAVGAVMMFVGFLGCYGAIQESQCLLGTFFTCLVILFACEVAAGIWGFVNKDQIA
       |||***|*||*||**|**|||||*|||||**||**||*****|||*|||*||||||||||
```

```
-continued
MT:  61 GIYTQTATGATMMYTGYQGCYGATQESQCQQGTYYTCQTTQACETAAGTWGFVNKDQIA WT: 121 KDVKQFYDQALQQAVVDDDANNAKAVVKTFHETLDCCGSSTLTALTTSVLKNNLCPSGSN
         ||||||||||||||||||||||||||||||||||||||||||||||||||||||||||||
MT: 121 KDVKQFYDQALQQAVVDDDANNAKAVVKTFHETLDCCGSSTLTALTTSVLKNNLCPSGSN WT: 181 IISNLFKEDCHQKIDDLFSGKLYLIGIAAIVVAVIMIFEMILSMVLCCGIRNSSVY
         |||||||||||||||||||||*|**|*||*||||||||||||||||||
MT: 181 IISNLFKEDCHQKIDDLFSGKQYQTGTAATTTATTMTYEMTQSMVLCCGIRNSSVY
```

The predicted transmembrane regions exemplify modified domains of the invention and include (SEQ ID NOs: 326, 327, 328, 329, 330, 331, 332, 333, respectively):

```
TM1-wt:    LFVFNFVFWLAGGVILGVALW
           ****|***|*|||***|*|*|
TM1-mt:    QYTYNYTYWQAGGTTQGTAQW

TM2-wt:    LIAVGAVMMFVGFLGCYGAIQ
           **|*||*||**|**||||||*|
TM2-mt:    QTATGATMMYTGYQGCYGATQ

TM3-wt:    LGTFFTCLVILFACEVAAGIWGF
           *||**||*****|||*|||*|||
TM3-mt:    QGTYYTCQTTQYACETAAGTWGF

TM4-wt:    YLIGIAAIVVAVIMIFEMILSMV
           |**|*||***|**|**||**|||
TM4-mt:    YQTGTAATTTATTMTYEMTQSMV
```

Thus, for example, the invention includes a transmembrane domain comprising each modified or "mt" domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native V, L I and F amino acids, as set forth in the wild type sequence.

The wild type sequence can be subject to the process as discussed above to select additional transmembrane domain variants as described in Example 1. Coding sequences can be designed, shuffled and proteins expressed. The expressed proteins can be assayed for ligand binding, as described herein.

Example 23: *E. coli* Expression of QTY Variants and a CXCR4-QTY Variant

1. Large-Scale Production of CXCR4-QTY in *E. coli* BL21 (DE3)

A water-soluble GPCR CXCR4 was produced it in *E. coli* with a yield estimated to be ~20 mg purified protein per liter of routine LB culture media. The estimated cost of production is about $0.25 per milligram. Advantageously, this approach can be used to easily obtain grams of quantity of water-soluble GPCRs, which in turn can facilitate their structural determinations.

2. Determining where the Water-Soluble CXCR4-QTY is Produced in *E. coli* Cells

A water-soluble CXCR4-QTY was cloned into pET vector. We first carried out a small-scale *E. coli* culture study to assess the location of produced CXCR4-QTY protein (150 ml culture). After culturing the cells, induced with IPTG at 24° C. for 4 hours, we collected and sonicated the cells and divided into 2 fractions through centrifugation at 14,637×g (12,000 rmp). We then used Western blot analysis of the specific anti-rho-tag monoclonal antibody to detect where the CXCR4-QTY protein was. We observed that the CXCR4-QTY protein was in the supernatant fraction and no protein was observed in the pellet fraction, thus suggesting the protein is fully water-soluble.

3. The Estimated Yield CXCR4-QTY Produced in Soluble Fraction of *E. coli* Cells We then carried out another 150 ml culture and obtained ~6 mg 1D4 monoclonal antibody-purified CXCR4-QTY. Because we under-estimated the yield (we did not anticipate the surprisingly high yield), we did not use enough affinity 1D4 rho-tag monoclonal antibody beads to capture the produced CXCR4-QTY. Thus, a significant amount CXCR4-QTY protein did not bind to the beads due to the fact that not enough beads were added during purification, and the protein was in the flow-through lane and was further washed out. Despite the significant loss, we are still able to obtain ~6 mg for the 150 ml culture as seen from the lanes 8-10 (Elution fractions).

4. Measuring the Thermo-Stability of Purified Water-Soluble CXCR4-QTY Protein

In most cases, structure determines function in proteins. Thus it is important to know if the purified CXCR4-QTY protein produced in *E. Coli* still folds correctly in the typical alpha-helical structure with ~50% alpha-helix. We performed secondary structural measurement using Circular dichroism (CD). We observed the CD spectra of purified CXCR4-QTY protein at various temperatures. We measured the thermo-stability of purified CXCR4-QTY protein. We observed that the purified CXCR4-QTY protein is relatively stable up to 55° C., the protein was only partially and gradually denatured, the CD signal reduction was ~15%. Between 55° C. and 65° C., the denaturation increased toward 65° C., the denaturation transition took place between 65° C. and 75° C. and the protein was nearly fully denatured at 75° C.

We plotted the temperature vs the ellipticity at 222 nm to obtain the melting temperature (Tm) of purified water-soluble CXCR4-QTY protein. From the plot, we estimated that the Tm for purified CXCR4-QTY protein is ~67° C. This Tm suggests the purified water-soluble CXCR4-QTY protein is quite stable compared to many other soluble proteins. This thermo-stability characteristics facilitates obtaining diffracting crystals, since it is known that the better the thermo-stability, the better the crystal lattice packing, and thus the better the chances to obtain structures.

5. Additional G Protein-Coupled Receptors

We selected 10 G protein-coupled receptors (GPCRs) to design the water-soluble form, using the QTY method that is described in Zhang et al., Water Soluble Membrane Proteins and Methods for the Preparation and Use Thereof, U.S. Patent Publication No. 2012/0252719 A ("Zhang"). Alternatively, the proteins described herein can be selected.

6. Molecular Cloning of the Genes.

We successfully verified the GPCR native and QTY genes in the cell-free protein expression plasmid vector pIVex2.3d and *E. Coli* pET28a and pET-duet-1 plasmid vectors.

7. Water-Soluble GPCR Productions

We have produced several native and QTY proteins. When producing native GPCR in the cell-free system, a detergent Brij35 is required, without the detergent, the proteins precipitate upon production. On the other hand, we tested QTY variants in the present and absent of detergent. Without the detergent, the cell-free system produced soluble proteins.

We cloned the QTY variants into *E. Coli* in vivo expression system, pET28a and pET-duet-1 plasmid vectors for *E. Coli* cell protein production in *E. Coli* BL21 (DE3) strain. We have purified several water-soluble GPCR proteins, including CXCR4 and CCR5, which we have used for secondary structural analysis. We have performed ligand-binding studies for CXCR4 with its natural ligand CCL12 (SDF1a). We carried out *E. Coli* production and purification of water-soluble GPCR CCR5e variant. The CCR5e variant had 58 amino acid changes (~18% change). The water-soluble GPCR CCR5e variant was purified to homogeneity using the specific monoclonal antibody rhodopsin-tag. The blue stain showed a single band on the SDS gel indicating the purity. Estimated from the protein size marker, it appears to be a pure homo-dimer (the native membrane-bound CXCR4 crystal structure was a dimer. The Western-blot verified the monomer and homo-dimmer of CCR5e variant that is common in GPCRs.

8. QTY CCR5e Secondary Structural Studies.

We obtained water-soluble QTY variant of GPCR CCR5e. Then we carried out secondary structural analyses using an Aviv Model 410 circular dichroism instrument and confirmed that the GPCR QTY CCR5-e variant has a typical alpha-helical structure. We also carried out experiments in various temperatures to determine the CCR5e variant Tm, namely, the thermo-stability of the water-soluble CCR5e variant. From the experiments, we determined the Tm of CCR5e variant is about 46° C. This Tm is good for crystal screen experiments.

9. Ligand-Binding Studies of CXCR4 with CCL12 (SDF1a).

In order to be certain the designed water-soluble QTY GPCRs still maintain their biological function, namely recognize and bind to their natural ligands, we first used an ELISA measurement to study water-soluble CXCR4 with its natural ligand CCL12 (also called SDF1a). The assay concentrations range from 50 nM to 10 µM. The measured Kd is ~80 nM. The Kd of native membrane-bound CXCR4 with SDF1a is about 100 nM. So the Kd of water-soluble CXCR4 is within acceptable range. Further experiments using more sensitive SPR or other measurement may produce more accurate Kd.

While this invention has been particularly shown and described with references to preferred embodiments thereof, it will be understood by those skilled in the art that various changes in form and details may be made therein without departing from the scope of the invention encompassed by the appended claims.

---

The invention claimed is:

1. A method for producing a water-soluble variant of a G Protein-Coupled Receptor (GPCR), the method comprising:
   (1) entering a sequence of the GPCR for analysis;
   (2) obtaining a variant of the GPCR, wherein substantially all of Leucine (L), Isoleucine (I), Valine (V), and Phenylalanine (F) in the transmembrane (TM) domain alpha-helical segments ("TM regions") of the GPCR are substituted, wherein:
      (a) each said Leucine (L) is independently substituted by Glutamine (Q), Asparagine (N), or Serine (S);
      (b) each said Isoleucine (I) and said Valine (V) are independently substituted by Threonine (T), Asparagine (N), or Serine (S); and,
      (c) each said Phenylalanine is substituted by Tyrosine (Y); and, subsequently,
   (3) obtaining an α-helical secondary structure result for the variant to verify maintenance of α-helical secondary structures in the variant;
   (4) obtaining a trans-membrane (TM) region result for the variant to verify water solubility of the variant, wherein said water solubility of said variant is verified when said TM region result predicts absence of TM regions or low propensity to form TM regions, based on the sequence of said variant, and,
   (5) selecting and producing the variant obtained in step (2) that has maintained α-helical secondary structures according to step (3), and is verified to have water solubility in step (4) as said water-soluble variant of the GPCR.

2. The method of claim 1, wherein step (3) is performed prior to, concurrently with, or after step (4).

3. The method of claim 1 further comprising performing the method with a data processor.

4. The method of claim 1, wherein about 96%, 97%, 98%, 99% or 100% of said leucines are substituted by glutamines, about 96%, 97%, 98%, 99% or 100% of said isoleucines are substituted by threonines, about 96%, 97%, 98%, 99% or 100% of said valines are substituted by threonines, or about 96%, 97%, 98%, 99% or 100% of said phenylalanines are substituted by tyrosines.

5. The method of claim 1, wherein 1, 2, or 3 of said leucines are not substituted, 1, 2, or 3 of said isoleucines are not substituted, 1, 2, or 3 of said valines are not substituted, or 1, 2, or 3 of said phenylalanines are not substituted.

6. The method of claim 1, wherein the TM regions of the GPCR are predicted using TMHMM 2.0 (TransMembrane prediction using Hidden Markov Models) software module.

7. A non-transitory computer readable medium having stored thereon a sequence of instructions to perform the method of claim 1.

8. The method of claim 1, wherein in step (2), all (100% of) said leucines in the TM regions are substituted by glutamines, all (100% of) said isoleucines in the TM regions are substituted by threonines, all (100% of) said valines in the TM regions are substituted by threonines, and all (100% of) said phenylalanines in the TM regions are substituted by tyrosines.

9. The method of claim 1, wherein all said leucines are substituted by glutamines, all said isoleucines are substituted by threonines, all said valines are substituted by threonines, or all said phenylalanines are substituted by tyrosines.

* * * * *